US010041068B2

(12) United States Patent
Avniel et al.

(10) Patent No.: US 10,041,068 B2
(45) Date of Patent: Aug. 7, 2018

(54) ISOLATED DSRNA MOLECULES AND METHODS OF USING SAME FOR SILENCING TARGET MOLECULES OF INTEREST

(71) Applicant: A.B. Seeds Ltd., Lod (IL)

(72) Inventors: Amir Avniel, Tel-Aviv (IL); Efrat Lidor-Nili, Nes Ziona (IL); Rudy Maor, Rechovot (IL); Ofir Meir, Doar-Na Emek Soreq (IL); Orly Noivirt-Brik, Givataim (IL); Osnat Yanai-Azulay, Rishon-LeZion (IL)

(73) Assignee: A. B. Seeds Ltd., Lod (IL)

( * ) Notice: Subject to any disclaimer, the term of this patent is extended or adjusted under 35 U.S.C. 154(b) by 846 days.

(21) Appl. No.: 14/143,748

(22) Filed: Dec. 30, 2013

(65) Prior Publication Data
US 2014/0296503 A1 Oct. 2, 2014

Related U.S. Application Data

(60) Provisional application No. 61/748,095, filed on Jan. 1, 2013, provisional application No. 61/748,101, filed on Jan. 1, 2013, provisional application No. 61/748,094, filed on Jan. 1, 2013, provisional application No. 61/748,099, filed on Jan. 1, 2013, provisional application No. 61/814,888, filed on Apr. 23, 2013, provisional application No. 61/814,892, filed on Apr. 23, 2013, provisional application No. 61/814,899, filed on Apr. 23, 2013, provisional application No. 61/814,890, filed on Apr. 23, 2013, provisional application No. 61/908,965, filed on Nov. 26, 2013, provisional application No. 61/908,855, filed on Nov. 26, 2013.

(51) Int. Cl.
C12N 15/82 (2006.01)
C12N 15/113 (2010.01)
A01H 3/04 (2006.01)
A01N 63/02 (2006.01)

(52) U.S. Cl.
CPC .............. *C12N 15/113* (2013.01); *A01H 3/04* (2013.01); *A01N 63/02* (2013.01); *C12N 15/8206* (2013.01); *C12N 15/8207* (2013.01); *C12N 15/8218* (2013.01); *C12N 15/8279* (2013.01)

(58) Field of Classification Search
CPC .............. C12N 15/113; C12N 15/8218; C12N 15/8279; C12N 15/8206; C12N 15/8201; C12N 15/8216; C12N 15/8286; C12N 2310/14
See application file for complete search history.

(56) References Cited

U.S. PATENT DOCUMENTS

| 3,687,808 | A | 8/1972 | Merigan et al. |
| 3,791,932 | A | 2/1974 | Schuurs et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,469,863 | A | 9/1984 | Ts'o et al. |
| 4,476,301 | A | 10/1984 | Imbach et al. |
| 4,535,060 | A | 8/1985 | Comai |
| 4,581,847 | A | 4/1986 | Hibberd et al. |
| 4,666,828 | A | 5/1987 | Gusella |
| 4,683,202 | A | 7/1987 | Mullis |
| 4,761,373 | A | 8/1988 | Anderson et al. |
| 4,769,061 | A | 9/1988 | Comai |

(Continued)

FOREIGN PATENT DOCUMENTS

| CN | 101279950 A | 10/2008 |
| CN | 101279951 A | 10/2008 |
| CN | 101914540 A | 12/2010 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |

(Continued)

OTHER PUBLICATIONS

Liu, Chenggang, Michael J. Axtell, and Nina V. Fedoroff. "The helicase and RNasellla domains of *Arabidopsis* Dicer-Like1 modulate catalytic parameters during microRNA biogenesis." Plant physiology 159.2 (2012): 748-758.*

(Continued)

*Primary Examiner* — Lee A Visone
*Assistant Examiner* — Weihua Fan
(74) *Attorney, Agent, or Firm* — Amanda Carmany-Rampey; David Marsh; Arnold & Porter Kaye Scholer

(57) ABSTRACT

An isolated dsRNA molecule comprising an antisense RNA sequence for regulating a target gene of interest in a plant or a phytopathogen of the plant, wherein the dsRNA sequence is flanked by two complementary sites to an smRNA or smRNAs expressed in the plant and wherein the dsRNA molecule further comprises a helicase binding site positioned so as to allow unwinding of the strands of the isolated dsRNA molecule to single stranded RNA (ssRNA) and recruitment of an RNA-dependent RNA polymerase so as to amplify the dsRNA molecule in the plant cell and generate secondary siRNA products of the dsRNA sequence.

28 Claims, 22 Drawing Sheets

(56) References Cited

U.S. PATENT DOCUMENTS

| | | |
|---|---|---|
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Feigner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Haberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischotherger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |

(56) References Cited

U.S. PATENT DOCUMENTS

| | | |
|---|---|---|
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 7/2002 | McElroy et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Driver et al. |
| 6,642,435 B1 | 11/2003 | Antoni et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,548,778 B1 | 10/2013 | Hart et al. |
| 8,554,490 B2 | 10/2013 | Tang et al. |
| 9,121,022 B2 | 9/2015 | Sammons et al. |
| 9,445,603 B2 | 9/2016 | Baum et al. |
| 2001/0006797 A1 | 7/2001 | Kumagai et al. |
| 2001/0042257 A1 | 11/2001 | Connor-Ward et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0127444 A1 | 7/2004 | Spradling et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1* | 12/2004 | Shukla .................. C07K 14/415 800/278 |
| 2005/0005319 A1 | 1/2005 | della-Cioppa et al. |
| 2005/0215435 A1 | 9/2005 | Menges et al. |
| 2005/0250647 A1 | 11/2005 | Hills et al. |
| 2006/0009358 A1 | 1/2006 | Kibler et al. |
| 2006/0021087 A1 | 1/2006 | Baum et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1* | 11/2007 | Heck .................. C12N 15/111 504/100 |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1* | 7/2009 | Axtell .................. C12N 15/8218 800/285 |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |

(56) References Cited

U.S. PATENT DOCUMENTS

| | | |
|---|---|---|
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0107355 A1 | 5/2012 | Harris et al. |
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0164205 A1 | 6/2012 | Baum et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |

FOREIGN PATENT DOCUMENTS

| | | |
|---|---|---|
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 157 991 A2 | 11/2001 |
| EP | 1 238 586 A1 | 9/2002 |
| EP | 1 416 049 A1 | 5/2004 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009067739 A | 4/2009 |
| JP | 2009114128 A | 5/2009 |
| JP | 2009126792 A | 6/2009 |
| JP | 2009137851 A | 6/2009 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/49816 A1 | 12/1997 |
| WO | WO 99/024585 A1 | 5/1999 |
| WO | WO 99/26467 | 6/1999 |
| WO | WO 99/26467 A1 | 6/1999 |
| WO | WO 99/27116 A2 | 6/1999 |
| WO | WO 99/32619 | 7/1999 |
| WO | WO 99/32619 A1 | 7/1999 |
| WO | WO 99/61631 A1 | 12/1999 |
| WO | WO 99/67367 A1 | 12/1999 |
| WO | WO 00/32757 A2 | 6/2000 |
| WO | WO 00/044914 A1 | 8/2000 |
| WO | WO 02/14472 A2 | 2/2002 |
| WO | WO 02/066660 A2 | 8/2002 |
| WO | WO 03/000679 A2 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A1 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |

(56) References Cited

FOREIGN PATENT DOCUMENTS

| | | |
|---|---|---|
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/039454 A1 | 4/2007 |
| WO | WO 2007/050715 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/096576 A1 | 8/2007 |
| WO | WO 2007/051462 A2 | 10/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/035150 A2 | 3/2009 |
| WO | WO 2009/046384 A1 | 4/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/152995 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A1 | 10/2014 |
| WO | WO 2014/164797 A2 | 10/2014 |
| WO | WO 2015/010026 A2 | 1/2015 |

OTHER PUBLICATIONS

Voinnet, Olivier. "Origin, biogenesis, and activity of plant microRNAs." Cell 136.4 (2009): 669-687.*
Chen R, Jiang N, Jiang Q, Sun X, Wang Y, et al. (2014) Exploring MicroRNA-Like Small RNAs in the Filamentous Fungus Fusarium oxysporum. PLoS ONE 9(8): e104956. doi:10.1371/journal.pone.0104956.*
Zhang, Zhanyuan J. "Artificial trans-acting small interfering RNA: a tool for plant biology study and crop improvements." Planta 239.6 (2014): 1139-1146.*
Communication pursuant to Article 94(3) EPC dated Jan. 14, 2016, in European Patent Application No. 12 832 415.9.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.

(56) References Cited

OTHER PUBLICATIONS

Extended European Search Report dated Jan. 20, 2016, in European Patent Application No. 13 794 339.5.
First Office Action dated Aug. 31, 2015, in Chinese Patent Application No. 201280053985.3.
First Office Action dated Sep. 9, 2015, in Chinese Patent Application No. 201280055409.2.
Fukunaga et al., "dsRNA with 5' overhangs v contributes to endogenous and antiviral RNA silencing pathways in plants," *The EMBO Journal*, 28(5):545-555 (2009).
GenBank Accession No. CB377464, "CmaE1_37_J02_T3 Cowpea weevil larvae Lambda Zap Express Library Callosobruchus maculatus cDNA, mRNA sequence," (2007).
GenBank Accession No. EW765249, "ST020010B10C12 Normalized and subtracted western corn rootworm female head cDNA library Diabrotica virgifera virgifera cDNA clone STO20010B10C12 5-, mRNA sequence," (2007).
GenBank Accession No. EW771198, "ST020010B10C12 Normalized and subtracted western corn rootworm female head cDNA library Diabrotica virgifera virgifera cDNA clone STO20010B10C12 5-, mRNA sequence," (2007).
GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. GU120406, "Chrysomela tremulae ribosomal protein L7 (RpL7) mRNA, complete cds" (2009).
GenBank Accession No. HD315444, "Sequence 192160 from Patent EP2213738" (2010).
GenBank Accession No. Q4GXM3_BIPLU, "Ribosomal protein L7e" (2006).
GenBank Accession No. Y08611.1, "P.sativum mRNA for dihydropterin pyrophosphokinase/dihydropteroate synthase." (2006).
Gudkov, "Minireview: The L7/L12 ribosomal domain of the ribosome: structural and functional studies," *FEBS Letters*, 407:253-256 (1997).
Heffer et al., "Rapid isolation of gene homologs across taxa: Efficient identification and isolation of gene orthologs from non-model organism genomes, a technical report," *EvoDevo Journal*, 2(7):1-5 (2011).
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/US2015/037015.
Knudsen, "Promoter2.0: for the recognition of PolI promoter sequences," *Bioniformatics*, 15(5):356-361 (1999).
Lein et al., "Target-based discovery of novel herbicides," *Current Opinion in Plant Biology*, 7:219-225 (2004).
Migge et al., "Greenhouse-grown conditionally lethal tobacco plants obtained by expression of plastidic glutamine synthetase antisense RNA may contribute to biological safety," *Plant Science* 153:107-112 (2000).
Nord-Larsen et al., "Cloning, characterization and expression analysis of tonoplast intrinsic proteins and glutamine synthetase in ryegrass (*Lolium perenne* L.)," *Plant Cell Reports*, 28(10):1549-1562 (2009).
Office Action dated Aug. 28, 2013, in Chinese Patent Application No. 201180012795.2.
Office Action dated Feb. 24, 2014, in Eurasian Patent Application No. 201201264.
Office Action dated Oct. 5, 2015, in Eurasian Patent Application No. 201201264/28.
Patent Examination Report No. 1 dated Feb. 8, 2016, in Australian Patent Application No. 2014262189.
Patent Examination Report No. 1 dated Nov. 11, 2013, in Australian Patent Application No. 2011224570.
Promoter Prediction for SEQ ID No. 1702 from 13/612929/MK/, Promoter 2.0 Prediction Results, pp. 1-4 (2016).
Salanenka et al., "Seedcoat Permeability: Uptake and Post-germination Transport of Applied Model Tracer Compounds," *HortScience*, 46(4):622-626 (2011).
Scott et al., Botanical Insecticides for Controlling Agricultural Pests: Piperamides and the Colorado Potato Beetle Leptinotarsa decemlineata Say (Coleoptera: Chrysomelidae), Archives of Insect Biochemistry and Physiology, 54:212-225 (2003).
Second Office Action dated Feb. 25, 2016, in Chinese Patent Application No. 201280054179.8.
Second Office Action dated Mar. 4, 2016, in Chinese Patent Application No. 201280054820.8.
Shintani et al., "Antisense Expression and Overexpression of Biotin Carboxylase in Tobacco Leaves," Plant Physiol., 114:881-886 (1997).
Written Opinion dated Apr. 7, 2016, in Singapore Patent Application No. 201206152-9.
Zhang et al., "Development and Validation of Endogenous Reference Genes for Expression Profiling of Medaka (*Oryzias latipes*) Exposed to Endocrine Disrupting Chemicals by Quantitative Real-Time RT-PCR," Toxicological Sciences, 95(2):356-368 (2007).
Agrios, *Plant Pathology* (Second Edition), 2:466-470 (1978).
Axtell et al., "A Two-Hit Trigger for siRNA Biogenesis in Plants," *Cell*, 127:565-577 (2006).
Bai et al., "Naturally Occurring Broad-Spectrum Powdery Mildew Resistance in a Central American Tomato Accession is Caused by Loss of Mlo Function," *MPMI*, 21(1):30-39 (2008).
Bourgeois et al., "Field and producer survey of ACCase resistant wild oat in Manitoba," *Canadian Journal of Plant Science*, 709-715 (1997).
Brugière et al., "Glutamine Synthetase in the Phloem Plays a Major Role in Controlling Proline Production," *The Plant Cell*, 11:1995-2011 (1999).
Campbell et al., "Gene-knockdown in the honey bee mite *Varroa destructor* by a non-invasive approach: studies on a glutathione S-transferase," *Parasites & Vectors*, 3(1):73, pp. 1-10 (2010).
Chang et al., "Cellular Internalization of Fluorescent Proteins via Arginine-rich Intracellular Delivery Peptide in Plant Cells," *Plant Cell Physiol.*, 46(3):482-488 (2005).
Chee et al., "Transformation of Soybean (*Glycine max*) by Infecting Germinating Seeds with *Agrobacterium tumefaciens*," *Plant Physiol.*, 91:1212-1218 (1989).
Chupp et al., "Chapter 8: White Rust," *Vegetable Diseases and Their Control*, The Ronald Press Company, New York, pp. 267-269 (1960).
Communication pursuant to Article 94(3) EPC dated Jun. 26, 2015, as received in European Patent Application No. 11 753 916.3.
Dalmay et al., "An RNA-Depenedent RNA Polymerase Gene in *Arabidopsis* is Required for Posttranscriptional Gene Silencing Mediated by a Transgene but Not by a Virus," *Cell*, 101:543-553 (2000).
Desai et al., "Reduction in deformed wing virus infection in larval and adult honey bees (*Apis mellifera* L.) by double-stranded RNA ingestion," *Insect Molecular Biology*, 21(4):446-455 (2012).
Emery et al., "Radial Patterning of *Arabidopsis* Shoots by Class III HD-ZIP and KANADI Genes," *Current Biology*, 13:1768-1774 (2003).
Extended European Search Report dated Jun. 29, 2015, in European Patent Application No. 12 831 494.5.
Final Office Action dated Nov. 10, 2015, in U.S. Appl. No. 13/612,985.
Final Office Action dated Nov. 7, 2013, in U.S. Appl. No. 13/042,856.
First Office Action dated May 27, 2015, in Chinese Patent Application No. 201280054179.8.
Fukuhara et al., "Enigmatic Double-Stranded RNA in Japonica Rice," *Plant Molecular Biology*, 21:1121-1130 (1993).
Fukuhara et al., "The Unusual Structure of a Novel RNA Replicon in Rice," *The Journal of Biological Chemistry*, 270(30):18147-18149 (1995).
International Preliminary Report on Patentability (Chapter II) dated Jul. 24, 2015, in International Application No. PCT/US2014/047204.

(56) References Cited

OTHER PUBLICATIONS

International Search Report and the Written Opinion dated Oct. 1, 2013, in International Application No. PCT/IL2013/050447.
International Search Report and Written Opinion dated Jul. 8, 2015, in International Application No. PCT/US2015/011408.
International Search Report and Written Opinion dated Mar. 26, 2015, in International Application No. PCT/US2014/069353.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Jofre-Garfias et al., "*Agrobacterium*-mediated transformation of Amaranthus *hypochondriacus*: light- and tissue-specific expression of a pea chlorophyll a/b-binding protein promoter," *Plant Cell Reports*, 16:847-852 (1997).
Khan et al., "Matriconditioning of Vegetable Seeds to Improve Stand Establishment in Early Field Plantings," *J. Amer. Soc. Hort. Sci.*, 117(1):41-47 (1992).
Kim et al., "Synthetic dsRNA Dicer substrates enhance RNAi potency and efficacy," *Nature Biotechnology*, 23(2):222-226 (2005).
Klahre et al., "High molecular weight RNAs and small interfering RNAs induce systemic posttranscriptional gene silencing in plants," *Proc. Natl. Acad. Sci. USA*, PNAS, 99(18):11981-11986 (2002).
Leopold et al., "Chapter 4: Moisture as a Regulator of Physiological Reaction in Seeds," *Seed Moisture, CSSA Special Publication No. 14*, pp. 51-69 (1989).
MacKenzie et al., "Transgenic *Nicotiana debneyii* expressing viral coat protein are resistant to potato virus S infection," *Journal of General Virology*, 71:2167-2170 (1990).
Maori et al., "IAPV, a bee-affecting virus associated with Colony Collapse Disorder can be silenced by dsRNA ingestion," *Insect Molecular Biology*, 18(1):55-60 (2009).
Molina et al., "Inhibition of protoporphyrinogen oxidase expression in *Arabidopsis* causes a lesion-mimic phenotype that induces systemic acquired resistance," *The Plant Journal*, 17(6):667-678 (1999).
Moriyama et al., "Double-stranded RNA in rice: a novel RNA replicon in plants," *Molecular & General Genetics*, 248(3):364-369 (1995).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Notice of Allowance dated Oct. 5, 2015, in U.S. Appl. No. 13/583,302.
Office Action dated Jul. 23, 2015, in Ukrainian Patent Application No. 201211548.
Office Action dated Sep. 9, 2015, in Chinese Patent Application No. 201280055409.2.
Orbović et al., "Foliar-Applied Surfactants and Urea Temporarily Reduce Carbon Assimilation of Grapefruit Leaves," *J. Amer. Soc. Hort. Sci.*, 126(4):486-490 (2001).
Pratt et al., "Amaranthus rudis and A. tuberculatus, One Species or Two?, *Journal of the Torrey Botanical Society*," 128(3):282-296 (2001).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 2, 2012, in U.S. Appl. No. 13/042,856.
Restriction Requirement dated Oct. 21, 2014, in U.S. Appl. No. 13/583,302.
Riggins et al., "Characterization of de novo transcriptome for waterhemp (*Amaranthus tuberculatus*) using GS-FLX 454 pyrosequencing and its application for studies of herbicide target-site genes," *Pest Manag. Sci.*, 66:1042-1052 (2010).
Rose et al., "Functional polarity is introduced by Dicer processing of short substrate RNAs," *Nucleic Acids Research*, 33(13):4140-4156 (2005).
Rothnie et al., Pararetroviruses and Retroviruses: A Comparative Review of Viral Structure and Gene Expression Strategies, *Advances in Virus Research*, 44:1-67 (1994).
Schweizer et al., "Double-stranded RNA interferes with gene function at the single-cell level in cereals," *The Plant Journal*, 24(6):895-903 (2000).
Senthil-Kumar et al., "A systematic study to determine the extent of gene silencing in *Nicotiana benthamiana* and other *Solanaceae* species when heterologous gene sequences are used for virus-induced gene silencing," *New Phytologist*, 176:782-791 (2007).
Snead et al., "Molecular basis for improved gene silencing by Dicer substrate interfering RNA compared with other siRNA variants," *Nucleic Acids Research*, 41(12):6209-6221 (2013).
Stevens et al., "New Formulation Technology—SILWET® Organosilicone Surfactants Have Physical and Physiological Properties Which Enhance the Performance of Sprays," *Proceedings of the 9th Australian Weeds Conference*, pp. 327-331 (1990).
Street, "Why is DNA (and not RNA) a stable storage form for genetic information?," *Biochemistry Revisited*, pp. 1-4 (2008).
Sutton et al., "Activity of mesotrione on resistant weeds in maize," *Pest Manag. Sci.*, 58:981-984 (2002).
Tank Mixing Chemicals Applied to Peanut Crops: Are the Chemicals Compatible?, College of Agriculture & Life Sciences, NC State University, AGW-653, pp. 1-11 (2004).
Taylor, "Seed Storage, Germination and Quality," *The Physiology of Vegetable Crops*, pp. 1-36 (1997).
Tranel et al., "Resistance of weeds to ALS-inhibiting herbicides: what have we learned?," *Weed Science*, 50:700-712 (2002).
Tsugawa et al., "Efficient transformation of rice protoplasts mediated by a synthetic polycationic amino polymer," *Theor Appl Genet*, 97:1019-1026 (1998).
Vermeulen et al., "The contributions of dsRNA structure to Dicer specificity and efficiency," *RNA*, 11(5):674-682 (2005).
Wang et al., "Foliar uptake of pesticides—Present status and future challenge," ScienceDirect, 87:1-8 (2007).
Written Opinion dated May 8, 2014, in International Application No. PCT/IL2013/050447.
Chee et al., "Transformation of Soybean (*Glycine Max*) by Infecting Germination Seeds With *Agrobacterium Tumefaciens*," *Plant Physiology*, 91:1212-1218 (1989).

(56) References Cited

OTHER PUBLICATIONS

Dalmay et al., "An RNA-Dependent RNA Polymerase Gene in *Arabidopsis* is Required for Posttranscriptional Gene Silencing Mediated by A Transgene But Not by A Virus," Cell, 101(5):543-553 (2000).
International Search Report and the Written Opinion Dated Oct. 1, 2013 From the International Searching Authority Re. Application No. PCT/IL2013/050447.
Agricultural Chemical Usage 2006 Vegetables Summary, Agricultural Statistics Board, NASS, USDA, pp. 1-372 (2007).
Al-Kaff et al., "Plants rendered herbicide-susceptible by cauliflower mosaic virus-elicited suppression of a 35S promoter-regulated transgene," Nature Biotechnology, 18:995-999 (2000).
Andersen et al., "Delivery of siRNA from lyophilized polymeric surfaces,"Biomaterials, 29:506-512 (2008).
Anonymous, "A handbook for high-level expression and purification of 6xHis-tagged proteins," The QiaExpressionist, (2003).
Artymovich, "Using RNA interference to increase crop yield and decrease pest damage," MMG 445 Basic Biotech., 5(1):7-12(2009).
Bachman et al., "Characterization of the spectrum of insecticidal activity of a double-stranded RNA with targeted activity against Western Corn Rootworm (Diabrotica virgifera LeConte)," Transgenic Res., pp. 1-16 (2013).
Balibrea et al., "Extracellular Invertase is an Essential Component of Cytokinin-Mediated Delay of Senescence," The Plant Cell, 16(5):1276-1287 (2004).
Bart et al., "A novel system for gene silencing using siRNAs in rice leaf and stem-derived protoplasts," Plant Methods, 2(13):1-9 (2006).
Basu et al., "Weed genomics: new tools to understand weed biology," Trends in Plant Science, 9(8):391-398 (2004).
Busch et al., "RNAi for discovery of novel crop protection products," Pflanzenschutz-Nachrichten Bayer, 58(1):34-50 (2005).
Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).
Chen et al., "Transfection and Expression of Plasmid DNA in Plant Cells by an Arginine-Rich Intracellular Delivery Peptide without Protoplast Preparation," FEBS Letters 581, pp. 1891-1897 (2007).
Colliver et al.. "Differential modification of flavonoid and isoflavonoid biosynthesis with an antisense chalcone synthase construct in transgenic Lotus corniculatus," Plant Molecular Biology, 35:509-522 (1997).
Communication pursuant to Article 94(3) EPC dated Jun. 26, 2015, in European Patent Application No. 11 753 916.3.
Concise Descriptions of Relevance filed by a third party dated Nov. 29, 2012, in U.S. Appl. No. 13/042,856.
Dalakouras et al., "Induction of Silencing in Plants by High-Pressure Spraying of In vitro-Synthesized Small RNAs," Frontiers in Plant Science, 7(1327):1-5 (2016).
Dawson et al., "cDNA cloning of the complete genome of tobacco mosaic virus and production of infectious transcripts," Proc. Natl. Acad. Sci. USA, 83:1832-1836 (1986).
Extended European Search Report dated Oct. 8, 2013, in European Patent Application No. 11753916.3.
Extended European Search Report dated Sep. 29, 2016, in European Patent Application No. 14778840.0.
Feuillet et al., "Crop genome sequencing: lessons and rationales," Trends Plant Sci., 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2016, in U.S. Appl. No. 13/583,302.
Final Office Action dated Nov. 19, 2015, in U.S. Appl. No. 13/612,941.
Final Office Action dated Nov. 30, 2015, in U.S. Appl. No. 13/612,948.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 9, 2016, in U.S. Appl. No. 13/612,954.
Final Office Action dated Sep. 9, 2016, in U.S. Appl. No. 14/608,951.
Final Office Action dated Sep. 9, 2016, in U.S. Appl. No. 14/603,347.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054819.5.
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Further Examination Report dated May 16, 2014, in New Zealand Patent Application No. 601784.
Gan et al., "Inhibition of Leaf Senescence by Autoregulated Production of Cytokinin," Science, 270:1986-1988 (1995).
Gao et al., "Nonviral Methods for siRNA Delivery," Molecular Pharmaceutics, 6(3):651-658 (2008).
GenBank Accession No. AY545657.1 (2004).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EU024568, "Amaranthus hypochondriacus acetolacate synthase (ALS) gene" (2007).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. U87257.1, "Daucus carota 4-hydroxyphenylpyruvate dioxygenase mRNA, complete cds" (1997).
Genbank Accession No. XM_014456745.1, PREDICTED: Myotis lucifugus ribonucleoprotein, PTB-binding 2 (RAVER2), transcript variant X3, mRNA,: (2015).
GenEmbl Accession No. FJ861243 (2010).
Gossamer Threads, Compendium of Herbicide Adjuvants: Organo-Sillicone Surfactant, p. 1-4 (1998).
Hajirezaei et al., "Impact of elevated cytosolic and apoplastic invertase activity on carbon metabolism during potato tuber development," Journal of Experimental Botany, 51:439-445 (2000).
Holtra et al., "Assessment of the Physiological Condition of *Salvinia natans* L. Exposed to Copper(II) Ions," Environ. Protect. Eng., 41:147-158 (2015).
International Preliminary Report on Patentability dated Sep. 11, 2012, in International Application No. PCT/US2011/027528.

(56) References Cited

OTHER PUBLICATIONS

International Preliminary Report on Patentability dated Sep. 11, 2014, in International Application No. PCT/IL2013/050447.
International Rice Genome Sequencing Project, The map-based sequence of the rice genome, Nature, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated May 10, 2011, in International Application No. PCT/US2011/027528.
International Search Report and the Written Opinion dated Aug. 25, 2014, in International Application No. PCT/US2014/023503.
International Search Report and the Written Opinion dated Aug. 27, 2014, in International Application No. PCT/US2014/023409.
International Search Report and the Written Opinion dated Feb. 23, 2015, in International Application No. PCT/US2014/063832.
International Search Report dated Mar. 12, 2013, in International Application No. PCT/US2012/054789.
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Kaloumenos et al., "Identification of a Johnsongrass (*Sorghum halepense*) Biotype Resistant to ACCase-Inhibiting Herbicides in Northern Greece," Weed Technol, 23:470-476 (2009).
Kambiranda et al., "Relationship Between Acid Invertase Activity and Sugar Content in Grape Species," Journal of Food Biochemistry, 35:1646-1652 (2011).
Kim et al., "Optimization of Conditions for Transient Agrobacterium-Mediated Gene Expression Assays in *Arabidopsis*," Plant Cell Reports, 28:1159-1167 (2009).
Kirkwood, "Herbicides and Plants," Botanical Journal of Scotland, 46(3):447-462 (1993).
Liu et al., "Identification and Application of a Rice Senescence-Associated Promoter," Plant Physiology, 153:1239-1249 (2010).
Liu, "Influence of Sugars on the Foliar Uptake of Bentazone and Glyphosate," New Zealand Plant Protection, 55:159-162 (2002).
Luque et al., "Water Permeability Isolated Cuticular Membranes: A Structural Analysis," Archives of Biochemistry and Biophysics, 317(2):417-422 (1995).
Mora et al., "How Many Species are There on Earth and in the Ocean?," PLOS Biol., 9(8):e100127, p. 1-8 (2011).
Mount et al., "Gene and Metabolite Regulatory Network Analysis of Early Developing Fruit Tissues Highlights New Candidate Genes for the Control of Tomato Fruit Composition and Development," Plant Physiology, 149:1505-1528 (2009).
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Mar. 1, 2016, in U.S. Appl. No. 13/612,954.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856
Office Action dated Apr. 13, 2016, in Chinese Application No. 201280053985.3.
Office Action dated Aug. 25, 2016, in Eurasian Patent Application No. 201201264.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 15, 2016, in Ukrainian Patent Application No. a 2014 03849.
Office Action dated Dec. 27, 2016, in Ukrainian Patent Application No. a 2014 11548.
Office Action dated Jul. 18, 2016, in Indonesian Patent Application No. W00201203610.
Office Action dated Jun. 20, 2016, in Chinese Patent Application No. 201280054819.5.
Office Action dated Jun. 24, 2016, in Chinese Patent Application No. 201280053984.9.
Office Action dated Nov. 15, 2016, in Mexican Patent Application No. MX/a/2014/003068.
Office Action dated Sep. 5, 2016, in Ukrainian Patent Application No. a 2014 03846.
Office Action dated Nov. 3, 2014, in Chinese Patent Application No. 201180012795.2.

(56) References Cited

OTHER PUBLICATIONS

Patent Examination Report No. 1 dated Jun. 17, 2016, in Austrailian Patent Application No. 2012308659.
Patent Examination Report No. 1 dated Jun. 17, 2016, in Austrailian Patent Application No. 2012308660.
Promoter Prediction for SEQ ID No. 4 from 13/612995/MK/, Promoter 2.0 Prediction Results, pp. 1-3 (2016).
Promoter Prediction for SEQ ID No. 7 from 13/612936/MK/, Promoter 2.0 Prediction Results, pp. 1-2 (2016).
Promoter Prediction for SEQ ID No. 8 from 13/612,925/MK/, Promoter 2.0 Prediction Results, pp. 1-6 (2016).
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Oct. 13, 2016, in U.S. Appl. No. 14/206,707.
Restriction Requirement dated Oct. 28, 2015, in U.S. Appl. No. 14/603,347.
Restriction Requirement dated Sep. 2, 2015, in U.S. Appl. No. 14/532,596.
Roberts, "Fast-track applications: The potential for direct delivery of proteins and nucleic acids to plant cells for the discovery of gene function," Plant Methods, 1(12):1-3 (2005).
Robson et al., "Leaf senescence is delayed in maize expressing the Agrobacterium IPT gene under the control of a novel maize senescence-enhanced promoter," Plant Biotechnology Journal, 2:101-112 (2004).
Roitsch et al., "Extracellular invertase: key metabolic enzyme and PR protein," Journal of Experimental Botany, 54(382):513-524 (2003).
Roitsch et al., "Function and regulation of plant invertases: sweet sensations," Trades in Plant Science, 9(12):606-613 (2004).
Ruan et al., "Suppression of Sucrose Synthase Gene Expression Represses Cotton Fiber Cell Initiation, Elongation, and Seed Development," The Plant Cell, 15:952-964 (2003).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Second Chinese Office Action dated Jun. 10, 2014, in Chinese Patent Application No. 201180012795.2.
Shaoquan, "The action target of herbicide and the innovation of a new variety," Chemical Industry Press, pp. 23-24 (2001).
Showalter, "Structure and Function of Plant Cell Wall Proteins," The Plant Cell, 5:9-23 (1993).
Song et al., "Herbicide," New Heterocyclic Pesticide, Chemical Industry Press, 354-356 (2011).
Stevens, "Organosilicone Surfactants as Adjuvants for Agrochemicals," Journal of Pesticide Science, 38:103-122 (1993).
Tang et al., "Efficient delivery of small interfering RNA to plant cells by a nanosecond pulsed laser-induced stress wave for post-transcriptional gene silencing," Plant Science, 171:375-381 (2006).
Temple et al., "Can glutamine synthetase activity levels be modulated in transgenic plants by the use of recombinant DNA technology?" Transgenic Plants and Plant Biochemistry, 22(4):915-920 (1994).
Tenllado et al., "Double-Stranded RNA-Mediated Interference with Plant Virus Infection," Journal of Virology, 75(24):12288-12297 (2001).
Thomas et al., "Size constraints for targeting post-transcriptional gene silencing and for RNA-directed methylation in Nicotiana benthamiana using a potato virus X vector," The Plant Journal, 25(4):417-425 (2001).
Tomlinson et al., "Evidence that the hexose-to-sucrose ratio does not control the switch to storage product accumulation in oilseeds: analysis of tobacco seed development and effects of overexpressing apoplastic invertase," Journal of Experimental Botany.
Unniraman et al., "Conserved Economics of Transcription Termination in Eubacteria," Nucleic Acids Research, 30(3):675-684 (2002).
Voinnet et al., "Systemic Spread of Sequence-Specific Transgene RNA Degradation in Plants is Initiated by Localized Introduction of Ectopic Promoterless DNA," Cell, 95:177-187 (1998).
Widholm et al., "Glyphosate selection of gene amplification in suspension cultures of 3 plant species," Physiologia Plantarum, 112:540-545 (2001).
Wiesman et al., "Novel cationic vesicle platform derived from veronia oil for efficient delivery of DNA through plant cuticle membranes," Journal of Biotechnology, 130:85-94 (2007).
Wild Carrot, Noxious Weed Control Board (NWCB) of Washington State (2010) <www.nweb.wa.gov/detail.asp?weed=46>.
Zhang et al., "Chapter 10: New Characteristics of Pesticide Research & Development," New Progress of the world agriculture chemicals, p. 209 (2010).
Abad et al., "Genome sequencing of the metazoan plant-parasitic nematode *Meloidogyne incognita*," Nature Biotechnology, 26:909-915 (2008).
Ahlquist et al., "Nucleotide Sequence of the Brome Mosaic Virus Genome and its Implications for Viral Replication," J. Mol. Biol., 172:369-383 (1984).
Berrie et al., "Complete nucleotide sequence and host range of South African cassava mosaic virus: further evidence for recombination amongst begomoviruses," J. Gen. Virol., 82:53-58 (2001).
Bogdanove et al., "Two New Complete Genome Sequences Offer Insight Into Host and Tissue Specificity of Plant Pathogenic *Xanthomonas* spp.," Journal of Bacteriology, 193:5450-5464 (2011).
Boutros et al., "Genome-Wide RNAi Analysis of Growth and Viability in *Drosophila* Cells," Science, 303:832-835 (2004).
Dietzl et al., "A genome-wide transgenic RNAi library for conditional gene inactivation in *Drosophila*," Nature, 448:151-156 (2007).
Frank et al., "Nucleotide Sequence of Cauliflower Mosaic Virus DNA," Cell, 21:285-294 (1980).
Goelet et al., "Nucleotide sequence of tobacco mosaic virus RNA," Proc. Natl. Acad. Sci. USA, 79:5818-5822 (1982).
Goff et al., "A Draft Sequence of the Rice Genome (*Oryza sativa* L. ssp. *japonica*)," Science, 296:92-100.
Hearne et al., "The Complete Genome Structure and Synthesis of Infectious RNA from Clones of Tomato Bushy Stunt Virus," Virology, 177:141-151 (1990).
Huisman et al., "The Complete Nucleotide Sequence of Potato Virus X and Its Homologies at the Amino Acid Level with Various Plus-stranded RNA Viruses," J. Gen. Virol., 69:1789-1798 (1988).
Jalan et al., "Comparative genomic and transcriptome analyses of pathotypes of *Xanthomonas citri* subsp. Citri provide insights into mechanisms of bacterial virulence and host range," BMC Genomics, 14:551-568 (2013).
Karasev et al., "Complete Sequence of the Citrus Tristeza Virus RNA Genome," Virology, 208:511-520 (1995).
Kuromori et al., "A trial of phenome analysis using 4000 Ds-insertional mutants in gene-coding regions of *Arabidopsis*," Plant Journal, 47:640-651 (2006).
Lee et al., "A systematic RNAi screen identifies a critical role for mitochondria in *C. elegans* longevity," Nature Genetics, 33:40-48 (2002).
Maiss et al., "The Complete Nucleotide Sequence of Plum Pox Virus RNA," J. Gen. Virol., 70:513-524 (1989).
Miller et al., "Sequence and organization of barley yellow dwarf virus genomic RNA," Nucleic Acids Research, 16:6097-6111 (1988).
Navot et al., "Tomato Yellow Leaf Curl Virus: A Whitefly-Transmitted Geminivirus with a Single Genomic Component," Virology, 185:151-161 (1991).
Opperman et al., "Sequence and genetic map of Meloidogyne hapla: A compact nematode genome for plant parasitism," Proc. Natl. Acad. Sci. USA, 105:14802-14807 (2008).
Paterson et al., "The Sorghum bicolor genome and the diversification of grasses," Nature, 457:551-556 (2009).

(56) References Cited

OTHER PUBLICATIONS

Robaglia et al., "Nucleotide Sequence of Potato Virus Y (N Strain) Genomic RNA," *J. Gen. Virol.*, 70:935-947 (1989).
Schnable et al., "The B73 Maize Genome: Complexity, Diversity, and Dynamics," *Science*, 326:1112-1115 (2009).
Stover et al., "Complete genome sequence of *Pseudomonas aeruginosa* PA01, an opportunistic pathogen," *Nature*, 406:959-964 (2000).
Studholme et al., "Draft Genome Sequence of *Xanthomoas sacchari* and Two Banana-Associated Xanthomonads Reveal Insights into the *Xanthomonas* Group 1 Clade," *Genes*, 2:1050-1065 (2011).
The Tomato Genome Consortium, "The tomato genome sequence provides insights into fleshy fruit evolution," *Nature*, 485:635-641 (2012).
Triplett et al., "Genome Analysis of *Xanthomonas oryzae* Isolates from Rice Grown in the United States Reveals Substantial Divergence from Known X. oryzae Pathovars," *Applied and Environmental Microbiology*, 77:3930-3937 (2011).
Van der Wilk et al., "Nucleotide sequence and organization of potato leafroll virus genomic RNA," *FEBS Letters*, 245:51-56 (1989).
Alarcón-Reverte et al., "Resistance to ACCase-inhibiting herbicides in the weed *Lolium multiflorum*," *Comm. Appl. Biol. Sci.*, 73(4):899-902 (2008).
Amarzguioui et al., "An algorithm for selection of functional siRNA sequences," *Biochemical and Biophysical Research Communications*, 316:1050-1058 (2004).
Ambrus et al., "The Diverse Roles of RNA Helicases in RNAi," *Cell Cycle*, 8(21):3500-3505 (2009).
An et al., "Transient RNAi Induction against Endogenous Genes in *Arabidopsis* Protoplasts Using in Vitro-Prepared Double-Stranded RNA," *Biosci Biotechnol Biochem*, 69(2):415-418 (2005).
Andersson et al., "A novel selection system for potato transformation using a mutated AHAS gene," *Plant Cell Reports*, 22(4):261-267 (2003).
Anonymous, "A handbook for high-level expression and purification of 6xHis-tagged proteins," *The QUIexpressionist*, (2003).
Anonymous, "Agronomy Facts 37: Adjuvants for enhancing herbicide performance," n.p., 1-8, (Jan. 26, 2000), Web, (Jan. 21, 2014).
Anonymous, "Devgen, The mini-Monsanto," KBC Securities (2006).
Anonymous, "Do Monsanto have the next big thing?," *Austalian Herbicide Resistance Initiative (AHRI)*, (Apr. 23, 2013) Web. (Jan. 19, 2015).
Aoki et al., "In Vivo Transfer Efficiency of Antisense Oligonucleotides into the Myocardium Using HVJ—Liposome Method," *Biochem Biophys Res Commun*, 231:540-545 (1997).
Arpaia et al., "Production of transgenic eggplant (*Solanum melongena* L.) resistant to Colorado Potato Beetle (*Leptinotarsa decemlineata* Say)," (1997) *Theor. Appl. Genet.*, 95:329-334 (1997).
Artmymovich, "Using RNA interference to increase crop yield and decrease pest damage," *MMG 445 Basic Biotech.*, 5(1):7-12 (2009).
Australian Patent Examination report No. 1 dated Nov. 11, 2013, in Australian Application No. 2011224570.
Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).
Bannerjee et al., "Efficient production of transgenic potato (*S. tuberosum* L. ssp. *andigena*) plants via *Agrobacterium tumefaciens*-mediated transformation," *Plant Sci.*, 170:732 738 (2006).
Baulcombe, "RNA silencing and heritable epigenetic effects in tomato and *Arabidopsis*," Abstract 13th Annual Fall Symposium, Plant Genomes to Phenomes, Donald Danforth Plant Science Center, 28-30 (2011).
Bayer et al., "Programmable ligand-controlled riboregulators of eukaryotic gene expression," *Nature Biotechnol.*, 23(3):337-343 (2005).
Beal, et al., "Second Structural Motif for Recognition of DNA by Oligonucleotide-Directed Triple-Helix Formation," *Science*, 251:1360-1363 (1992).

Becker et al., "Fertile transgenic wheat from microprojectile bombardment of scutellar tissue," *The Plant Journal*, 5(2):299-307 (1994).
Bhargava et al., "Long double-stranded RNA-mediated RNA interference as a tool to achieve site-specific silencing of hypothalamic neuropeptides," *Brain Research Protocols*, 13:115-125 (2004).
Boletta et al., "High Efficient Non-Viral Gene Delivery to the Rat Kidney by Novel Polycationic Vectors," *J. Am Soc. Nephrol.*, 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," *FEBS Letters*, 580:789-794 (2006).
Breaker et al., "A DNA enzyme with $Mg^{2+}$-dependent RNA phosphoesterase activity," *Chemistry and Biology*, 2:655-660 (1995).
Brodersen et al., "The diversity of RNA silencing pathways in plants," *Trends in Genetics*, 22(5):268-280 (2006).
Busi et al., "Gene flow increases the initial frequency of herbicide resistance alleles in unselectedpopulations," *Agriculture, Ecosystems and Environments*, Elsevier, Amsterdam, NL, 142(3):403-409 (2011).
Butler et al., "Priming and re-drying improve the survival of mature seeds of *Digitalis purpurea* during storage," *Annals of Botany*, 103:1261-1270 (2009).
Bytebier et al., "T-DNA organization in tumor cultures and transgenic plants of the monocotyledon *Asparagus officinalis*," *Proc. Natl. Acad. Sci. U.S.A.*, 84:5345-5349 (1987).
Chabbouh et al., "Cucumber mosaic virus in artichoke," *FAO Plant Protection Bulletin*, 38:52-53 (1990).
Chakravarty et al., "Genetic Transformation in Potato: Approaches and Strategies," *Amer J Potato Res*, 84:301 311 (2007).
Chen et al., "In Vivo Analysis of the Role of atTic20 in Protein Import into Chloroplasts," *The Plant Cell*, 14:641-654 (2002).
Cheng et al., "Production of fertile transgenic peanut (*Arachis hypogaea* L.) plants using *Agrobacterium tumefaciens*," *Plant Cell Reports*, 15:653-657 (1996).
Chi et al., "The Function of RH22, a DEAD RNA Helicase, in the Biogenesis of the 50S Ribosomal Subunits of *Arabidopsis* Chloroplasts," *Plant Physiology*, 158:693-707 (2012).
Chinese Office Action dated Aug. 28, 2013 in Chinese Application No. 201180012795.2.
Clough et al., "Floral dip: a simplified method for Agrobacterium-mediated transformation of *Arabidopsis thaliana*," *The Plant Journal*, 16(6):735-743 (1998).
CN101914540 Patent Diclosure, "Introduction of RNA into plant by interference," (2010).
Colbourne et al., "The Ecoresponsive Genome of Daphnia pulex," *Science*, 331(6017):555-561 (2011).
Colombian Office Action dated Aug. 2, 2013 in Application No. 12 152898.
Colombian Office Action dated Feb. 21, 2014 in Application No. 12 152898.
Cooney et al., "Site-Specific Oligonucleotide Binding Represses Transcription of the Human c-myc Gene in Vitro," *Science*, 241:456-459 (1988).
COST Action FA0806 progress report "Plant virus control employing RNA-based vaccines: A novel non-transgenic strategy" (2010).
Coticchia et al., "Calmodulin modulates Akt activity in human breast cancer cell Breast lines," *Breast Cancer Res. Treat*, 115:545-560 (2009).
Database EMBL CBIB Daphnia—XP-002732239 (2011).
Davidson et al., "Engineering regulatory RNAs," *TRENDS in Biotechnology*, 23(3):109-112 (2005).
De Block, et al. "Engineering herbicide resistance in plants by expression of a detoxifying enzyme," *EMBO J.* 6(9):2513-2519 (1987).
De Framond, "MINI-Ti: A New Vector Strategy for Plant Genetic Engineering," *Nature Biotechnology*, 1:262-269 (1983).

(56) References Cited

OTHER PUBLICATIONS

Della-Cioppa et al., "Import of a precursor protein into chloroplasts is inhibited by the herbicide glyphosate," *The EMBO Journal*, 7(5):1299-1305 (1988).
Diallo et al., "Long Endogenous dsRNAs Can Induce Complete Gene Silencing in Mammalian Cells and Primary Cultures," *Oligonucleotides*, 13:381-392 (2003).
Dietemann et al.,"*Varroa destructor*: research avenues towards sustainable control," *Journal of Apicultural Research*, 51(1):125-132 (2012).
Du et al., "A systematic analysis of the silencing effects of an active siRNA at all single-nucleotide mismatched target sites," *Nucleic Acids Research*, 33(5):1671-1677 (2005).
Dunoyer et al., "Small RNA Duplexes Function as Mobile Silencing Signals Between Plant Cells," *Science*, 328:912-916 (2010).
Ellington et al., "In vitro selection of RNA molecules that bind specific ligands," *Nature*, 346:818-822 (1990).
Eurasian Office Action dated Feb. 24, 2014, in Application No. 201201264.
European Cooperation in the field of Scientific and Technical Research—Memorandum of Understanding for COST Action FA0806 (2008).
European Supplemental Search Report dated Oct. 8, 2013 in Application No. 11753916.3.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Feb. 2, 2015, in European Patent Application No. 12 830 932.5.
Extended European Search Report dated Feb. 3, 2015, in European Patent Application No. 12 831 945.6.
Extended European Search Report dated Feb. 27, 2015, in European Patent Application No. 12 832 160.1.
Extended European Search Report dated Mar. 3, 2015, in European Patent Application No. 12 831 166.9.
Extended European Search Report dated Mar. 17, 2015, in European Patent Application No. 12 831 684.1.
Partial Supplementary European Search Report dated Mar. 2, 2015, in European Patent Application No. 12 831 494.5.
Farooq et al., "Rice seed priming," *IPRN*, 30(2):45-48 (2005).
Fire et al., "Potent and specific genetic interference by double-stranded RNA in *Caenorhabditis elegans*," *Nature*, 391:806-811 (1998).
First Examination Report dated Apr. 23, 2013, in New Zealand Patent Application No. 601784.
First Examination Report dated Jul. 28, 2014, in New Zealand Patent Application No. 627060.
Fukuhara et al., "The wide distribution of endornaviruses, large double-stranded RNA replicons with plasmid-like properties," *Archives of Virology*, 151:995-1002 (2006).
Further Examination Report issued in New Zealand Patent Application No. 601784 dated May 16, 2014.
Gaines et al., "Gene amplification confers glypho sate resistance in *Amaranthus palmeri*," *Proc. Natl. Acad. Sci. USA*, 107(3):1029-1034 (2010).
Gallie et al., "Identification of the motifs within the tobacco mosaic virus 5'-leader responsible for enhancing translation," *Nucleic Acids Res.*, 20(17):4631-4638 (1992).
Gan et al. "Bacterially expressed dsRNA protects maize against SCMV infection," *Plant Cell Rep*, 11:1261-1268 (2010).
Gao et al., "Down-regulation of acetolactate synthase compromises 01-1-mediated resistance to powdery mildew in tomato," *BMC Plant Biology*, 14 (2014).
Garbian et al., "Bidirectional Transfer of RNAi between Honey Bee and *Varroa destructor*: *Varroa* Gene Silencing Reduces*Varroa* Population," 8(12):1-9:e1003035 (2012).
Ge et al., "Rapid vacuolar sequestration: the horseweed glyphosate resistance mechanism," *Pest Management Sci.*, 66:345-348 (2010).

GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank accession No. AY545657.1, published 2004.
GenBank accession No. GI:186478573, published Jan. 22, 2014.
GenEmbl FJ861243, published Feb. 3, 2010.
Gong et al., "Silencing of Rieske iron-sulfur protein using chemically synthesised siRNA as a potential biopesticide against Plutella xylostella," *Pest Manag Sci*, 67:514-520 (2011).
Gressel et al., "A strategy to provide long-term control of weedy rice while mitigating herbicide resistance transgene flow, and its potential use for other crops with related weeds," *Pest Manag Sci*, 65(7):723-731 (2009).
Gutensohn et al., "Functional analysis of the two *Arabidopsis* homologues of Toc34, a component of the chloroplast protein import apparatus," *The Plant Journal*, 23(6):771-783 (2000).
Haigh, "The Priming of Seeds: Investigation into a method of priming large quantities of seeds using salt solutions," Thesis submitted to Macquarie University (1983).
Hamilton et al., "Guidelines for the Identification and Characterization of Plant Viruses," *J. gen. Virol.*, 54:223-241 (1981).
Hamilton et al., "Two classes of short interfering RNA in RNA silencing," *EMBO J.*, 21(17):4671-4679 (2002).
Han et al., "Molecular Basis for the Recognition of Primary microRNAs by the Drosha-DGCR8 Complex," *Cell*, 125(5):887-901 (2006).
Hannon, "RNA interference," *Nature*,481:244-251 (2002).
Hardegree, "Drying and storage effects on germination of primed grass seeds," *Journal of Range Management*, 47(3):196-199 (1994).
Harrison et al., "Does Lowering Glutamine Synthetase Activity in Nodules Modigy Nitrogen Metabolism and Growth of *Lotus japonicus?*," *Plant Physiology*, 133:253-262 (2003).
Herman et al., "A three-component dicamba O-demethylase from *Pseudomonas maltophilia*, strain DI-6: gene isolation, characterization, and heterologous expression," *J. Biol. Chem.*, 280: 24759-24767 (2005).
Hewezi et al., "Local infiltration of high- and low-molecular-weight RNA from silenced sunflower (*Helianthus annuus* L.) plants triggers post-transcriptional gene silencing in non-silenced plants," *Plant Biotechnology Journal*, 3:81-89 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem. Physiol.*, 57:137-146 (1997).
Himber et al., "Transitivity-dependant and—independent cell-to-cell movement of RNA silencing," *The EMBO Journal*, 22(17):4523-4533 (2003).
Hirschberg et al., "Molecular Basis of Herbicide Resistance in *Amaranthus hybridus*," *Science*, 222:1346-1349 (1983).
Hoekema et al., "A binary plant vector strategy based on separation of *vir*- and T-region of the *Agrobacterium tumefaciens* Ti-plasmid," *Nature*, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.*, 107(2):469-477 (1995).
Hsieh et al., "A library of siRNA duplexes targeting the phosphoinositide 3-kinase pathway: determinants of gene silencing for use in cell-based screens," *Nucleic Acids Res.*, 32(3):893-901 (2004).
Huesken et al., "Design of a genome-wide siRNA library using an artificial neural network," *Nature Biotechnology*, 23(8): 995-1001 (2005).

(56) References Cited

OTHER PUBLICATIONS

Hunter et al., "RNA Interference Strategy to suppress Psyllids & Leafhoppers," *International Plant and Animal Genome XIX*, 15-19 (2011).
Ichihara et al., "Thermodynamic instability of siRNA duplex is a prerequisite for dependable prediction of siRNA activities," *Nucleic Acids Res.*, 35(18):e123 (2007).
International Preliminary Report on Patentability dated Sep. 11, 2014, in International Application No. PCT/IL13/50447.
International Search Report and the Written Opinion dated May 10, 2011, in International Application No. PCT/US 11/27528.
International Search Report and the Written Opinion dated Feb. 25, 2013, in International Application No. PCT/US 12/54883.
International Search Report and the Written Opinion dated Feb. 27, 2013, in International Application No. PCT/US 12/54814.
International Search Report and the Written Opinion dated Feb. 27, 2013, in International Application No. PCT/US 12/54842.
International Search Report and the Written Opinion dated Feb. 27, 2013, in International Application No. PCT/US 12/54862.
International Search Report and the Written Opinion dated Feb. 27, 2013, in International Application No. PCT/US 12/54894.
International Search Report and the Written Opinion dated Feb. 27, 2013, in International Application No. PCT/US 12/54974.
International Search Report and the Written Opinion dated Feb. 27, 2013, in International Application No. PCT/US 12/54980.
International Search Report and the Written Opinion dated Jul. 15 2014, in International Application No. PCT/US2014/025305.
International Search Report and the Written Opinion dated Jul. 22 2014, in International Application No. PCT/IL2013/051083.
International Search Report and the Written Opinion dated Jul. 22 2014, in International Application No. PCT/IL2013/051085.
International Search Report and the Written Opinion dated Jul. 24 2014, in International Application No. PCT/US2014/026036.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report dated Mar. 12, 2013, in International Application No. PCT/US 12/54789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Isaacs et al., "Engineered riboregulators enable post-transcriptional control of gene expression," *Nature Biotechnology*, 22(7):841-847 (2004).
Ji et al., "Regulation of small RNA stability: methylation and beyond," *Cell Research*, 22:624-636 (2012).
Jones-Rhoades et al., "MicroRNAs and Their Regulatory Roles in Plants," *Annu. Rev. Plant Biol.*, 57:19-53 (2006).
Josse et al., "A DELLA in Disguise: SPATULA Restrains the Growth of the Developing *Arabidopsis* Seedling," *Plant Cell*, 23:1337-1351 (2011).
Kam et al., "Nanotube Molecular Transporters: Internalization of Carbon Nanotube—Protein Conjugates into Mammalian Cells," *J. Am. Chem. Soc.*, 126(22):6850-6851 (2004).
Katoh et al., "Specific residues at every third position of siRNA shape its efficient RNAi activity," *Nucleic Acids Res.*, 35(4): e27 (2007).
Kertbundit et al., "In vivo random β-glucuronidase gene fusions in *Arabidopsis thaliana*," *Proc. Natl. Acad. Sci. U S A.*, 88:5212-5216 (1991).

Khachigian, "DNAzymes: Cutting a path to a new class of therapeutics," *Curr Opin Mol Ther* 4(2):119-121 (2002).
Khodakovskaya et al., "Carbon Nanotubes are Able To Penetrate Plant Seed Coat and Dramatically Affect Seed Germination and Plant Growth," *ACS Nano*, 3(10):3221-3227 (2009).
Kirkwood, "Use and Mode of Action of Adjuvants for Herbicides: A Review of some Current Work," *Pestic Sci.*, 38:93-102 (1993).
Kronenwett et al., "Oligodeoxyribonucleotide Uptake in Primary Human Hematopoietic Cells is Enhanced by Cationic Lipids and Depends on the Hematopoietic Cell Subset," *Blood*, 91(3):852-862 (1998).
Kumar et al., "Sequencing, *De Novo* Assembly and Annotation of the Colorado Potato Beetle, *Leptinotarsa decemlineata*,Transcriptome," *PLoS One*, 9(1):e86012 (2014).
Kusaba et al., "*Low glutelin content1*: A Dominant Mutation That Suppresses the *Glutelin* Multigene Family via RNA Silencing ni Rice," *The Plant Cell*, 15(6):1455-1467 (2003).
Kusaba, "RNA interference in crop plants," *Curr Opin Biotechnol*, 15(2):139-143 (2004).
Lavigne et al., "Enhanced antisense inhibition of human immunodeficiency virus type 1 in cell cultures by DLS delivery system," *Biochem Biophys Res Commun*, 237:566-571 (1997).
Lee et al., "Aptamer Database," *Nucleic Acids Research*, 32:D95-D100 (2004).
Lermontova et al., "Reduced activity of plastid protoporphyrinogen oxidase causes attenuated photodynamic damage during high-light compared to low-light exposure," *The Plant Journal*, 48(4):499-510 (2006).
Lesnik et al., "Prediction of rho-independent transcriptional terminators in *Escherichia coli*," *Nucleic Acids Research*, 29(17):3583-3594 (2001).
Li et al., "Establishment of a highly efficient transformation system for pepper (*Capsicum annuum* L.)," *Plant Cell Reports*, 21: 785-788 (2003).
Li et al., "The FAST technique: a simplified Agrobacterium-based transfaimation method for transient gene expression analysis in seedlings of *Arabidopsis* and other plant species," *Plant Methods*, 5(6):1-15 (2009).
Liu et al., "Carbon Nanotubes as Molecular Transporters for Walled Plant Cells," *Nano Letters*, 9(3):1007-1010 (2009).
Liu et al., "Comparative study on the interaction of DNA with three different kinds of surfactants and the founation of multilayer films," *Bioelectrochemistry*, 70:301-307 (2007).
Liu et al., "DNAzyme-mediated recovery of small recombinant RNAs from a 5S rRNA-derived chimera expressed in *Escherichia coli*," *BMC Biotechnology*, 10:85 (2010).
Llave et al., "Endogenous and Silencing-Associated Small RNAs in Plants," *The Plant Cell*, 14:1605-1619 (2002).
Lu et al., "RNA silencing in plants by the expression of siRNA duplexes," *Nucleic Acids Res.*, 32(21):e171 (2004).
Lu et al., "OligoWalk: an online siRNA design tool utilizing hybridization thermodynamics," *Nucleic Acids Research*, 36:W104-W108 (2008).
Luft, "Making sense out of antisense oligodeoxynucleotide delivery: getting there is half the fun," *J Mol Med*, 76:75-76 (1998).
Maas et al., "Mechanism and optimized conditions for PEG mediated DNA transfection into plant protoplasts," *Plant Cell Reports*, 8:148-149 (1989).
Maher III et al., "Inhibition of DNA binding proteins by oligonucleotide-directed triple helix formation," *Science*, 245(4919):725-730 (1989).
Makkouk et al., "Virus Diseases of Peas, Beans, and Faba Bean in the Mediterranean region," *Adv Virus Res*, 84:367-402 (2012).
Mandal et al., "Adenine riboswitches and gene activation by disruption of a transcription terminator,", *Nature Struct. Mol. Biol.*, 11(1):29-35 (2004).
Mandal et al., "Gene Regulation by Riboswitches," *Nature Reviews | Molecular Cell Biology*, 5:451-463 (2004).
Manoharan, "Oligonucleotide Conjugates as Potential Antisense Drugs with Improved Uptake, Biodistribution, Targeted Delivery, and Mechanism of Action," *Antisense & Nucleic Acid Drug Development*, 12:103-128 (2002).

(56) References Cited

OTHER PUBLICATIONS

Masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," *Transgenic Research*, 5:313-323 (1996).
Matveeva et al., "Prediction of antisense oligonucleotide efficacy by in vitro methods," *Nature Biotechnology*, 16:1374-1375 (1998).
Meinke, et al., "Identifying essential genes in *Arabidopsis thaliana*," *Trends Plant Sci.*, 13(9):483-491 (2008).
Meins et al., "RNA Silencing Systems and Their Relevance to Plant Development," *Annu. Rev. Cell Dev. Biol.*, 21:297-318 (2005).
Melnyk et al., "Intercellular and systemic movement of RNA silencing signals," *The EMBO Journal*, 30:3553-3563 (2011).
Misawa et al., "Functional expression of the *Erwinia uredovora* carotenoid biosynthesis gene *crtI* in transgenic plants showing an increase of β-carotene biosynthesis activity and resistance to the bleaching herbicide norflurazon," *The Plant Journal*, 4(5):833-840 (1993).
Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal*, 6(4):481-489 (1994).
Miura et al., "The Balance between Protein Synthesis and Degradation in Chloroplasts Determines Leaf Variegation in *Arabidopsis yellow variegated* Mutants," *The Plant Cell*, 19:1313-1328 (2007).
Molnar et al., "Plant Virus-Derived Small Interfering RNAs Originate redominantly from Highly Structured Single-Stranded Viral RNAs," *Journal of Virology*, 79(12):7812-7818 (2005).
Molnar et al., "Small Silencing RNAs in Plants are Mobile and Direct Epigenetic Modification in Recipient Cells," *Science*, 328:872-875 (2010).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Morrissey et al., "Potent and persistent in vivo anti-HBV activity of chemically modified siRNAs," *Nat Biotechnol.* 23(8):1002-1007 (2005).
Moser et al., "Sequence-Specific Cleavage of Double Helical DNA by Triple Helix Formation," *Science*, 238:645-646 (1987).
Nowak et al., "A new and efficient method for inhibition of RNA viruses by DNA interference," *The FEBS Journal*, 276:4372-4380 (2009).
Office Action dated Feb. 17, 2014, in Mexican Patent Application No. MX/a/2012/010479.
Office Action dated Jan. 6, 2015, in Japanese Patent Application No. 2012-557165.
Office Action dated Nov. 19, 2014, in Eurasian Patent Application No. 201201264/28.
Office Action issued dated Nov. 3, 2014, in Chinese Patent Application No. 201180012795.2.
Ongvarrasopone et al., "A Simple and Cost Effective Method to Generate dsRNA for RNAi Studies in Invertebrates," *Science Asia*, 33:35-39 (2007).
Ouellet et al., "Members of the Acetohydroxyacid Synthase Muligene Family of Brassica Napus Have Divergent Patterns of Expression," *The Plant Journal*, Blackwell Scientific Publications, Oxford, GB, 2(3):321-330 (1992).
Paddison et al., "Stable suppression of gene expression by RNAi in mammalian cells," *Proc. Nall Acad. Sci. USA*, 99(3):1443-1448 (2002).
Palauqui et al., "Activation of systemic acquired silencing by localised introduction of DNA," *Current Biology*, 9:59-66 (1999).
Parera et al., "Dehydration Rate after Solid Matrix Priming Alters Seed Performance of *Shrunken*-2 Corn," *J. Amer. Soc. Hort. Sci.*, 119(3):629-635 (1994).
Paungfoo-Lonhienne et al., "DNA is Taken up by Root Hairs and Pollen, and Stimulates Root and Pollen Tube Growth," *Plant Physiology*, 153:799-805 (2010).
Paungfoo-Lonhienne et al., "DNA uptake by *Arabidopsis* induces changes in the expression of CLE peptides which control root morphology," *Plant Signaling & Behavior*, 5(9):1112-1114 (2010).
Pei et al., "On the art of identifying effective and specific siRNAs," *Nature Methods*, 3(9):670-676 (2006).
Peretz et al., "A Universal Expression/Silencing Vector in Plants," *Plant Physiology*, 145:1251-1263 (2007).
Pornprom et al., "Glutamine synthetase mutation conferring target-site-based resistance to glufosinate in soybean cell selections," *Pest Manag Sci*, 2009; 65(2):216-222 (2009).
Preston et al., "Multiple effects of a naturally occurring proline to threonine substitution within acetolactate synthase in two herbicide-resistant populations of *Lactuca serriola*," *Pesticide Biochem. Physiol.*, 84(3):227-235 (2006).
Qiwei," Advance in DNA interference," *Progress in Veterinary Medicine*, 30(1):71-75 (2009).
Rajur et al., "Covalent Protein—Oligonucleotide Conjugates for Efficient Delivery of Antisense Molecules," *Bioconjug Chem.*, 8;935-940 (1997).
Reddy et al "Organosilicone Adjuvants Increased the Efficacy of Glyphosate for Control of Weeds in Citrus (*Citrus* spp.)" *HortScience* 27(9):1003-1005 (1992).
Reddy et al., "Aminomethylphosphonic Acid Accumulation in Plant Species Treated with Glyphosate," *J. Agric. Food Chem.*, 56(6):2125-2130 (2008).
Reither et al., "Specificity of DNA triple helix formation analyzed by a FRET assay," *BMC Biochemistry*, 3:27 (2002).
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Reynolds et al., "Rational siRNA design for RNA interference," *Nature Biotechnology*, 22:326-330 (2004).
Ryabov et al., "Cell-to-Cell, but Not Long-Distance, Spread of RNA Silencing That Is Induced in Individual Epidemial Cells," *Journal of Virology*, 78(6):3149-3154 (2004).
Ryan, "Human endogenous retroviruses in health and disease: a symbiotic perspective," *Journal of the Royal Society of Medicine*, 97:560-565 (2004).
Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. Columbia," *Nucleic Acids Research*, 18(8):2188-2193 (1990).
Schwab et al., "RNA silencing amplification in plants: Size matters," *PNAS*, 107(34):14945-14946 (2010).
Schwember et al., "Drying Rates following Priming Affect Temperature Sensitivity of Germination and Longevity of Lettuce Seeds," *HortScience*, 40(3):778-781 (2005).
Second Chinese Office Action issued in Chinese Patent Application No. 201180012795.2, dated Jun. 10, 2014.
Seidman et al., "The potential for gene repair via triple helix formation," *J Clin Invest.*, 112(4):487-494 (2003).
Selvarani et al., "Evaluation of seed priming methods to improve seed vigour of onion (*Allium cepa cv. Aggregatum*) and carrot (*Daucus carota*)," *Journal of Agricultural Technology*, 7(3):857-867 (2011).
Sharma et al., "A simple and efficient *Agrobacterium*-mediated procedure for Transformation of tomato," *J. Biosci.*, 34(3):423 433 (2009).
Sijen et al., "On the Role of RNA Amplification in dsRNA-Triggered Gene Silencing," *Cell*, 107:465-476 (2001).
Silwet L-77 Spray Adjuvant for agricultural applications, product description from Momentive Performance Materials, Inc. (2003).
Singh et al., "Absorption and translocation of glyphosate with conventional and organosilicone adjuvants," *Weed Biology and Management*, 8:104-111 (2008).
Steeves et al., "Transgenic soybeans expressing siRNAs specific to a major sperm protein gene suppress *Heterodera glycines* reproduction," *Funct. Plant Biol.*, 33:991-999 (2006).
Stock et al., "Possible Mechanisms for Surfactant-Induced Foliar Uptake of Agrochemicals," *Pestic. Sci.*, 38:165-177 (1993).

(56) References Cited

OTHER PUBLICATIONS

Strat et al., "Specific and nontoxic silencing in mammalian cells with expressed long dsRNAs," *Nucleic Acids Research*, 34(13):3803-3810 (2006).
Sudarsan et al., "Metabolite-binding RNA domains are present in the genes of eukaryotes," *RNA*, 9:644-647 (2003).
Sun et al., "Antisense oligodeoxynucleotide inhibition as a potent strategy in plant biology: identification of SUSIBA2 as a transcriptional activator in plant sugar signalling," *The Plant Journal*, 44:128-138 (2005).
Sun et al., "A Highly efficient Transformation Protocol for Micro-Tom, a Model Cultivar for Tomato Functional Genomics," *Plant Cell Physiol.*, 47(3):426-431 (2006).
Sun et al., "Sweet delivery—sugar translocators as ports of entry for antisense oligodeoxynucleotides in plant cells," *The Plant Journal*, 52:1192-1198 (2007).
Takasaki et al., "An Effective Method for Selecting siRNA Target Sequences in Mammalian Cells," *Cell Cycle*, 3:790-795 (2004).
Temple et al., "Can glutamine synthetase activity levels be modulated in transgenic plants by the use of recombinant DNA technology?" *Transgenic Plants and Plant Biochemistry*, 22:915-920 (1994).
Temple et al., "Down-regulation of specific members of the glutamine synthetase gene family in Alfalfa by antisense RNA technology," *Plant Molecular Biology*, 37:535-547 (1998).
Templeton et al., "Improved DNA: liposome complexes for increased systemic delivery and gene expression," *Nature Biotechnology*, 15:647-652 (1997).
Tenllado et al., "Crude extracts of bacterially expressed dsRNA can be used to protect plants against virus infection," *BMC Biotechnology*, 3(3):1-11 (2003).
Tenllado et al., "RNA interference as a new biotechnological tool for the control of virus diseases in plants," *Virus Research*, 102:85-96 (2004).
Tepfer, "Risk assessment of virus resistant transgenic plants," *Annual Review of Phytopathology*, 40:467-491 (2002).
The Seed Biology Place, Website Gerhard Leubner Lab Royal Holloway, University of London, <http://www.seedbiology.de/seedtechnology.asp.
Third Party Submission filed Nov. 29, 2012 in U.S. Appl. No. 13/042,856.
Thompson, et al., "CLUSTAL W: improving the sensitivity of progressive multiple sequence alignment through sequence weighting, position-specific gap penalties and weight matrix choice," *Nucl. Acids Res.*, 22(22):4673-4680 (1994).
Timmons et al., "Specific interference by ingested dsRNA," *Nature*, 395:854 (1998).
Tomari et al., "Perspective: machines for RNAi," *Genes & Dev.*, 19:517-529 (2005).
Töpfer et al., "Uptake and Transient Expression of Chimeric Genes in Seed-Derived Embryos," *Plant Cell*, 1:133-139 (1989).
Toriyama et al., "Transgenic Rice Plants After Direct Gene Transfer Into Protoplasts," *Bio/Technology*, 6:1072-1074 (1988).
Tran et al., "Control of specific gene expression in mammalian cells by co-expression of long complementary RNAs," *FEBS Lett.*; 573(1-3):127-134 (2004).
Tarina et al., "Tospoviruses in the Mediterranean Area," *Advances in Virus Research*, 84:403-437 (2012).
Tuschl, "RNA Interference and Small Interfering RNAs," *ChemBiochem.* 2(4):239-245 (2001).
Tuschl, "Expanding small RNA interference," *Nature Biotechnol.*, 20: 446-448 (2002).
Ui-Tei et al., "Guidelines for the selection of highly effective siRNA sequences for mammalian and chick RNA interference," *Nucleic Acids Res.*, 32(3): 936-948 (2004).
Unnamalai et al., "Cationic oligopeptide-mediated delivery of dsRNA for post-transcriptional gene silencing in plant cells," *FEBS Letters*, 566:307-310 (2004).
Unniraman et al., "Alternate Paradigm for Intrinsic Transcription Termination in Eubacteria," *The Journal of Biological Chemistry*, 276(45)(9):41850-41855 (2001).
Urayama et al., "Knock-down of *OsDCL2* in Rice Negatively Affects Maintenance of the Endogenous dsRNA Virus, *Oryza sativa* Endornavirus," *Plant and Cell Physiology*, 51(1):58-67 (2010).
Van de Wetering et al., "Specific inhibition of gene expression using a stably integrated, inducible small-interfering-RNA vector," *EMBO Rep.*, 4(6):609-615 (2003).
Vasil et al., "Herbicide Resistant Fertile Transgenic Wheat Plants Obtained by Microprojectile Bombardment of Regenerable Embryogenic Callus," *Bio/Technology*,10:667-674 (1992).
Vaucheret, "Post-transcriptional small RNA pathways in plants: mechanisms and regulations," *Genes Dev.*, 20:759-771 (2006).
Vencill et al., "Resistance of Weeds to Herbicides," *Herbicides and Environment*, 29:585-594 (2011).
Verma et al., "Modified oligonucleotides: synthesis and strategy for users," *Annu. Rev. Biochem.*, 67:99-134 (1998).
Vert et al., "An accurate and interpretable model for siRNA efficacy prediction," *BMC Bioinformatics*, 7:520 (2006).
Vionnet et al., "Systemic Spread of Sequence-Specific Transgene RNA Degradation in Plants is Initiated by Localized Introduction of Ectopic Promoterless DNA," *Cell*, 95:177-187 (1998).
Wakelin et al., "A target-site mutation is present in a glyphosate-resistant *Lolium rigidum* population," *Weed Res.* (Oxford), 46(5):432-440 (2006).
Walton et al., "Prediction of antisense oligonucleotide binding affinity to a structured RNA target," *Biotechnol Bioeng* 65(1):1-9 (1999).
Wan et al., "Generation of Large Numbers of Independently Transformed Fertile Barley Plants," *Plant Physiol.*, 104:37-48 (1994).
Wardell, "Floral Induction of Vegetative Plants Supplied a Purified Fraction of Deoxyribonucleic Acid from Stems of Flowering Plants," *Plant Physiol*, 60:885-891 (1977).
Wardell,"Floral Activity in Solutions of Deoxyribonucleic Acid Extracted from Tobacco Stems," *Plant Physiol*, 57:855-861 (1976).
Waterhouse et al., "Virus resistance and gene silencing in plants can be induced by simultaneous expression of sense and antisense RNA," *Proc Natl Acad Sci USA*, 95 13959-13964 (1998).
Welch et al., "Expression of ribozymes in gene transfer systems to modulate target RNA levels," *Curr Opin Biotechnol.* 9(5):486-496 (1998).
Wilson, et al., "Transcription termination at intrinsic terminators: The role of the RNA hairpin," *Proc. Natl. Acad. Sci. USA*, 92:8793-8797 (1995).
Winkler et al., "Thiamine derivatives bind messenger RNAs directly to regulate bacterial gene expression," *Nature*, 419:952-956 (2002).
Written Opinion dated Sep. 1, 2014, in Singapore Patent Application No. 201206152-9.
Xu et al., Characterization and Functional Analysis of the Calmodulin-Binding Domain of Rac1 GTPase, *Plos One*, 7(8)1-12:e42975 (2012).
Yin et al., "Production of double-stranded RNA for interference with TMV infection utilizing a bacterial prokaryotic expression system," *Appl. Microbiol. Biotechnol.*, 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "A novel rice gene, NRR responds to macronutrient deficiency and regulates root growth," *Mol Plant*, 5(1):63-72 (2012).
Zhang et al., "*Agrobacterium*-mediated transformation of *Arabidopsis thaliana* using the floral dip method," *Nature Protocols*, 1(2):1-6 (2006).

(56) References Cited

OTHER PUBLICATIONS

Zhang et al., "Cationic lipids and polymers mediated vectors for delivery of siRNA," *Journal of Controlled Release*, 123:1-10 (2007).
Zhang et al., "DEG: a database of essential genes," *Nucleic Acids Res.*, 32:D271-D272 (2004).
Zhang et al., "Transgenic rice plants produced by electroporation-mediated plasmid uptake into protoplasts," *The Plant Cell Rep.*, 7:379-384 (1988).
Zhao et al., "*Phyllotreta striolata* (Coleoptera: Chrysomelidae):Arginine kinase cloning and RNAi-based pest control," *European Journal of Entomology*, 105(5):815-822 (2008).
Zhu et al., "Ingested RNA interference for managing the populations of the Colorado potato beetle, *Leptinotarsa decemlineata*," *Pest Manag Sci*, 67:175-182 (2010).

\* cited by examiner

*SOLANUM LYCOPERSICON TAS3:* dsRNA CONSTRUCT #1 - EXOGENOUS TRIGGER CONTROL dsRNA CONSTRUCT #2 - DUAL Mir390BS
ON SENSE STRAND + EXOGENOUS SEQUENCE dsRNA CONSTRUCT #3 - DUAL Mir390BS BOTH
ON THE SENSE AND ANTISENSE STRANDS dsRNA CONSTRUCT #4 - miR390BS AS OVERHANGS
SENSE 5'->3'

ANTI SENSE 3'->5' dsRNA CONSTRUCT #5 - DUAL Mir390BS + HELICASE INSIDE

* GFP234

* TASMir390

* GFP234Mir390 - Mir390BS ON SENSE STRAND

* GFP234Mir390 HELICASE

* GFP234Mir390_Mir4376

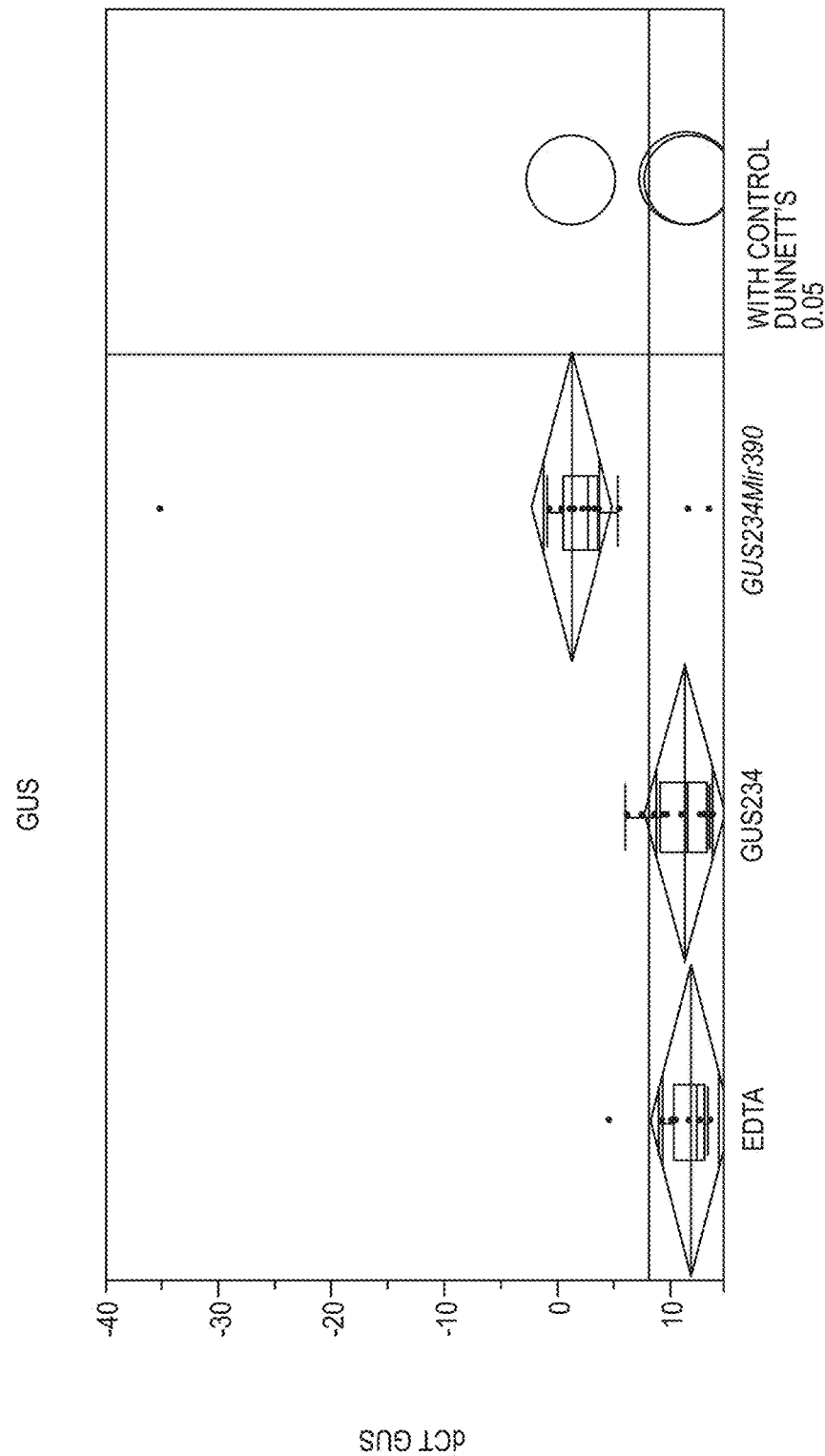

ISOLATED DSRNA MOLECULES AND METHODS OF USING SAME FOR SILENCING TARGET MOLECULES OF INTEREST

CROSS REFERENCE TO RELATED APPLICATIONS

This application claims benefit of provisional applications 61/748,095, filed Jan. 1, 2013, 61/748,101, filed Jan. 1, 2013, 61/748,094, filed Jan. 1, 2013, 61/748,099, filed Jan. 1, 2013, 61/814,888, filed Apr. 23, 2013, 61/814,892, filed Apr. 23, 2013, 61/814,899, filed Apr. 23, 2013, 61/814,890, filed Apr. 23, 2013, 61/908,965, filed Nov. 26, 2013, and 61/908,855, filed Nov. 26, 2013, each of which is herein incorporated by reference.

SEQUENCE LISTING STATEMENT

The ASCII file, entitled p34097may292014st25.txt, created on May 29, 2014, comprising 71,663 bytes, is incorporated herein by reference.

FIELD OF THE DISCLOSURE

The present disclosure provides for, and includes, methods and compositions for silencing target molecules of plants and plant pathogens. Also provided are plants, plant parts and seeds having dsRNAs and methods of introducing dsRNAs into seeds.

BACKGROUND

The present disclosure, in some embodiments thereof, relates to isolated dsRNA molecules and methods of using same for silencing target molecules of interest.

RNA interference (RNAi) has been shown effective in silencing gene expression in a broad variety of species, including plants, with wide ranging implications for cancer, inherited disease, infectious disease in plants and animals. Studies in a variety of organisms have shown that effectors of RNAi include dsRNA and related small interfering RNAs (siRNAs; also called "short interfering RNAs" and "silencing RNAs"). Studies have also shown in a variety of organisms that dsRNA or their siRNA derivatives can be used to arrest, retard or even prevent a variety of pathogens, most notably viral diseases (see, for example, PCT Patent Application Publication No. WO/2003/004649).

It has been shown in some species that RNAi mediated interference spreads from the initial site of dsRNA delivery, producing interference phenotypes throughout the injected animal. Recently the same spreading effect of dsRNA has been demonstrated in bee larva. In addition, homologs of transmembrane proteins called systemic RNA interference defective proteins (SID) have been detected in, for example, humans, mouse and *C. elegans*. It is thought that SID transmembrane channels are responsible for endocytic uptake and spreading effect of dsRNA (Aronstein et al., J. Apic Res and Bee World, 2006; 45:20-24; see also van Roessel P, Brand A H., "Spreading silence with Sid," Genome Biol. 5(2):208 (2004)).

Application of RNA interference technology for insects that are plant pests and other plant pests has been suggested. Moderate RNAi-type silencing of insect genes by feeding has been demonstrated (Turner et al., Insect Mol Biol 2006; 15:383; and Araujo et al., Insect Mol. Biol. 2006; 36:683). Various publications have since then focused on the incorporation of dsRNA in plants as pesticides. Such incorporation methods can be divided into transgenic gene expression and coating such as a seed coating.

U.S. Pat. No. 6,326,193 refers to the use of recombinant insect viruses such as baculoviruses expressing dsRNA to silence selected insect genes for pest control. PCT Patent Application Publication No. WO 99/32619 describes the use of dsRNA for reducing crop destruction by plant pathogens or pests such as arachnids, insects, nematodes, protozoans, bacteria, or fungi. PCT Patent Application Publication No. WO 2004/005485 describes RNAi sequences and transgenic plants designed to control plant-parasitic nematodes.

U.S. Patent Application Publication No. 20030154508 describes pest control with a dsRNA against a cation-amino acid transporter/channel protein. PCT Patent Application Publication No. WO 02/14472 describes an inverted repeat and a sense or antisense nucleic acids for inhibiting target gene expression in a sucking insect. U.S. Patent Application Publication No. 20030150017 describes the use of RNA molecules homologous or complementary to a nucleotide sequence of a plant pest such as nematodes and insects.

Raemakers et al. (PCT Patent Application Publication Nos. WO 2007/080127 and WO 2007/080126) have disclosed transgenic plants expressing RNAi for controlling pest infestation by insects, nematodes, fungus and other plant pests. Among the sequences taught are sequences targeting essential genes of insects. Waterhouse et al. (U.S. Patent Application Publication No. 20060272049) and Van De Craen (U.S. Patent Application Publication No. 2010068172) also disclosed transgenic plants expressing dsRNA directed to essential genes of plant insect pests, for use as pesticides and insecticides. Boukharov et al. (U.S. Patent Application Publication No. 20070250947) disclosed dsRNA in transgenic plants for targeting plant parasitic nematodes.

U.S. Patent Application Publication No. 20080022423 describes the control of fungal and oomycete plant pathogens by inhibiting one or more biological functions. The disclosure provides methods and compositions for such control. By feeding one or more recombinant double stranded RNA molecules provided by the disclosure to the pathogen, a reduction in disease may be obtained through suppression of gene expression. The disclosure is also directed to methods for making transgenic plants that express the double stranded RNA molecules, and to particular combinations of transgenic agents for use in protecting plants from pathogen infection. Also described is a seed coating with the dsRNA anti-pathogenic compositions.

PCT Patent Application Publication No. WO 2011112570 describes a method of regulating target endogenous gene expression in growing plants/plant organs involving topically coating onto plants/organs, a composition comprising polynucleotide having sequence of specific contiguous nucleotides, and a transferring agent.

U.S. Pat. No. 8,143,480 refers to methods for knock-down of a target genes in plants, particularly efficient and specific methods for knock-down of a target gene in plants. This disclosure also relates to methods for silencing endogenous plant genes or plant pathogen genes. It further relates to nucleic acid constructs (DNA, RNA) which comprise a nucleic acid sequence that corresponds to a target gene or fragment thereof flanked by two complementary sites to an smRNA, e.g., a miRNA (one complementary site is on either side of the nucleic acid sequence), resulting in, for example the configuration: complementary site—nucleic acid sequence that corresponds to a target gene—complementary site. Axtell and Bartell describe siRNA biogenesis in *Arabidopsis* (Axtell and Bartel Cell. 2006 Nov. 3; 127(3):565-77.).

It has been reported that an autonomous dsRNA sequence derived from endovirus is found in every tissue of an infected plant and at every developmental stage. Thus, in 1993 Fukuhara et al. (Plant Mol. Biol. 21(6):1121-1130) identified a linear, 16 kb, dsRNA in symptomless *Japonica* rice that is not found in *Indica* rice. The dsRNA was detected in every tissue and at every developmental stage and its copy number was approximately constant (about 20 copies/cell). A sequence of about 13.2 kb of the dsRNA was determined and two open reading frames (ORFs) were found. The larger ORF (ORF B) was more than 12,351 nucleotides long and encoded a polypeptide of more than 4,117 amino acid residues having an RNA helicase-like domain followed by an RNA dependent RNA Polymerase-like domain, as characterized in subsequent works published as Fukuhara et al. 1995 J. Biol. Chem. 270(30):18147-18149; and Moriyama et al. 1995 Mol. Gen. Genet. 248(3):364-369.

While not limited by theory, during RNA silencing, RNAs of about 21 to 24 nucleotides (nt) in length are generated, which are incorporated into a protein complex where they serve as guide RNAs to direct the down-regulation of gene expression at the transcriptional or posttranscriptional level. These small interfering RNAs, small silencing RNAs, or short interfering RNAs are called "siRNAs" or "microRNAs", depending upon their biogenesis: endogenous siRNAs derive from long double-stranded RNA and miRNAs derive from local hairpin structures within longer transcripts.

RNA silencing occurs in plants, insects, nematodes and other animals. In addition, new compositions (e.g., nucleic acid constructs) and methods of achieving RNA-based silencing would be useful, and plants in which expression of one or more genes of interest is modulated, e.g., inhibited, would be of great use. New compositions and rapid cost-effective methods of achieving RNA-based silencing by directly manipulating the plant seed are highly desirable.

SUMMARY OF THE INVENTION

The present disclosure provides for, and includes, methods and compositions for the regulation of gene expression in plants.

The present disclosure provides for, and includes, isolated double-stranded RNA molecules having a first RNA strand of at least one antisense RNA sequence for regulating a target gene of interest in a plant or a phytopathogen of a plant and a first heterologous RNA sequence corresponding to a first small RNA (smRNA) expressed in a plant (e.g., a first heterologous smRNA-binding sequence for binding a first smRNA expressed in a plant) and a second RNA strand that is a reverse complement of the at least one antisense RNA sequence.

The present disclosure provides for, and includes, isolated double-stranded RNA molecules having a first RNA strand of at least one antisense RNA sequence for regulating a target gene of interest in a plant or a phytopathogen of a plant, a first heterologous RNA sequence corresponding to a first small RNA (smRNA) expressed in the plant (e.g., a first heterologous smRNA-binding sequence for binding a first smRNA expressed in a plant), a helicase binding sequence and a second RNA strand that is a reverse complement of the at least one antisense RNA sequence.

The present disclosure provides for, and includes, isolated double-stranded RNA molecules having a first RNA strand of at least one antisense RNA sequence for regulating a target gene of interest in a plant or a phytopathogen of a plant and a first heterologous RNA sequence corresponding to a first small RNA (smRNA) expressed in the plant (e.g., a first heterologous smRNA-binding sequence for binding a first smRNA expressed in a plant) and a second RNA strand that is a reverse complement of the at least one antisense RNA sequence and the first heterologous RNA sequence.

The present disclosure provides for, and includes, isolated double-stranded RNA molecules having a first RNA strand of at least one antisense RNA sequence for regulating a target gene of interest in a plant or a phytopathogen of a plant, a first heterologous RNA sequence corresponding to a first small RNA (smRNA) expressed in a plant (e.g., a first heterologous smRNA-binding sequence for binding a first smRNA expressed in a plant), a helicase binding sequence and a second RNA strand that is a reverse complement of the at least one antisense RNA sequence and the first heterologous RNA sequence.

The present disclosure provides for, and includes, isolated double-stranded RNA molecules having a first RNA strand of at least one antisense RNA sequence for regulating a target gene of interest in a plant or a phytopathogen of a plant, a first heterologous RNA sequence corresponding to a first small RNA (smRNA) expressed in said plant (e.g., a first heterologous smRNA-binding sequence for binding a first smRNA expressed in a plant), a helicase binding sequence and a second RNA strand that is a reverse complement of the at least one antisense RNA sequence and the first heterologous RNA sequence.

The present disclosure provides for, and includes, isolated double-stranded RNA molecules having a first RNA strand of at least one antisense RNA sequence for regulating a target gene of interest in a plant or a phytopathogen of a plant, a first heterologous RNA sequence corresponding to a first small RNA (smRNA) expressed in said plant (e.g., a first heterologous smRNA-binding sequence for binding a first smRNA expressed in a plant), a helicase binding sequence and a second RNA strand that is a reverse complement of the at least one antisense RNA sequence, the first heterologous RNA sequence, and helicase binding sequence.

The present disclosure provides for, and includes, isolated double-stranded RNA molecules having a first RNA strand of at least one antisense RNA sequence for regulating a target gene of interest in a plant or a phytopathogen of a plant, a first heterologous RNA sequence corresponding to a first small RNA (smRNA) expressed in the plant (e.g., a first heterologous smRNA-binding sequence for binding a first smRNA expressed in a plant), a second heterologous RNA sequence corresponding to a second smRNA expressed in the plant (e.g., a second heterologous smRNA-binding sequence for binding a second smRNA expressed in a plant), where the first heterologous smRNA and said second heterologous smRNA flank the at least one antisense RNA sequence, and a second RNA strand that is a reverse complement of the at least one antisense RNA sequence.

The present disclosure provides for, and includes, isolated double-stranded RNA molecules having a first RNA strand of at least one antisense RNA sequence for regulating a target gene of interest in a plant or a phytopathogen of a plant, a first heterologous RNA sequence corresponding to a first small RNA (smRNA) expressed in the plant (e.g., a first heterologous smRNA-binding sequence for binding a first smRNA expressed in a plant), a second heterologous RNA sequence corresponding to a second smRNA expressed in the plant (e.g., a second heterologous smRNA-binding sequence for binding a second smRNA expressed in a plant), where the first heterologous smRNA and said second heterologous smRNA flank the at least one antisense RNA sequence, and a second RNA strand that is a reverse complement of the at least one antisense RNA sequence, and first heterologous RNA sequence.

The present disclosure provides for, and includes, isolated double-stranded RNA molecules having a first RNA strand of at least one antisense RNA sequence for regulating a target gene of interest in a plant or a phytopathogen of a plant, a first heterologous RNA sequence corresponding to a first small RNA (smRNA) expressed in the plant (e.g., a first heterologous smRNA-binding sequence for binding a first smRNA expressed in a plant), a second heterologous RNA sequence corresponding to a second smRNA expressed in the plant (e.g., a second heterologous smRNA-binding sequence for binding a second smRNA expressed in a plant), where the first heterologous smRNA and said second heterologous smRNA flank the at least one antisense RNA sequence, and a second RNA strand that is a reverse complement of the at least one antisense RNA sequence, first heterologous RNA sequence, and second heterologous RNA sequence.

The present disclosure provides for, and includes, isolated double-stranded RNA molecules having a first RNA strand of at least one antisense RNA sequence for regulating a target gene of interest in a plant or a phytopathogen of a plant, a helicase binding sequence, a first heterologous RNA sequence corresponding to a first small RNA (smRNA) expressed in the plant (e.g., a first heterologous smRNA-binding sequence for binding a first smRNA expressed in a plant), a second heterologous RNA sequence corresponding to a second smRNA expressed in the plant (e.g., a second heterologous smRNA-binding sequence for binding a second smRNA expressed in a plant), where the first heterologous smRNA and said second heterologous smRNA flank the at least one antisense RNA sequence, and a second RNA strand that is a reverse complement of the at least one antisense RNA sequence, first heterologous RNA sequence, and second heterologous RNA sequence.

According to some embodiments of the present disclosure there is provided an isolated dsRNA molecule comprising an antisense RNA sequence for regulating a target gene of interest in a plant or a phytopathogen of the plant, wherein the dsRNA sequence is flanked by two complementary sites to an smRNA or smRNAs expressed in the plant and wherein the dsRNA molecule further comprises a helicase binding site positioned so as to allow unwinding of the strands of the isolated dsRNA molecule to single stranded RNA (ssRNA) and recruitment of an RNA-dependent RNA Polymerase so as to amplify the dsRNA molecule in the plant cell and generate secondary siRNA products of the dsRNA sequence.

According to some embodiments of the present disclosure there is provided an isolated dsRNA molecule comprising an antisense RNA sequence for regulating a target gene of interest in a plant or a phytopathogen of the plant, wherein the dsRNA sequence is flanked by two complementary sites to an smRNA or smRNAs expressed in the plant.

According to an embodiment of some embodiments of the present disclosure there is provided an isolated dsRNA molecule comprising an antisense RNA sequence for regulating a target gene of interest in a plant or a phytopathogen of the plant, wherein the dsRNA molecule further comprises a complementary site to an smRNA expressed in the plant located upstream or downstream the dsRNA.

According to some embodiments of the disclosure, the isolated dsRNA molecule further comprises a helicase binding site positioned so as to allow unwinding of the strands of the isolated dsRNA molecule to single stranded RNA (ssRNA) and recruitment of an RNA-dependent RNA Polymerase so as to amplify the dsRNA molecule in the plant cell.

According to some embodiments of the disclosure, the complementary site to the smRNA is located downstream of the dsRNA sequence.

According to some embodiments of the disclosure, the complementary site to the smRNA is located upstream of the dsRNA sequence.

According to some embodiments of the disclosure, one of the two complementary sites to the smRNA or smRNAs comprises a mutation rendering it resistant to cleavage by the complementary smRNA.

According to some embodiments of the disclosure, the helicase binding site is positioned upstream of the dsRNA sequence.

According to some embodiments of the disclosure, wherein the helicase binding site is positioned in the dsRNA sequence for regulating a target gene of interest in the plant or the phytopathogen of the plant.

According to some embodiments of the disclosure, the helicase binding site is positioned upstream of the dsRNA sequence and the two complementary sites to the smRNA or smRNAs flank the helicase binding site.

According to some embodiments of the disclosure, the smRNA or smRNAs is selected from the group consisting of a miRNA and a siRNA.

According to some embodiments of the disclosure, the smRNA or smRNAs is a miRNA.

According to some embodiments of the disclosure, the miRNA is smRNA390.

According to some embodiments of the disclosure, the plant comprises a TAS locus that has a second smRNA complementary site.

According to some embodiments of the disclosure, the first and second complementary sites are naturally found flanking the TAS locus in the plant.

According to some embodiments of the disclosure, the smRNA is an smRNA for which complementary sites are naturally found flanking a TAS locus in a plant.

According to some embodiments of the disclosure, the two complementary sites are complementary sites for the same smRNA.

According to some embodiments of the disclosure, the two complementary sites comprise difference sequences.

According to some embodiments of the disclosure, the two complementary sites comprise the same sequence.

According to some embodiments of the disclosure, the smRNAs are non-identical.

According to some embodiments of the disclosure, the smRNA or smRNAs is selected from the group consisting of miR390, miR161.1, miR168, miR393, miR828 and miR173.

According to some embodiments of the disclosure, the plant is a crop plant.

According to an embodiment of some embodiments of the present disclosure there is provided a method of silencing expression of a target gene of interest in a plant, the method comprising introducing the isolated dsRNA molecule, and wherein the dsRNA sequence is for silencing the target gene of interest in the plant, thereby silencing expression of the target gene of interest in the plant.

According to an embodiment of some embodiments of the present disclosure there is provided a method of introducing dsRNA molecule into a seed, the method comprising contacting the seed with the isolated dsRNA molecule under conditions which allow penetration of the dsRNA molecule into the seed, thereby introducing the dsRNA molecule into the seed.

According to an embodiment of some embodiments of the present disclosure there is provided an isolated seed comprising the isolated dsRNA molecule.

According to some embodiments of the disclosure, the isolated seed is devoid of a heterologous promoter for driving expression of the dsRNA molecule in the plant.

According to an embodiment of some embodiments of the present disclosure there is provided a seed comprising the isolated dsRNA molecule and the secondary siRNA products.

According to an embodiment of some embodiments of the present disclosure there is provided a plant or plant part generated from the seed.

According to an embodiment of some embodiments of the present disclosure there is provided a seed containing device comprising a plurality of the seeds.

According to an embodiment of some embodiments of the present disclosure there is provided a sown field comprising a plurality of the seeds.

According to an embodiment of some embodiments of the present disclosure there is provided a method of producing a plant the method comprising: (a) providing the seed; and (b) germinating the seed so as to produce the plant.

According to an embodiment of some embodiments of the present disclosure there is provided a method of modulating gene expression in a plant, the method comprising: (a) contacting a seed of the plant with the dsRNA molecule, under conditions which allow penetration of the dsRNA molecule into the seed, thereby introducing the dsRNA molecule into the seed; and optionally (b) generating a plant of the seed.

According to some embodiments of the disclosure, the penetration is to an endosperm and alternatively or additionally an embryo of the seed.

According to an embodiment of some embodiments of the present disclosure there is provided a method of silencing expression of a target gene in a phytopathogenic organism, the method comprising providing to the phytopathogenic organism the plant or plant part, thereby silencing expression of a target gene in the phytopathogenic organism.

According to some embodiments of the disclosure, the phytopathogenic organism is selected from the group consisting of a fungus, a nematode, an insect, a bacteria and a virus.

According to an embodiment of some embodiments of the present disclosure there is provided a kit for introducing a dsRNA molecule to seeds comprising; (i) the dsRNA molecule; and (ii) a priming solution.

According to some embodiments of the disclosure, the dsRNA molecule and the priming solution are comprised in separate containers.

According to an embodiment of some embodiments of the present disclosure there is provided a pesticidal composition comprising the isolated dsRNA molecule.

According to some embodiments of the disclosure, the contacting is effected by inoculating the seed with the dsRNA molecule.

According to some embodiments of the disclosure, the method further comprises priming the seed prior to the contacting.

According to some embodiments of the disclosure, the priming is effected by: (i) washing the seed prior to the contacting; and (ii) drying the seed following step (i).

According to some embodiments of the disclosure, the washing is effected in the presence of double deionized water.

According to some embodiments of the disclosure, the washing is effected for 2-6 hours.

According to some embodiments of the disclosure, the washing is effected at 4-28° C.

According to some embodiments of the disclosure, the drying is effected at 25-30° C. for 10-16 hours.

According to some embodiments of the disclosure, the contacting is effected in a presence of the dsRNA molecule at a final concentration of 0.1-100 µg/µl.

According to some embodiments of the disclosure, the contacting is effected in a presence of the dsRNA molecule at a final concentration of 0.1-0.5 µg/µl.

According to some embodiments of the disclosure, the method further comprises treating the seed with an agent selected from the group consisting of a pesticide, a fungicide, an insecticide, a fertilizer, a coating agent and a coloring agent following the contacting.

According to some embodiments of the disclosure, the treating comprises coating the seed with the agent.

According to some embodiments of the disclosure, the conditions allow accumulation of the dsRNA molecule in the endosperm and alternatively or additionally embryo of the seed.

According to some embodiments of the disclosure, a concentration of the dsRNA molecule is adjusted according to a parameter selected from the group consisting of, seed size, seed weight, seed volume, seed surface area, seed density and seed permeability.

According to some embodiments of the disclosure, the contacting is effected prior to breaking of seed dormancy and embryo emergence.

According to some embodiments of the disclosure, the seed is a primed seed.

According to some embodiments of the disclosure, the seed comprises RNA dependent RNA polymerase activity for amplifying expression of the dsRNA molecule.

According to some embodiments of the disclosure, the seed is a hybrid seed.

According to an aspect of some embodiments of the present disclosure there is provided an isolated dsRNA molecule comprising a nucleic acid sequence which comprises in a sequential order from 5' to 3', an endovirus 5' UTR, an endovirus RNA Dependent RNA Polymerase (RDRP) coding sequence, an endovirus 3' UTR and a multiple cloning site flanked by the RDRP and the 3' UTR.

According to an aspect of some embodiments of the present disclosure there is provided an isolated dsRNA molecule comprising a nucleic acid sequence which comprises in a sequential order from 5' to 3', an endovirus 5' UTR, an endovirus RNA Dependent RNA Polymerase (RDRP) coding sequence, an endovirus 3' UTR and a nucleic acid sequence for regulating a target gene flanked by the RDRP and the 3' UTR.

According to some embodiments of the disclosure, the endovirus 5' UTR, endovirus RNA Dependent RNA Polymerase (RDRP) coding sequence and the endovirus 3' UTR are selected capable of autonomous replication in the plant cell.

According to some embodiments of the disclosure, the 5' UTR is as set forth in SEQ ID NO: 14.

According to some embodiments of the disclosure, the 3' UTR is as set forth ion SEQ ID NO: 22.

According to some embodiments of the disclosure, the endovirus RNA Dependent RNA Polymerase (RDRP) coding sequence is as set forth in SEQ ID NO: 23.

According to some embodiments of the disclosure, the nucleic acid sequence for regulating a target gene is 17-600 bp long.

According to some embodiments of the disclosure, the nucleic acid sequence for regulating a target gene is selected from the group consisting of a miRNA and a siRNA.

According to some embodiments of the disclosure, the nucleic acid sequence for regulating a target gene is a miRNA.

Unless otherwise defined, all technical and/or scientific terms used herein have the same meaning as commonly understood by one of ordinary skill in the art to which the disclosure pertains. Although methods and materials similar or equivalent to those described herein can be used in the practice or testing of embodiments of the disclosure, examples of methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the disclosure are herein described, by way of example only, with reference to the accompanying drawings. With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

FIGS. 15A-B presents graphs showing the results of real-time PCR analyses of GUS in shoots seven days (A) and 14 days (B) after seed treatment according to an embodiment of the present disclosure.

DETAILED DESCRIPTION

Figure 1:
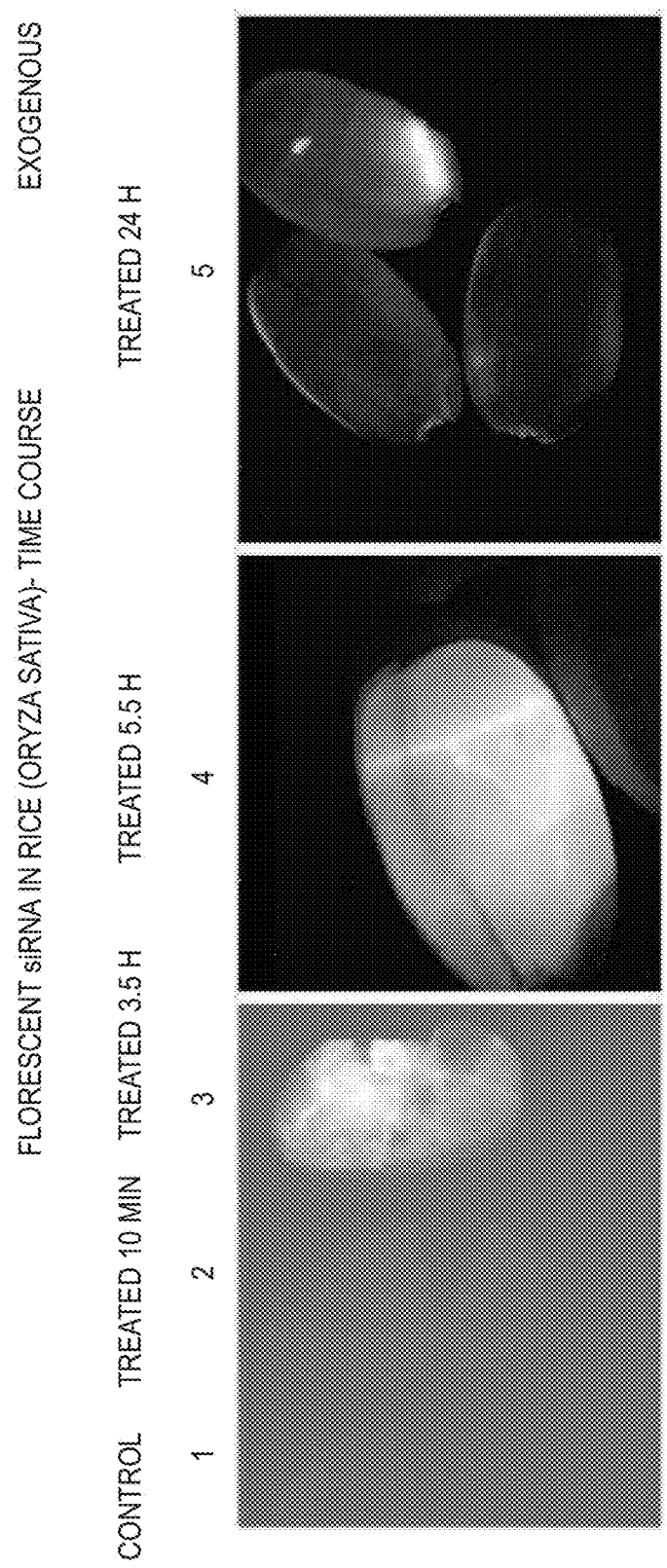
FIG. 1 presents fluorescent images of siGLO-treatment rice seeds over a 24 hour period according to embodiment of the present disclosure.

The present disclosure, in some embodiments thereof, relates to and provides for isolated dsRNA molecules and methods of using same for silencing target molecules of interest.

The present disclosure further includes and provides for compositions and methods for silencing gene expression.

The present disclosure provides for, and includes tools for overcoming the delivery obstacle and amplifying the small interfering RNA (siRNA) levels within the plant cell to thereby efficiently down-regulate target genes of interest.

Before explaining at least one embodiment of the disclosure in detail, it is to be understood that the disclosure is not necessarily limited in its application to the details set forth in the following description or exemplified by the Examples. The disclosure is capable of other embodiments or of being practiced or carried out in various ways.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 1 is expressed in a DNA sequence format (e.g., reciting T for thymine), but it can refer to either a DNA sequence that corresponds to a T7 DNA Dependent RNA Polymerase primer nucleic acid sequence, or the RNA sequence of an RNA molecule nucleic acid sequence. Similarly, though SEQ ID NO: 25 is expressed in a RNA sequence format (e.g., reciting U for uracil), depending on the actual type of molecule being described, SEQ ID NO: 25 can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

As used herein, the terms "homology" and "identity" when used in relation to nucleic acids, describe the degree of similarity between two or more nucleotide sequences. The percentage of "sequence identity" between two sequences is determined by comparing two optimally aligned sequences over a comparison window, such that the portion of the sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. An alignment of two or more sequences may be performed using any suitable computer program. For example, a widely used and accepted computer program for performing sequence alignments is CLUSTALW v1.6 (Thompson, et al. Nucl. Acids Res., 22: 4673-4680, 1994).

Homologous sequences include both orthologous and paralogous sequences. The term "paralogous" relates to gene-duplications within the genome of a species leading to paralogous genes. The term "orthologous" relates to homologous genes in different organisms due to ancestral relationship. For instance in this case, other plant RNA viruses.

Identity (e.g., percent homology) can be determined using any homology comparison software, including for example, the BlastN software of the National Center of Biotechnology Information (NCBI) such as by using default parameters.

According to some embodiments of the disclosure, the identity is a global identity, i.e., an identity over the entire nucleic acid sequences of the disclosure and not over portions thereof.

The degree of homology or identity between two or more sequences can be determined using various known sequence comparison tools. Following is a non-limiting description of such tools which can be used along with some embodiments of the disclosure.

As used herein, the terms "exogenous polynucleotide" and "exogenous nucleic acid molecule" relative to an organisms refer to a heterologous nucleic acid sequence which is not naturally expressed within that organism, for example a plant. An exogenous nucleic acid molecule may be introduced into an organism in a stable or transient manner. An exogenous nucleic acid molecule may comprise a nucleic acid sequence which is identical or partially homologous to an endogenous nucleic acid sequence of the organism. In certain embodiments, an "exogenous polynucleotide" and "exogenous nucleic acid molecule" may refer to a nucleic acid sequence expressed or present in a plant, either transiently or stably. As used herein, the terms "endogenous polynucleotide" and "endogenous nucleic acid" refers to nucleic acid sequences that are found in an organism's cell. In certain aspects, an endogenous nucleic acid may be part of the nuclear genome or the plastid genome. In other aspects, an endogenous nucleic acid may be found outside the nuclear or plastid genomes. As used herein, endogenous nucleic acids do not include viral, parasite or pathogen nucleic acids, for example an endovirus sequence. The present disclosure provides for, and includes, compositions comprising exogenous polynucleotides and exogenous nucleic acid molecules and methods for introducing them into a target organism. The present disclosure provides for, and includes, compositions comprising exogenous polynucleotides and exogenous nucleic acid molecules in combination with endogenous nucleic acids and polynucleotides and methods for introducing them into a target organism. The present disclosure provides for, and includes, compositions comprising recombinant endogenous nucleic acids and polynucleotides and methods for introducing them into a target organism.

The present disclosure provides for, and includes dsRNA molecules which are processed through the trans-acting siRNA (ta-siRNA) pathway. Transacting siRNAs are a subclass of siRNAs that function like miRNAs to repress expression of target genes. While not limited to any particular theory, trans-acting siRNAs form by transcription of ta-siRNA-generating genes found at trans-acting (TAS) loci. A ta-siRNA precursor is any nucleic acid molecule, including single-stranded or double-stranded DNA or RNA, that can be transcribed and/or processed to release a ta-siRNA. Cleavage of the primary transcript occurs through a guided RISC mechanism, conversion of one of the cleavage products to dsRNA, and processing of the dsRNA by dicer or dicer-like (DCL) enzymes. While not limited by any particular theory, it is thought that RNA-dependent RNA polymerase 6 (RDR6) (or related enzymes) function in posttranscriptional RNAi of sense transgenes, some viruses, and specific endogenous mRNAs that are targeted by trans-acting siRNAs (ta-siRNAs) (see Dalmay et al., Cell 101:543-553, 2000; Mourrain et al., Cell 101:533-542, 2000; Peragine et al., Genes & Dev 18:2369-2379, 2004; Vazquez et al., Mol Cell 16:69-79, 2004b; Yu et al., Mol Plant Microbe Interact 16:206-216, 2003). Again, while not being limited to any particular theory, it is thought that ta-siRNAs arise from transcripts that are recognized by RDR6, in cooperation with SGS3, as a substrate to form dsRNA. The dsRNA is processed accurately in 21-nucleotide steps by DCL1 to yield a set of "phased" ta-siRNAs. These ta-siRNAs interact with target mRNAs to guide cleavage by the same mechanism as do plant miRNAs (Peragine et al., Genes & Dev 18:2369-2379, 2004; Vazquez et al., Mol Cell 16:69-79, 2004; Allen et al., Cell 121:207-221, 2005). Trans-acting siRNAs are conserved among distantly related plant species and have been maintained over a long evolutionary period. The design and construction of ta-siRNA constructs and their use in the modulation of protein in transgenic plant cells is disclosed by Allen and Carrington in US Patent Application Publication US 2006/0174380 A1 (now U.S. Pat. No. 8,030,473) which is incorporated herein by reference.

As used herein, the term "dsRNA sequence" refers to, and includes, a double-stranded sequences having a first strand and a second strand that is a reverse complement of the first strand. It will be understood that reference to an antisense RNA sequence for regulating a target gene of interest and a sense RNA sequence for regulating a target gene of interest, would necessarily include a dsRNA sequences when included in a dsRNA molecule. For clarity, the sequences for targeting a gene of interest for regulation will be generally referenced as the antisense RNA sequence and provides for a standard reference point for the 5' and 3' ends. As used herein, the 'antisense strand' refers to the strand having the antisense RNA sequence for regulating (e.g., suppressing or silencing) a target gene of interest. One of ordinary skill in the art would further understand that reference to a single strand, whether the sense or antisense strand, provides a definition and sequence for the reverse complement strand. Further, it is well understood that a single nucleic acid strand and its reverse complement provide for a double-stranded nucleic acid. One of ordinary skill in the art would understand that an RNA and DNA sequence may be readily substituted using the well known base pairing rules and as provided above. One of ordinary skill in the art would further understand that binding can occur between two polynucleotide sequences that are characterized by having sufficient sequence complementarity (which need not be 100% complementarity) to allow hybridization between the two polynucleotides (e.g., binding or hybridization under common physiological conditions). Thus, a "heterologous smRNA-binding sequence for binding a first small RNA" need not be 100% complementary to the sequence of the first small RNA (for example, where the heterologous smRNA-binding sequence is complementary to the sequence of the first small RNA except for one or more mutations or mismatches at the site where cleavage mediated by the small RNA would normally occur), although in some embodiments the complementarity is 100%. The present disclosure provides for, and includes, an isolated dsRNA molecule comprising an antisense RNA sequence for regulating a target gene of interest in a plant or a phytopathogen of the plant, wherein the dsRNA sequence is flanked by two complementary sites to an smRNA expressed in the plant. In some embodiments, the dsRNA sequence may be flanked by two complementary sites from the same smRNA expressed in the plant. In other embodiments, the dsRNA sequence may be flanked by complementary sites from two different smRNAs. In yet other embodiments, the dsRNA sequence may be flanked by four complementary sites corresponding to one or more smRNAs expressed in a plant (e.g., two heterologous sequences on one side and two heterologous sequences on the other side of the dsRNA sequence. In certain embodiments, the dsRNA molecule further comprises a helicase binding site positioned so as to allow unwinding of the strands of the isolated dsRNA molecule to single stranded RNA (ssRNA) and amplification by recruitment of an RNA-dependent RNA Polymerase (RDRP) when introduced into a host cell. In other embodiments, the helicase and other proteins may be provided in vitro, for example as part of a cell extract. Methods of in vitro analysis are known in the art. In certain embodiments, the host cell is a plant cell. In some embodiments, introduction of the dsRNA molecule into a plant cell results in the recruitment of a helicase and RDRP and the generation of secondary siRNA products corresponding to the dsRNA sequence for regulating a target gene of interest in a plant or a phytopathogen of the plant. In certain embodiments, the target gene is silenced. In other embodiments, expression of the target gene is enhanced.

According to another embodiment of the disclosure there is provided, and included, an isolated dsRNA molecule comprising an antisense RNA sequence for regulating a target gene of interest in a plant or a phytopathogen of the plant, wherein the dsRNA sequence is flanked by two complementary sites to an smRNA or smRNAs expressed in the plant. In certain embodiments, the target gene is silenced. In other embodiments, expression of the target gene is enhanced.

According to a further embodiment of the disclosure there is provided, and included, an isolated dsRNA molecule comprising an antisense RNA sequence for regulating a target gene of interest in a plant or a phytopathogen of the plant, wherein the dsRNA molecule further comprises a complementary site to an smRNA expressed in the plant located upstream or downstream the dsRNA. In certain embodiments, the target gene is silenced. In other embodiments, expression of the target gene is enhanced.

Not to be limited by theory, a possible downstream mechanism for a dsRNA construct of the present disclosure having two flanking heterologous RNA sequences corresponding to an smRNA, with one sequence being a non-cleavable mutant (for example, mir390 BS and Mir390 Mut BS of FIG. 2C) includes unwinding of the dsRNA in the cell. Following the opening of the double stranded RNA into two single strands the sense strand may recruit an AGO7, or AGO7-like, protein to the flanking heterologous RNA sequences. This binding, in turn, may lead to cleavage at a the non-mutated heterologous RNA sequence (for example Mir390 BS of FIG. 2C) and localization of this single stranded RNA inside a cytoplasmic processing center (Evidence for such a processing center was reported in Kumakura et al. (2009). SGS3 and RDR6 interact and colocalize in cytoplasmic SGS3/RDR6-bodies. (2009). *FEBS Letters,* 583, 1261-1266 and Jouannet et al. (2012). Cytoplasmic *Arabidopsis* AGO7 accumulates in membrane-associated siRNA bodies and is required for to-siRNA biogenesis. *EMBO Journal*, 31, 1704-1713.). The antisense strand may then either be diced or cleaved but is not expected to take part in additional amplification of the exogenous sequence (e.g., the gene of interest of FIG. 2C).

Not to be limited by theory, an alternative downstream mechanism for dsRNA construct of the present disclosure having two flanking heterologous RNA sequences corresponding to an smRNA (for example, as provided in FIG. 2C) similarly starts with the unwinding of the dsRNA in a cell. In this non-limiting theoretical mechanism, the sense strand is translocated to a processing center that may have an accumulation of a RNA Dependent RNA Polymerase (RDRP) that is predicted to lead to the formation of antisense transcripts. Preferably, each template of sense RNA will serve for multiple rounds of antisense RNA production. Following antisense RNA accumulation, it may be that the mere localization of this transcript inside the processing center enables RDRP recruitment and creation of double-stranded RNAs (even though this strand may lack a recognizable element of the TAS system). Some of these double stranded RNAs may be translocated to the nucleus where to be diced into ta-siRNAs against an exogenous sequence and some of the double stranded RNA may remain in the processing center where it will unwind again and lead to further cycles of amplification. One possible mediator of the unwinding process inside the processing center is the SDE3 RNA helicase (see Garcia et al. (2012). Ago Hook and RNA Helicase Motifs Underpin Dual Roles for SDE3 in Antiviral Defense and Silencing of Nonconserved Intergenic Regions. *Mol Cell*, 48, 109-120.).

Not to be limited by theory, a possible downstream mechanism for dsRNA construct #3 (FIG. 3) also begins with unwinding of the dsRNA into two single strands.

Focusing on the outcome of the sense strand, it may be recognized by Mir390-Ago7 at both Mir390 Binding sites. The binding of this complex may lead to cleavage at the 3' Mir390BS and to the translocation of this truncated transcript into a processing center. Inside the processing center it may serve as a template for the creation of multiple transcripts of antisense strands. The newly created antisense strands may contain recognizable Mir390 binding sites and therefore may be able to recruit Ago7 and Mir390 to the 5' Mut Mir390BS. This binding is may enable efficient recruitment of RDRP and creation of double stranded RNAs. Some of this double stranded RNA may be translocated to the nucleus and diced into ta-siRNAs whereas other dsRNA may be expected to continue to additional rounds of unwinding and amplification.

Not to be limited by theory, in the alternative, dsRNA construct #3 may be unwound in the cell to a ssRNA. Focusing on the outcome of the antisense strand, it may be recognized by Mir390-Ago7 at both Mir390 Binding sites. The binding of this complex may lead to cleavage at the 3' Mir390BS and to the translocation of this truncated transcript into the processing center. Inside the processing center it may serve as a template for the creation of multiple transcripts of sense strands. The newly created sense strands will contain recognizable Mir390 binding sites and therefore may be able to recruit Ago7 and Mir390 to the 5' Mut Mir390BS. This binding may enable efficient recruitment of RDRP and creation of double stranded RNAs. Some of this double stranded RNA may be translocated to the nucleus and diced into ta-siRNAs whereas other dsRNA may continue to additional rounds of unwinding and amplification.

Not to be limited by theory, in another alternative mechanism, dsRNA construct #3 is undergoes strand unwinding in a cell. Newly synthesized sense and antisense strands (possibly resulting from the mechanisms described above may serve as templates for multiple rounds of RDRP recruitment and dsRNA amplification. This construct may lead to an optimal amplification due to the presence of the 5' Mut Mir390BS on both strands enabling ongoing recruitment of Mir390-Ago7 complex.

As used herein, the term "upstream" refers to positions that are 5' end of the polynucleotide. In certain aspects, upstream refers to the 5' location of sequences relative to an antisense sequence for regulating a target gene.

As used herein the term "isolated" refers to separated from its natural environment. In the case of a dsRNA molecule, separated from the cytoplasm or the nucleus, conversely, in the case of a plant part such as a seed, separated from the rest of the plant.

As used herein the term "isolated dsRNA molecule" refers to an isolated RNA molecule which is substantially in a double stranded form. As used herein, an isolated dsRNA molecule may be in solution and may include buffers. An isolated dsRNA molecule is substantially separated from other nucleic acid molecules including DNA.

As used herein the term "dsRNA" refers to two strands of anti-parallel polyribonucleic acids held together by base pairing (e.g., two sequences that are the reverse complement of each other in the region of base pairing). The two strands can be of identical length or of different lengths provided there is enough sequence homology between the two strands that a double stranded structure is formed with at least 80%, 90%, 95% or 100% complementarity over the entire length. As used herein, the term "overhang" refers to non-double stranded regions of a dsRNA molecule (i.e., single stranded RNA). According to an embodiment of the disclosure, there are no overhangs for the dsRNA molecule. According to another embodiment of the disclosure, the dsRNA molecule comprises one overhang. According to other embodiments, a dsRNA molecule may comprise two overhangs.

In embodiments according to the present disclosure, an isolated dsRNA molecule comprises a second strand having an RNA sequence that is at least 80%, 90%, 95% or 100% complementary over its entire length to an antisense RNA sequence. In some embodiments, an isolated dsRNA molecule comprises a second strand that is 99% complementary over its entire length to an antisense RNA sequence. In other embodiments, the double stranded region is 98% complementary over the entire length of an antisense RNA sequence. In yet other embodiments, the double stranded region is 97% complementary over the entire length of an antisense RNA sequence. In further embodiments, the double stranded region may comprise 96% of the entire length of an antisense RNA sequences. In certain embodiments the double stranded region is between 90 and 100% complementary over the entire length of antisense RNA sequence. In certain embodiments the double stranded region is between 95 and 100% complementary over the entire length of antisense RNA sequence.

The present disclosure provides for, and includes, embodiments of an isolated dsRNA molecule comprising a second strand having an RNA sequence that is nearly 100% complementary over its entire length to an antisense RNA sequence but having 1 mismatch. In some embodiments, the nearly 100% complementary dsRNA region may have 2 mismatches. In some embodiments, the nearly 100% complementary dsRNA region may have 3 mismatches. Some embodiments according to the present disclosure provide for 4, 5 or 6 mismatches in a dsRNA region. In some embodiments, the nearly 100% complementary dsRNA region may have 1 or more, 2 or more, or 3 or more mismatches.

According to an embodiment, an overhang may be 5' to a double stranded region comprising at least one antisense RNA sequence and its reverse complement (e.g., 5' to said antisense RNA sequence). According to an embodiment, an overhang may be 3' to a double stranded region comprising at least one antisense RNA sequence and its reverse complement (e.g., 3' to said antisense RNA sequence). In other embodiments according to the present disclosure, a dsRNA molecule may comprise two overhang regions flanking a double stranded region.

According to other embodiments, an overhang region comprises less than 10 bases. In certain embodiments, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. In an embodiment, a less than 10 base overhang may be a 5' overhang (relative to the 5' and 3' positions on the end of a double stranded RNA region). In another embodiment, a less than 10 base overhang may be a 3' overhang. Relative to a dsRNA molecule having at least one antisense RNA sequence, the 5' overhang may be located at 5' of said antisense RNA sequences. In other embodiments, the 5' overhang may be located 3' of said antisense RNA sequence (e.g., the 5' overhang is on the complementary strand). Also provided by the present disclosure are embodiments wherein the 3' overhang is located 3' of said antisense RNA sequence or wherein the 3' overhang is located 5' of said antisense RNA sequence. According to embodiments of the present disclosure, a 5' overhanging sequence may be 9 bases. In an embodiment, a 3' overhanging sequence may be 9 bases. According to embodiments of the present disclosure, a 5' overhanging sequence may be 8 bases. In an embodiment, a 3' overhanging sequence may be 8 bases. According to embodiments of the present disclosure, a 5' overhanging sequence may be 7 bases. In an embodiment, a 3' overhanging sequence may be 7 bases. According to embodiments of the present disclosure, a 5' overhanging sequence may be 6 bases. In an embodiment, a 3' overhanging sequence may be 6 bases. In some embodiments, a single stranded overhanging sequence may be less than 5 bases. According to embodiments of the present disclosure, a 5' overhanging sequence may be 5 bases. In an embodiment, a 3' overhanging sequence may be 5 bases. According to embodiments of the present disclosure, a 5' overhanging sequence may be 4 bases. In an embodiment, a 3' overhanging sequence may be 4 bases. According to embodiments of the present disclosure, a 5' overhanging sequence may be 3 bases. In an embodiment, a 3' overhanging sequence may be 3 bases. According to embodiments of the present disclosure, a 5' overhanging sequence may be 2 bases. In an embodiment, a 3' overhanging sequence may be 2 bases.

As will be appreciated by one of ordinary skill in the art, a dsRNA molecule of the present disclosure may refer to either strand of the anti-parallel nucleic acids. As will also be appreciated by one of ordinary skill in the art, a dsRNA molecule of the present disclosure includes both a 'sense' and 'antisense' strand and that the sense and antisense strands are reverse complements of each other in a region of base pairing. As used herein the sequence of a dsRNA molecule for regulating a target gene of interest is provided as the 'antisense' orientation with respect to the target gene of interest. Thus, one of ordinary skill in the art would appreciate that the 5' end of a dsRNA molecule for regulating a target gene of interest corresponds to sequences towards the 3' end of the target gene of interest. Similarly, the 3' end of a dsRNA molecule for regulating a target gene of interest corresponds to sequences towards the 5' end of a target gene of interest. As used herein, "the reverse complement of a dsRNA molecule for regulating a target gene of interest" refers to a nucleic acid sequence in the 'sense' orientation.

The term "corresponding to the target gene of interest" or "dsRNA for regulating a target gene of interest" means that the dsRNA sequence contains an RNA silencing agent to the target gene.

As used herein, the term "RNA silencing agent" refers to a nucleic acid which is capable of inhibiting or "silencing" the expression of a target gene. In certain aspects, the RNA silencing agent is capable of preventing complete processing (e.g., the full translation and/or expression) of an mRNA molecule through a post-transcriptional silencing mechanism. RNA silencing agents can be single- or double-stranded RNA or single- or double-stranded DNA or double-stranded DNA/RNA hybrids or modified analogues thereof. In some aspects, the RNA silencing agents are selected from the group consisting of (a) a single-stranded RNA molecule (ssRNA), (b) a ssRNA molecule that self-hybridizes to form a double-stranded RNA molecule, (c) a double-stranded RNA molecule (dsRNA), (d) a single-stranded DNA molecule (ssDNA), (e) a ssDNA molecule that self-hybridizes to form a double-stranded DNA molecule, and (f) a single-stranded DNA molecule including a modified Pol III gene that is transcribed to an RNA molecule, (g) a double-stranded DNA molecule (dsDNA), (h) a double-stranded DNA molecule including a modified Pol III promoter that is transcribed to an RNA molecule, (i) a double-stranded, hybridized RNA/DNA molecule, or combinations thereof. In some aspects these polynucleotides include chemically modified nucleotides or non-canonical nucleotides. In some aspects, the RNA silencing agents are noncoding RNA molecules, for example RNA duplexes comprising paired strands, as well as precursor RNAs from which such small non-coding RNAs can be generated. In some aspects, the RNA silencing agents are dsRNAs such as siRNAs, miRNAs and shRNAs. In one aspect, the RNA silencing agent is capable of inducing RNA interference. In another aspect, the RNA silencing agent is capable of mediating translational repression. As used herein, an RNA silencing agent is a type of agent for regulating a target gene.

In some embodiments, the dsRNA molecule is subject to amplification by RNA-Dependant RNA Polymerase (RDRP). According to some embodiments, a dsRNA molecule comprises a first strand having at least one antisense RNA sequence for regulating a target gene, one or two heterologous RNA sequences corresponding to a smRNA, a helicase binding site and a sequence encoding an RDRP, and a second complementary strand. According to some embodiments, a dsRNA molecule comprises a first strand having at least one antisense RNA sequence for regulating a target gene, one or two heterologous RNA sequences corresponding to a smRNA, a helicase binding site and a sequence encoding an RDRP and further including flanking 3' UTR and 5' UTR sequences from an endovirus and a second RNA strand that is the reverse complement.

As used herein, "small RNA" or "smRNA" refers to RNA molecules that function to modulate (e.g., inhibit) gene expression, and are present in diverse eukaryotic organisms, including plants. As known to those of skill in the art, smRNAs may be defined as low-molecular weight RNAs associated with gene silencing and in some embodiments may be further described as short (generally 21 to 26 nucleotides). Small RNAs include siRNAs and miRNAs, which function in RNA silencing, also sometimes referred to as RNA interference (RNAi). RNA silencing encompasses a broad range of phenomena in which large, double-stranded RNA, fold-back structures, or stem-loop precursors are processed to about 21-26 nucleotide (nt) small RNAs (e.g., siRNAs or miRNAs, which are described further below) that then guide the cleavage of cognate RNAs, block productive translation thereof, or induce methylation of specific target DNAs (Meins, F., et al., Annu Rev. Cell Dev. Biol., 21:297-318, 2005).

As used herein, a small RNA is an RNA molecule that is at least 15 base pairs in length, generally 15-30 nucleotides long, preferably 20-24 nucleotides long. In some aspects, In aspects according to the present disclosure, a "small RNA" is greater than 30 base pairs in length. In an aspect, the small RNA is greater than 30 base pairs in length but less than about 600 base pairs. In an aspect, the small RNA is greater than 100 base pairs in length but less than about 600 base pairs. In an aspect, the small RNA is greater than 200 base pairs in length but less than about 600 base pairs. A small RNA can be either double-stranded or single-stranded. Small RNA includes, without limitation, miRNA (micro-RNA), ta-siRNA (trans activating siRNA), siRNA, activating RNA (RNAa), nat-siRNA (natural anti-sense siRNA), hc-siRNA (heterochromatic siRNA), cis-acting siRNA, lmiRNA (long miRNA), lsiRNA (long siRNA) and easiRNA (epigenetically activated siRNA) and their respective precursors. Preferred siRNA molecules of the disclosure are miRNA molecules, to-siRNA molecules and RNAa molecules and their respective precursors. A small RNA may be processed in vivo by an organism to an active form. According to aspects of the present disclosure, a selective insecticide may be a small RNA. In embodiments according to the present disclosure a small RNA is a dsRNA.

As provided for and included in the present disclosure, a dsRNA molecule may comprise an antisense RNA sequence for regulating a target gene of interest. In some embodiments, a dsRNA molecule for regulating a target gene of interest may comprise an antisense RNA sequence that is greater than 30 base pairs in length to allow processing of the dsRNA in a plant cell and generation of secondary siRNA molecules. In other embodiments, a dsRNA molecule for regulating a target gene of interest may comprise an antisense RNA sequence that is from 30 to 600 bp in length to allow processing of the dsRNA in a plant cell and generation of secondary siRNA molecules. As used herein, "secondary siRNA", "phase RNA" and "ta-siRNA" or refer to dsRNA molecules generated after processing a dsRNA molecule. In certain embodiments, the target gene regulation is silencing. In other embodiments, expression of the target gene is enhanced.

The present disclosure also includes and provides for embodiments having dsRNA molecules having various lengths of dsRNA sequences, whereby the shorter version i.e., x is shorter or equals 50 bp (e.g., 17-50), is referred to as siRNA or miRNA sequences. Longer dsRNA sequences of 51-600 nucleotides are referred to herein as dsRNA, which can be further processed for siRNA molecules.

The term "siRNA" generally refers to small inhibitory RNA duplexes (generally between 17-30 base pairs, but also longer e.g., 31-50 bp) that induce the RNA interference (RNAi) pathway. In certain embodiments, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. Without being limited by any theory, a role of siRNA is its involvement in the RNA interference (RNAi) pathway, where it interferes with the expression of a specific gene. Though not to be limiting, the observed increased potency obtained using longer RNAs in triggering RNAi is theorized to result from providing Dicer with a substrate (27mer) instead of a product (21mer) and that this improves the rate or efficiency of entry of the siRNA duplex into the RNA-induced silencing complex (RISC).

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

In some embodiments, the strands of a double-stranded interfering RNA (e.g., an siRNA) may be connected to form a hairpin or stem-loop structure (e.g., an shRNA). Thus, as mentioned the RNA silencing agent of some embodiments of the disclosure may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, 5 to 15, 7 to 13, 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

As used herein, the phrase "microRNA (also referred to herein interchangeably as "miRNA" or "miR") or a precursor thereof" refers to a microRNA (miRNA) molecule acting as a post-transcriptional regulator. Typically, the miRNA molecules are RNA molecules of about 20 to 22 nucleotides in length which can be loaded into a RISC complex and which direct the cleavage of another RNA molecule, wherein the other RNA molecule comprises a nucleotide sequence essentially complementary to the nucleotide sequence of the miRNA molecule.

While not limited by a particular theory, a miRNA molecule is often processed from a "pre-miRNA" or as used herein a precursor of a miRNA molecule by proteins, such as DCL proteins. Pre-microRNA molecules are typically processed from pri-microRNA molecules (primary transcripts). The single-stranded RNA segments flanking the pre-microRNA are important for processing of the pri-miRNA into the pre-miRNA. The cleavage site appears to be determined by the distance from the stem-ssRNA junction (Han et al., 2006, *Cell,* 125:887-901). In some embodiments, a miRNA molecule is loaded onto a RISC complex where it can guide the cleavage of the target gene of interest.

Pre-microRNA molecules are typically processed from pri-microRNA molecules (primary transcripts). The single stranded RNA segments flanking the pre-microRNA are important for processing of the pri-miRNA into the pre-miRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides which can adopt a secondary structure comprising an imperfect double stranded RNA stem and a single stranded RNA loop (also referred to as "hairpin") and further comprising the nucleotide sequence of the miRNA (and its complement sequence) in the double stranded RNA stem. According to a specific embodiment, the miRNA and its complement are located about 10 to about 20 nucleotides from the free ends of the miRNA double stranded RNA stem. The length and sequence of the single stranded loop region are not critical and may vary considerably, e.g. between 30 and 50 nucleotides in length. The complementarity between the miRNA and its complement need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

In some embodiments according to the present disclosure, naturally occurring miRNA molecules may be comprised within their naturally occurring pre-miRNA molecules. In other embodiments, a miRNA can be introduced into a non-natural heterologous pre-miRNA molecule scaffold by exchanging the nucleotide sequence of the miRNA molecule. Thus, when processed the recombinant pre-miRNA produces an miRNA having a replaced sequence. In some embodiments, the scaffold of the pre-miRNA can also be completely synthetic. Likewise, synthetic miRNA molecules may be comprised within, and processed from, existing pre-miRNA molecule scaffolds or synthetic pre-miRNA scaffolds. Some pre-miRNA scaffolds may be preferred over others for their efficiency to be correctly processed into the designed microRNAs, particularly when expressed as a chimeric gene. In some aspects a chimeric pre-miRNA gene may include other DNA regions, such as untranslated leader sequences, transcription termination and polyadenylation regions that are incorporated in the primary transcript in addition to the pre-microRNA.

According to the present teachings, the dsRNA sequences may be naturally occurring or synthetic.

The dsRNA sequence for regulating a target gene of interest may contain multiple discrete portions or regions that correspond to the target gene, separated by portions that do not correspond to the target gene. In some embodiments, portions that do not correspond to the target gene may optionally correspond to a second, third, or fourth target gene. It will be appreciated that the portions that correspond to the target gene may have different lengths, different degrees of sequence identity to the target gene, and may correspond to regions located anywhere within the target gene.

In embodiments according to the present disclosure, an antisense RNA sequence may be flanked by two nucleic acid sequences that are complementary to an smRNA expressed in the plant. In some embodiments, the two flanking nucleic acid sequences may be complementary to two different smRNAs. In yet other embodiments, the two flanking nucleic acid sequences may comprise sequences that are complementary to more than two smRNAs. In further embodiments, the smRNAs may comprise two copies of one smRNA and a nucleic acid sequence complementary to a different smRNA.

The present disclosure provides for an includes dsRNA molecules comprising an antisense RNA sequence and one or two nucleic acid sequences that are complementary to an smRNA expressed in the plant. The present disclosure provides for embodiments having the composition and orientation of one or two nucleic acid sequences that are complementary to an smRNA expressed in the plant of dsRNA molecules as shown in Table 1 below. In certain embodiments, the dsRNA molecules of Table 1 further comprise a helicase binding sequence. In some embodiments, the dsRNA molecules of Table 1, further comprise a helicase binding sequence and a RDRP polypeptide encoding sequence.

TABLE 1

Embodiments of first strands of dsRNA molecules having a first and second nucleic acid sequence complementary to an smRNA expressed in a plant

| Construct | 5' smRNA$_2$ | 5' smRNA$_1$ | Antisense RNA sequence | 3' smRNA$_1$ | 3' smRNA$_2$ |
|---|---|---|---|---|---|
| A01[1] | None | None | Present | None | None |
| A02 | None | Direct | Present | Direct | None |
| A03 | None | Direct | Present | Direct Mut | None |
| A04 | None | Direct | Present | R/C | None |
| A05 | None | Direct | Present | R/C Mut | None |
| A06 | None | Direct Mut | Present | Direct | None |
| A07 | None | Direct Mut | Present | Direct Mut | None |
| A08 | None | Direct Mut | Present | R/C | None |
| A09 | None | Direct Mut | Present | R/C Mut | None |
| A10 | None | R/C | Present | Direct | None |
| A11 | None | R/C | Present | DirectMut | None |
| A12 | None | R/C | Present | R/C | None |
| A13 | None | R/C | Present | R/C Mut | None |
| A14 | None | R/C Mut | Present | Direct | None |
| A15 | None | R/C Mut | Present | Direct Mut | None |
| A16 | None | R/C Mut | Present | R/C | None |
| A17 | None | R/C Mut | Present | R/C Mut | None |
| B01 | Direct | Direct | Present | Direct | Direct |
| B02 | Direct | Direct | Present | Direct | Direct Mut |
| B03 | Direct | Direct | Present | Direct | R/C |
| B04 | Direct | Direct | Present | Direct | R/C Mut |
| B05 | Direct | Direct | Present | Direct Mut | Direct |
| B06 | Direct | Direct | Present | Direct Mut | Direct Mut |
| B07 | Direct | Direct | Present | Direct Mut | R/C |
| B08 | Direct | Direct | Present | Direct Mut | R/C Mut |
| B09 | Direct | Direct | Present | R/C | Direct |
| B10 | Direct | Direct | Present | R/C | Direct Mut |

TABLE 1-continued

Embodiments of first strands of dsRNA molecules having a first and second nucleic acid sequence complementary to an smRNA expressed in a plant

| Construct | 5' smRNA₂ | 5' smRNA₁ | Antisense RNA sequence | 3' smRNA₁ | 3' smRNA₂ |
|---|---|---|---|---|---|
| B11 | Direct | Direct | Present | R/C | R/C |
| B12 | Direct | Direct | Present | R/C | R/C Mut |
| B13 | Direct | Direct | Present | R/C Mut | Direct |
| B14 | Direct | Direct | Present | R/C Mut | Direct Mut |
| B15 | Direct | Direct | Present | R/C Mut | R/C |
| B16 | Direct | Direct | Present | R/C Mut | R/C Mut |
| B17 | Direct | Direct Mut | Present | Direct | Direct |
| B18 | Direct | Direct Mut | Present | Direct | Direct Mut |
| B19 | Direct | Direct Mut | Present | Direct | R/C |
| B20 | Direct | Direct Mut | Present | Direct | R/C Mut |
| B21 | Direct | Direct Mut | Present | Direct Mut | Direct |
| B22 | Direct | Direct Mut | Present | Direct Mut | Direct Mut |
| B23 | Direct | Direct Mut | Present | Direct Mut | R/C |
| B24 | Direct | Direct Mut | Present | Direct Mut | R/C Mut |
| B25 | Direct | Direct Mut | Present | R/C | Direct |
| B26 | Direct | Direct Mut | Present | R/C | Direct Mut |
| B27 | Direct | Direct Mut | Present | R/C | R/C |
| B28 | Direct | Direct Mut | Present | R/C | R/C Mut |
| B29 | Direct | Direct Mut | Present | R/C Mut | Direct |
| B30 | Direct | Direct Mut | Present | R/C Mut | Direct Mut |
| B31 | Direct | Direct Mut | Present | R/C Mut | R/C |
| B32 | Direct | Direct Mut | Present | R/C Mut | R/C Mut |
| B33 | Direct | R/C | Present | Direct | Direct |
| B34 | Direct | R/C | Present | Direct | Direct Mut |
| B35 | Direct | R/C | Present | Direct | R/C |
| B36 | Direct | R/C | Present | Direct | R/C Mut |
| B37 | Direct | R/C | Present | R/C | Direct |
| B38 | Direct | R/C | Present | R/C | Direct Mut |
| B39 | Direct | R/C | Present | R/C | R/C |
| B40 | Direct | R/C | Present | R/C | R/C Mut |
| B41 | Direct | R/C | Present | R/C Mut | Direct |
| B42 | Direct | R/C | Present | R/C Mut | Direct Mut |
| B43 | Direct | R/C | Present | R/C Mut | R/C |
| B44 | Direct | R/C | Present | R/C Mut | R/C Mut |
| B45 | Direct | R/C Mut | Present | Direct | Direct |
| B46 | Direct | R/C Mut | Present | Direct | Direct Mut |
| B47 | Direct | R/C Mut | Present | Direct | R/C |
| B48 | Direct | R/C Mut | Present | Direct | R/C Mut |
| B49 | Direct | R/C Mut | Present | Direct Mut | Direct |
| B50 | Direct | R/C Mut | Present | Direct Mut | Direct Mut |
| B51 | Direct | R/C Mut | Present | Direct Mut | R/C |
| B52 | Direct | R/C Mut | Present | Direct Mut | R/C Mut |
| B53 | Direct | R/C Mut | Present | R/C | Direct |
| B54 | Direct | R/C Mut | Present | R/C | Direct Mut |
| B55 | Direct | R/C Mut | Present | R/C | R/C |
| B56 | Direct | R/C Mut | Present | R/C | R/C Mut |
| B57 | Direct | R/C Mut | Present | R/C Mut | Direct |
| B58 | Direct | R/C Mut | Present | R/C Mut | Direct Mut |
| B59 | Direct | R/C Mut | Present | R/C Mut | R/C |
| B60 | Direct | R/C Mut | Present | R/C Mut | R/C Mut |
| C01 | Direct Mut | Direct | Present | Direct | Direct |
| C02 | Direct Mut | Direct | Present | Direct | Direct Mut |
| C03 | Direct Mut | Direct | Present | Direct | R/C |
| C04 | Direct Mut | Direct | Present | Direct | R/C Mut |
| C05 | Direct Mut | Direct | Present | Direct Mut | Direct |
| C06 | Direct Mut | Direct | Present | Direct Mut | Direct Mut |
| C07 | Direct Mut | Direct | Present | Direct Mut | R/C |
| C08 | Direct Mut | Direct | Present | Direct Mut | R/C Mut |
| C09 | Direct Mut | Direct | Present | R/C | Direct |
| C10 | Direct Mut | Direct | Present | R/C | Direct Mut |
| C11 | Direct Mut | Direct | Present | R/C | R/C |
| C12 | Direct Mut | Direct | Present | R/C | R/C Mut |
| C13 | Direct Mut | Direct | Present | R/C Mut | Direct |
| C14 | Direct Mut | Direct | Present | R/C Mut | Direct Mut |
| C15 | Direct Mut | Direct | Present | R/C Mut | R/C |
| C16 | Direct Mut | Direct | Present | R/C Mut | R/C Mut |
| C17 | Direct Mut | Direct Mut | Present | Direct | Direct |
| C18 | Direct Mut | Direct Mut | Present | Direct | Direct Mut |
| C19 | Direct Mut | Direct Mut | Present | Direct | R/C |
| C20 | Direct Mut | Direct Mut | Present | Direct | R/C Mut |
| C21 | Direct Mut | Direct Mut | Present | Direct Mut | Direct |
| C22 | Direct Mut | Direct Mut | Present | Direct Mut | Direct Mut |
| C23 | Direct Mut | Direct Mut | Present | Direct Mut | R/C |
| C24 | Direct Mut | Direct Mut | Present | Direct Mut | R/C Mut |
| C25 | Direct Mut | Direct Mut | Present | R/C | Direct |
| C26 | Direct Mut | Direct Mut | Present | R/C | Direct Mut |
| C27 | Direct Mut | Direct Mut | Present | R/C | R/C |
| C28 | Direct Mut | Direct Mut | Present | R/C | R/C Mut |
| C29 | Direct Mut | Direct Mut | Present | R/C Mut | Direct |
| C30 | Direct Mut | Direct Mut | Present | R/C Mut | Direct Mut |
| C31 | Direct Mut | Direct Mut | Present | R/C Mut | R/C |
| C32 | Direct Mut | Direct Mut | Present | R/C Mut | R/C Mut |
| C33 | Direct Mut | R/C | Present | Direct | Direct |
| C34 | Direct Mut | R/C | Present | Direct | Direct Mut |
| C35 | Direct Mut | R/C | Present | Direct | R/C |
| C36 | Direct Mut | R/C | Present | Direct | R/C Mut |
| C37 | Direct Mut | R/C | Present | R/C | Direct |
| C38 | Direct Mut | R/C | Present | R/C | Direct Mut |
| C39 | Direct Mut | R/C | Present | R/C | R/C |
| C40 | Direct Mut | R/C | Present | R/C | R/C Mut |
| C41 | Direct Mut | R/C | Present | R/C Mut | Direct |
| C42 | Direct Mut | R/C | Present | R/C Mut | Direct Mut |
| C43 | Direct Mut | R/C | Present | R/C Mut | R/C |
| C44 | Direct Mut | R/C | Present | R/C Mut | R/C Mut |
| C45 | Direct Mut | R/C Mut | Present | Direct | Direct |
| C46 | Direct Mut | R/C Mut | Present | Direct | Direct Mut |
| C47 | Direct Mut | R/C Mut | Present | Direct | R/C |
| C48 | Direct Mut | R/C Mut | Present | Direct | R/C Mut |
| C49 | Direct Mut | R/C Mut | Present | Direct Mut | Direct |
| C50 | Direct Mut | R/C Mut | Present | Direct Mut | Direct Mut |
| C51 | Direct Mut | R/C Mut | Present | Direct Mut | R/C |
| C52 | Direct Mut | R/C Mut | Present | Direct Mut | R/C Mut |
| C53 | Direct Mut | R/C Mut | Present | R/C | Direct |
| C54 | Direct Mut | R/C Mut | Present | R/C | Direct Mut |
| C55 | Direct Mut | R/C Mut | Present | R/C | R/C |
| C56 | Direct Mut | R/C Mut | Present | R/C | R/C Mut |
| C57 | Direct Mut | R/C Mut | Present | R/C Mut | Direct |
| C58 | Direct Mut | R/C Mut | Present | R/C Mut | Direct Mut |
| C59 | Direct Mut | R/C Mut | Present | R/C Mut | R/C |
| C60 | Direct Mut | R/C Mut | Present | R/C Mut | R/C Mut |
| D01 | R/C | Direct | Present | Direct | Direct |
| D02 | R/C | Direct | Present | Direct | Direct Mut |
| D03 | R/C | Direct | Present | Direct | R/C |
| D04 | R/C | Direct | Present | Direct | R/C Mut |
| D05 | R/C | Direct | Present | Direct Mut | Direct |
| D07 | R/C | Direct | Present | Direct Mut | R/C |
| D08 | R/C | Direct | Present | Direct Mut | R/C Mut |
| D10 | R/C | Direct | Present | R/C | Direct Mut |
| D11 | R/C | Direct | Present | R/C | R/C |
| D12 | R/C | Direct | Present | R/C | R/C Mut |
| D13 | R/C | Direct | Present | R/C Mut | Direct |
| D14 | R/C | Direct | Present | R/C Mut | Direct Mut |
| D15 | R/C | Direct | Present | R/C Mut | R/C |
| D16 | R/C | Direct | Present | R/C Mut | R/C Mut |
| D17 | R/C | Direct Mut | Present | Direct | Direct |
| D18 | R/C | Direct Mut | Present | Direct | Direct Mut |
| D19 | R/C | Direct Mut | Present | Direct | R/C |
| D20 | R/C | Direct Mut | Present | Direct | R/C Mut |
| D21 | R/C | Direct Mut | Present | Direct Mut | Direct |
| D22 | R/C | Direct Mut | Present | Direct Mut | Direct Mut |
| D23 | R/C | Direct Mut | Present | Direct Mut | R/C |
| D24 | R/C | Direct Mut | Present | Direct Mut | R/C Mut |
| D25 | R/C | Direct Mut | Present | R/C | Direct |
| D26 | R/C | Direct Mut | Present | R/C | Direct Mut |
| D27 | R/C | Direct Mut | Present | R/C | R/C |
| D28 | R/C | Direct Mut | Present | R/C | R/C Mut |
| D29[3] | R/C | Direct Mut | Present | R/C Mut | Direct |
| D30 | R/C | Direct Mut | Present | R/C Mut | Direct Mut |
| D31 | R/C | Direct Mut | Present | R/C Mut | R/C |
| D32 | R/C | Direct Mut | Present | R/C Mut | R/C Mut |
| D33 | R/C | R/C | Present | Direct | Direct |
| D34 | R/C | R/C | Present | Direct | Direct Mut |
| D35 | R/C | R/C | Present | Direct | R/C |
| D36 | R/C | R/C | Present | Direct | R/C Mut |

TABLE 1-continued

Embodiments of first strands of dsRNA molecules having a first and second nucleic acid sequence complementary to an smRNA expressed in a plant

| Construct | 5' smRNA₂ | 5' smRNA₁ | Antisense RNA sequence | 3' smRNA₁ | 3' smRNA₂ |
|---|---|---|---|---|---|
| D37 | R/C | R/C | Present | R/C | Direct |
| D38 | R/C | R/C | Present | R/C | Direct Mut |
| D39 | R/C | R/C | Present | R/C | R/C |
| D40 | R/C | R/C | Present | R/C | R/C Mut |
| D41 | R/C | R/C | Present | R/C Mut | Direct |
| D42 | R/C | R/C | Present | R/C Mut | Direct Mut |
| D43 | R/C | R/C | Present | R/C Mut | R/C |
| D44 | R/C | R/C | Present | R/C Mut | R/C Mut |
| D45 | R/C | R/C Mut | Present | Direct | Direct |
| D46 | R/C | R/C Mut | Present | Direct | Direct Mut |
| D47 | R/C | R/C Mut | Present | Direct | R/C |
| D48 | R/C | R/C Mut | Present | Direct | R/C Mut |
| D49 | R/C | R/C Mut | Present | Direct Mut | Direct |
| D50 | R/C | R/C Mut | Present | Direct Mut | Direct Mut |
| D51 | R/C | R/C Mut | Present | Direct Mut | R/C |
| D52 | R/C | R/C Mut | Present | Direct Mut | R/C Mut |
| D53 | R/C | R/C Mut | Present | R/C | Direct |
| D54 | R/C | R/C Mut | Present | R/C | Direct Mut |
| D55 | R/C | R/C Mut | Present | R/C | R/C |
| D56 | R/C | R/C Mut | Present | R/C | R/C Mut |
| D57 | R/C | R/C Mut | Present | R/C Mut | Direct |
| D58 | R/C | R/C Mut | Present | R/C Mut | Direct Mut |
| D59 | R/C | R/C Mut | Present | R/C Mut | R/C |
| D6 | R/C | Direct | Present | Direct Mut | Direct Mut |
| D60 | R/C | R/C Mut | Present | R/C Mut | R/C Mut |
| D9 | R/C | Direct | Present | R/C | Direct |
| E01 | R/C Mut | Direct | Present | Direct | Direct |
| E02 | R/C Mut | Direct | Present | Direct | Direct Mut |
| E03 | R/C Mut | Direct | Present | Direct | R/C |
| E04 | R/C Mut | Direct | Present | Direct | R/C Mut |
| E05 | R/C Mut | Direct | Present | Direct Mut | Direct |
| E06 | R/C Mut | Direct | Present | Direct Mut | Direct Mut |
| E07 | R/C Mut | Direct | Present | Direct Mut | R/C |
| E08 | R/C Mut | Direct | Present | Direct Mut | R/C Mut |
| E09 | R/C Mut | Direct | Present | R/C | Direct |
| E10 | R/C Mut | Direct | Present | R/C | Direct Mut |
| E11 | R/C Mut | Direct | Present | R/C | R/C |
| E12 | R/C Mut | Direct | Present | R/C | R/C Mut |
| E13 | R/C Mut | Direct | Present | R/C Mut | Direct |
| E14 | R/C Mut | Direct | Present | R/C Mut | Direct Mut |
| E15 | R/C Mut | Direct | Present | R/C Mut | R/C |
| E16 | R/C Mut | Direct | Present | R/C Mut | R/C Mut |
| E17 | R/C Mut | Direct Mut | Present | Direct | Direct |
| E18 | R/C Mut | Direct Mut | Present | Direct | Direct Mut |
| E19 | R/C Mut | Direct Mut | Present | Direct | R/C |
| E20 | R/C Mut | Direct Mut | Present | Direct | R/C Mut |
| E21 | R/C Mut | Direct Mut | Present | Direct Mut | Direct |
| E22 | R/C Mut | Direct Mut | Present | Direct Mut | Direct Mut |
| E23 | R/C Mut | Direct Mut | Present | Direct Mut | R/C |
| E24 | R/C Mut | Direct Mut | Present | Direct Mut | R/C Mut |
| E25 | R/C Mut | Direct Mut | Present | R/C | Direct |
| E26 | R/C Mut | Direct Mut | Present | R/C | Direct Mut |
| E27 | R/C Mut | Direct Mut | Present | R/C | R/C |
| E28 | R/C Mut | Direct Mut | Present | R/C | R/C Mut |
| E29 | R/C Mut | Direct Mut | Present | R/C Mut | Direct |
| E30 | R/C Mut | Direct Mut | Present | R/C Mut | Direct Mut |
| E31 | R/C Mut | Direct Mut | Present | R/C Mut | R/C |
| E32 | R/C Mut | Direct Mut | Present | R/C Mut | R/C Mut |
| E33 | R/C Mut | R/C | Present | Direct | Direct |
| E34 | R/C Mut | R/C | Present | Direct | Direct Mut |
| E35 | R/C Mut | R/C | Present | Direct | R/C |
| E36 | R/C Mut | R/C | Present | Direct | R/C Mut |
| E37 | R/C Mut | R/C | Present | Direct | Direct |
| E38 | R/C Mut | R/C | Present | R/C | Direct Mut |
| E39 | R/C Mut | R/C | Present | R/C | R/C |
| E40 | R/C Mut | R/C | Present | R/C | R/C Mut |
| E41 | R/C Mut | R/C | Present | R/C Mut | Direct |
| E42 | R/C Mut | R/C | Present | R/C Mut | Direct Mut |
| E43 | R/C Mut | R/C | Present | R/C Mut | R/C |
| E44 | R/C Mut | R/C | Present | R/C Mut | R/C Mut |
| E45 | R/C Mut | R/C Mut | Present | Direct | Direct |
| E46 | R/C Mut | R/C Mut | Present | Direct | Direct Mut |
| E47 | R/C Mut | R/C Mut | Present | Direct | R/C |
| E48 | R/C Mut | R/C Mut | Present | Direct | R/C Mut |
| E49 | R/C Mut | R/C Mut | Present | Direct Mut | Direct |
| E50 | R/C Mut | R/C Mut | Present | Direct Mut | Direct Mut |
| E51 | R/C Mut | R/C Mut | Present | Direct Mut | R/C |
| E52 | R/C Mut | R/C Mut | Present | Direct Mut | R/C Mut |
| E53 | R/C Mut | R/C Mut | Present | R/C | Direct |
| E54 | R/C Mut | R/C Mut | Present | R/C | Direct Mut |
| E55 | R/C Mut | R/C Mut | Present | R/C | R/C |
| E56 | R/C Mut | R/C Mut | Present | R/C | R/C Mut |
| E57 | R/C Mut | R/C Mut | Present | R/C Mut | Direct |
| E58 | R/C Mut | R/C Mut | Present | R/C Mut | Direct Mut |
| E59 | R/C Mut | R/C Mut | Present | R/C Mut | R/C |
| E60 | R/C Mut | R/C Mut | Present | R/C Mut | R/C Mut |

Figure 2A:
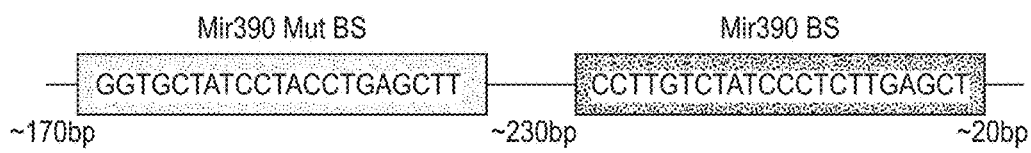
FIG. 2A presents a schematic representation of the Solanum Lycopersicum (*Lycopersicon esculentum*) TAS3 gene according to an embodiment of the present disclosure. Mir390BS is displayed in a darker gray box (SEQ ID NO. 319). The light gray box represents the 5' Mut Mir390BS (SEQ. ID NO. 318).
Figure 2B:
FIG. 2B presents a schematic representation of dsRNA construct #1 having an exogenous trigger control according to an embodiment of the present disclosure. The construct includes a 234 bp exogenous sequence provided in Table 5 (e.g., Trigger #1).
Figure 2C:
FIG. 2C presents a schematic representation of dsRNA construct #2 having a dual Mir390BS sequence on the sense strand and an exogenous sequence according to an embodiment of the present disclosure. The construct is comprises 3 parts from 5' to 3': a 5' Mut Mir390BS sequence, a 234 bp exogenous sequence in reverse complement orientation, and a 3' Mir390BS. The sequences are presented in Table 5 (e.g., Trigger #2).
Figure 4:
FIG. 4 presents a schematic representation of dsRNA construct #4 having miR390S as overhangs. This construct is composed of two different strands. The sense strand is composed of 3 parts from 5' to 3': 5' Mut Mir390BS, a 234 bp exogenous sequence in the reverse complement orientation, 3' Mir390BS. The antisense is composed of only one part: a 234 bp exogenous sequence in the sense orientation. For sequences, see Table 5 (Sense-Trigger#4, Antisense-Trigger #5).
Figure 4:
Figure 8:
FIG. 8 presents a schematic representation of dsRNA construct #8 an Endogenous Trigger Control. This construct is composed of one part: a 234 bp of the endogenous TAS3 sequence. For sequence, see Table 5 (Trigger #10).
Figure 9:
FIG. 9 presents a schematic representation of dsRNA construct #9–Mir390BS+Endogenous insert. This construct is composed of 3 parts from 5' to 3': 5' Mut Mir390BS, a 234 bp of the endogenous TAS3 sequence and 3' Mir390BS. For sequence, see Table 5 (Trigger #11).

₁see construct #1, FIG. 2B and construct #8, FIG. 8;
₂See construct #2, FIG. 2A and 2C; construct #4 FIG. 4; construct #9 FIG. 9
₃see construct, #3 and construct #6
As used herein, "Direct" means the direct sequence (i.e., a sequence having the same order of nucleotides and in the same orientation) of a smRNA; "Direct Mut" means the direct sequence of an smRNA having a mutation that renders it resistant to cleavage; "R/C" means the reverse complement of an smRNA; and "R/C Mut" means a reverse complement of an smRNA having a mutation that renders it resistant to cleavage.

In embodiments according to the present disclosure, the sequences of the embodiments of Table 1 include, but are not limited to combinations of SEQ ID NOs: 26 to 35, and 41 to 288, their complements, and non-cleavable mutants thereof. In some embodiments, RNA sequence for regulating a target gene of interest comprises a nucleic acid having 90 to 100% homology to a sequence selected from the group consisting of SEQ ID NOs:8, 11, 12, 36 to 38, and their complements thereof. It is understood that the present disclosure provides for, and includes, dsRNA constructs of Table 1 having a second reverse complementary strand at least to the antisense RNA sequence. The present disclosure further provides dsRNA constructs having a second reverse complimentary strand comprising an antisense RNA sequence and a 5' smRNA₁ sequence. The present disclosure further provides dsRNA constructs having a second reverse complimentary strand comprising an antisense RNA sequence, a 5' smRNA₁ sequence and a 3' smRNA₁ sequence. The present disclosure further provides dsRNA constructs having a second reverse complimentary strand comprising an antisense RNA sequence, a 5' smRNA₁ sequence, a 5' smRNA₂ sequence and a 3' smRNA₁ sequence. The present disclosure further provides dsRNA constructs having a second reverse complimentary strand comprising an antisense RNA sequence, a 5' smRNA₁ sequence, a 5' smRNA₂ sequence, a 3' smRNA₁ sequence and a 4' smRNA₂ sequence.

The present disclosure provides for and includes second reverse complementary strand of the constructs of Table 1 having mismatches. In some embodiments, the second reverse complementary strand provides for a double stranded region comprising a smRNA and its non-cleavable mutant. Accordingly it is understood, the dsRNA comprises one or more mismatches corresponding to the mismatch between the smRNA and it's non-cleavable mutant. The present disclosure provides for combinations of the first strands of Table 1 to produce dsRNA molecules. Accordingly, it is understood that construct A02 may be combined with, for example, the reverse complement of A02 to prepare a dsRNA of the present disclosure. In other embodiments, for example, construct A02 may be combined with the reverse complement of construct A06 to prepare a dsRNA of the present disclosure having a mismatch sequence at the non-cleavable site. One of ordinary skill in the art would recognize that additional combinations of the constructs of Table 1 may be prepared in accordance with the present disclosure.

In embodiments according to the present disclosure, the sequence complementarity may be, but are not required to be, 100%. In certain embodiments of the disclosure the degree of complementarity, e.g., percent complementarity, need only be sufficient to provide for stable binding of a smRNA to the complementary site. In certain embodiments of the disclosure the degree of complementarity need only be sufficient such that the smRNA pairs to the complementary site and mediates cleavage of the target mRNA. For example, in certain embodiments of the disclosure the degree of complementarity is at least 70%, at least 80%, or at least 90%. In certain embodiments of the disclosure the number of mismatched or unpaired nucleotides in the siRNA strand or miRNA, following binding to the complementary site, is between 0 and 5, e.g., 1, 2, 3, 4, or 5.

In other embodiments according to the present disclosure, the sequence complementarity of an smRNA may be greater than 90%. In some embodiments, the sequence complementarity of an smRNA may be greater than 91%. In some embodiments, the sequence complementarity of an smRNA may be greater than 92%. In other embodiments, the sequence complementarity of an smRNA may be greater than 93%. In some embodiments, the sequence complementarity of an smRNA may be greater than 94%. In some embodiments, the sequence complementarity of an smRNA may be greater than 95%. In other embodiments, the sequence complementarity of an smRNA may be greater than 96%. In some embodiments, the sequence complementarity of an smRNA may be greater than 97%. In some embodiments, the sequence complementarity of an smRNA may be greater than 98%. In other embodiments, the sequence complementarity of an smRNA may be greater than 99%. In some embodiments, the sequence complementarity of an smRNA may be 100%. In embodiments according to the present disclosure, sequence complementarity may be between 90 and 100% or 95 and 100%. According to embodiments of the present disclosure the smRNAs may be selected from the group consisting of SEQ ID NOs 26 to 35, 41 to 288, and non-cleavable mutants thereof.

As used herein, the terms "complementarity" and "complementary" refer to a nucleic acid that can form one or more hydrogen bonds with another nucleic acid sequence by either traditional Watson-Crick or other non-traditional types of interactions. It will be recognized that complementarity and homology or identity are related terms. That is, a homology describes the degree of similarity between two or more nucleotide sequences when examined in the same 5' to 3' orientation. In contrast, complementarity describes the degree of similarity between two or more nucleotide sequences when comparing a sequence having a 5' to 3' orientation to a sequence having a 3' to 5' orientation. Thus, a first and second sequence having 90% homology will also have 90% complementarity when the first sequence is compared to the reverse complement of the second sequences. In reference to the nucleic molecules of the presently disclosed subject matter, the binding free energy of a nucleic acid molecule with its complementary sequence is sufficient to allow the relevant function of the nucleic acid to proceed, in some embodiments, to form a duplex structure under physiological conditions in a plant cell, to mediate ribonuclease activity, etc. For example, the degree of complementarity between the sense and antisense strands of an miRNA precursor can be the same or different from the degree of complementarity between the miRNA-containing strand of an miRNA precursor and the target nucleic acid sequence. Determination of binding free energies for nucleic acid molecules is well known in the art. See e.g., Freier et al., 1986; Turner et al., 1987. One of ordinary skill in the art would be able to test for sufficiency of complementarity by random or site directed mutagenesis and screening of silencing activity and dsRNA molecule stability in vivo.

In certain embodiments, the phrase "percent complementarity" refers to the percentage of residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). The terms "100% complementary", "fully complementary", and "perfectly complementary" indicate that all of the contiguous residues of a nucleic acid sequence can hydrogen bond with the same number of contiguous residues in a second nucleic acid sequence. It will be appreciated that the nucleic acids may have different lengths and/or that there may be bulges when the two nucleic acids are optimally aligned for maximum complementarity over a given portion of either sequence. Percent complementarity can, in various embodiments of the disclosure, disregard such bulges in the computation or consider the percentage complementarity to be the number of paired (hydrogen bonded) residues divided by the total number of residues over a given length, which may be the length of the shorter or the longer nucleic acid in different embodiments.

Any complementary sequence for a smRNA may be used in various embodiments of the present disclosure. The sequence may be complementary to an miRNA or siRNA. The sequence may be perfectly (100%) complementary or may have imperfect complementarity as described herein and known in the art. The complementary sequence may be one that is naturally found in a trans-acting-siRNA-producing (TAS) locus or to-siRNA precursor RNA, flanking the portion of the RNA that is cleaved to produce ta-siRNAs. The complementary sequence may be any smRNA complementary sequence that is found on one side of a nucleic acid sequence that is cleaved to produce siRNA, wherein a second smRNA complementary sequence is found on the other side of the nucleic acid sequence. In various embodiments of the disclosure the complementary sequence is recognized by a smRNA selected from the group consisting of:

miR390: (SEQ ID NO: 25) AAGCUCAGGAGGGAUAGCGCC;

miR161.1: (SEQ ID NO: 26) UUGAAAGUGACUACAUCGGGG;

miR400: (SEQ ID NO: 27) UAUGAGAGUAUUAUAAGUCAC;

TAS2 3'D6(−): (SEQ ID NO: 28) AUAUCCCAUUUCUACCAUCUG;

TAS 1b 3'D4(−): (SEQ ID NO: 29) UUCUUCUACCAUCCUAUCAAU;

TAS3 5'D7(+): (SEQ ID NO: 30) UUCUUGACCUUGUAAGACCCC;

TAS3 5'D8(+): (SEQ ID NO: 31) UUCUUGACCUUGUAAGGCCUU;

miR168: (SEQ ID NO: 32) UCGCUUGGUGCAGGUCGGGAA;

miR828 (SEQ ID NO: 33) UCUUGCUUAAAUGAGUAUUCCA; and miR393: (SEQ ID NO: 34) UCCAAAGGGAUCGCAUUGAUC.

In one embodiment, the miRNA is UUCGCUUGCAGAGAGAAAUCAC (SEQ ID NO: 35). Note that these sequences may have been identified in one or more plants, e.g., *Arabidopsis*, most land plants, moss, etc. It will be appreciated that in some cases the sequences are conserved across multiple species while in other cases there could be minor variations. Such variations are encompassed within the present disclosure. It will be appreciated that homologous siRNAs or miRNAs from other plant species than those listed could be used. Optionally, recognition of the complementary sequence by the cognate miRNA or siRNA leads to cleavage. One of skill in the art could determine whether binding and/or cleavage of a smRNA to a candidate complementary sequence occurs in vivo (in living cells or organisms) or in vitro, e.g., under conditions approximating physiological intercellular conditions. In other embodiments, an smRNA may be selected from the group consisting of SEQ ID NOs:41 to 288 (see, Table 1 of U.S. Pat. No. 8,143,480).

The length of the complementary sequence could vary. The length of a complementary sequence may be defined as equal to the length of the smRNA that binds to it, but it will be appreciated that a complementary sequence could differ in length from that of the smRNA, e.g., it may be shorter than the length of the smRNA. Typically the complementary sequence is sufficiently long such that the smRNA can bind (e.g., hybridize) to the sequence with reasonable specificity and, optionally, direct cleavage within a duplex structure formed upon binding. Such cleavage may occur at a position within the duplex typical of cleavage directed by smRNAs, (e.g., in certain embodiments at position 10 or 11 of the smRNA). For example, a complementary sequence could be between 15 and 24 nucleotides in length, or any intervening number, wherein there are 1, 2, 3, 4, or 5 mismatches when the smRNA is paired with the complementary sequence in the case of a 15 nucleotide sequence and up to 6, 7, or 8 mismatches in the case of a 24 nucleotide complementary sequence. Similar considerations would apply for other smRNA complementary sequence. It will be appreciated that there may be "bulges" in the duplex formed when an smRNA pairs with its complementary sequence. In such instances a bulge could be considered equivalent to a single mismatch or, in various embodiments of the disclosure a bulge of X nucleotides could be considered equivalent to X mismatches. It will also be appreciated that the specificity of binding of the smRNA to the complementary sequence need not be completely specific, e.g., the smRNA may bind to different sequence having either a lesser or greater degree of complementarity.

In embodiments according to the present disclosure, a first or second complementary sequence may be between 15 and 30 nt, between 18 and 24 nt, between 20 and 22, or exactly 21 nt in length. In some embodiments a first or second complementary sequence may comprise any intervening range or specific value within the foregoing ranges in certain embodiments of the disclosure. In certain non-limiting embodiments of the disclosure the number of mismatched or unpaired nucleotides in the siRNA strand or miRNA, following binding to the complementary sequence, is between 0 and 5, e.g., 1, 2, 3, 4, or 5. In certain non-limiting embodiments of the disclosure the number of mismatched or unpaired nucleotides (including those in both strands) in a duplex structure formed between the smRNA and its complementary sequence, is between 0 and 10, e.g., 1, 2, 3, 4, 5, 6, 7, 8, 9, or 10. The mismatches or bulges may occur at any position within the duplex structure, in various embodiments of the disclosure. In certain embodiments the mismatches or bulges are located at positions known in the art not to typically inhibit or prevent smRNA-directed cleavage. In other embodiments the mismatches or bulges are located at such positions. One or more mismatches or bulges may occur, for example, at any position with respect to the 5' end of a smRNA depicted in the figures herein or contemplated when an smRNA described herein pairs with a sequence complementary to it. The mismatch may be any mismatch known in the art. In certain embodiments a mismatch is said to occur when a nucleotide within an at least partly double-stranded structure is not paired in a conventional G-C, A-T, or A-U base pair. In certain embodiments a mismatch is said to occur when a nucleotide in an at least partly double-stranded structure is not paired in a Watson-Crick base pair. It will be appreciated that the aforementioned mismatches may exclude "bulges", wherein a nucleotide bulges outward from an otherwise duplex region by being located between two nucleotides that are base paired with adjacent nucleotides on the opposite strand of the duplex.

The present disclosure further includes and provides for embodiments wherein a first and a second complementary sequence are the same length. In other embodiments, a first complementary sequence may be a different length than a second complementary sequence.

The portion of the smRNA that is complementary to the complementary sequence could vary. For example, in certain embodiments the complementary site is at least 70%, at least 80%, or at least 90% complementary to the first 16 nucleotides of the smRNA. In certain embodiments the complementary sequence is at least 70%, at least 80%, or at least 90% complementary to the first 17, 18, or 19 nucleotides of the smRNA. In certain embodiments the complementary sequence is a subsequence of a complementary sequence, wherein said subsequence is at least 16, 17, 18, 19, 20, or 21 nucleotides in length. In some embodiments the subsequence is the last 16, 17, 18, 19, 20, or 21 nucleotides of the listed sequence. In some embodiments the subsequence is at least 70%, at least 80%, at least 90%, or 100% complementary to the first 16, 17, 18, 19, 20, or 21 nucleotides of an smRNA.

The present disclosure also includes, and provides for, dsRNA molecules having a single smRNA complementary sequence and an antisense RNA sequence for regulating a target gene of interest. In embodiments according to the present disclosure, where the dsRNA molecule is presented as an antisense sequence, an smRNA sequence on the 5' end is an upstream sequences. In other embodiments, an smRNA sequence on the 3' end is a downstream sequence. Not to be limited by theory, a smRNA complementary sequence binds (hybridizes) to a complementary smRNA and the duplex recruits an RDRP, such as RNA-dependent RNA polymerase 6 (RDR6). The dsRNA molecule can be further processed by Dicer-like enzymes such as dicer-like protein 4 (DCL4) to produce the siRNAs. It will be appreciated that the presence of a second complementary sequence (e.g., flanking sequences) depends on the sequence of smRNA that the complementary sequence recognizes. In some instances (i.e., miR390) it is required whereas in others it is not required (i.e., miR173). In some aspects, for smRNAs that do not require a second complementary sequence (flanking sequence), the inclusion of a second complementary sequence may increase the propensity, efficiency or rate of generating siRNAs.

When only one smRNA complementary sequence is present in a dsRNA molecule, then it can be upstream (5') or downstream (3') to the dsRNA sequence for silencing the target gene (where the dsRNA sequence is referenced in the antisense orientation). According to a specific embodiment, this smRNA complementary sequence is functional and is located 3' to the dsRNA sequence for silencing the target gene. According to another specific embodiment, this smRNA complementary sequence is functional (e.g., miR173) and is located 5' to the dsRNA sequence for silencing the target gene.

When two complementary sequences to one or more an smRNAs are included, one sequence (e.g., the first site) is located 5' to the dsRNA sequence for silencing the target gene (where the dsRNA sequence is referenced in the antisense orientation), and the second site is located 3' to the dsRNA sequence for silencing the target gene (e.g., flanking smRNA sequences). Alternatively, the present disclosure also provides for dsRNA molecules having the second site located 5' to the dsRNA sequence for silencing the target gene, and the first site located 3' to dsRNA sequence for silencing the target gene.

It will be appreciated that the complementary sequences can be positioned on one strand (sense) and the other on the other strand (antisense). It will be further appreciated that in the presence of two complementary sequences to an smRNA or smRNAs, one of said sequences can mediate binding of the smRNA but not cleavage of the dsRNA sequence for silencing the target gene. Thus, one of the complementary binding sequences is essentially an smRNA mimic sequence (e.g. sufficient for binding but not cleavage).

The smRNA mimic sequence is essentially complementary to the microRNA or siRNA provided that one or more mismatches are allowed: thus, a mismatch between the complementary nucleotides at position 10 or position 11 of the microRNA and the corresponding nucleotide sequence in the micro-RNA resistant site. As used herein, the term "smRNA mimic," "smRNA mutant," and "miRNA Mut" are used interchangeably and refer to smRNAs that are not cleaved in a cell. Not to be limited by any particular theory, mimic or mutant are thought mediate binding of the machinery, such as the Argonaute protein family, but are not processed, for example by a dicer-like protein. Accordingly, smRNA mimics or mutants interact with the RISC complex but can not be cleaved. Thus a non-cleavable target mimic of a smRNA acts to sequester the corresponding target miRNA and arrest its activity. By incorporating a miRNA target mimic having a non-cleavable target site the accumulation of all MIR gene family members may be reduced. Methods for preparing smRNA mutants or mimics are known. See Todesco et al., "A Collection of Target Mimics for Comprehensive Analysis of MicroRNA Function in *Arabidopsis thaliana*," PLOS Genetics 6(7):e1001031 (2010); Wang Z., "The guideline of the design and validation of MiRNA mimics," Methods Mol. Biol. 676:211-23 (2011);

The complementary sequences may be identical or different and may be recognized by the same or different smRNAs, which may be miRNA or siRNA, or both, in any combination.

The complementary sequences(s) can be immediately adjacent to (i.e., contiguous with) the dsRNA sequence for silencing the target gene. Alternatively, the complementary sequence (or at least one of same) may be separated from the dsRNA sequence for silencing the target gene by an intervening spacer or functional sequence (e.g., Helicase binding site).

As used herein a "helicase binding site" refers to a binding site of an RNA helicase. RNA helicases are essential for most processes of RNA metabolism such as ribosome biogenesis, pri-mRNA splicing and translation initiation. Sequence information is available from the RNA Helicase Database, available on the internet at wwwdotrnahelicasedotorg/. According to a specific embodiment, the helicase may be a DEAD RNA helicase (DEAD RH), such as described in Chi et al. (2012). "The Function of RH22, a DEAD RNA Helicase, in the Biogenesis of the 50S Ribosomal Subunits of *Arabidopsis* Chloroplasts," *Plant Physiology*, 158, 693-707. In certain embodiments, a helicase binding site may be positioned so as to allow unwinding of the strands of a dsRNA molecule to single stranded RNA (ssRNA) and allow recruitment of an RNA-dependent RNA Polymerase such as RDR6. Unwinding and recruitment of an RDRP provides for amplification of a dsRNA molecule in the plant cell. Other proteins that are known to be cytosolic proteins and have helicase or helicase-like activity include the Argonaute protein family, which are a key components of the RISC complex (RNA Induced Silencing Complex). Alternatively a helicase binding site may includes sequences recognized by the plant homolog of RNA helicase RIG-I (Yoneyama et al. 2004 Nat. Immun. 5:730-737). Alternatively or additionally, the present disclosure provides for helicase binding site sequences as described in Garcia et al. 2012 Mol. Cell. 48(1):109-20, which is hereby incorporated by reference in its entirety.

According to a specific embodiment, the helicase binding site is positioned upstream or downstream of the dsRNA sequence for silencing expression of the target gene (where the dsRNA sequence is referenced in the antisense orientation).

According to a specific embodiment, the helicase binding site is positioned upstream or downstream of the dsRNA sequence (where the dsRNA sequence is referenced in the antisense orientation) and the two complementary sites to the smRNA or smRNAs flank the helicase binding site.

According to a further specific embodiment, the helicase binding site is located within the dsRNA sequence corresponding to the target site.

"Flanked by" as used herein, does not require that the smRNA complementary sequences are contiguous with the dsRNA sequence for silencing the target gene. All that is necessary is that there is an smRNA complementary sequences on at least one side or in case of two complementary sequences on each side of the dsRNA sequence for silencing the target gene. Either or both smRNA complementary sequences may, in various embodiments of the disclosure, be located contiguously with the dsRNA sequence for silencing the target gene. In certain embodiments either or both smRNA complementary sequences may, in various embodiments of the disclosure, be separated from the dsRNA sequence for silencing the target gene by between 1 nt and 2 kB, e.g., between 1 nt and 1 kB, between 1 nt and 500 nt, between 1 nt and 250 nt, between 1 nt and 100 nt, etc. In certain embodiments either or both smRNA complementary sequences are separated from a portion of the nucleic acid sequence that corresponds to the target gene by between 10 and 20 nt, between 10 and 50 nt, or between 10 and 100 nt. Thus the spacer between either smRNA complementary sequences and the closest nucleotide that corresponds to a portion of a target gene may, in various embodiments of the disclosure, be between 1 nt and 2 kB, e.g., between 1 nt and 1 kB, between 1 nt and 500 nt, between 1 nt and 250 nt, between 1 nt and 100 nt, between 10 and 20 nt, between 10 and 50 nt, or between 10 and 100 nt in length.

Without being bound to theory, it is suggested that following introduction into the plant, the dsRNA molecule is unwound either by the binding of a helicase to a "helicase binding site" when present or by endogenous RNA helicases that recognize and unwind the dsRNA molecule in a manner similar to antiviral response in a case where it is absent.

Without being bound to a particular theory, once a single stranded molecule is formed is processed by miRNA-guided-cleavage. One product of the cleaved transcript may be stabilized possibly by Suppressor of Gene Silencing 3 (SGS3) and converted to dsRNA by RNA-Dependent RNA Polymerase 6 (RDR6). The resulting dsRNA may be processed through Dicer-Like 4 (DCL4) into 21-nt siRNA duplexes in register with the miRNA-cleavage site. One strand of each smRNA duplex may be selectively sorted to one or more Argonaute (AGO) proteins according to the 5' nucleotide sequence while the other is used as a template for RNA dependent RNA polymerase, thereby constantly generating more phase siRNA molecule.

Thus, the dsRNA molecule is designed for specifically targeting a target gene of interest. It will be appreciated that the dsRNA can be used to down-regulate one or more target genes. In some embodiments, a single isolated dsRNA molecule can target a number of different genes.

The present disclosure provides for and includes heterogenic compositions of dsRNA molecules. In certain embodiments wherein a dsRNA molecule targets a single target gene of interest, heterogenic compositions comprising two or more dsRNA molecules that target two or more target genes of interest may be prepared. A heterogenic composition comprises a plurality of dsRNA molecules for targeting a number of target genes may be prepared. In some embodiments, a plurality of dsRNA molecules may be separately applied to the seeds (but not as a single composition).

The present disclosure provides for an includes dsRNA molecules comprising a sequence, wherein said nucleic acid sequence shares between 100% and 90% sequence identity to a nucleic acid sequence selected from the group consisting of SEQ ID NO: 289-299. In other embodiments according to the present disclosure, a dsRNA molecule comprises a sequence that shares more than 90% sequence identity to a nucleic acid sequence selected from the group consisting of SEQ ID NO: 289-299. In other embodiments according to the present disclosure, a dsRNA molecule comprises a sequence that shares more than 91% sequence identity to a nucleic acid sequence selected from the group consisting of SEQ ID NO: 289-299. In other embodiments according to the present disclosure, a dsRNA molecule comprises a sequence that shares more than 92% sequence identity to a nucleic acid sequence selected from the group consisting of SEQ ID NO: 289-299. In other embodiments according to the present disclosure, a dsRNA molecule comprises a sequence that shares more than 93% sequence identity to a nucleic acid sequence selected from the group consisting of SEQ ID NO: 289-299. In other embodiments according to the present disclosure, a dsRNA molecule comprises a sequence that shares more than 94% sequence identity to a nucleic acid sequence selected from the group consisting of SEQ ID NO: 289-299. In other embodiments according to the present disclosure, a dsRNA molecule comprises a sequence that shares more than 95% sequence identity to a nucleic acid sequence selected from the group consisting of SEQ ID NO: 289-299. In other embodiments according to the present disclosure, a dsRNA molecule comprises a sequence that shares more than 96% sequence identity to a nucleic acid sequence selected from the group consisting of SEQ ID NO: 289-299. In other embodiments according to the present disclosure, a dsRNA molecule comprises a sequence that shares more than 97% sequence identity to a nucleic acid sequence selected from the group consisting of SEQ ID NO: 289-299. In other embodiments according to the present disclosure, a dsRNA molecule comprises a sequence that shares more than 98% sequence identity to a nucleic acid sequence selected from the group consisting of SEQ ID NO: 289-299. In other embodiments according to the present disclosure, a dsRNA molecule comprises a sequence that shares more than 99% sequence identity to a nucleic acid sequence selected from the group consisting of SEQ ID NO: 289-299. In other embodiments according to the present disclosure, a dsRNA molecule comprises a sequence that shares more than 100% sequence identity to a nucleic acid sequence selected from the group consisting of SEQ ID NO: 289-299.

While conceiving the present disclosure, the present inventors realized that the long dsRNA identified by Fukuhara et al. is able to survive autonomously in rice cells, and as such can be used as a cassette (a building block) for introducing dsRNA sequenced for RNA silencing of a target gene of interest (endogenous to the plant or exogenous thereto). Such a dsRNA molecule is expressed throughout the plant's life cycle, does not become integrated into the plant genome (plastid or nuclear), and does not get reverse-transcribed into DNA.

Thus, in some embodiments of the present disclosure provide for endovirus-derived sequences which have evolved to co-exist in plant cells in a dsRNA form, maintaining a near exact copy number in all cells.

As used herein the term "endovirus" refers to a dsRNA symbiotic virus which propagates in the plant cell and maintains a relatively stable copy number throughout the life cycle of the plant.

As used herein the term "5' UTR" refers to an untranslated region derived from the endovirus sequence (13,716 nucleotides, available from GSDB, DDBJ, EMBL, and NCBI nucleotide sequence data bases with accession number D32136, according to Fukuhara 1995 supra), adjacent (in a 5' orientation) to its RDRP sequence.

As used herein the term "3' UTR" refers to an untranslated region derived from the endovirus sequence (13,716 nucleotides, available from GSDB, DDBJ, EMBL, and NCBI nucleotide sequence data bases with accession number D32136, according to Fukuhara 1995 supra), adjacent (in a 3' orientation) to its RDRP sequence.

As used herein the term "RNA dependent RNA Polymerase" refers to the RDRP-like sequence derived from the 13,716 nucleotides described in Fukuhara et al. 1995 supra.

According to a specific embodiment said 5' UTR is as set forth in SEQ ID NO: 14. It will be appreciated that the sequences are provided in the form of DNA but will be made RNA upon subjecting to T7 activity. In some embodiments, the 5' UTR shares between 90% and 100% sequences identity to a nucleic acid sequence of SEQ ID NO:14.

According to a specific embodiment said 3' UTR is as set forth ion SEQ ID NO: 22.

According to a specific embodiment said endovirus RNA Dependent RNA Polymerase (RDRP) coding sequence is as set forth in SEQ ID NO: 23.

According to some embodiments of the disclosure, the nucleic acid sequence is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% identical to the nucleic acid sequence of SEQ ID NO: 14, 22 or 23 (or a combination of same). It is understood that combinations of SEQ ID NOs: 14, 22, or 23 having differing percent homology are envisioned. As a non-limiting example, a combination dsRNA molecule may comprise a sequence having 85% homology to SEQ ID NO:14, 90% homology to SEQ ID NO:22 and 99% homology to SEQ ID NO:23. Any number of such combinations are contemplated and provided for in the present disclosure.

One of ordinary skill in the art would understand that certain nucleotide positions of a polynucleotide sequence play critical roles while other nucleotide positions may vary without significant effect. This understanding is well illustrated for polypeptide encoding sequences. For example, the first and second nucleotide of an amino acid encoding codon largely determine the identity of an amino acid in a polypeptide chain. In contrast, the third "wobble" position can vary, sometimes without limitation. Accordingly, one of ordinary skill in the art can substitute approximately 30% of the nucleic acid sequence without affecting the amino acid sequence. A similar dependence for non-coding sequences, including 3' and 5' UTRs exists, though the positions of importance may not be predictable. However, one of ordinary skill in the art may mutagenize (randomly or through site directed) positions in a nucleic acid sequence and confirm their activity using the functional assays disclosed in the present application (See, Examples below).

According to some embodiments, a nucleic acid sequence may encode a protein that shares between 70% and 100% homology with an RNA Dependent RNA Polymerase (RDRP) polypeptide sequence according to SEQ ID NO: 300. A nucleic acid sequence according to the present disclosure may encode a protein having 70 to 75% homology to a polypeptide sequence according to SEQ ID NO: 300. In another embodiment, a nucleic acid sequence may encode a protein having 75 to 80% homology to a polypeptide sequence according to SEQ ID NO: 300. In another embodiment, a nucleic acid sequence may encode a protein having 80 to 85% homology to a polypeptide sequence according to SEQ ID NO: 300. In an embodiment, a nucleic acid sequence may encode a protein having 85 to 90% homology to a polypeptide sequence according to SEQ ID NO: 300. In another embodiment, a nucleic acid sequence may encode a protein having 90 to 95% homology to a polypeptide sequence according to SEQ ID NO: 300. In an embodiment, a nucleic acid sequence may encode a protein having 95 to 100% homology to a polypeptide sequence according to SEQ ID NO: 300. In another embodiment, a nucleic acid sequence may encode a protein having 97 to 100% homology to a polypeptide sequence according to SEQ ID NO: 300. In an embodiment, a nucleic acid sequence may encode a protein having 98 to 100% homology to a polypeptide sequence according to SEQ ID NO: 300. In another embodiment, a nucleic acid sequence may encode a protein having 99 to 100% homology to a polypeptide sequence according to SEQ ID NO: 300.

Homologous sequences to the above can also be used according to the present teachings, as long as their main characteristics are maintained, i.e., amplification by RDRP and maintenance of stable copy number in the cell throughout the plant life cycle.

The present disclosure further provides for, and includes, an isolated dsRNA molecule comprising a nucleic acid sequence in a sequential order from 5' to 3', an endovirus 5' UTR, an endovirus RNA Dependent RNA Polymerase (RDRP) coding sequence, an endovirus 3' UTR and a cloning site flanked by said RDRP and said 3' UTR.

The present disclosure further provides for, and includes, an isolated dsRNA molecule comprising a nucleic acid sequence in a sequential order from 5' to 3', an endovirus 5' UTR, an endovirus RNA Dependent RNA Polymerase (RDRP) coding sequence, an endovirus 3' UTR and a nucleic acid sequence for regulating a target gene flanked by said RDRP and said 3' UTR.

In some embodiments, a heterologous dsRNA sequence corresponding to a target gene is constructed such that it is flanked by the RDRP sequence and the 3' UTR. Alternatively, in other embodiments, a heterologous dsRNA sequence corresponding to the target gene is constructed such that it is flanked by the RDRP sequence and the 5' UTR. When introduced into the plant (e.g., directly to the seed), and once germination has initiated, gene expression occurs including expression of endogenous plant helicases, RDRPs and other components of the silencing machinery. Not to be limited by theory, at any given time, a portion of the dsRNA molecules is recognized and processed by the plant's dicer like (DCL) proteins into siRNA of different lengths. In certain embodiments, this recognition and processing includes processing of the gene targeted for silencing, which is flanked between the 5' and the 3' UTR. In certain embodiments, the gene targeted for silencing and the RDRP sequence is flanked between the 5' and the 3' UTR. Not all of the heterologous dsRNA sequence is processed and a portion remains in double-stranded, full length form. Not to be limited by theory, it is thought that plant helicases recognize unique features in the 5' UTR and the 3' UTR of the dsRNA and unwind the dsRNA into two ssRNA molecules. Again, not limited by theory, the same or other feature in the 5' and 3' UTR are thought to also recruit and activate an RDRP. In some embodiments, the RDRP may be an RDRP that is encoded by the dsRNA. In other embodiments, the RDRP may be an endogenous RDRP, naturally occurring in the plant or introduced as a transgene.

Though not limited by theory, it is thought that the RDRP uses each of the ssRNA molecules thought to be produced by the activity of a helicase as templates to produce a dsRNA molecule identical to the original dsRNA molecule.

Accordingly, and not to be limited by theory, as long as a ratio between processed and un-processed dsRNA molecules is maintained, the cycle can go on and repeat throughout the plant's life cycle. Also not to be limited by theory, it is thought that some features in the 5' and 3' UTR can assist to maintain a stable copy number of the dsRNA in cells, in a similar manner to the endovirus which is maintained at a stable copy number.

As used herein the term "sequential" refers to multiple nucleic acid segments (e.g., 5' UTR, RDRP and 3' UTR) arranged in sequence. In this case, from 5' to 3. Each of the specified nucleic acid segments can be directly attached to each other and contiguous, however intervening nucleic acids can be implanted therebetween such that the segments are not directly attached to each other and are discontinuous.

According to an embodiment of the disclosure the target gene is endogenous to the plant. Downregulating such a gene is typically important for conferring the plant with an improved, agricultural, horticultural, nutritional trait ("improvement" or an "increase" is further defined hereinbelow).

As used herein, the terms "suppress," "repress," and "downregulate" when referring to the expression or activity of a nucleic acid molecule in a plant cell are used equivalently herein and mean that the level of expression or activity of the nucleic acid molecule in a plant, a plant part, or plant cell after applying a method of the present disclosure is lower than its expression or activity in the plant, part of the plant, or plant cell before applying the method, or compared to a control plant lacking a dsRNA molecule of the disclosure.

The terms "suppressed," "repressed" and "downregulated" as used herein are synonymous and mean herein lower, preferably significantly lower, expression or activity of the nucleic acid molecule to be expressed.

As used herein, a "suppression," "repression," or "downregulation" of the level or activity of an agent such as a protein, mRNA, or RNA means that the level or activity is reduced relative to a substantially identical plant, part of a plant, or plant cell grown under substantially identical conditions, lacking a dsRNA molecule of the disclosure, for example, lacking an RNA sequence for regulating a target gene of interest. As used herein, "suppression," "repression," or "downregulation" of the level or activity of an agent, such as, for example, a preRNA, mRNA, rRNA, tRNA, snoRNA, snRNA expressed by the target gene, and/or of the protein product encoded by it, means that the amount is reduced by 10% or more, for example, 20% or more, preferably 30% or more, more preferably 50% or more, even more preferably 70% or more, most preferably 80% or more, for example, 90%, relative to a cell or organism lacking a dsRNA molecule of the disclosure.

As used herein "a suppressive amount" refers to an amount of dsRNA molecule which is sufficient to down regulate the target gene by at least 20%. In an aspect, a suppressive amount according to the present disclosure is an amount sufficient to downregulate a target gene by 30% or more. In an aspect, a suppressive amount according to the present disclosure is an amount sufficient to downregulate a target gene by 40% or more. In an aspect, a suppressive amount according to the present disclosure is an amount sufficient to downregulate a target gene by at least 50%. In other aspects, a suppressive amount according to the present disclosure is an amount sufficient to downregulate a target gene by 60% or more. In an aspect, a suppressive amount according to the present disclosure is an amount sufficient to downregulate a target gene by at least 70%. In an aspect, a suppressive amount according to the present disclosure is an amount sufficient to downregulate a target gene by 80% or more. In an aspect, a suppressive amount according to the present disclosure is an amount sufficient to downregulate a target gene by greater than 90%. In certain aspects, a suppressive amount according to the present disclosure is an amount sufficient to downregulate a target gene by 100% (e.g., wherein the remaining amount of the target gene is not detectable). The suppressive amount can be a result of the formation of amplification in the plant or the phytopathogen.

As used herein "endogenous" refers to a gene which expression (mRNA or protein) takes place in the plant. Typically, the endogenous gene is naturally expressed in the plant or originates from the plant. Thus, the plant may be a wild-type plant. However, the plant may also be a genetically modified plant (transgenic).

Downregulation of the target gene may be important for conferring improved one of, or at least one of (e.g., two of or more), biomass, vigor, yield, abiotic stress tolerance, biotic stress tolerance or improved nitrogen use efficiency.

Examples of target genes include, but are not limited to, an enzyme, a structural protein, a plant regulatory protein, an miRNA target gene, or a non-coding RNA such as a miRNA of the plant. WO2011067745, WO 2009125401 and WO 2012056401 provide examples of miRNA sequences or targets of miRNAs (e.g., miRNA167, miRNA169, miRNA 156, miR164 and targets thereof ARF, NFY, SPL17 and NAC, respectively) which expression can be silenced to improve a plant trait.

The target gene may comprise a nucleic acid sequence which is transcribed to an mRNA which codes for a polypeptide.

Alternatively, the target gene can be a non-coding gene such as an miRNA or a siRNA.

For example, in order to silence the expression of an mRNA of interest, synthesis of the dsRNA molecule suitable for use with some embodiments of the disclosure can be selected as follows. First, the mRNA sequence may be scanned including the 3' UTR and the 5' UTR.

Second, the mRNA sequence may be compared to an appropriate genomic database using any sequence alignment software, such as the BLAST software available from the NCBI server (available on the internet at wwwdotncbidotnlmdotnihdotgov/BLAST/). Putative regions in the mRNA sequence which exhibit significant homology to other coding sequences may be filtered out.

Qualifying target sequences may be selected as for the preparation of dsRNA templates for dsRNA molecule synthesis. Preferred sequences are those that have as little homology to other genes in the genome to reduce an "off-target" effect.

It will be appreciated that the RNA regulating or silencing agent of some embodiments of the disclosure need not be limited to those molecules containing only RNA, but further encompasses chemically-modified nucleotides and non-nucleotides.

The dsRNA molecules of the present disclosure may be synthesized using any method known in the art, including either enzymatic syntheses or solid-phase syntheses. These are especially useful in the case of short polynucleotide sequences with or without modifications as explained above. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning", John Wiley & Sons, New York; and Gait, M. J., ed. (1984), "Oligonucleotide Synthesis"; utilizing solid-phase chemistry, e.g., cyanoethyl phosphoramidite followed by deprotection, desalting, and purification by, for example, an automated trityl-on method or HPLC.

The nucleic acids of the present disclosure may comprise heterocylic nucleosides consisting of purines and the pyrimidines bases, bonded in a 3' to 5' 5phosphodiester linkage. Preferably used nucleic acids are those modified in either backbone, internucleoside linkages or bases, as is broadly described hereinunder.

Specific examples of preferred nucleic acids useful according to this aspect of the present disclosure include nucleic acids containing modified backbones or non-natural internucleoside linkages. Nucleic acids having modified backbones include those that retain a phosphorus atom in the backbone, as disclosed in U.S. Pat. Nos. 4,469,863; 4,476, 301; 5,023,243; 5,177,196; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,306; 5,550,111; 5,563,253; 5,571, 799; 5,587,361; and 5,625,050.

Preferred modified polynucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,216,141; 5,235,033; 5,264,562; 5,264,564; 5,405,938; 5,470,967; 5,489,677; 5,541,307; 5,561,225; 5,596,086; 5,602,240; 5,602,240; 5,608,046; 5,610,289; 5,618,704; 5,623,070; 5,663,312; 5,214,134; 5,466,677; 5,610,289; 5,633,360; 5,677,437; and 5,677,439.

Other nucleic acids which can be used according to the present disclosure, are those modified in both sugar and the internucleoside linkage, i.e., the backbone, of the nucleotide units are replaced with novel groups. The base units are maintained for complementation with the appropriate polynucleotide target. An example for such an polynucleotide mimetic, includes peptide nucleic acid (PNA). A PNA polynucleotide refers to a polynucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present disclosure are disclosed in U.S. Pat. No. 6,303,374.

Polynucleotide agents of the present disclosure may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 613, and those disclosed by Sanghvi, Y. S., Chapter 15, Antisense Research and Applications, pages 289-2, Crooke, S. T. and Lebleu, B., ed., CRC Press, 1993. Such bases are particularly useful for increasing the binding affinity of the oligomeric compounds of the disclosure. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi Y S et al. (1993) Antisense Research and Applications, CRC Press, Boca Raton 276-278) and are presently preferred base substitutions, even more particularly when combined with 2'-O-methoxyethyl sugar modifications.

Following synthesis, the polynucleotide agents of the present disclosure may optionally be purified. For example, polynucleotides can be purified from a mixture by extraction with a solvent or resin, precipitation, electrophoresis, chromatography, or a combination thereof. Alternatively, polynucleotides may be used with no, or a minimum of, purification to avoid losses due to sample processing. The polynucleotides may be dried for storage or dissolved in an aqueous solution. The solution may contain buffers or salts to promote annealing, and/or stabilization of the duplex strands.

It will be appreciated that a polynucleotide agent of the present disclosure may be provided per se, or as a nucleic acid construct comprising a nucleic acid sequence encoding the polynucleotide agent. Typically, the nucleic acid construct comprises a promoter sequence which is functional in the host cell, as detailed herein below.

The polynucleotide sequences of the present disclosure, under the control of an operably linked promoter sequence, may further be flanked by additional sequences that advantageously affect its transcription and/or the stability of a resulting transcript. Such sequences are generally located upstream of the promoter and/or downstream of the 3' end of the expression construct.

The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

The present disclosure provides for and includes DNA templates for the preparation of dsRNA molecules. As used herein, "dsRNA template" refers to a DNA sequence having the same sequence as the corresponding dsRNA molecule. In certain embodiments, a dsRNA template may further include additional sequences, such as promoters, sufficient for the expression of one or more RNA molecules via transcription. In some embodiments the promoters are bacteriophage promoters, for example but not limited to, SP6, T3 and T7. In some embodiments a promoter may be a bacterial or a eukaryotic promoters.

In certain embodiments, a dsRNA template according to the present teachings may be used as a cassette for the cloning of a nucleic acid sequence corresponding to a target gene of interest (exogenous to the plant or endogenous thereto) for silencing expression of same when expressed as a dsRNA molecule.

Thus according to an embodiment of the disclosure, a dsRNA template may comprise a cloning site (multiple cloning site for instance) to which a nucleic sequence for silencing a target gene of interest is ligated while being flanked by the RDRP encoding and the 3'UTR encoding nucleic acid sequences. In other aspects according to present disclosure, a dsRNA molecule may be prepared by chemical synthesis using methods known in the art. In other embodiments, a dsRNA template may comprise a plasmid vector having the dsRNA molecule coding sequences. In certain embodiments, the dsRNA template may be a linear polynucleotide having a RNA polymerase promoter at one end. It will be appreciated that such a template produces a single strand RNA.

In certain embodiments, a dsRNA template may comprise a mixture of two linear polynucleotides having the same dsRNA coding sequence but promoters at opposite ends. It will be appreciated that transcription results in the production of two complementary RNA strands from the separate template that may be annealed and recovered, or recovered and annealed. By providing separate transcription templates, and recovering annealed double stranded dsRNA molecules according to the present disclosure, asymmetric dsRNA molecules may be produced. As provided below, dsRNA construct #4 provides for a dsRNA region corresponding to a region of a target gene of interest and having non-double stranded Mir390 Mut BS and Mir390BS sequences. As used herein, the term "overhang" refers to non-double stranded regions of a dsRNA molecule (i.e., single stranded RNA). Accordingly dsRNA construct #4 has two overhang regions comprising Mir390 Mut BS and Mir390 BS sequences respectively. Similarly, dsRNA construct #6 provides for an asymmetric dsRNA having a non-double stranded helicase binding sequence or overhang.

In other aspects, a dsRNA template may have two promoters flanking the dsRNA coding sequences. It will be appreciated that, like the separate templates, two complementary strands are produced that may be annealed and recovered, or recovered and annealed. The promoters of the dsRNA templates of some embodiments may be the same or different.

As mentioned, in certain embodiments, the dsRNA molecule may be directly contacted with the seed.

The seed may be of any plant, such as of the Viridiplantae super family including monocotyledon and dicotyledon plants. Other plants are listed below. According to an embodiment of the disclosure, the cells of the plant comprise RNA dependent RNA polymerase activity and the target RNA molecule of the dsRNA to ensure amplification of the dsRNA.

The term "plant" as used herein encompasses whole plants, ancestors and progeny of the plants and plant parts, including seeds, shoots, stems, roots (including tubers), and isolated plant cells, tissues and organs. The plant may be in any form including suspension cultures, embryos, meristematic regions, callus tissue, leaves, gametophytes, sporophytes, pollen, and microspores. It will be appreciated, that the plant or seed thereof may be transgenic plants.

As used herein the phrase "plant cell" refers to plant cells which are derived and isolated from disintegrated plant cell tissue or plant cell cultures.

As used herein the phrase "plant cell culture" refers to any type of native (naturally occurring) plant cells, plant cell lines and genetically modified plant cells, which are not assembled to form a complete plant, such that at least one biological structure of a plant is not present. Optionally, the plant cell culture of this embodiment of the present disclosure may comprise a particular type of a plant cell or a plurality of different types of plant cells. It should be noted that optionally plant cultures featuring a particular type of plant cell may be originally derived from a plurality of different types of such plant cells. In certain embodiments according to the present disclosure, the plant cell is a non-sexually producing plant cell. In other aspects, a plant cell of the present disclosure is a non-photosynthetic plant cell.

Any commercially or scientifically valuable plant is envisaged in accordance with some embodiments of the disclosure. Plants that are particularly useful in the methods of the disclosure include all plants which belong to the super family Viridiplantae, in particular monocotyledonous and dicotyledonous plants including a fodder or forage legume, ornamental plant, food crop, tree, or shrub selected from the list comprising Acacia spp., Acer spp., Actinidia spp., Aesculus spp., Agathis australis, Albizia amara, Alsophila tricolor, Andropogon spp., Arachis spp, Areca catechu, Astelia fragrans, Astragalus cicer, Baikiaea plurijuga, Betula spp., Brassica spp., Bruguiera gymnorrhiza, Burkea africana, Butea frondosa, Cadaba farinosa, Calliandra spp, Camellia sinensis, Canna indica, Capsicum spp., Cassia spp., Centroema pubescens, Chacoomeles spp., Cinnamomum cassia, Coffea arabica, Colophospermum mopane, Coronillia varia, Cotoneaster serotina, Crataegus spp., Cucumis spp., Cupressus spp., Cyathea dealbata, Cydonia oblonga, Cryptomeria japonica, Cymbopogon spp., Cynthea dealbata, Cydonia oblonga, Dalbergia monetaria, Davallia divaricata, Desmodium spp., Dicksonia squarosa, Dibeteropogon amplectens, Dioclea spp, Dolichos spp., Dorycnium rectum, Echinochloa pyramidalis, Ehraffia spp., Eleusine coracana, Eragrestis spp., Erythrina spp., Eucalyptus spp., Euclea schimperi, Eulalia vi/losa, Pagopyrum spp., Feijoa sellowlana, Fragaria spp., Flemingia spp, Freycinetia banksli, Geranium thunbergii, GinAgo biloba, Glycine javanica, Gliricidia spp, Gossypium hirsutum, Grevillea spp., Guibourtia coleosperma, Hedysarum spp., Hemaffhia altissima, Heteropogon contoffus, Hordeum vulgare, Hyparrhenia rufa, Hypericum erectum, Hypeffhelia dissolute, Indigo incamata, Iris spp., Leptarrhena pyrolifolia, Lespediza spp., Lettuca spp., Leucaena leucocephala, Loudetia simplex, Lotonus bainesli, Lotus spp., Macrotyloma axillare, Malus spp., Manihot esculenta, Medicago saliva, Metasequoia glyptostroboides, Musa sapientum, Nicotianum spp., Onobrychis spp., Ornithopus spp., Oryza spp., Peltophorum africanum, Pennisetum spp., Persea gratissima, Petunia spp., Phaseolus spp., Phoenix canariensis, Phormium cookianum, Photinia spp., Picea glauca, Pinus spp., Pisum sativam, Podocarpus totara, Pogonarthria fleckii, Pogonaffhria squamosa, Populus spp., Prosopis cineraria, Pseudotsuga menziesii, Pterolobium stellatum, Pyrus communis, Quercus spp., Rhaphiolepis umbellata, Rhopalostylis sapida, Rhus natalensis, Ribes grossularia, Ribes spp., Robinia pseudoacacia, Rosa spp., Rubus spp., Salix spp., Schyzachyrium sanguineum, Sciadopitys vefficillata, Sequoia sempervirens, Sequoiadendron giganteum, Sorghum bicolor, Spinacia spp., Sporobolus fimbriatus, Stiburus alopecuroides, Stylosanthos

*humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present disclosure.

According to some embodiments of the disclosure, the plant used by the method of the disclosure is a crop plant including, but not limited to, cotton, *Brassica* vegetables, oilseed rape, sesame, olive tree, palm oil, banana, wheat, corn or maize, barley, alfalfa, peanuts, sunflowers, rice, oats, sugarcane, soybean, turf grasses, barley, rye, sorghum, sugar cane, chicory, lettuce, tomato, zucchini, bell pepper, eggplant, cucumber, melon, watermelon, beans, hibiscus, okra, apple, rose, strawberry, chili, garlic, pea, lentil, canola, mums, *Arabidopsis*, broccoli, cabbage, beet, quinoa, spinach, squash, onion, leek, tobacco, potato, sugar beet, papaya, pineapple, mango, *Arabidopsis thaliana*, and also plants used in horticulture, floriculture or forestry, such as, but not limited to, poplar, fir, eucalyptus, pine, an ornamental plant, a perennial grass and a forage crop, coniferous plants, moss, algae, as well as other plants available on the internet at, for example, wwwdotnationmasterdotcom/encyclopedia/Plantae.

According to a specific embodiment, the plant is selected from the group consisting of corn, rice, wheat, tomato, cotton and sorghum. In certain embodiments, the plant is a corn plant. In certain embodiments, the plant is a rice plant. In certain embodiments, the plant is a wheat plant. In certain embodiments, the plant is a cotton plant. In certain embodiments, the plant is a sorghum plant.

Introduction of the compositions of the present disclosure can be performed to any organs/cells of the plant (as opposed to seeds) using conventional delivery methods such as particle bombardment, grafting, soaking and the like.

According to a specific embodiment, the composition is introduced directly to the seed.

According to a specific embodiment, the seed is an uncoated or fresh seed that hasn't been subjected to chemical/physical treatments. In certain embodiments, the seed is a corn seed. In certain embodiments, the seed is a rice seed. In certain embodiments, the seed is a wheat seed. In certain embodiments, the seed is a cotton seed. In certain embodiments, the seed is a sorghum seed.

The seed may be subjected to priming or washing prior to contacting with the dsRNA.

In embodiments according to the present disclosure, washing of the seeds is effected for 30 min to 4 hours. In other embodiments, the seeds may be washed up to 5 hours. In an embodiment a seed may be washed up 6, 7 or 8 hours. In another embodiment, seeds are washed for less than 4 or less than 3 hours. In some embodiments, a seed may be washed less than two hours or less than one hour.

The present disclosure provides for and includes washing of a seed between 1 minute and 1 hours. Also included are brief washes comprising less than 1 minute wherein the seed is completely wet and then removed from the wash. In some embodiments, a seed may be washed from 1 minute to 10 minutes. In another embodiment, a seed may be washed from 1 minute to 10 minutes. In an embodiment, a seed may be washed from 10 to 30 minutes. In yet another embodiment, a seed may be washed from 1 to 30 minutes. In certain embodiments, a seed may be washed from 5 to 10 minutes or 5 to 15 minutes. In some embodiments, a seed may be washed from 15 to 30 minutes or 10 to 25 minutes.

In some embodiments according to the present disclosure, the wash solution may include a weak detergent such as Tween-20, or its equivalents. In some embodiments, the detergent may be less than 1% by volume. In other embodiments, the detergent may be less than 0.5% by volume. In some embodiments, the detergent may be less than 0.25% or 0.2% by volume. In other embodiments, the detergent may be less than 0.1% or 0.05% by volume. In embodiments according to the present disclosure, the wash solution may contain a detergent at between 0.01 to 0.2% or 0.2 to 1%. In other embodiments, the wash solution may contain a detergent at between 0.05 to 0.5% or 0.5 to 1.5%.

As used herein the term "priming" refers to controlling the hydration level within seeds so that the metabolic activity necessary for germination can occur but radicle emergence is prevented. Different physiological activities within the seed occur at different moisture levels (Leopold and Vertucci, 1989; Taylor, 1997). The last physiological activity in the germination process is radicle emergence. The initiation of radicle emergence requires a high seed water content. By limiting seed water content, all the metabolic steps necessary for germination can occur without the irreversible act of radicle emergence. Prior to radicle emergence, the seed is considered desiccation tolerant, thus the primed seed moisture content can be decreased by drying. After drying, primed seeds can be stored until time of sowing.

Several different priming methods are used commercially. Among them, liquid or osmotic priming and solid matrix priming appear to have the greatest following (Khan et al., 1991).

According to an embodiment of the disclosure, priming is effected in the presence of salt, a chelating agent, polyethylene glycol or a combination of same (e.g., chelating agent and salt).

Alternatively priming is effected in the presence of water such as deionized water or double deionized water (ddW). According to a specific embodiment, the priming is effected in the presence of 100% ddW.

Several types of seed priming are commonly used:

Osmopriming (osmoconditioning) is a standard priming technique. Seeds are incubated in well aerated solutions with a low water potential, and afterwards washes and dried. The low water potential of the solutions can be achieved by adding osmotica like mannitol, polyethyleneglycol (PEG) or salts like KCl. In embodiments according to the present disclosure, the seeds are osmoprimed. In certain embodiments, the osmoprimed seed is a corn seed. In certain embodiments, the osmoprimed seed is a rice seed. In certain embodiments, the osmoprimed seed is a wheat seed. In certain embodiments, the osmoprimed seed is a cotton seed. In certain embodiments, the osmoprimed seed is a sorghum seed.

Hydropriming (drum priming) is achieved by continuous or successive addition of a limited amount of water to the seeds. A drum is used for this purpose and the water can also be applied by humid air. 'On-farm steeping' is a cheap and useful technique that is practiced by incubating seeds (cereals, legumes) for a limited time in warm water. In embodiments according to the present disclosure, the seeds are hydroprimed. In certain embodiments, the hydroprimed seed is a corn seed. In certain embodiments, the hydroprimed seed is a rice seed. In certain embodiments, the hydroprimed seed is a wheat seed. In certain embodiments, the hydroprimed seed is a cotton seed. In certain embodiments, the hydroprimed seed is a sorghum seed.

Matrixpriming (matriconditioning) is the incubation of seeds in a solid, insoluble matrix (vermiculite, diatomaceous earth, cross-linked highly water-absorbent polymers) with a limited amount of water. This method confers a slow imbibition. In embodiments according to the present disclosure, the seeds are matriconditioned. In certain embodiments, the matriconditioned seed is a corn seed. In certain embodiments, the matriconditioned seed is a rice seed. In certain embodiments, the matriconditioned seed is a wheat seed. In certain embodiments, the matriconditioned seed is a cotton seed. In certain embodiments, the matriconditioned seed is a sorghum seed.

Pregerminated seeds may be used in certain embodiments however not all species can be primed using this method. In contrast to normal priming, seeds are allowed to perform radicle protrusion. This is followed by sorting for specific stages, a treatment that reinduces desiccation tolerance, and drying. The use of pregerminated seeds causes rapid and uniform seedling development.

Thus, according to one embodiment, the seeds are primed seeds.

Of note, it may be possible that the seeds are treated with water (double-distilled water, ddW), prior to contacting with the dsRNA without effecting any priming on the seeds. For instance, treatment for a short while with water (e.g., 30 seconds to 1 hours, 30 seconds to 0.5 hour, 30 seconds to 10 min, 30 seconds to 5 min or 45 seconds to 5 min).

Thus, according to one embodiment, the seeds are non-primed seeds.

A non-limiting example of a method of introducing the dsRNA into the seed is provided in Example 1, which is considered as an integral part of the specification.

The temperature at the washing/priming and drying steps may be the same or differ.

According to one embodiment, the temperature for washing/priming is between 4 and 28° C. In some embodiments, the washing/priming temperature is less than 28° C. In some embodiments, the washing/priming temperature is less than 25° C. In some embodiments, the washing/priming temperature is less than 20° C. In some embodiments, the washing/priming temperature is less than 15° C. In some embodiments, the washing/priming temperature is less than 10° C. In some embodiments, the washing/priming temperature is between 4 and 10° C. In an embodiment the washing/priming temperature is between 10 and 15° C. In an another embodiment the washing/priming temperature is between 15 and 20° C. or 15 and 25° C. In an another embodiment the washing/priming temperature is between 10 and 20° C. or 10 and 25° C.

According to one embodiment, the priming/washing solution or the dsRNA containing solution is devoid of a solid carrier.

According to one embodiment, the priming/washing solution or the dsRNA containing solution is devoid of a transferring agent such as a surfactant or a salt.

According to a further embodiment of the disclosure, the seeds subject to contacting with the dsRNA molecule are washed in order to remove agents, to which the seeds have been subjected, such as a pesticide, a fungicide, an insecticide, a fertilizer, a coating agent and a coloring agent.

Thus, according to one embodiment, the seeds (prior to treatment with dsRNA) are substantially free (i.e., do not comprise effective amounts) of pesticide, a fungicide, an insecticide, a fertilizer, a coating agent and a coloring agent.

The seeds are then subjected to drying.

According to one embodiment, the drying temperature is between 20 to 37° C. In another embodiment, the drying temperature is between 20 to 30° C. In another embodiment, the drying temperature is between 22 and 37° C. In another embodiment, the drying temperature is between 15 to 22° C. or 20 to 25° C. In embodiments according to the present disclosure, the drying time at a temperature of the present disclosure may be for 10 to 20 hours. In other embodiments the drying time may be from 10 to 16 hours. In other embodiments, the drying time may be 2 to 5 hours.

Various considerations are to be taken when calculating the concentration of the dsRNA in the contacting solution. Considerations include, but are not limited to, at least one of the group consisting of seed size, seed weight, seed volume, seed surface area, seed density and seed permeability.

For example, related to seed size, weight, volume and surface area, it is estimated that corn seeds will require longer treatment than *Arabidopsis* and tomato seeds. Regarding permeability and density, it is estimated that wheat seeds will require longer treatments at higher concentrations than tomato seeds.

Examples of concentrations of dsRNA in the treating solution include, but are not limited to 0.1 to 100 micrograms ($1\times10^{-6}$ grams) per microliter ($1\times10^{-6}$ liter) (µg/µl). In an embodiment the dsRNA concentration in the treating solution may be 0.04 to 0.15 µg/µl. In an another embodiment the dsRNA concentration in the treating solution may be 0.1 to 50 µg/µl. In certain embodiments, the dsRNA concentration in the treating solution may be 0.1 to 10 µg/µl. In yet other embodiments the dsRNA concentration in the treating solution may be 0.1 to 5 µg/µl. In some embodiments the dsRNA concentration in the treating solution may be 0.1 to 1 µg/µl. In an embodiment the dsRNA concentration in the treating solution may be 0.1 to 0.5 µg/µl. Also included and provided for in the present disclosure are embodiments having a dsRNA concentration in the treating solution of between 0.15 and 0.5 µg/µl. In an embodiment the dsRNA concentration in the treating solution may be 0.1 to 0.3 µg/µl. In an embodiment the dsRNA concentration in the treating solution may be 0.01 to 0.1 µg/µl. In an embodiment the dsRNA concentration in the treating solution may be 0.01 to 0.05 µg/µl. In an embodiment the dsRNA concentration in the treating solution may be 0.02 to 0.04 µg/µl. In an embodiment the dsRNA concentration in the treating solution may be 0.001 to 0.02 µg/µl. According to a specific embodiment, the concentration of the dsRNA in the treating solution is 0.04 to 0.15 µg/µl.

According to a specific embodiment, the contacting with the dsRNA is effected in the presence of a chelating agent such as EDTA or another chelating agent such as DTPA (0.01 to 0.1 mM).

The contacting solution may comprise a transferring agent such as a surfactant or a salt.

Examples of such transferring agents include but are not limited salts such as sodium or lithium salts of fatty acids (such as tallow or tallowamines or phospholipids lipofectamine or lipofectin (1 to 20 nM, or 0.1 to 1 nM)) and organosilicone surfactants. Other useful surfactants include organosilicone surfactants including nonionic organosilicone surfactants, e.g., trisiloxane ethoxylate surfactants or a silicone polyether copolymer such as a copolymer of polyalkylene oxide modified heptamethyl trisiloxane and allyloxypolypropylene glycol methylether (commercially available as Silwet™ L-77 surfactant having CAS Number 27306-78-1 and EPA Number: CAL.REG.NO. 5905-50073-AA, currently available from Momentive Performance Materials, Albany, N.Y.).

Useful physical agents can include (a) abrasives such as carborundum, corundum, sand, calcite, pumice, garnet, and the like, (b) nanoparticles such as carbon nanotubes or (c) a physical force. Carbon nanotubes are disclosed by Kam et al. (2004) J. Am. Chem. Soc., 126 (22):6850-6851, Liu et al. (2009) Nano Lett., 9(3):1007-1010, and Khodakovskaya et al. (2009) ACS Nano, 3(10):3221-3227. Physical force agents can include heating, chilling, the application of positive pressure, or ultrasound treatment. Agents for laboratory conditioning of a plant to permeation by polynucleotides include, e.g., application of a chemical agent, enzymatic treatment, heating or chilling, treatment with positive or negative pressure, or ultrasound treatment. Agents for conditioning plants in a field include chemical agents such as surfactants and salts.

Contacting of the seeds with the dsRNA molecule can be effected using any method known in the art as long as a suppressive amount of the dsRNA molecule enters the seeds. These examples include, but are not limited to, soaking, spraying or coating with powder, emulsion, suspension, or solution; similarly, the polynucleotide molecules are applied to the plant by any convenient method, e.g., spraying or wiping a solution, emulsion, or suspension.

According to a specific embodiment contacting may be effected by soaking (i.e., inoculation) so that shaking the seeds with the treating solution may improve penetration and soaking and therefore reduce treatment time. Shaking is typically performed at 50 to 150 RPM and depends on the volume of the treating solution. Shaking may be effected for 4 to 24 hours (1 to 4 hours, 10 minutes to 1 hour or 30 seconds to 10 minutes). The incubation takes place in the dark at 4 to 28° C. or 15 to 22° C. (e.g., 8 to 15° C., 4 to 8° C., 22 to 28° C.).

According to a specific embodiment, contacting occurs prior to breaking of seed dormancy and embryo emergence.

Following contacting, preferably prior to breaking of seed dormancy and embryo emergence, the seeds may be subjected to treatments (e.g., coating) with the above agents (e.g., pesticide, fungicide etc.).

Contacting is effected such that the dsRNA molecule enters the embryo, endosperm, the coat, or a combination of the three.

After contacting with the treatment solution, the seeds may be subjected to drying for up to 30 hours at 25 to 37° C.

According to a specific embodiment, the seed (e.g., isolated seed) comprises the exogenous dsRNA and wherein at least 10 or 20 molecules of the dsRNA are in the endosperm of the isolated seed.

As used herein the term "isolated" refers to separation from the natural physiological environment. In the case of seed, the isolated seed is separated from other parts of the plant. In the case of a nucleic acid molecule (e.g., dsRNA) separated from the cytoplasm.

According to a specific embodiment, the dsRNA molecule is not expressed from the plant genome, thereby not being an integral part of the genome.

Methods of qualifying successful introduction of the dsRNA molecule include but are not limited to, RT-PCR (e.g., quantifying the level of the target gene or the dsRNA), phenotypic analysis such as biomass, vigor, yield and stress tolerance, root architecture, leaf dimensions, grain size and weight, oil content, cellulose, as well as cell biology techniques.

Seeds may be stored for 1 day to several months prior to planting (e.g., at 4 to 10° C.).

The resultant seed can be germinated in the dark so as to produce a plant.

Thus there is provided a plant or plant part comprising an exogenous dsRNA molecule and devoid of a heterologous promoter for driving expression of the dsRNA molecule in the plant.

As used herein "devoid of a heterologous promoter for driving expression of the dsRNA" means that the plant or plant cell doesn't include a cis-acting regulatory sequence (e.g., heterologous) transcribing the dsRNA in the plant.

As used herein, the term "heterologous" means not naturally occurring together. In some embodiments, the term "heterologous" refers to exogenous, not-naturally occurring within the native plant cell (such as by position of integration, or being non-naturally found within the plant cell). Thus the isolated seed in the absence of a heterologous promoter sequence for driving expression of the dsRNA in the plant, comprises a homogenic (prior to amplification) or heterogenic (secondary siRNAs, following amplification) population of plant non-transcribable dsRNA. In embodiments according to the present disclosure, an antisense RNA sequence may be a heterologous sequence.

The present methodology can be used for modulating gene expression such as in a plant, the method comprising: (a) contacting a seed of the plant with a dsRNA, under conditions which allow penetration of the dsRNA into the seed, thereby introducing the dsRNA into the seed; and optionally (b) generating a plant of the seed.

When used for down-regulating a plant gene, the dsRNA is designed of the desired specificity using bioinformatic tools which are well known in the art (e.g., BLAST).

This methodology can be used in various applications starting from basic research such as in order to asses gene function and lasting in generating plants with altered traits which have valuable commercial use.

Such plants can exhibit agricultural beneficial traits including altered morphology, altered flowering, altered tolerance to stress (i.e., biotic and/or abiotic), altered biomass vigor and/or yield and the like.

The phrase "abiotic stress" as used herein refers to any adverse effect on metabolism, growth, viability and/or reproduction of a plant. Abiotic stress can be induced by any of suboptimal environmental growth conditions such as, for example, water deficit or drought, flooding, freezing, low or high temperature, strong winds, heavy metal toxicity, anaerobiosis, high or low nutrient levels (e.g. nutrient deficiency), high or low salt levels (e.g. salinity), atmospheric pollution, high or low light intensities (e.g. insufficient light) or UV irradiation. Abiotic stress may be a short term effect (e.g. acute effect, e.g. lasting for about a week) or alternatively may be persistent (e.g. chronic effect, e.g. lasting for example 10 days or more). The present disclosure contemplates situations in which there is a single abiotic stress condition or alternatively situations in which two or more abiotic stresses occur.

According to one embodiment the abiotic stress refers to salinity.

According to another embodiment the abiotic stress refers to drought.

According to another embodiment the abiotic stress refers to a temperature stress.

As used herein the phrase "abiotic stress tolerance" refers to the ability of a plant to endure an abiotic stress without exhibiting substantial physiological or physical damage (e.g. alteration in metabolism, growth, viability and/or reproducibility of the plant).

As used herein the phrase "nitrogen use efficiency (NUE)" refers to a measure of crop production per unit of nitrogen fertilizer input. Fertilizer use efficiency (FUE) is a measure of NUE. Crop production can be measured by biomass, vigor or yield. The plant's nitrogen use efficiency is typically a result of an alteration in at least one of the uptake, spread, absorbance, accumulation, relocation (within the plant) and use of nitrogen absorbed by the plant. Improved NUE is with respect to that of a non-transgenic plant (i.e., lacking the transgene of the transgenic plant) of the same species and of the same developmental stage and grown under the same conditions.

As used herein the phrase "nitrogen-limiting conditions" refers to growth conditions which include a level (e.g., concentration) of nitrogen (e.g., ammonium or nitrate) applied which is below the level needed for optimal plant metabolism, growth, reproduction and/or viability.

As used herein the term/phrase "biomass", "biomass of a plant" or "plant biomass" refers to the amount (e.g., measured in grams of air-dry tissue) of a tissue produced from the plant in a growing season. An increase in plant biomass can be in the whole plant or in parts thereof such as aboveground (e.g. harvestable) parts, vegetative biomass, roots and/or seeds or contents thereof (e.g., oil, starch etc.).

As used herein the term/phrase "vigor", "vigor of a plant" or "plant vigor" refers to the amount (e.g., measured by weight) of tissue produced by the plant in a given time. Increased vigor could determine or affect the plant yield or the yield per growing time or growing area. In addition, early vigor (e.g. seed and/or seedling) results in improved field stand.

As used herein the term/phrase "yield", "yield of a plant" or "plant yield" refers to the amount (e.g., as determined by weight or size) or quantity (e.g., numbers) of tissues or organs produced per plant or per growing season. Increased yield of a plant can affect the economic benefit one can obtain from the plant in a certain growing area and/or growing time.

According to one embodiment the yield is measured by cellulose content, oil content, starch content and the like.

According to another embodiment the yield is measured by oil content.

According to another embodiment the yield is measured by protein content.

According to another embodiment, the yield is measured by seed number, seed weight, fruit number or fruit weight per plant or part thereof (e.g., kernel, bean).

A plant yield can be affected by various parameters including, but not limited to, plant biomass; plant vigor; plant growth rate; seed yield; seed or grain quantity; seed or grain quality; oil yield; content of oil, starch and/or protein in harvested organs (e.g., seeds or vegetative parts of the plant); number of flowers (e.g. florets) per panicle (e.g. expressed as a ratio of number of filled seeds over number of primary panicles); harvest index; number of plants grown per area; number and size of harvested organs per plant and per area; number of plants per growing area (e.g. density); number of harvested organs in field; total leaf area; carbon assimilation and carbon partitioning (e.g. the distribution/allocation of carbon within the plant); resistance to shade; number of harvestable organs (e.g. seeds), seeds per pod, weight per seed; and modified architecture [such as increase stalk diameter, thickness or improvement of physical properties (e.g. elasticity)].

Improved plant NUE is translated in the field into either harvesting similar quantities of yield, while implementing less fertilizers, or increased yields gained by implementing the same levels of fertilizers. Thus, improved NUE or FUE has a direct effect on plant yield in the field.

As used herein "biotic stress" refers stress that occurs as a result of damage done to plants by other living organisms, such as bacteria, viruses, fungi, parasites, beneficial and harmful insects, weeds, and cultivated or native plants. Example 7 of the Examples section which follows, implements the present teachings towards conferring resistance to *Spodoptera littoralis*.

As used herein the term "improving" or "increasing" refers to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90% or greater increase in NUE, in tolerance to stress, in yield, in biomass or in vigor of a plant, as compared to a native or wild-type plants (i.e., isogenic plants (not modified to comprise the dsRNA)) of the disclosure.

As mentioned the target gene of the dsRNA may not be an endogenous plant gene but rather a gene exogenous to the plant such as of a phytopathogenic organism which feeds on the plant or depends thereon for growth/replication (e.g., bacteria or viruses) and survival.

As used herein. The term "phytopathogen" refers to an organism that benefits from an interaction with a plant, and has a negative effect on that plant.

Thus, according to an embodiment of the disclosure there is provided a method of inhibiting expression of a target gene in a phytopathogenic organism, the method comprising providing (e.g., feeding or contacting under infecting conditions) to the phytopathogenic organism the plant as described herein (at least part thereof includes the dsRNA), thereby inhibiting expression of a target gene in the phytopathogenic organism.

The phytopathogenic organism refers to a multicellular organism e.g., insects, fungi, animals or a microorganism that can cause plant disease, including viruses, bacteria, fungi as well as oomycetes, chytrids, algae, and nematodes.

Reference herein to a "nematode" refers to a member of the phylum Nematoda. Members of the family Heteroderidae are sedentary parasites that form elaborate permanent associations with the target host organism. They deprive nutrients from cells of an infected organism through a specialized stylet. The cyst nematodes (genera *Heterodera* and *Globodera*) and root-knot nematodes (genus *Meliodogyne*), in particular, cause significant economic loss in plants, especially crop plants. Examples of cyst nematodes include, inter alia, *H. avenae* (cereal cyst nematodes), *H. glycines* (beet cyst nematode) and *G. pallida* (potato cyst nematode). Root-knot nematodes include, for example, *M. javanica, M. incognita* and *M. arenaria*. These pathogens establish "feeding sites" in the plant, by causing the morphological transformation of root cells into giant cells. Hence, nematode "infestation" or "infection" refers to invasion of and feeding upon the tissues of the host plant. Other nematodes that cause significant damage include the lesion nematodes such as *Pratylenchus*, particularly *P. penetrans*, which infects maize, rice and vegetables, *P. brachyurus* which infects pineapple and *P. thornei* which infects inter alia, wheat.

Insects that may cause damage and disease in plants belong to three categories, according to their method of feeding: chewing, sucking and boring. Major damage is caused by chewing insects that eat plant tissue, such as leaves, flowers, buds and twigs. Examples from this large insect category include beetles and their larvae (grubs), web-worms, bagworms and larvae of moths and sawflies (caterpillars). By comparison, sucking insects insert their mouth parts into the tissues of leaves, twigs, branches, flowers or fruit and suck out the plant's juices. Typical examples of sucking insects include but are not limited to aphids, mealy bugs, thrips and leaf-hoppers. Damage caused by these pests is often indicated by discoloration, drooping, wilting and general lack of vigor in the affected plant.

According to a specific embodiment, the phytopathogen is prodentia of the family Noctuidae e.g., *Spodoptera littoralis*.

Examples of significant bacterial plant pathogens include, but are not limited to, *Burkholderia*, *Proteobacteria* (*Xanthomonas* spp. and *Pseudomonas* spp, *Pseudomonas syringae* pv. tomato).

A number of virus genera are transmitted, both persistently and non-persistently, by soil borne zoosporic protozoa. These protozoa are not phytopathogenic themselves, but parasitic. Transmission of the virus takes place when they become associated with the plant roots. Examples include *Polymyxa graminis*, which has been shown to transmit plant viral diseases in cereal crops and *Polymyxa betae* which transmits Beet necrotic yellow vein virus. Plasmodiophorids also create wounds in the plant's root through which other viruses can enter.

Specific examples of viruses which can be targeted according to the present teachings includes, but are not limited to:

(1) Tobacco mosaic virus (TMV, RNA virus) which infects plants, especially tobacco and other members of the family Solanaceae.

(2) Tomato spotted wilt virus (TSWV, RNA virus) which causes serious diseases of many economically important plants representing 35 plant families, including dicots and monocots. This wide host range of ornamentals, vegetables, and field crops is unique among plant-infecting viruses. Belongs to tospoviruses in the Mediterranean area, affect vegetable crops, especially tomato, pepper and lettuce (Turina et al., 2012, Adv Virus Res 84; 403-437).

(3) Tomato yellow leaf curl virus (TYLCV) which is transmitted by whitefly, mostly affects tomato plants. Geminiviruses (DNA viruses) in the genus *Begomovirus* (including sweepoviruses and legumoviruses)—most devastating pathogens affecting a variety of cultivated crops, including cassava, sweet potato, beans, tomato, cotton and grain legumes (Rey et al. 2012, Viruses 4; 1753-1791). Members include TYLCV above and tomato leaf curl virus (ToLCV).

(4) Cucumber mosaic virus (CMV)—CMV has a wide range of hosts and attacks a great variety of vegetables, ornamentals, and other plants (as many as 191 host species in 40 families). Among the most important vegetables affected by cucumber mosaic are peppers (*Capsicum annuum* L.), cucurbits, tomatoes (*Lycopersicon esculentum* Mill.), and bananas (*Musa L.* spp.).

Other vegetable hosts include: cucumber, muskmelon, squash, tomato, spinach, celery, peppers, water cress, beet, sweet potato, turnip, chayote, gherkin, watermelon, pumpkin, citron, gourd, lima bean, broad bean, onion, groundcherry, eggplant, potato, rhubarb, carrot, dill, fennel, parsnip, parsley, luffa, and artichoke (Chabbouh and Chemf, 1990, FAO Plant Prot. Bull. 38:52-53.).

Ornamental hosts include: China aster, chrysanthemum, delphinium, salvia, geranium, gilia, gladiolus, heliotrope, hyacinth, larkspur, lily, marigold, morning glory, nasturtium, periwinkle, petunia, phlox, snapdragon, tulip, and zinnia (Chupp and Sherf, 1960; Agrios, 1978).

(5) Potato virus Y (PVY)—one of the most important plant viruses affecting potato production.

(6) Cauliflower mosaic virus (CaMV, DNA virus (Rothnie et al., 1994)).

(7) African cassaya mosaic virus (ACMV).

(8) Plum pox virus (PPV) is the most devastating viral disease of stone fruit from the genus *Prunus*.

(9) Brome mosaic virus (BMV)—commonly infects *Bromus inermis* and other grasses, can be found almost anywhere wheat is grown.

(10) Potato virus X (PVX) There are no insect or fungal vectors for this virus. This virus causes mild or no symptoms in most potato varieties, but when Potato virus Y is present, synergy between these two viruses causes severe symptoms in potato.

Additional viruses:

Citrus tristeza virus (CTV)—causes the most economically damaging disease to Citrus, including sour orange (*Citrus aurantium*), and any Citrus species grafted onto sour orange root stock, sweet orange (*C. sinensis*), grapefruit (*C. paradisi*), lime and Seville orange (*C. aurantifolia*), and mandarin (*C. reticulatas*). CTV is also known to infect *Aeglopsis chevalieri*, *Afraegle paniculata*, *Pamburus missionis*, and *Passiflora gracilis*. CTV is distributed worldwide and can be found wherever citrus trees grow.

Barley yellow dwarf virus (BYDV)—most widely distributed viral disease of cereals. It affects the economically important crop species barley, oats, wheat, maize, triticale and rice.

Potato leafroll virus (PLRV) infects potatoes and other members of the family Solanaceae.

Tomato bushy stunt virus (TBSV), RNA virus, a member of the genus Tombusvirus and mostly affects tomatoes and eggplant.

Additional reviews:

Hamilton et al., 1981, J Gen Virol 54; 223-241—mentions TMV, PVX, PVY, CMV, CaMV Additional scientific papers:

Makkouk et al., 2012, Adv Virus Res 84; 367-402—Viruses affecting peas and beans with narrow (Faba bean necrotic yellow virus (FBNYN)) and wide (alfalfa mosaic virus (AMV) and CMV) host range.

Insect pests causing plant disease include those from the families of, for example, Apidae, Curculionidae, Scarabaeidae, Tephritidae, Tortricidae, amongst others.

The target gene of the phytopathogenic organism encodes a product essential to the viability and/or infectivity of the pathogen, therefore its down-regulation (by the dsRNA) results in a reduced capability of the pathogen to survive and infect host cells. Hence, such down-regulation results in a "deleterious effect" on the maintenance viability and/or infectivity of the phytopathogen, in that it prevents or reduces the pathogen's ability to feed off and survive on nutrients derived from host cells. By virtue of this reduction in the phytopathogen's viability and/or infectivity, resistance and/or enhanced tolerance to infection by a pathogen is facilitated in the cells of the plant. Genes in the pathogen may be targeted at the mature (adult), immature (juvenile) or embryo stages.

Examples of genes essential to the viability and/or infectivity of the pathogen are provided herein. Such genes may include genes involved in development and reproduction, e.g. transcription factors (see, e.g. Xue et al., 1993; Finney et al., 1988), cell cycle regulators such as wee-1 and ncc-1 proteins (see, e.g. Wilson et al., 1999; Boxem et al., 1999) and embryo-lethal mutants (see, e.g. Schnabel et al., 1991); proteins required for modeling such as collagen, ChR3 and LRP-1 (see, e.g. Yochem et al., 1999; Kostrouchova et al., 1998; Ray et al., 1989); genes encoding proteins involved in the motility/nervous system, e.g. acetycholinesterase (see, e.g. Piotee et al., 1999; Talesa et al., 1995; Arpagaus et al., 1998), ryanodine receptor such as unc-68 (see, e.g. Maryon et al., 1998; Maryon et al., 1996) and glutamate-gated chloride channels or the avermeetin receptor (see, e.g., Cully et al., 1994; Vassilatis et al., 1997; Dent et al., 1997); hydrolytic enzymes required for deriving nutrition from the host, e.g. serine proteinases such as HGSP-1 and HGSP-III (see, e.g. Lilley et al., 1997); parasitic genes encoding proteins required for invasion and establishment of the feeding site, e.g. cellulases (see, e.g. de Boer et al., 1999; Rosso et al., 1999) and genes encoding proteins that direct production of stylar or amphidial secretions such as sec-1 protein (see, e.g. Ray et al., 1994; Ding et al., 1998); genes encoding proteins required for sex or female determination, e.g. tra-1, tra-2 and egl-1, a suppressor of ced9 (see, e.g. Hodgkin, 1980; Hodgkin, 1977; Hodgkin, 1999; Gumienny et al., 1999; Zarkower et al., 1992); and genes encoding proteins required for maintenance of normal metabolic function and homeostasis, e.g. sterol metabolism, embryo lethal mutants (see, e.g. Schnabel et al., 1991) and trans-spliced leader sequences (see, e.g. Ferguson et al, 1996), pos-1, cytoplasmic Zn finger protein; pie-1, cytoplasmic Zn finger protein; mei-1, ATPase; dif-1, mitochondrial energy transfer protein; rba-2, chromatin assembly factor; skn-1, transcription factor; plk-1, kinase; gpb-1, G-protein B subunit; par-1, kinase; bir-1, inhibitor of apoptosis; mex-3, RNA-binding protein, unc-37, G-protein B subunit; hlh-2, transcription factor; par-2, dnc-1, dynactin; par-6, dhc-1, dynein heavy chain; and pal-1, homeobox. Such genes have been cloned from parasitic nematodes such as *Meliodogyne* and *Heterodera* species or can be identified by one of skill in the art using sequence information from cloned *C. elegans* orthologs (the genome of *C. elegans* has been sequenced and is available, see The *C. elegans* Sequencing Consortium (1998)).

As used herein, a "pathogen resistance" trait is a characteristic of a plant that causes the plant host to be resistant to attack from a pathogen that typically is capable of inflicting damage or loss to the plant. Once the phytopathogen is provided with the plant material comprising the dsRNA, expression of the gene within the target pathogen is suppressed by the dsRNA, and the suppression of expression of the gene in the target pathogen results in the plant being resistant to the pathogen.

In this case, the target gene can encode an essential protein or transcribe an non-coding RNA which, the predicted function is for example selected from the group consisting of ion regulation and transport, enzyme synthesis, maintenance of cell membrane potential, amino acid biosynthesis, amino acid degradation, development and differentiation, infection, penetration, development of appressoria or haustoria, mycelial growth, melanin synthesis, toxin synthesis, siderophore synthesis, sporulation, fruiting body synthesis, cell division, energy metabolism, respiration, and apoptosis, among others.

According to a specific embodiment, the phytopathogenic organism is selected from the group consisting of a fungus, a nematode, a virus, a bacteria and an insect.

To substantiate the anti-pest activity, the present teachings also contemplate observing death or growth inhibition and the degree of host symptomatology following said providing.

To improve the anti-phytopathogen activity, embodiments of the present disclosure further provide a composition that contains two or more different agents each toxic to the same plant pathogenic microorganism, at least one of which comprises a dsRNA described herein. In certain embodiments, the second agent can be an agent selected from the group consisting of inhibitors of metabolic enzymes involved in amino acid or carbohydrate synthesis; inhibitors of cell division; cell wall synthesis inhibitors; inhibitors of DNA or RNA synthesis, gyrase inhibitors, tubulin assembly inhibitors, inhibitors of ATP synthesis; oxidative phosphorylation uncouplers; inhibitors of protein synthesis; MAP kinase inhibitors; lipid synthesis or oxidation inhibitors; sterol synthesis inhibitors; and melanin synthesis inhibitors.

In addition, plants generated according to the teachings of the present disclosure or parts thereof can exhibit altered nutritional or therapeutic efficacy and as such can be employed in the food or feed and drug industries. Likewise, the plants generated according to the teachings of the present disclosure or parts thereof can exhibit altered oil or cellulose content and as such can be implemented in the construction or oil industry.

The seeds of the present disclosure can be packed in a seed containing device which comprises a plurality of seeds at least some of which (e.g., 5%, 10% or more) containing an exogenous dsRNA, wherein the seed is devoid of a heterologous promoter for driving expression of the dsRNA.

The seed containing device can be a bag, a plastic bag, a paper bag, a soft shell container or a hard shell container.

Reagents of the present disclosure can be packed in a kit including the dsRNA, instructions for introducing the dsRNA into the seeds and optionally a priming solution. According to one embodiment, the dsRNA and priming solution are comprised in separate containers.

Compositions of some embodiments of the disclosure may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for introduction to the seed.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

Various embodiments and embodiments of the present disclosure as delineated hereinabove and as claimed in the claims section below find experimental support in the following examples.

EXAMPLES

Reference is now made to the following examples, which together with the above descriptions, illustrate some embodiments of the disclosure in a non limiting fashion.

Generally, the nomenclature used herein and the laboratory procedures utilized in the present disclosure include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Protocols for dsRNA Production and Seed Treatment

Generating dsRNA/siRNA Sequences

The dsRNA sequences were custom-created for each gene using in vitro transcription of PCR products. Part of the mRNA, including either the ORF, 3' UTR or 5' UTR for which dsRNA to be produced was PCR-amplified using gene-specific primers, which contain the sequence of the T7 promoter on either side. This product was used as a template for dsRNA production using commercial kits such as the MaxiScript dsRNA kit (Life Technologies) or T7 High Yield RNA Synthesis kit (NEB). Next, the sample is treated with DNase Turbo at 37° C. for 15-30 min followed by phenol treatment and nucleic acid precipitation. Next, one of two different reactions is carried out: (1) dsRNA is ready to use, (2) processing of the dsRNA with Dicer (Shortcut RNase III (NEB)) to create small interfering RNAs (siRNA).

Either dsRNA or a combination of dsRNA and siRNA were used for seed treatments as described below.

General Seed Treatment Protocol for Gene Silencing Using a dsRNA/siRNA Mixture

Uncoated organic corn seeds were from variety "popcorn", uncoated organic whole grain rice seeds, organic soybean and wheat seeds were purchased from Nitsat Haduvdevan (Israel), Fresh tomato seeds were retrieved from M82 tomato fruits, which are propagated in-house. Uncoated or fresh plant seeds were washed with double distilled water (DDW) prior to treatment for four hours. Next, seeds were dried at 30° C. for 10-16 hours. Following the drying step, seeds were treated with a solution containing the dsRNA formulation, which is made of dsRNA at a final concentration of 40-150 µg/ml in 0.1 mM EDTA. Treatment was performed by gently shaking the seeds in the solution for 24 hours in a dark growth chamber at 15° C. Finally, seeds were washed twice briefly and planted on soil or dried for 0-30 hours and germinated at 25° C. in a dark growth chamber and planted in soil or planted directly in soil. Control seeds were treated in a similar way, with a formulation that lacked the dsRNA or with non-specific dsRNA.

Example 2

Stability of the DSRNA in Seedlings of Rice, Tomato and Sorghum

As an example for an exogenous gene that is not present/expressed in plants, the ORFs encoding the replicase and coat protein of CGMMV (accession number AF417242) were used to as targets for dsRNA treatment of plant seeds using the protocol described in Example 1. Rice, tomato and sorghum seeds were washed for 4 hours at 20° C., tomato and sorghum were dried at 30° C. and rice at 20° C. for overnight. Seeds were immediately treated at 15° C. with 132.7 µg/ml dsRNA (final concentration) for 39 hours for rice, 93.8 µg/ml dsRNA (final concentration) for 48 hours for tomato, and 75 µg/ml dsRNA (final concentration) for 40 hours for sorghum.

Briefly, the virus-derived ORFs were amplified by PCR with specifically designed forward and reverse primers that contain the T7 sequence (5'-TAATACGACTCACTATAGGG-3', SEQ ID NO: 1) at their 5' (see Table 2, below). PCR products were purified from agarose gel and since they carry T7 promoters at both ends they were used as templates for T7-dependent in-vitro transcription, resulting in dsRNA product of the CGMMV genes. PCR on a housekeeping gene, tubulin, was used as a positive control (forward primer 5'-GGTGCTCTGAACGTGGATG-3' (SEQ ID NO: 2), and reverse primer 5'-CATCATCGCCATCCTCATTCTC-3' (SEQ ID NO: 3)).

TABLE 2

PCR primers served as Templates for in vitro Transcription and detection of CGMMV, and CGMMV dsRNA products.

| Virus Name | Product Name | Product Sequence/SEQ ID NO: | Forward primer/SEQ ID NO: | Reverse primer/SEQ ID NO: |
|---|---|---|---|---|
| | | TAATACGACTCACTATAGGGGGTAAGCG | | Set 1: |
| | | GCATTCTAAACCTCCAAATCGGAGGTTGG | | TAATACGA |
| | | ACTCTGCTTCTGAAGAGTCCAGTTCTGTT | TAATACGACT | CTCACTATA |
| | | TCTTTTGAAGATGGCTTACAATCCGATCA | CACTATAGGG | GGGGAAGA |
| | | CACCTAGCAAACTTATTGCGTTTAGTGCT | GGTAAGCGGC | CCCTCGAA |
| | | TCTTATGTTCCCGTCAGGACTTTACTTAAT | ATTCTAAACC/ | ACTAAGC/ |
| | | TTTCTAGTTGCTTCACAAGGTACCGCTTTC | (SEQ ID NO: 5) | (SEQ ID NO: 4) |
| | | CAGACTCAAGCGGGAAGAGATTCTTTCCG | | |
| | | CGAGTCCCTGTCTGCGTTACCCTCGTCTG | | |
| | | TCGTAGATATTAATTCTAGATTCCCAGAT | | |
| | | GCGGGTTTTTACGCTTTCCTCAACGGTCC | | |
| | | TGTGTTGAGGCCTATCTTCGTTTCGCTTCT | | |
| | | CAGCTCCACGGATACGCGTAATAGGGTC | | |
| | | ATTGAGGTTGTAGATCCTAGCAATCCTAC | | |
| | | GACTGCTGAGTCGCTTAACGCCGTAAAGC | | |
| 1) | | GTACTGATGACGCGTCTACGGCCGCTAGG | | |
| CGMMV | | GCTGAGATAGATAATTTAATAGAGTCTAT | | |
| (NCBI | | TTCTAAGGGTTTTGATGTTTACGATAGGG | Set 2: | |
| Accession | | CTTCATTTGAAGCCGCGTTTTCGGTAGTC | ACTCAGCA | |
| number CGMVV | | TGGTCAGAGGCTACCACCTCGAAAGCTTA | CTTCTTATGT | GTCGTAGG |
| AF417242) dsRNA | | GTTTCGAGGGTCTTCCCCTATAGTGAGTC | TCCCGTCAGG/ | ATTG/(SEQ |
| product 1 | | GTATTA/(SEQ ID NO: 8) | (SEQ ID NO: 7) | ID NO: 6) |
| | | TAATACGACTCACTATAGGGGCTTTACCG | | |
| | | CCACTAAGAACTCTGTACACTCCCTTGCG | | |
| | | GGTGGTCTGAGGCTTCTTGAATTGGAATA | | |

TABLE 2-continued

PCR primers served as Templates for in vitro Transcription and detection of CGMMV, and CGMMV dsRNA products.

| Virus Name | Product Name | Product Sequence/SEQ ID NO: | Forward primer/SEQ ID NO: | Reverse primer/SEQ ID NO: |
|---|---|---|---|---|
| | | TATGATGATGCAAGTGCCCTACGGCTCAC | | |
| | | CTTGTTATGACATCGGCGGTAACTATACG | | |
| | | CAGCACTTGTTCAAAGGTAGATCATATGT | | |
| | | GCATTGCTGCAATCCGTGCCTAGATCTTA | | |
| | | AAGATGTTGCGAGGAATGTGATGTACAA | | |
| | | CGATATGATCACGCAACATGTACAGAGG | | |
| | | CACAAGGGATCTGGCGGGTGCAGACCTC | | |
| | | TTCCAACTTTCCAGATAGATGCATTCAGG | | |
| | | AGGTACGATAGTTCTCCCTGTGCGGTCAC | | |
| | | CTGTTCAGACGTTTTCCAAGAGTGTTCCT | | |
| | | ATGATTTTGGGAGTGGTAGGGATAATCAT | | |
| | | GCAGTCTCGTTGCATTCAATCTACGATAT | | Set 3: |
| | | CCCTTATTCTTCGATCGGACCTGCTCTTCA | | TAATACGA |
| | | TAGGAAAAATGTGCGAGTTTGTTATGCAG | TAATACGACT | CTCACTATA |
| | | CCTTTCATTTCTCGGAGGCATTGCTTTTAG | CACTATAGGG | GGGCATCA |
| | | GTTCGCCTGTAGGTAATTTAAATAGTATT | GCTTTACCGC | CCATCGAC |
| CGMVV dsRNA product 2 | | GGGGCTCAGTTTAGGGTCGATGGTGATGC CCTATAGTGAGTCGTATTA/(SEQ ID NO: 11) | CACTAAGAAC/ (SEQ ID NO: 10) | CCTAAAC/ (SEQ ID NO: 9) | dsRNA homologous to green mottle mosaic virus was observed to be stable in rice seedlings. Rice seeds were treated at 15° C. with 132.7 µg/ml dsRNA (final concentration) for 39 hours and dsRNA was detected_bp real time polymerase chain reaction (RT-PCR) 1 week post germination. Detection of tubulin cDNA serves as a positive control for the cDNA quality. At two weeks post germination, dsRNA was detectable in 10 out of 10 seedlings. At 3 weeks post germination, dsRNA homologous to green mottle mosaic virus was detected in 5 out of 5 samples of rice seedlings.

Tomato seeds were treated at 15° C. with 93.8 µg/ml dsRNA (final concentration) for 48 hours and sorghum seeds treated at 5 µg/ml dsRNA (final concentration) for 40 hours. CGMMV dsRNA was detected by RT-PCR in 5 out of 13 tomato seedlings tested at 10 day post-germination and 3 out of four sorghum seedlings 4 weeks after germination.

The exogenous dsRNA was found to be stable for at least three weeks in rice seedlings and at least 10 days in tomato seedlings and four weeks in *Sorghum* plants.

Example 3

The dsRNA is not Integrated into the Genome of Rice

Rice seeds were treated with an exogenous dsRNA as in Example 2. Plants were germinated and grown for five weeks, DNA was extracted and PCR reactions were performed to demonstrate that the dsRNA did not integrate into the Rice's genome. Two sets of primers that gave a positive reaction when checked on the RNA level were used, set 1 (see Table 2) of primers were the set of primers used to amplify the template (all the dsRNA sequence). Set 2 (see Table 3) are the primers that were used in the PCR above. A Rice endogenous housekeeping gene (tubulin) was used as a positive control for the PCR reaction (see Table 3).

Three different DNA PCR reactions were carried out on dsRNA treated and untreated plants. No amplified DNA corresponding to CGMMV was detected in any treated or untreated plant.

TABLE 3

Tubulin Primers Used for PCR Amplification.

| Primer Name and Direction | Primer Sequence/(SEQ ID NO:) | Primer Length |
|---|---|---|
| osa_TubA1_736F | GGTGCTCTGAACGTGGATG (SEQ ID NO: 12) | 19 |
| osa_TubA1_1342R | CATCATCGCCATCCTCATTCTC (SEQ ID NO: 13) | 22 |

Example 4

Exogenous dsRNA Molecules are Highly Stable in Solution and do not get Incorporated into the Genome of Treated Plants Corn seeds were treated using the protocol described in Example 1, seeds were washed for 4 h at 20° C., dried at 30° C. overnight and immediately treated with 40 µg/ml dsRNA (final concentration) directed against the β-glucuronidase (GUS) reporter gene for 60 hours at 15° C., dried and were germinated. Leaves and roots were harvested from control and dsGUS-treated plants 7 and 15 days following germination. RNA was extracted from the harvested tissues and RT-PCR with specific GUS primers was run (Table 4). In addition, a corn endogenous housekeeping gene (ubiquitin) was used as a positive control for the PCR reaction. The GUS dsRNA molecules were found to be extremely stable in the treated seeds, and can be detected in corn plants 7 and 15 days post germination of the seeds.

GUS dsRNA was detected in corn seedlings by RT-PCR at 7 and 15 days after germination according to an aspect of the present disclosure. At one week, GUS dsRNA was detected in shoots of nine of eleven corn seedlings tested. GUS dsRNA was not detected in untreated plants. At 1 week post-germination, GUS dsRNA was detected in five of five corn seedlings' roots. At 15 days post germination, GUS dsRNA was detected in corn seedlings' roots. GUS dsRNA molecules do not get incorporated in the genome of treated corn plants one week after germination as determined by agarose gel electrophoresis of DNA PCR reactions using GUS primers on DNA isolated from treated corn plants.

Example 5

Fluorescence Microscopy of siRNA Sequences in Various Plant Seeds

Plant seeds as per the protocol described in example 1. Seeds were washed for 4 h at 20° C., dried at 25° C. and were immediately treated with a fluorescent siRNA (siGLO, 2 µM final concentration, Thermo Scientific) at 15° C. for 24 h. The quality of the siGLO before application to a plant seed was verified by gel electrophoresis analysis. Bands corresponding to the expected size of 20-24 bp of the fluorescent siRNA molecules was detected.

Fluorescent pictures of the seeds were taken 24-48 hours post treatment using an Olympus microscope at the lowest objective magnification (5× for bigger seeds such as rice and tomato seeds, and 10× for smaller seeds such as *Arabidopsis* seeds). To eliminate the possibility of non-specific autofluorescence, dsRNA-treated seeds were compared to control untreated seeds. Penetration of fluorescent siRNA molecules into plant seeds was observed at 24 hours after seed treatment with siRNA at 2 µM final concentration in rice seeds and tomato seeds.

Penetration of fluorescent siRNA molecules into rice seeds was observed at 24 hours following treatment with siGLO dsRNA.

In order to evaluate the distribution efficiency of the fluorescent siRNA inside the seeds, different plant seeds were cut into slices and imaged with a fluorescent micro-

TABLE 4

Primers for PCR Amplification of GUS and Ubiquitin Genes and GUS dsRNA product.

| Primer Length | Primer Sequence/SEQ ID NO: | Primer Name |
|---|---|---|
| GUS_T7_For | TAATACGACTCACTATAGGGAGATCGACGGCCTGTGGGCATTC/ (SEQ ID NO: 15) | |
| GUS_T7_Rev | TAATACGACTCACTATAGGGAGCATTCCCGGCGGGATAGTCTG/ (SEQ ID NO: 16) | 43 |
| GUS208For | CAGCGCGAAGTCTTTATACC/ (SEQ ID NO: 17) | 43 |
| GUS289Rev | CTTTGCCGTAATGAGTGACC/ (SEQ ID NO: 18) | 20 |
| zmaUBQ-947F | CCATAACCCTGGAGGTTGAG/ (SEQ ID NO: 19) | 20 |
| zmaUBQ1043R | ATCAGACGCTGCTGGTCTGG/ (SEQ ID NO: 20) | 20 |
| GUS dsRNA product | TAATACGACTCACTATAGGGAGATCGACGGCCTGTGGGCATTC AGTCTGGATCGCGAAAACTGTGGAATTGATCAGCGTTGGTGG GAAAGCGCGTTACAAGAAAGCCGGGCTATTGCTGTGCCAGGC AGTTTTAACGATCAGTTCGCCGATGCAGATATTCGTAATTATG CGGGCAACGTCTGGTATCAGCGCGAAGTCTTTATACCGAAAG GTTGGGCAGGCCAGCGTATCGTGCTGCGTTTCGATGCGGTCAC TCATTACGGCAAAGTGTGGGTCAATAATCAGGAAGTGATGGA GCATCAGGGCGGCTATACGCCATTTGAAGCCGATGTCACGCC GTATGTTATTGCCGGGAAAAGTGTACGTATCACCGTTTGTGTG AACAACGAACTGAACTGGCAGACTATCCCGCCGGGAATGCTC CCTATAGTGAGTCGTATTA/ (SEQ ID NO: 21) | | scope 48 hours after treatment. Each treated seed was imaged alongside a control untreated seed. Light and fluorescent images were taken where applicable for rice, tomato, cucumber, bean, sorghum and wheat seed samples.

Penetration of fluorescent siRNA molecules into rice seeds was observed at 48 hours following treatment with siGLO dsRNA. siGLO-treated and control rice seeds were sliced to view the interior distribution of the fluorescent dsRNA using a fluorescent microscope and fluorescent siRNA molecules detected in the treated seed. Fluorescent siGLO RNA is detected throughout the seed.

Penetration of fluorescent siRNA molecules into tomato seeds was observed at 48 hours following treatment with siGLO dsRNA. siGLO-treated and control tomato seeds were sliced to view the interior distribution of the fluorescent dsRNA using a fluorescent microscope. Fluorescent siGLO RNA is detected in the endosperm and the embryo.

Penetration of fluorescent siRNA molecules into cucumber seeds was observed at 48 hours following treatment with siGLO dsRNA. siGLO-treated and control cucumber seeds were sliced to view the interior distribution of the florescent dsRNA using a fluorescent microscope. Penetration of fluorescent siRNA molecules into cucumber seeds was observed at Fluorescent siGLO RNA is detected in the endosperm and the embryo.

Penetration of fluorescent siRNA molecules is detected in sliced seeds of various plant species, including bean, tomato, sorghum and wheat, 48 hours following treatment with siGLO dsRNA. siGLO-treated and control seeds were sliced to view the interior distribution of the fluorescent dsRNA using a fluorescent microscope. Light images were also taken for each seed and are shown alongside the fluorescent image of the seed for reference.

FIG. 1 presents fluorescent images of siGLO-treatment rice seeds over a 24 hour period. The effect of incubation time with siGLO dsRNA on fluorescence intensity, indicating quantity and quality of dsRNA penetration, was tested. Control seeds that were left untreated (1), were imaged along with seeds treated with siGLO dsRNA for four different incubation times; 10 min (2), 3.5 hours (3), 5.5 hours (4), and 24 hours (5).

It is clear that the siRNA is distributed at various levels between the embryo and the endosperm. Accordingly, dsRNA molecules enter the embryo directly. Though not to be limited by any particular theory, the dsRNA molecules are carried by the water-based solution used for the seed treatment. The dsRNA molecules enter the endosperm as part of the endosperm's water-absorption process. These molecules then are transferred to the embryo as it develops as part of the endosperm to embryo nutrient flow during germination and seed development.

These present findings suggest the RNA molecules used to treat the seeds both penetrate the embryo and function in the embryo as it develops and also penetrate the endosperm and feed the embryo following germination.

Example 6

Time Course Experiment with siGLO Treatment

A time course experiment was performed on rice seeds to monitor the kinetics of siGLO penetration into the seeds following the seed treatment (FIG. 1). The results indicate that the siRNA efficiently penetrates the plant seeds using the protocol described in Example 1.

Example 7

Example Embodiments of dsRNA Molecules

Example 7A provides A backbone sequence with two smRNA complementary sites and a helicase binding site: 5' GCATCCTCATCTTAATCTCGGTGCTATCCTACCTGA-GCTTGATATC<u>TAGGCGAAGCAGCCCGAATGCTGCA-CCCTAGATGGCGAAAGTCCAGTAGCGATATCGAAT</u>-TCCTCGAGGGATCCAAGCTT<u>CCTTGTCTATCCCTC-CTGAGCT</u>GTTGATTTTATTCCATGT 3' (SEQ ID NO: 14). This example contains a sequence for mutated microRNA 390 binding (bold), followed by a helicase binding site (bold and underlined) and a microRNA 390 binding sequence (underlined). DNA sequences for restriction enzyme recognition are added for cloning of the sequence to be silenced.

Example 7B is the same as example 7A, without the helicase binding site:

(SEQ ID NO: 22)
GCATCCTCATCTTAATCTCGGTGCTATCCTACCTGAGCTTGATATCGAT

ATCGAATTCCTCGAGGGATCCAAGCTT<u>CCTTGTCTATCCCTCCTGAGCT</u>

GTTGATTTTATTCCATGT.

Example 7C provides a backbone sequence with two smRNA complementary sites and an helicase binding site:
GCATCCTCATCTTAATCTCGTGATTTTTCTCTACA-AGCGAAGATATC<u>TAGGCGAAGCAGCCCGAATGCT-GGCACCCTAGATGGCGAAAGTCCAGTAGCGATATC</u>-GAATTCCTCGAGGGATCCAAGCTT<u>TCTTGCTCAAA-TGAGTATTCCA</u>GTTGATTTTATTCC ATGT (SEQ ID NO: 23). Example 7C contains a sequence for microRNA 173 binding (bold), followed by a helicase binding site (bold and underlined) and the reverse-complement sequence of microRNA 828 binding sequence (underlined). DNA sequences for restriction enzyme recognition are added for cloning of the sequence to be silenced. In this case a single complementary site is sufficient (i.e., miR173BS) yet a second complementary site is placed on the complementary strand (i.e., miR828BS) so as to enhance amplification from both strands.

Example 7D is the same as Example 7C, without the helicase binding site:

(SEQ ID NO: 24)
GCATCCTCATCTTAATCTCGTGATTTTTCTCTACAAGCGAAGATATCGA

TATCGAATTCCTCGAGGGATCCAAGCTT<u>TCTTGCTCAAATGAGTATTCC</u>

<u>A</u>GTTGATTTTATTCCATGT.

Example 8

Schematic Representation of the Solanum Lycopersicum TAS3 Gene

FIG. 2A presents a schematic representation of the Solanum Lycopersicum (*Lycopersicon esculentum*) TAS3 gene. This gene contains two Mir390 binding sites (BS). The 5' Mir390BS has mutations in critical positions for Mir390 dependent cleavage and therefore it is bound by Mir390 but not cleaved (will be referred hereafter as 5' Mut Mir390BS). The 3' Mir390 does lead to Mir390 binding and cleavage. In between these two sequences there is a 234 bp sequence that contains all the different ta-siRNAs that will be created following RDRP recruitment, RNA dependent RNA polymerization and dicing (Allen et al. (2005). MicroRNA-Directed Phasing during Trans-Acting siRNA Biogenesis in Plants. *Cell,* 121, 207-221., Axtell et al. (2006). A Two-Hit Trigger for siRNA Biogenesis in Plants. *Cell,* 127, 565-577., Montgomery et al. (2008). Specificity of ARGONAUTE7-miR390 Interaction and Dual Functionality in TAS3 Trans-Acting siRNA Formation. Cell, 133, 128-141).

Example 9

Additional dsRNA Constructs According to the Present Disclosure

Example 9A provides dsRNA Construct #1 that is an exogenous trigger control. FIG. 2B presents a schematic representation of dsRNA Construct #1 that will serve as a control for the other experiments since it contains only the exogenous sequence with no additional features that should lead to its amplification. The length of the exogenous sequence is 234 bp, the same size of the original insert between the two Mir390BS in TAS3.

Example 9B provides dsRNA Construct #2 having a dual Mir390BS on sense strand and an exogenous sequence. FIG. 2C presents schematic representation of dsRNA Construct #2 having a dual Mir390BS on sense strand and an exogenous sequence. Double-stranded RNA Construct #2 is based on the dual Mir390BS from the TAS3 gene with an exogenous sequence replacing the original insert between the two Mir390BS.

Figure 3:
FIG. 3 presents a schematic representation of dsRNA construct#3 having a dual Mir390BS on both on the sense and antisense strands. The construct is composed of 5 parts from 5' to 3': 3' Mir390BS in the reverse complement orientation, 5' Mut Mir390BS, a 234 bp exogenous sequence in the reverse complement orientation, 5' Mut Mir390BS in the reverse complement orientation and 3' Mir390BS. For sequence, see Table 5 (Trigger #3).

Example 9C provides dsRNA construct #3 having a Dual Mir390BS both on the sense and antisense strands. FIG. 3 presents a schematic of dsRNA construct #3. This construct contains dual Mir390BS on both the sense and antisense strands and therefore we hypothesize that it will continuously recruit Mir390-Ago7 and RDRP to both strands. As a result, it is predicted to lead to long lasting amplification of the exogenous sequence and to ongoing production of its ta-siRNAs.

Example 9D provides dsRNA construct #4 having miR390BS as overhangs. FIG. 4 presents dsRNA construct #4 composed of two different strands. Having the Mir390BS present as overhangs will ease the initial requirement for the unwinding of the dsRNA since the Mir390BS will already be accessible for mir390 and Ago7 binding. The Mir390BS sequences will facilitate the unwinding and as a result the translocation into the processing center and the initiation of the entire process as explained in example #3 above.

Figure 5:
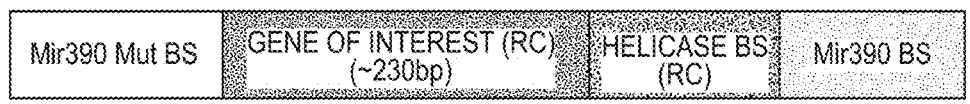
FIG. 5 presents a schematic representation of dsRNA construct #5 having miR390BS and a helicase binding sequence (Helicase BS). This construct is composed of 4 parts from 5' to 3': 5' Mut Mir390BS, a 234 bp exogenous sequence in the reverse complement orientation, Helicase BS in the reverse complement orientation, 3' Mir390BS. For sequence see Table 5 (Trigger #6).

Example 9E provides dsRNA construct #5 having Dual miR390BS sequences and helicase binding sequences. FIG. 5 presents dsRNA construct #5. The presence of the helicase binding sequences will enable more efficient unwinding of the dsRNA through active recruitment of a helicase and therefore leading to a strong and efficient amplification.

Figure 6:
FIG. 6 presents a schematic representation of dsRNA construct #6 having Mir390BS on both strands and Helicase BS as an overhang. This construct is composed of two different strands. The sense strand is composed of 5 parts from 5' to 3: '3' Mir390BS in the reverse complement orientation, 5' Mut Mir390BS, a 234 bp exogenous sequence in the reverse complement orientation, 5' Mut Mir390BS in the reverse complement orientation, and 3'Mir390BS. The antisense is composed of 6 parts from 5' to 3': 3'Mir390BS in the reverse complement orientation, 5' Mut Mir390BS, a 234 bp exogenous sequence in the sense orientation, 5' Mut Mir390BS in the reverse complement orientation, 3' Mir390BS and an Helicase BS as an overhang. For sequences, see Table 5 (Sense-Trigger #7, Antisense-Trigger #8).

Example 9F provides dsRNA construct #6 having Mir390BS on both strands and a helicase binding sequence (helicase BS) overhang. FIG. 6 presents dsRNA construct #6 having Mir390BS on both strands and a helicase overhang. This dsRNA construct #6 is composed of two different strands. The sense strand is the same as in construct #3 and the antisense strand is the same as construct #3 with an addition of an overhang of a helicase BS at the 3' end. The helicase BS leads to recruitment of a helicase that will unwind the dsRNA and enable efficient initiation of the entire process. Each of the strands will contains Mir390-Ago7 sequences for binding and localization into the processing center enabling long lasting amplification.

Figure 7:
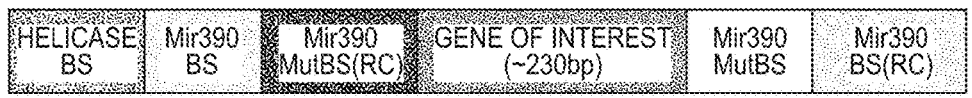
FIG. 7 presents a schematic representation of dsRNA construct #7 having Sense dual Mir390BS coupled with Antisense Mir4376BS. This construct is composed of 5 parts from 5' to 3': 5' Mut Mir390BS, a 234 bp exogenous sequence in the reverse complement orientation, Mir4376BS in the reverse complement orientation and 3' Mir390BS. For sequence, see Table 5 (Trigger #9).

Example 9G provides dsRNA construct #7 having a sense dual Mir390BS sequence coupled with an antisense Mir4376BS. FIG. 7 presents dsRNA construct #7 containing a dualMir390BS on its sense strand and a single Mir4376BS on its antisense strand. The presence of ta-siRNA inducing miRNAs on both strands will lead to ongoing amplification.

Example 9H provides dsRNA construct #8 having an Endogenous Trigger Control. FIG. 8 presents dsRNA construct #8 that is based on an exact endogenous insert sequence (the insert is the region between the two Mir390BS) in order to serve as an endogenous trigger control for the dsRNA construct #9 of Example 9I.

Example 9I presents dsRNA construct #9 having a Mir390BS sequence and an the Endogenous insert of Example 9H. FIG. 9 presents a schematic of dsRNA construct #9. Construct #9 maintains the endogenous sequence of the Mir390BS including the original insert region. This construct result in production of ta-siRNAs targeting ARF3 and ARF4.

Example 10

Treatment of Seeds with Ta-siRNA Constructs and Analysis of RNA Levels

Tomato seeds were treated with dsRNA molecules corresponding to the constructs and sequences of Table 5. Table 5.

TABLE 5

| Trigger # | Trigger alias | Sequence (5'-3') | Length | DS/SS | S/AS | SEQ ID |
|---|---|---|---|---|---|---|
| 1 | GFP234 | CTAATACGACTCACTATAGGGAGATTTCCG | 282 | DS | Sense | 320 |
| | | TCCTCCTTGAAATCAATTCCCTTAAGCTCG | | | | |
| | | ATCCTGTTGACGAGGGTGTCTCCCTCAAAC | | | | |
| | | TTGACTTCAGCACGTGTCTTGTAGTTCCCG | | | | |
| | | TCGTCCTTGAAAGAGATGGTCCTCTCCTGC | | | | |
| | | ACGTATCCCTCAGGCATGGCGCTCTTGAAG | | | | |
| | | AAGTCGTGCCGCTTCATATGATCTGGGTAT | | | | |

TABLE 5-continued

| Trigger # | Trigger alias | Sequence (5'-3') | Length | DS/SS | S/AS | SEQ ID |
|---|---|---|---|---|---|---|
| | | CTTGAAAAGCATTGAACACCATAAGAGAA | | | | |
| | | AGTAGTGACAAGTGTTGGCTCTCCCTATAG | | | | |
| | | TGAGTCGTATTAG | | | | |
| 2 | GFP234 Mir390 | CTAATACGACTCACTATAGGGAGAGGTGC TATCCTACCTGAGCTTTTTCCGTCCTCCTTG AAATCAATTCCCTTAAGCTCGATCCTGTTG ACGAGGGTGTCTCCCTCAAACTTGACTTCA GCACGTGTCTTGTAGTTCCCGTCGTCCTTG AAAGAGATGGTCCTCTCCTGCACGTATCCC TCAGGCATGGCGCTCTTGAAGAAGTCGTGC CGCTTCATATGATCTGGGTATCTTGAAAAG CATTGAACACCATAAGAGAAAGTAGTGAC AAGTGTTGGCCCTTGTCTATCCCTCCTGAG CTTCTCCCTATAGTGAGTCGTATTAG | 325 | DS | Sense | 321 |
| 3 | GFP234 Mir390 X2 | CTAATACGACTCACTATAGGGAGAAGCTC AGGAGGGATAGACAAGGGGTGCTATCCTA CCTGAGCTTTTTCCGTCCTCCTTGAAATCA ATTCCCTTAAGCTCGATCCTGTTGACGAGG GTGTCTCCCTCAAACTTGACTTCAGCACGT GTCTTGTAGTTCCCGTCGTCCTTGAAAGAG ATGGTCCTCTCCTGCACGTATCCCTCAGGC ATGGCGCTCTTGAAGAAGTCGTGCCGCTTC ATATGATCTGGGTATCTTGAAAAGCATTGA ACACCATAAGAGAAAGTAGTGACAAGTGT TGGCAAGCTCAGGTAGGATAGCACCCCTT GTCTATCCCTCCTGAGCTTCTCCCTATAGT GAGTCGTATTAG | 368 | DS | Sense | 322 |
| 4 | GFP234 Mir390_Sense | CTAATACGACTCACTATAGGGAGAGGTGC TATCCTACCTGAGCTTTTTCCGTCCTCCTTG AAATCAATTCCCTTAAGCTCGATCCTGTTG ACGAGGGTGTCTCCCTCAAACTTGACTTCA GCACGTGTCTTGTAGTTCCCGTCGTCCTTG AAAGAGATGGTCCTCTCCTGCACGTATCCC TCAGGCATGGCGCTCTTGAAGAAGTCGTGC CGCTTCATATGATCTGGGTATCTTGAAAAG CATTGAACACCATAAGAGAAAGTAGTGAC AAGTGTTGGCCCTTGTCTATCCCTCCTGAG CT | 301 | SS | Sense | 323 |

TABLE 5-continued

| Trigger # | Trigger alias | Sequence (5'-3') | Length | DS/SS | S/AS | SEQ ID |
|---|---|---|---|---|---|---|
| 5 | GFP234 Mir390_Antisense | CTAATACGACTCACTATAGGGAGAGCCAA CACTTGTCACTACTTTCTCTTATGGTGTTCA ATGCTTTTCAAGATACCCAGATCATATGAA GCGGCACGACTTCTTCAAGAGCGCCATGCC TGAGGGATACGTGCAGGAGAGGACCATCT CTTTCAAGGACGACGGGAACTACAAGACA CGTGCTGAAGTCAAGTTTGAGGGAGACAC CCTCGTCAACAGGATCGAGCTTAAGGGAA TTGATTTCAAGGAGGACGGAAA | 258 | SS | Antisense | 324 |
| 6 | GFP234 Mir390_Helicase | CTAATACGACTCACTATAGGGAGAGGTGC TATCCTACCTGAGCTTTTTCCGTCCTCCTTG AAATCAATTCCCTTAAGCTCGATCCTGTTG ACGAGGGTGTCTCCCTCAAACTTGACTTCA GCACGTGTCTTGTAGTTCCCGTCGTCCTTG AAAGAGATGGTCCTCTCCTGCACGTATCCC TCAGGCATGGCGCTCTTGAAGAAGTCGTGC CGCTTCATATGATCTGGGTATCTTGAAAAG CATTGAACACCATAAGAGAAAGTAGTGAC AAGTGTTGGCGCTACTGGACTTTCGCCATC TAGGGTGCAGCATTCGGGCTGCTTCGCCTA CCTTGTCTATCCCTCCTGAGCTTCTCCCTAT AGTGAGTCGTATTAG | 375 | DS | Sense | 325 |
| 7 | GFP234 Mir390_Helicase_Sense | CTAATACGACTCACTATAGGGAGAAGCTC AGGAGGGATAGACAAGGGGTGCTATCCTA CCTGAGCTTTTTCCGTCCTCCTTGAAATCA ATTCCCTTAAGCTCGATCCTGTTGACGAGG GTGTCTCCCTCAAACTTGACTTCAGCACGT GTCTTGTAGTTCCCGTCGTCCTTGAAAGAG ATGGTCCTCTCCTGCACGTATCCCTCAGGC ATGGCGCTCTTGAAGAAGTCGTGCCGCTTC ATATGATCTGGGTATCTTGAAAAGCATTGA ACACCATAAGAGAAAGTAGTGACAAGTGT TGGCAAGCTCAGGTAGGATAGCACCCCTT GTCTATCCCTCCTGAGCT | 344 | SS | Sense | 326 |
| 8 | GFP234 Mir390_Helicase_AntiSense | CTAATACGACTCACTATAGGGAGAAGCTC AGGAGGGATAGACAAGGGGTGCTATCCTA CCTGAGCTTGCCAACACTTGTCACTACTTT CTCTTATGGTGTTCAATGCTTTTCAAGATA CCCAGATCATATGAAGCGGCACGACTTCTT | 394 | SS | Antisense | 327 |

TABLE 5-continued

| Trigger # | Trigger alias | Sequence (5'-3') | Length | DS/SS | S/AS | SEQ ID |
|---|---|---|---|---|---|---|
| | | CAAGAGCGCCATGCCTGAGGGATACGTGC | | | | |
| | | AGGAGAGGACCATCTCTTTCAAGGACGAC | | | | |
| | | GGGAACTACAAGACACGTGCTGAAGTCAA | | | | |
| | | GTTTGAGGGAGACACCCTCGTCAACAGGA | | | | |
| | | TCGAGCTTAAGGGAATTGATTTCAAGGAG | | | | |
| | | GACGGAAAAAGCTCAGGTAGGATAGCACC | | | | |
| | | CCTTGTCTATCCCTCCTGAGCTTAGGCGAA | | | | |
| | | GCAGCCCGAATGCTGCACCCTAGATGGCG | | | | |
| | | AAAGTCCAGTAGC | | | | |
| 9 | GFP2234 Mir390_Mir4376 | CTAATACGACTCACTATAGGGAGAGGTGC | 347 | DS | Sense | 328 |
| | | TATCCTACCTGAGCTTTTTCCGTCCTCCTTG | | | | |
| | | AAATCAATTCCCTTAAGCTCGATCCTGTTG | | | | |
| | | ACGAGGGTGTCTCCCTCAAACTTGACTTCA | | | | |
| | | GCACGTGTCTTGTAGTTCCCGTCGTCCTTG | | | | |
| | | AAAGAGATGGTCCTCTCCTGCACGTATCCC | | | | |
| | | TCAGGCATGGCGCTCTTGAAGAAGTCGTGC | | | | |
| | | CGCTTCATATGATCTGGGTATCTTGAAAAG | | | | |
| | | CATTGAACACCATAAGAGAAAGTAGTGAC | | | | |
| | | AAGTGTTGGCTCGCAGGAGAGATGACACC | | | | |
| | | AGACCTTGTCTATCCCTCCTGAGCTTCTCC | | | | |
| | | CTATAGTGAGTCGTATTAG | | | | |
| 10 | TAS3 | CTAATACGACTCACTATAGGGAGATTTCTC | 282 | DS | Sense | 329 |
| | | ACCGCTTTTTTTTTCTGTTGTGTATTCTCT | | | | |
| | | TTTTTGACTTGTTGCCTTTCGTTCCTCTACC | | | | |
| | | TACCCCATTCTTCTTGACCTTGTAAGACCTT | | | | |
| | | TTCTTGACCTTGTAAGACCCCGTGTTATCT | | | | |
| | | CTTACGTCTTTATGTTTTGTTTTTTGCAAA | | | | |
| | | TCTTACGTCATGACTTCTTCATGTAAGCTTT | | | | |
| | | GTTTGGTCTCCTTCTTCTTTCCTACTCAACT | | | | |
| | | CTCGTTCTCCTTTCTCCCTATAGTGAGTCGT | | | | |
| | | ATTAG | | | | |
| 11 | TAS3Mir390 | CTAATACGACTCACTATAGGGAGAGGTGC | 325 | DS | Sense | 330 |
| | | TATCCTACCTGAGCTTTTTCTCACCGCTTTT | | | | |
| | | TTTTTTCTGTTGTGTATTCTCTTTTTTGACT | | | | |
| | | TGTTGCCTTTCGTTCCTCTACCTACCCCATT | | | | |
| | | CTTCTTGACCTTGTAAGACCTTTTCTTGACC | | | | |
| | | TTGTAAGACCCCGTGTTATCTCTTACGTCTT | | | | |
| | | TATGTTTTGTTTTTTGCAAATCTTACGTCA | | | | |
| | | TGACTTCTTCATGTAAGCTTTGTTTGGTCTC | | | | |

TABLE 5-continued

| Trigger # | Trigger alias | Sequence (5'-3') | Length | DS/SS | S/AS | SEQ ID |
|---|---|---|---|---|---|---|
| | | CTTCTTCTTTCCTACTCAACTCTCGTTCTCC | | | | |
| | | TTCCTTGTCTATCCCTCCTGAGCTTCTCCCT | | | | |
| | | ATAGTGAGTCGTATTAG | | | | |
| 12 | GUS234 | GCCACTTGCAAAGTCCCGCTAGTGCCT | 236 | DS | Sense | 331 |
| | | TGTCCAGTTGCAACCACCTGTTGATCC | | | | |
| | | GCATCACGCAGTTCAACGCTGACATCA | | | | |
| | | CCATTGGCCACCACCTGCCAGTCAACA | | | | |
| | | GACGCGTGGTTACAGTCTTGCGCGACA | | | | |
| | | TGCGTCACCACGGTGATATCGTCCACC | | | | |
| | | CAGGTGTTCGGCGTGGTGTAGAGCATT | | | | |
| | | ACGCTGCGATGGATTCCGGCATAGTTA | | | | |
| | | AAGAAATCATGGAAGTAAGC | | | | |
| 13 | GUS234Mir390 | GGTGCTATCCTACCTGAGCTTCCACTT | 278 | DS | Sense | 332 |
| | | GCAAAGTCCCGCTAGTGCCTTGTCCAG | | | | |
| | | TTGCAACCACCTGTTGATCCGCATCAC | | | | |
| | | GCAGTTCAACGCTGACATCACCATTGG | | | | |
| | | CCACCACCTGCCAGTCAACAGACGCGT | | | | |
| | | GGTTACAGTCTTGCGCGACATGCGTCA | | | | |
| | | CCACGGTGATATCGTCCACCCAGGTGT | | | | |
| | | TCGGCGTGGTGTAGAGCATTACGCTGC | | | | |
| | | GATGGATTCCGGCATAGTTAAAGAAAT | | | | |
| | | CATGGAAGTAAGCCTTGTCTATCCCTC | | | | |
| | | CTGAGCTC | | | | |

Figure 10A:
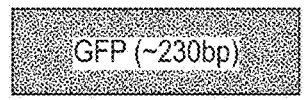
FIGS. 10A-E are schematic representations of dsRNA constructs of the present disclosure.
Figure 10B:
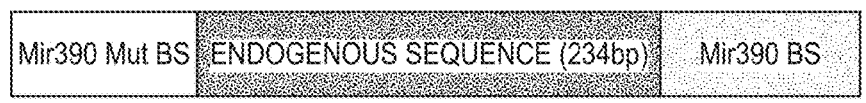
Figure 10C:
Figure 10D:
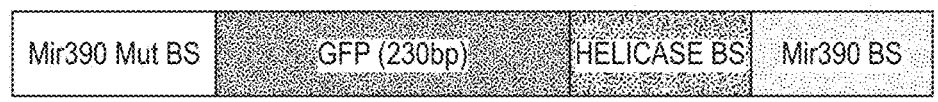
Figure 10E:
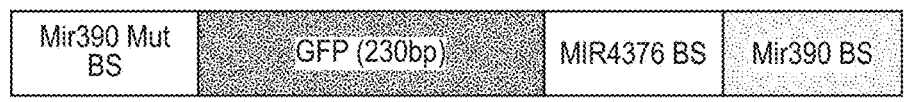

GFP234 (FIG. 10A; Trigger #1), GFP234Mir390 (Trigger #2), TAS3 (Trigger #10) and TAS3Mir390 (FIG. 10B, Trigger #11) were prepared as provided in Example 1. A final concentration of 50 μg/ml dsRNA diluted with 0.1 mM EDTA was used. Treatment was performed by gently shaking the seeds in the solution for 24 hours in a dark growth chamber at 15° C. followed by washing with water three times for one minute. After treatment, seeds were germinated either on wet paper or in soil and grown at about 25° C. with a 16 hour photoperiod. The plants germinated in soil were watered with tap water as necessary. Seeds that were treated with a similar solution not containing dsRNA (e.g., 0.1 mM EDTA "EDTA") were germinated and grown alongside the treated plants as a control.

Total RNA was extracted from whole seedlings, leaves or roots of germinated seeds seven, 14 and 30 days post treatment. For seeds that were germinated on paper, the entire seedling was harvested after seven days. For seeds that were germinated in soil, the leaves and roots were harvested and analyzed separately 14 and 30 days after treatment.

cDNA was prepared using oligo-dT primers and the expression levels of TAS3, ARF3 and ARF4 was determined by real-time PCR with SYBR Green (Quanta BioSciences).

Figure 11A:
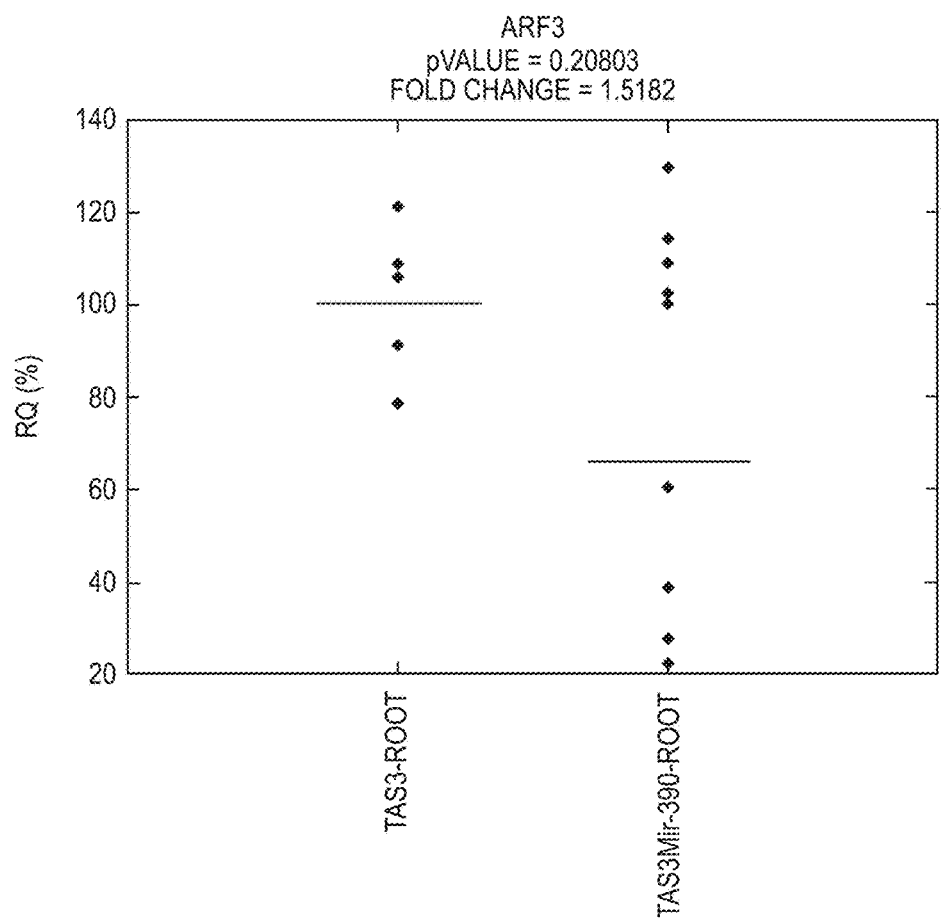
FIGS. 11A-B present graphs showing real-time PCR analyses of ARF3 and ARF4 mRNA expression in roots 14 days after seed treatment according to an embodiment of the present disclosure.
Figure 11B:
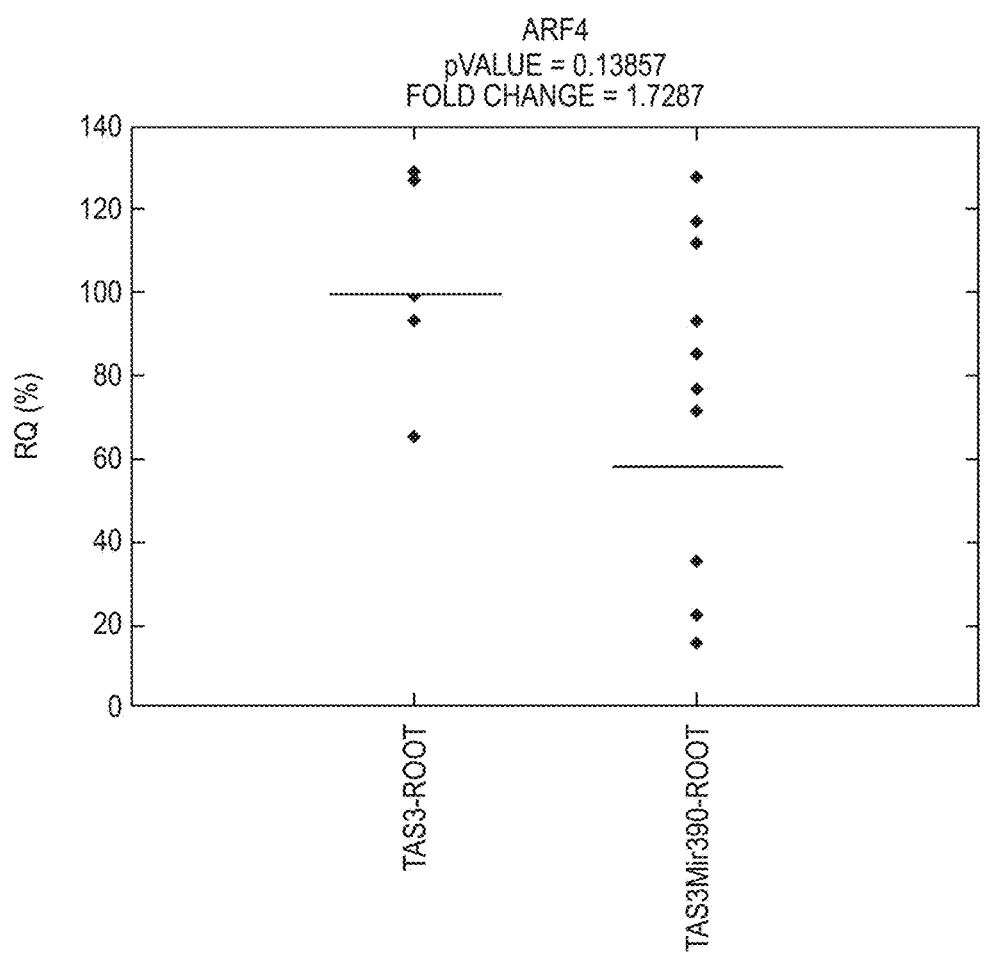

The results are presented in FIG. 11A-E. The house-keeping genes Expressed and Tip41 were used as endogenous control genes to normalize for input RNA amounts. ARF3 and ARF4 genes are regulated by the TAS3 system and their expression is predicted to decrease following TAS3Mir390 treatment. No significant difference in TAS3, ARF3 or ARF4 expression was detected in seedlings when comparing the TAS3 construct with the TAS3Mir390 construct seven days after treatment (t-test, p-value>0.05). Similarly, no significant difference in TAS3, ARF3 or ARF4 expression was detected in leaves when comparing the two constructs 14 days after treatment. When comparing expression levels in roots 14 days after treatment, a down-regulation trend was observed for ARF3 and ARF4 genes following treatment with the TAS3Mir390 construct (FIGS. 11A-B). FIG. 11A shows relative quantification of ARF3 mRNA following treatment with either TAS3 Insert or Mir390BS TAS3 dsRNA constructs. Each point represents the expression value per individual plant. Expression values were normalized to the average expression values of all plants treated with TAS3 Insert, which was set to 100%. The red line represents the normalized average expression values for each treatment. FIG. 11B shows the same analysis for ARF4 mRNA levels.

Figure 11C:
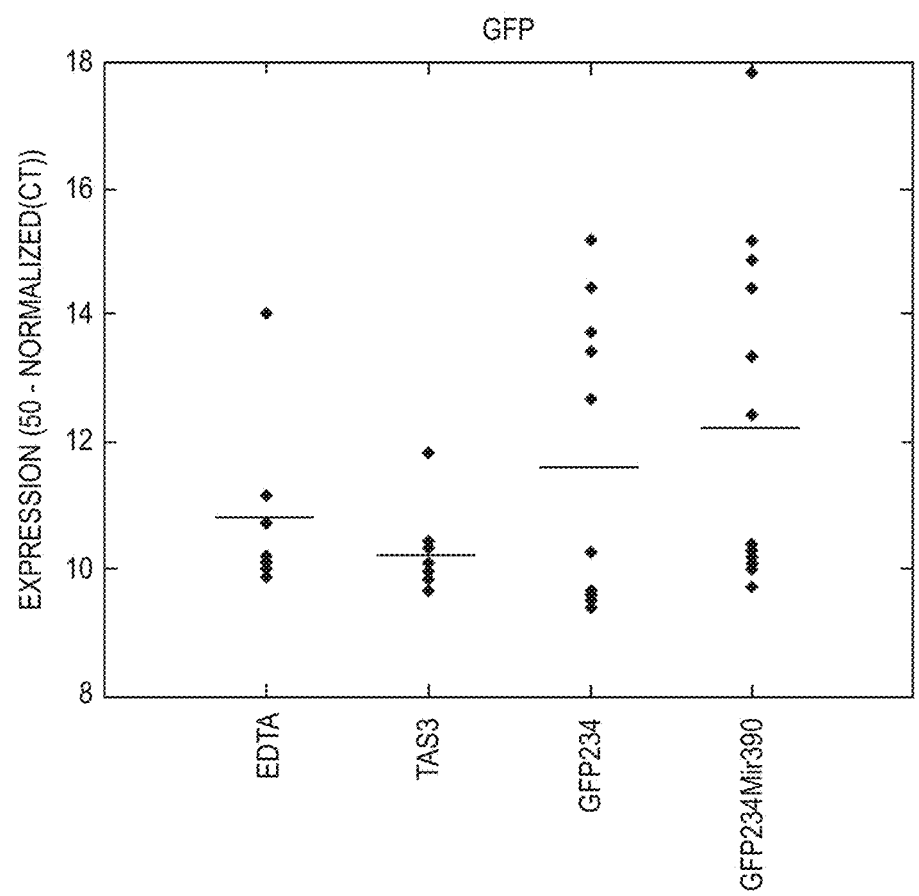
FIGS. 11C-E present graphs showing the results of real-time PCR analyses of GFP in seedlings seven days after seed treatment according to an embodiment of the present disclosure.
Figure 11D:
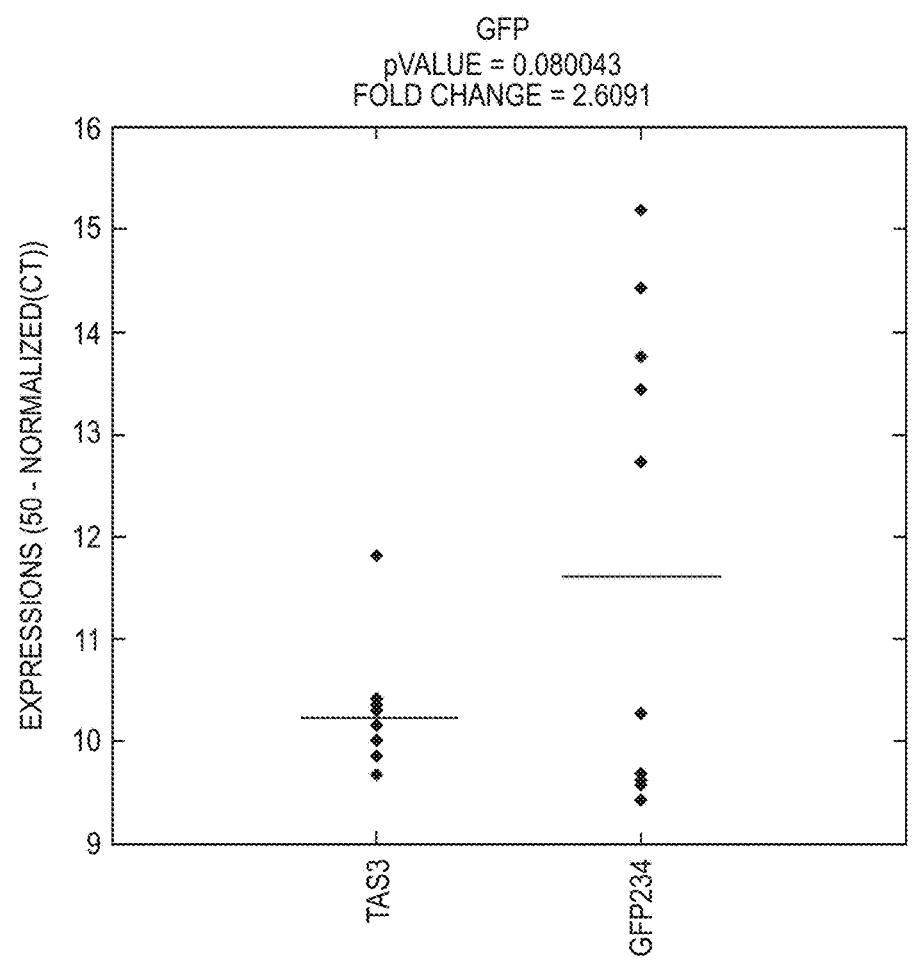
Figure 11E:
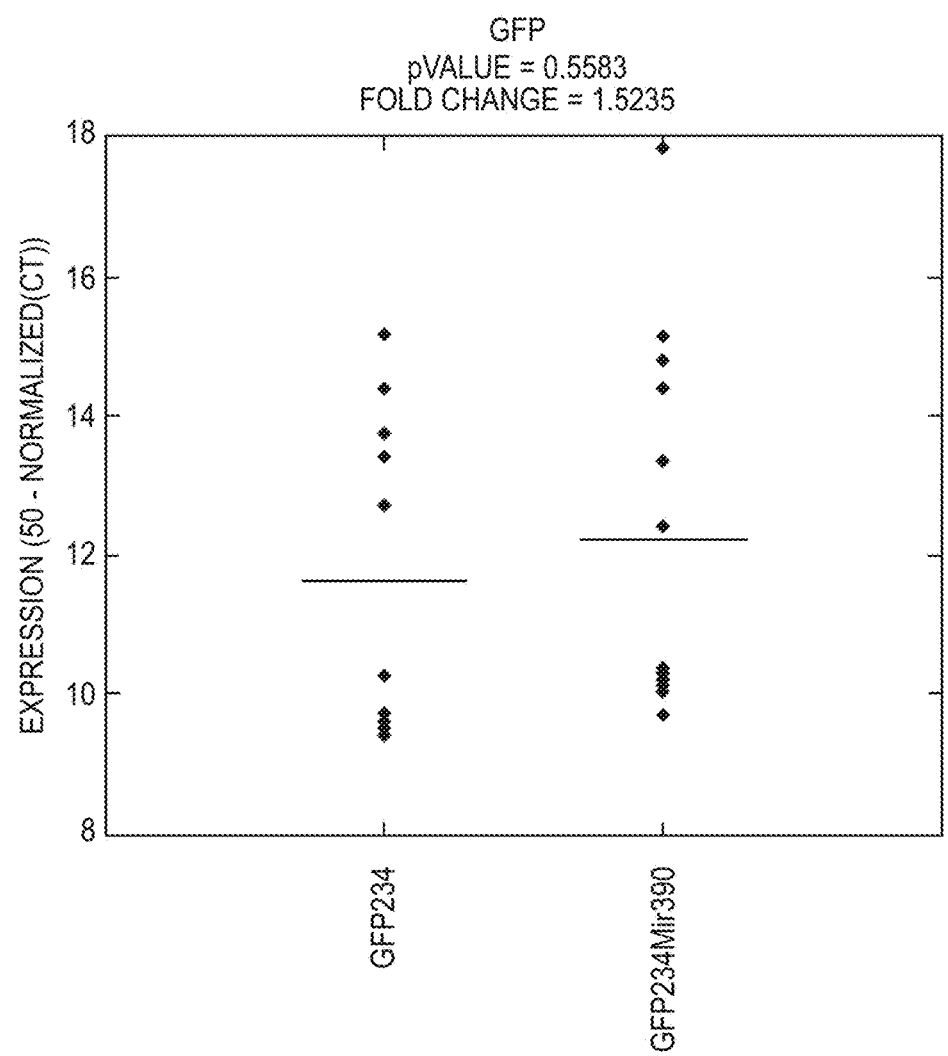
Figure 11F:
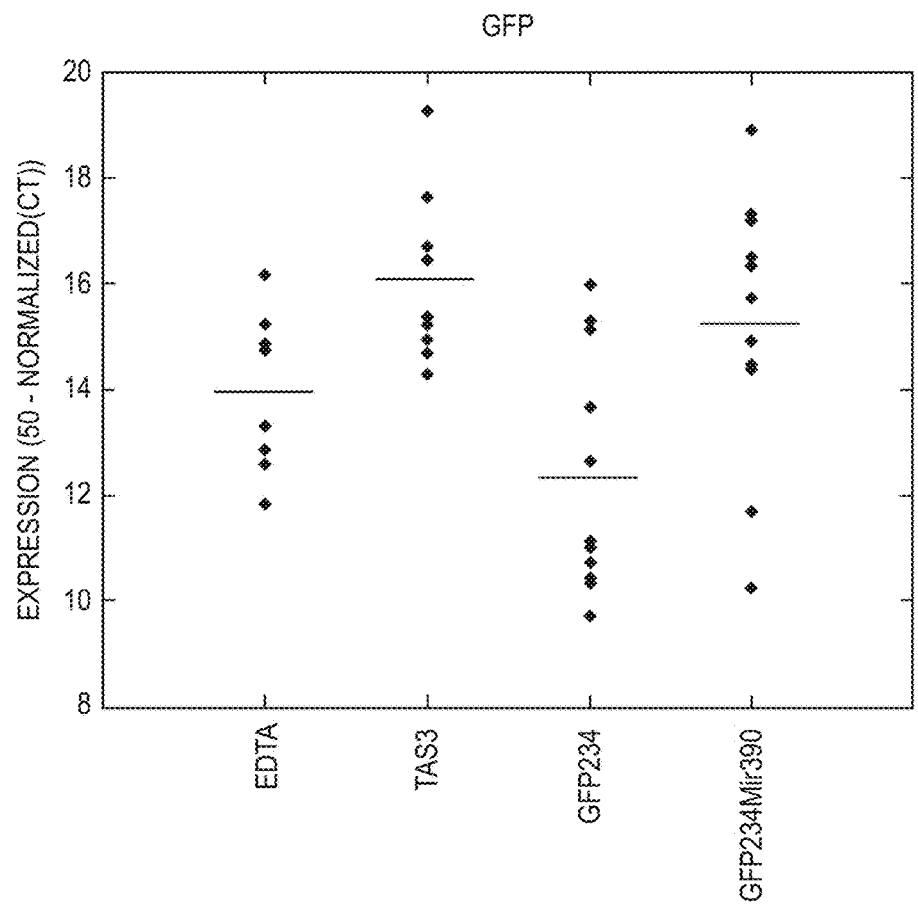
FIG. 11F presents a graph showing the results of real-time PCR analyses of GFP in leaves 30 days after seed treatment according to an embodiment of the present disclosure.

The RNA extracted from seven-day old seedlings, as well as RNA extracted from 30-day old roots and 30-day old leaves was used in a second cDNA reaction with random primers and then subjected to real-time PCR with SYBR Green (Quanta BioSciences). The primers used for real-time were derived from the GFP sequence that appears in the dsRNA constructs. Therefore, this analysis provides an indication for the presence of the dsRNA that was used for seed treatment and/or for RNA that was synthesized from this dsRNA in the plant tissue. Expressed and Tip41 were used as endogenous control genes. For seven day old seedlings, a 2.6 fold difference in GFP level was observed in plants treated with GFP234 compared to plants treated with TAS3 (t-test, p-value=0.08). However, no significant difference in GFP level was observed when comparing between GFP234 and GFP234Mir390 treatments (FIGS. 11C-E). FIG. 11C shows normalized Ct values for all treatments analyzed; for each RNA sample tested, the Ct value obtained from the real-time amplification plot was normalized to the average Ct value of the two endogenous control genes. This value was then subtracted from the number 50 to assign larger values for higher expression levels. Each dot represents one plant and the red line represents the average value per treatment. RNA samples that gave no Ct values were assigned a value of 40. FIG. 11D shows a comparison between GFP234 and TAS3 treatments. FIG. 11E shows a comparison between GFP234 and GFP234Mir390 treatments. For 30 day old roots, no significant difference in GFP level was observed when comparing between GFP234 and GFP234Mir390 treatments. For 30 day old leaves, a significant (t-test, p-value=0.005), 7.1-fold difference in GFP level was observed in plants treated with GFP234Mir390 compared to plants treated with GFP234 (FIG. 11F).

Example 11

Detection of GFP Sequence in Plants Following Seed Treatment with TA-SI dsRNA Constructs In a second experiment, tomato seeds were treated with dsRNA molecules corresponding to GFP234 (Trigger#1), GFP234Mir390 (Trigger#2), GFP234Mir390X2 (Trigger#3), GFP234Mir390 Helicase (Trigger#6), GFP234Mir390 Mir4376 (Trigger#9), TAS3 (Trigger#10) and TAS3Mir390 (Trigger#11) as provided above in Example 10 and Table 5, according to the protocol described in Example 10. A final concentration of 50 µg/ml dsRNA diluted with 0.1 mM EDTA was used. Treatment was performed by gently shaking the seeds in the solution for 24 hours in a dark growth chamber at 15° C. followed by washing with water three times for one minute. After treatment, seeds were germinated on wet paper and grown at about 25° C. with 16 hours photoperiod. Seeds that were treated with EDTA solution alone were germinated and grown alongside the treated plants as a control.

Figure 12A:
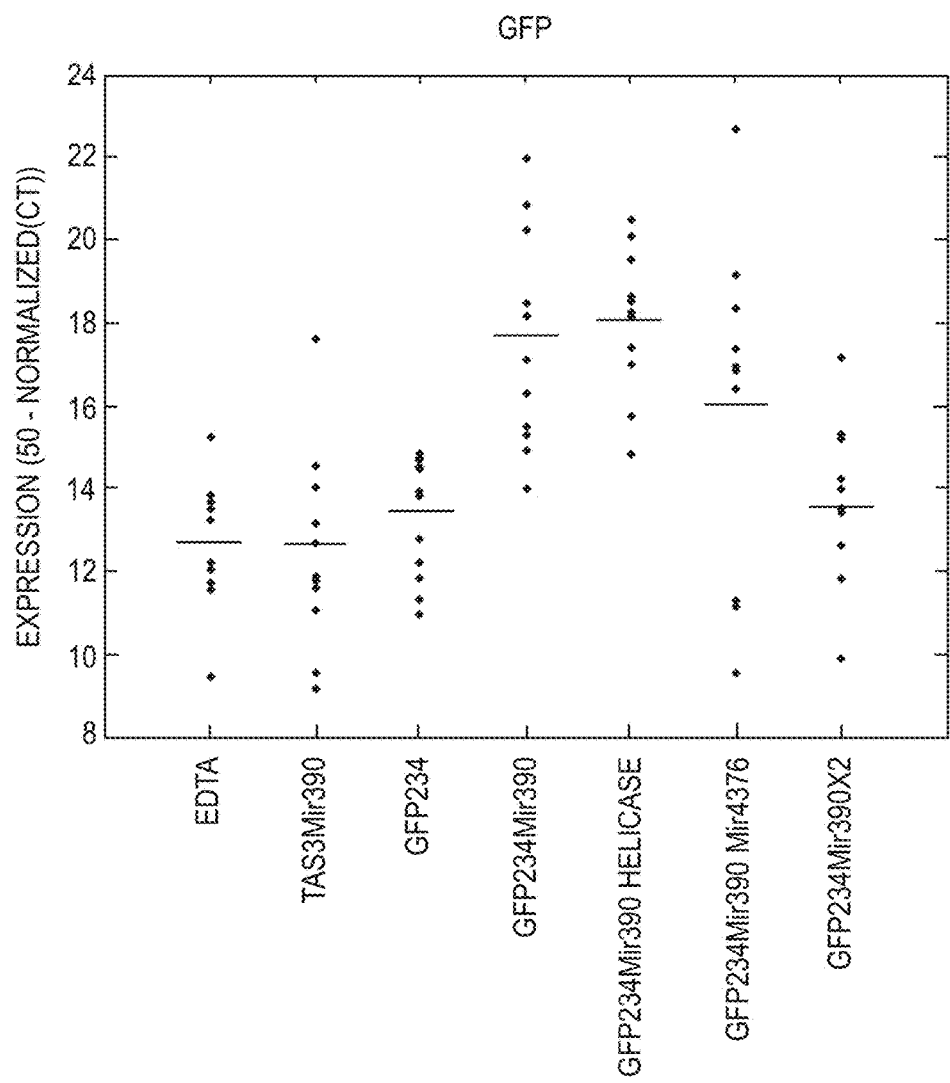
FIGS. 12A-E present graphs showing the results of real-time PCR analyses of GFP in shoots seven days after seed treatment according to an embodiment of the present disclosure.
Figure 12B:
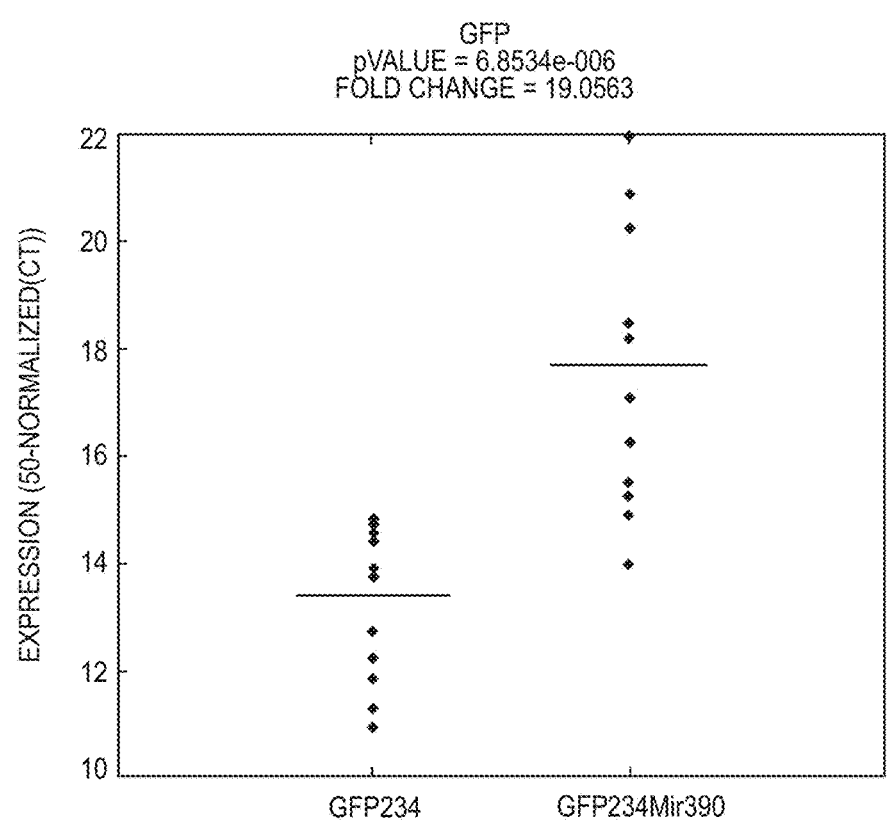
Figure 12C:
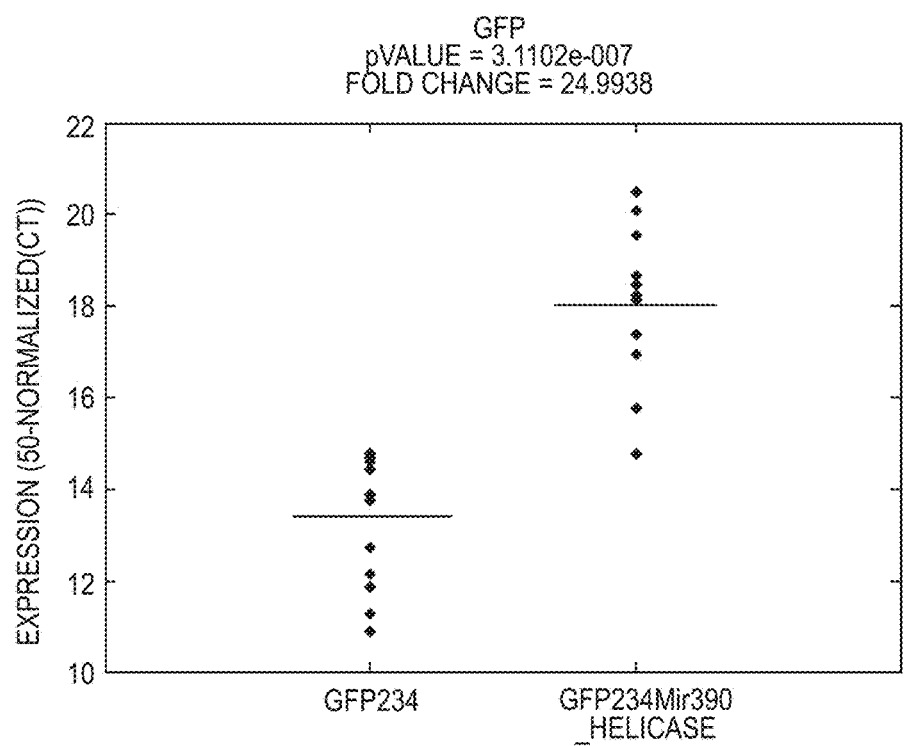
Figure 12D:
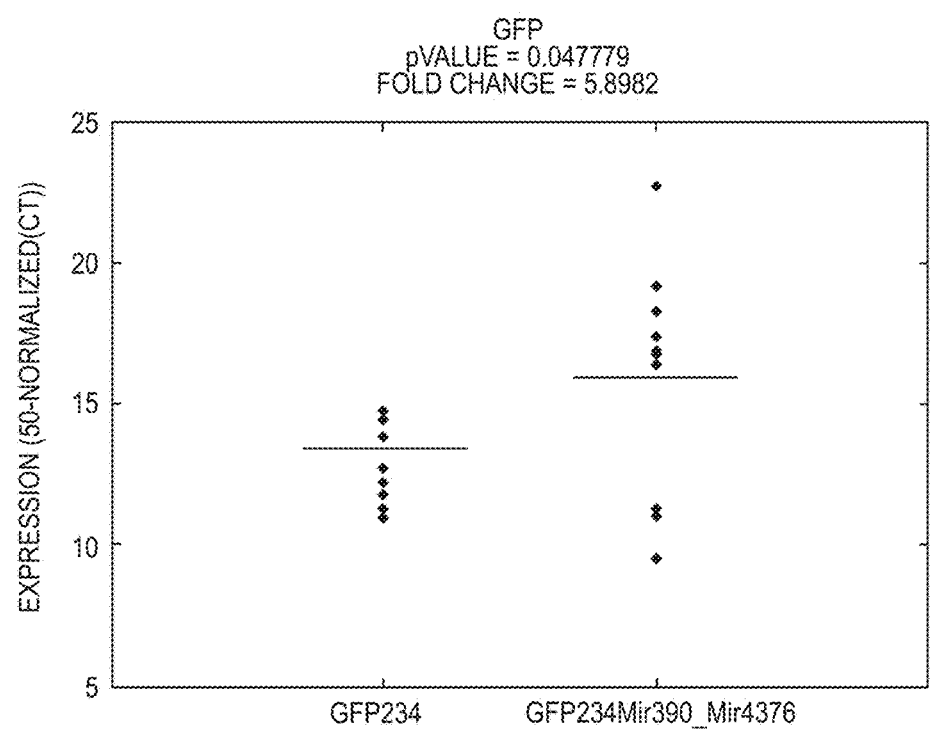
Figure 12E:
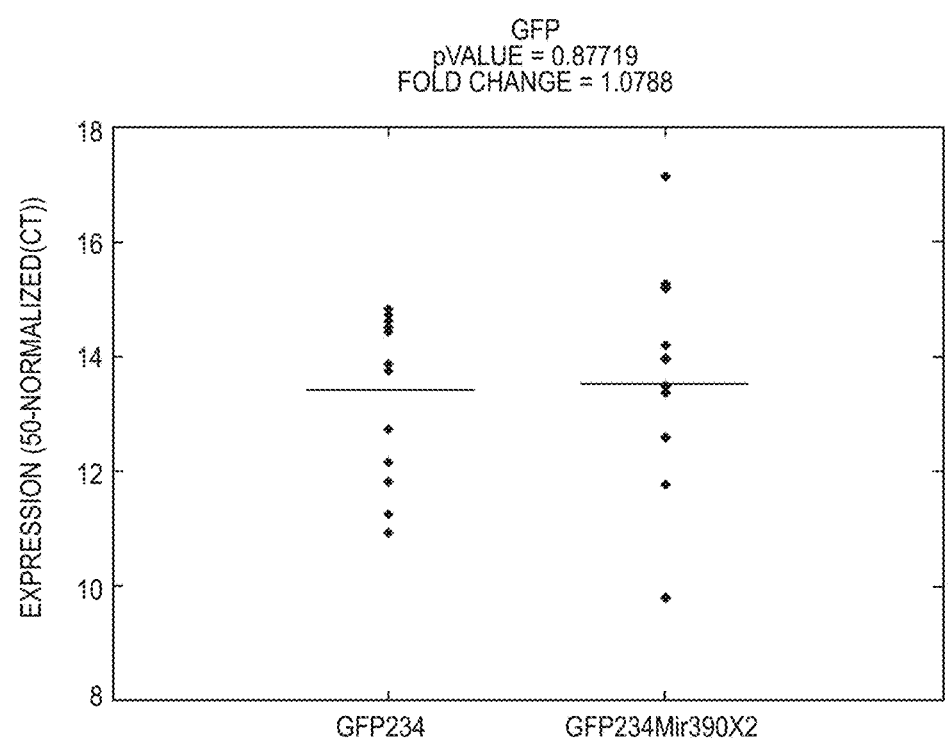

Total RNA was extracted from shoots (including hypocotyl, cotyledon and shoot apical meristem) seven and fourteen days after treatment. cDNA was prepared using random primers and the presence of the GFP sequence was determined and quantified by real-time PCR as described in Example 10. A significant difference in GFP level was observed in plants seven days after treatment with GFP234Mir390, GFP234Mir390_Helicase or GFP234Mir390_Mir4376 dsRNAs compared to treatment with GFP234, TAS3Mir390 or EDTA. The GFP level detected was between 5.9 fold (following treatment with GFP234Mir390_Mir4376) to 25 fold (following treatment with GFP234Mir390 Helicase) higher compared to plants treated with GFP234, with a p-value<0.05 (t-test). No significant difference was detected when comparing GFP234Mir390X2 to GFP234 treatment (FIGS. 12A-E). The analyses were performed as described for FIGS. 11C-F of Example 10. FIG. 12A shows normalized Ct values for all treatments. FIG. 12B shows a comparison between GFP234 and GFP234Mir390 treatments. FIG. 12C shows a comparison between GFP234 and GFP234Mir390_Helicase treatments. FIG. 12D shows a comparison between GFP234 and GFP234Mir390_Mir4376 treatments. FIG. 12E shows a comparison between GFP234 and GFP234Mir390X2 treatments.

Figure 13A:
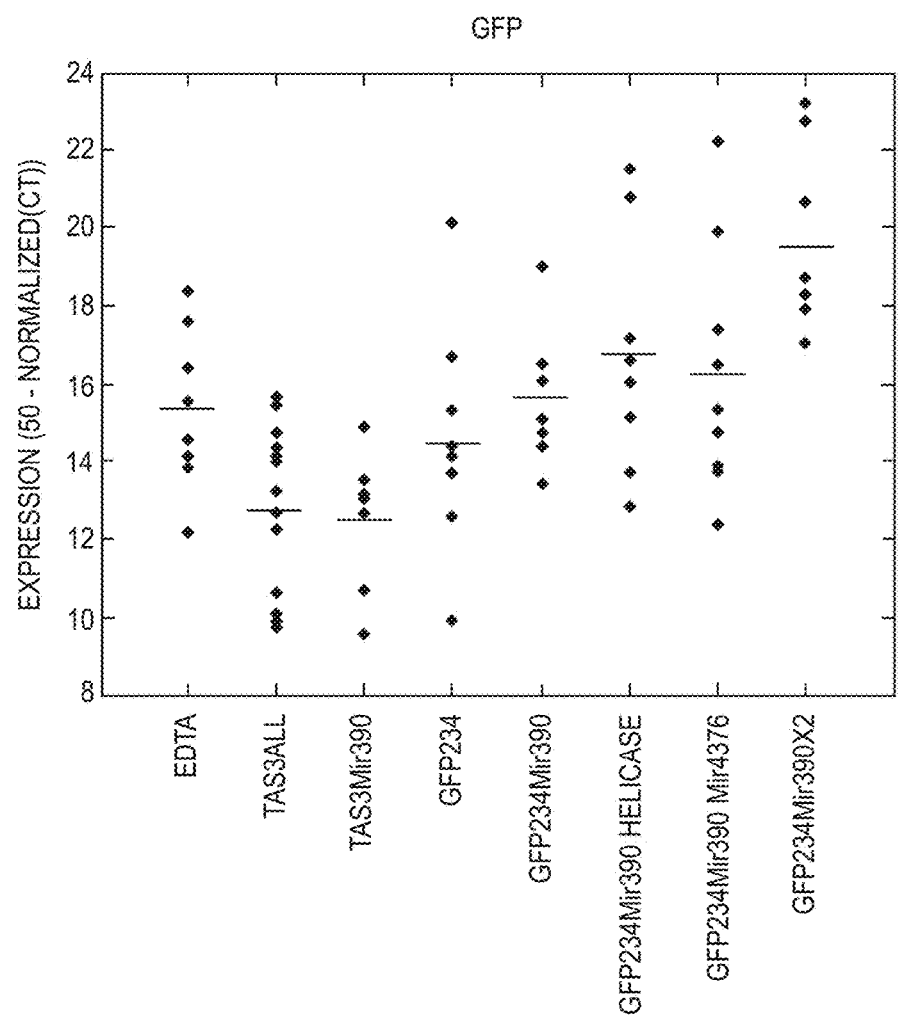
FIGS. 13A-B presents graphs showing the results of real-time PCR analyses of GFP in shoots 14 days after seed treatment according to an embodiment of the present disclosure.
Figure 13B:
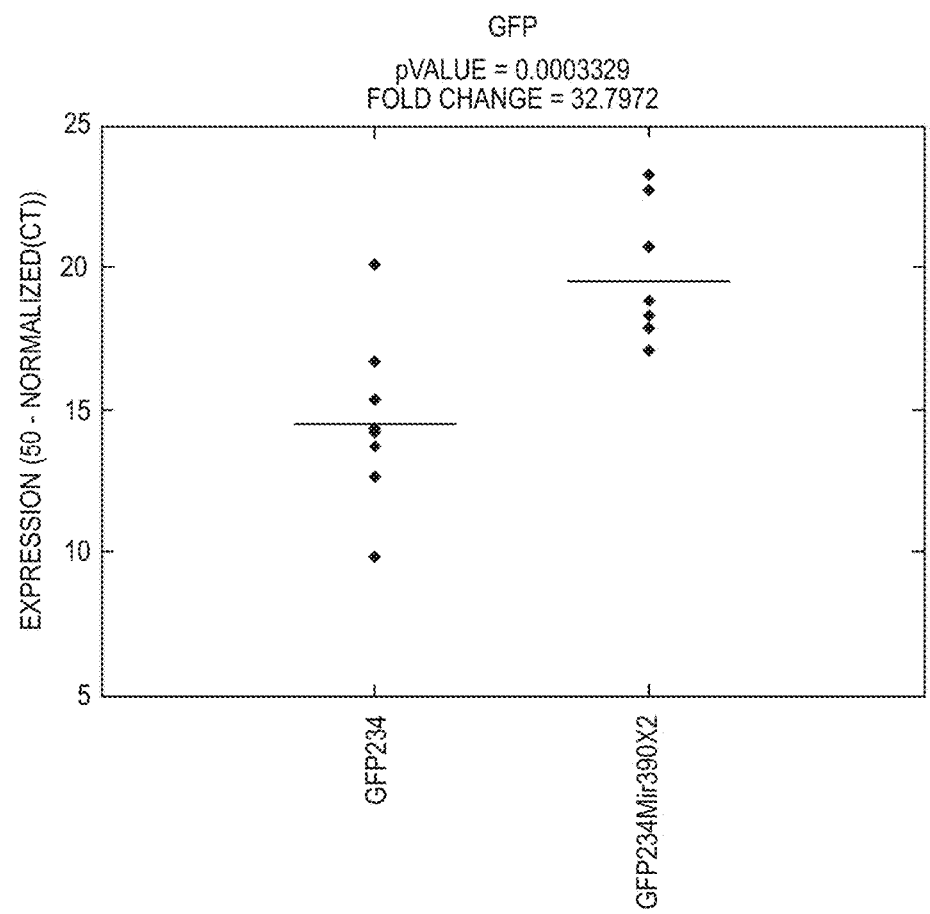

A significant, 33 fold difference in GFP level was observed in plants 14 days after treatment with GFP234Mir390X2 dsRNA compared to treatment with GFP234 (t-test, p-value<0.05). Higher levels of GFP were also detected for GFP234Mir390, GFP234Mir390_Helicase and GFP234Mir390_Mir4376 treatments compared to GFP234 treatment, but with no significant difference (FIGS. 13A-B). The analyses were performed as described for FIGS. 11C-F. FIG. 13A shows normalized Ct values for all treatments. FIG. 13B shows a comparison between GFP234 and GFP234Mir390X2 treatments.

The same cDNA prepared from RNA extracted from seven-day old seedlings, was used in a second real-time PCR, where the expression levels of TAS3, ARF3 and ARF4 was determined as described in Example 10 (except that random primers, and not oligo-dT primers were used in the cDNA reaction). No significant difference in TAS3, ARF3 or ARF4 expression was detected in seedlings when comparing between TAS3 and TAS3Mir390 treatments (t-test, p-value>0.05).

Example 12

Detection of GFP Sequence in Plants Following Seed Treatment with TA-SI dsRNA Constructs Tomato seeds were treated with dsRNA molecules corresponding to GFP234 (Trigger#1), GFP234Mir390_Helicase (Trigger#6) and GFP234Mir390_Mir4376 (Trigger#9), as provided above in Example 10 and Table 4, according to the protocol described in Example 1. A final concentration of 50 µg/ml dsRNA diluted with 0.1 mM EDTA was used. Treatment was performed by gently shaking the seeds in the solution for 24 hours in a dark growth chamber at 15° C. followed by washing with water three times for one minute. After treatment, seeds were germinated on wet paper and grown at about 25° C. with 16 hours photoperiod. Seeds that were treated with EDTA solution alone were germinated and grown alongside the treated plants as a control.

Total RNA was extracted from shoots (including hypocotyl, cotyledon and shoot apical meristem) seven days after treatment. cDNA was prepared using random primers and the presence of the GFP sequence was determined and quantified by real-time PCR as described in Example 10. No significant difference in GFP levels was observed when comparing the GFP234 treated plants to the GFP234Mir390_Helicase or GFP234Mir390_Mir4376 treated plants (Dunnett's test).

Example 13

Detection of GFP Sequence in Plants Following Seed Treatment with TA-SI dsRNA Constructs Tomato seeds were treated with dsRNA molecules corresponding to GFP234 (Trigger#1), GFP234Mir390 (Trigger#2), GFP234Mir390X2 (Trigger#3), GFP234Mir390_Helicase (Trigger#6), GFP234Mir390_Mir4376 (Trigger#9), TAS 3 (Trigger#10) and TAS3Mir390 (Trigger#11) as provided above in Example 10 and Table 5, according to the protocol described in Example 1. A final concentration of 50 µg/ml dsRNA diluted with 0.1 mM EDTA was used. Treatment was performed by gently shaking the seeds in the solution for 24 hours in a dark growth chamber at 15° C. followed by washing with water three times for one minute. After treatment, seeds were germinated on wet paper and grown at about 25° C. with 16 hours photoperiod. Seeds that were treated with EDTA solution alone were germinated and grown alongside the treated plants as a control.

Figure 14A:
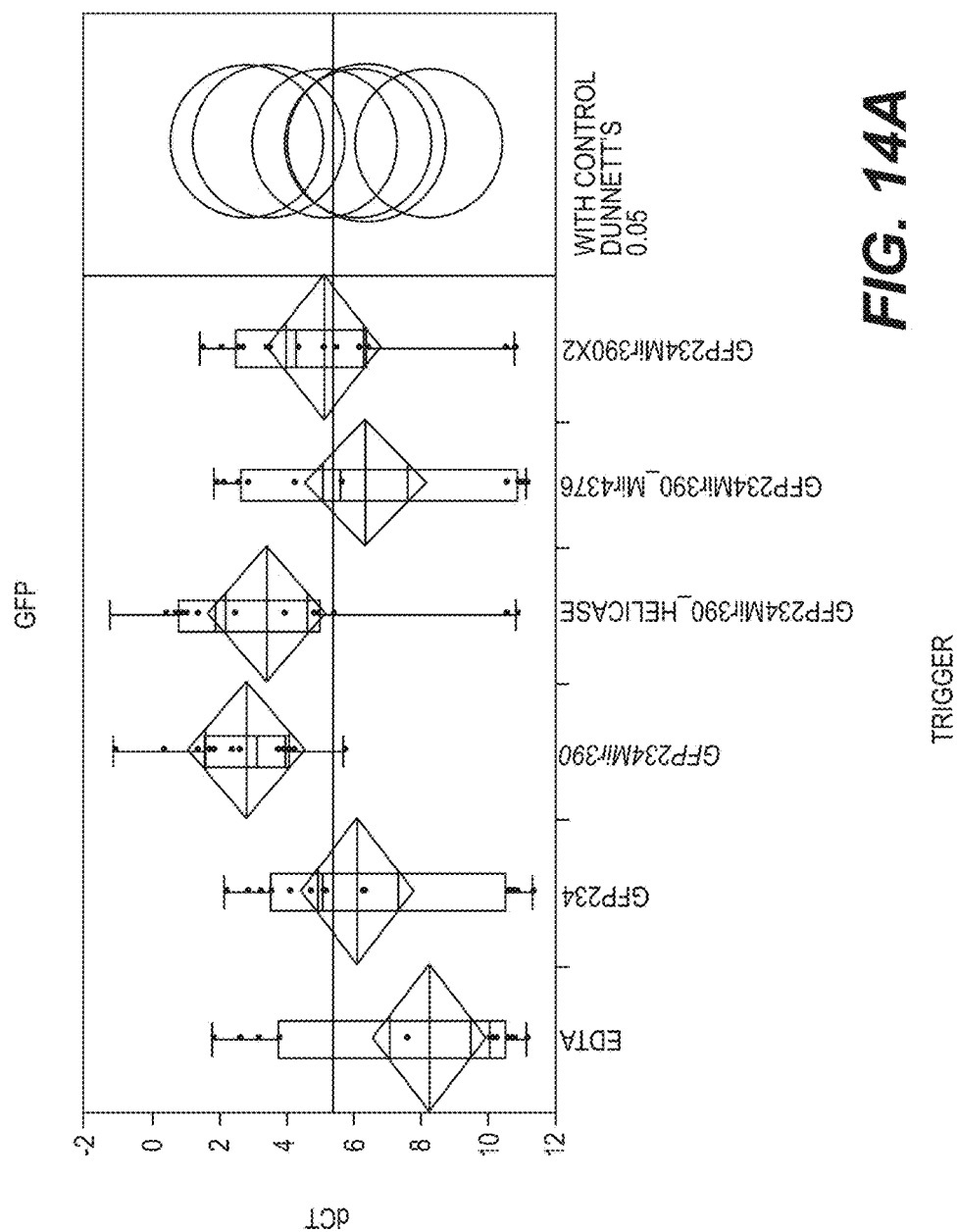
FIGS. 14A-B presents graphs showing the results of real-time PCR analyses of GFP in shoots seven days (A) and 14 days (B), according to an embodiment of the present disclosure.
Figure 14B:
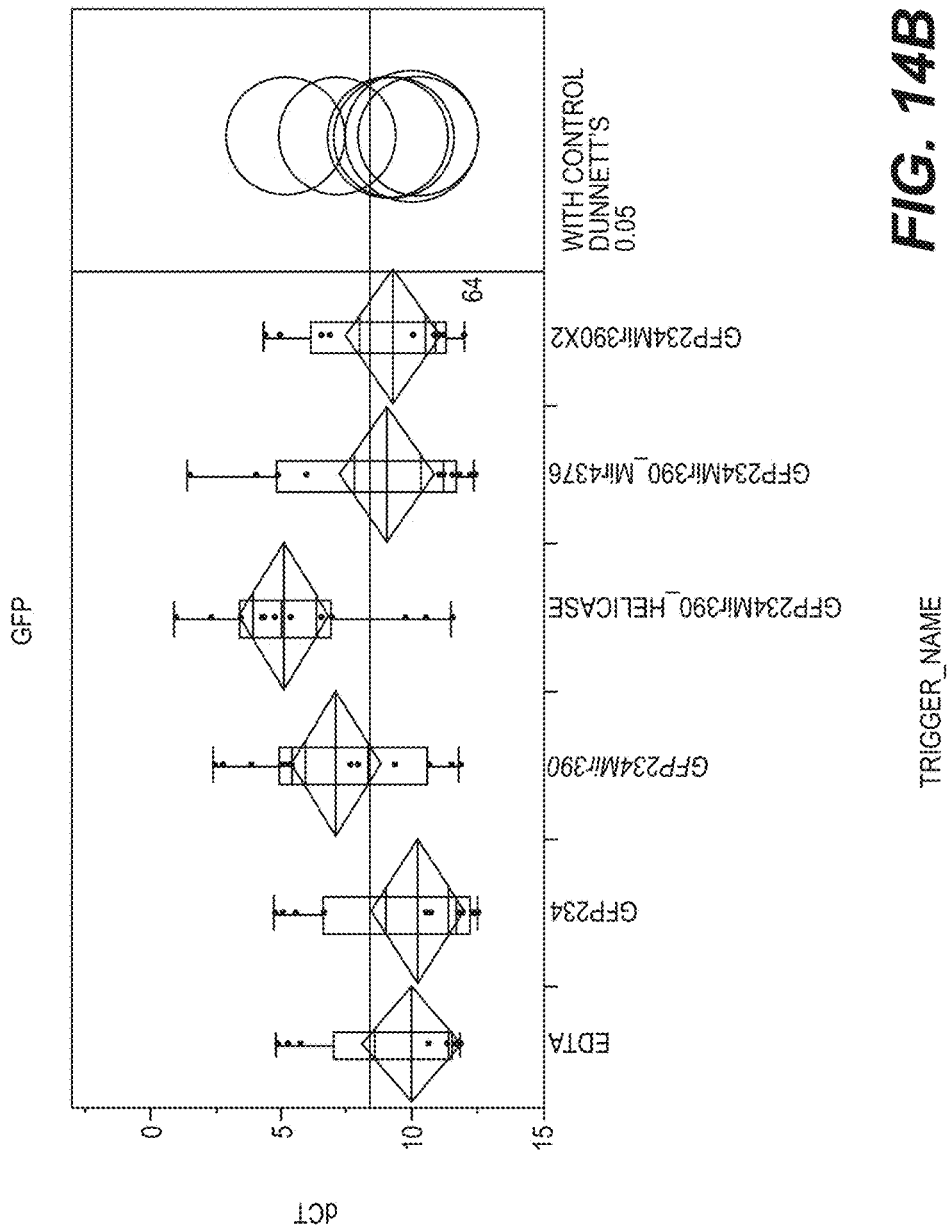

Total RNA was extracted from shoots (including hypocotyl, cotyledon and shoot apical meristem) seven and 14 days after treatment. cDNA was prepared using random primers and the presence of the GFP sequence was determined and quantified by real-time PCR as described in Example 10. Seven days after treatment, a significant, 10-fold difference in GFP level was observed in plants treated with GFP234Mir390 compared to plants treated with GFP234 (Dunnett's test, p-value=0.035). A 6.6-fold difference in GFP level was observed in plants following treatment with GFP234Mir390_Helicase compared to treatment with GFP234 (Dunnett's test, p-value=0.11). For 14 days old plants, a significant, 34-fold difference in GFP level was observed in plants treated with GFP234Mir390_Helicase compared to plants treated with GFP234 (Dunnett's test, p-value=0.0004). An 8.5-fold difference in GFP level was observed in plants following treatment with GFP234Mir390 compared to treatment with GFP234 (Dunnett's test, p-value=0.058). FIG. 14A shows normalized Ct values seven days after treatment. FIG. 14B shows normalized Ct values 14 days after treatment. The analysis was performed essentially as described for FIG. 11C-F, except that instead of subtracting the normalized Ct values from the number 50 to assign larger values for higher GFP levels, an inverse y-axis is presented.

RNA extracted from seven-day old shoots treated with TAS3 (Trigger#10) and TAS3Mir390 (Trigger#11) dsRNAs was used in a second real-time PCR to determine the expression levels of TAS3, ARF3 and ARF4 as described in Example 11. A significant, 1.3-fold up-regulation in ARF4 expression was detected in plants following treatment with TAS3Mir390 compared to treatment with TAS3 (Dunnett's test, p-value=0.05). No significant difference in TAS3 or ARF3 expression was detected in those plants.

Example 14

Detection of GUS Sequence in Plants Following Seed Treatment with TA-SI dsRNA Constructs Tomato seeds were treated with dsRNA molecules corresponding to GUS234 (Trigger#12) and GUS234Mir390 (Trigger#13), as provided above in Example 10 and Table 5, according to the protocol described in Example 1. A final concentration of 50 µg/ml dsRNA diluted with 0.1 mM EDTA was used. Treatment was performed by gently shaking the seeds in the solution for 24 hours in a dark growth chamber at 15° C. followed by washing with water three times for one minute. After treatment, seeds were germinated on wet paper and grown at about 25° C. with 16 hours photoperiod. Seeds that were treated with EDTA solution alone were germinated and grown alongside the treated plants as a control.

Figure 15B:
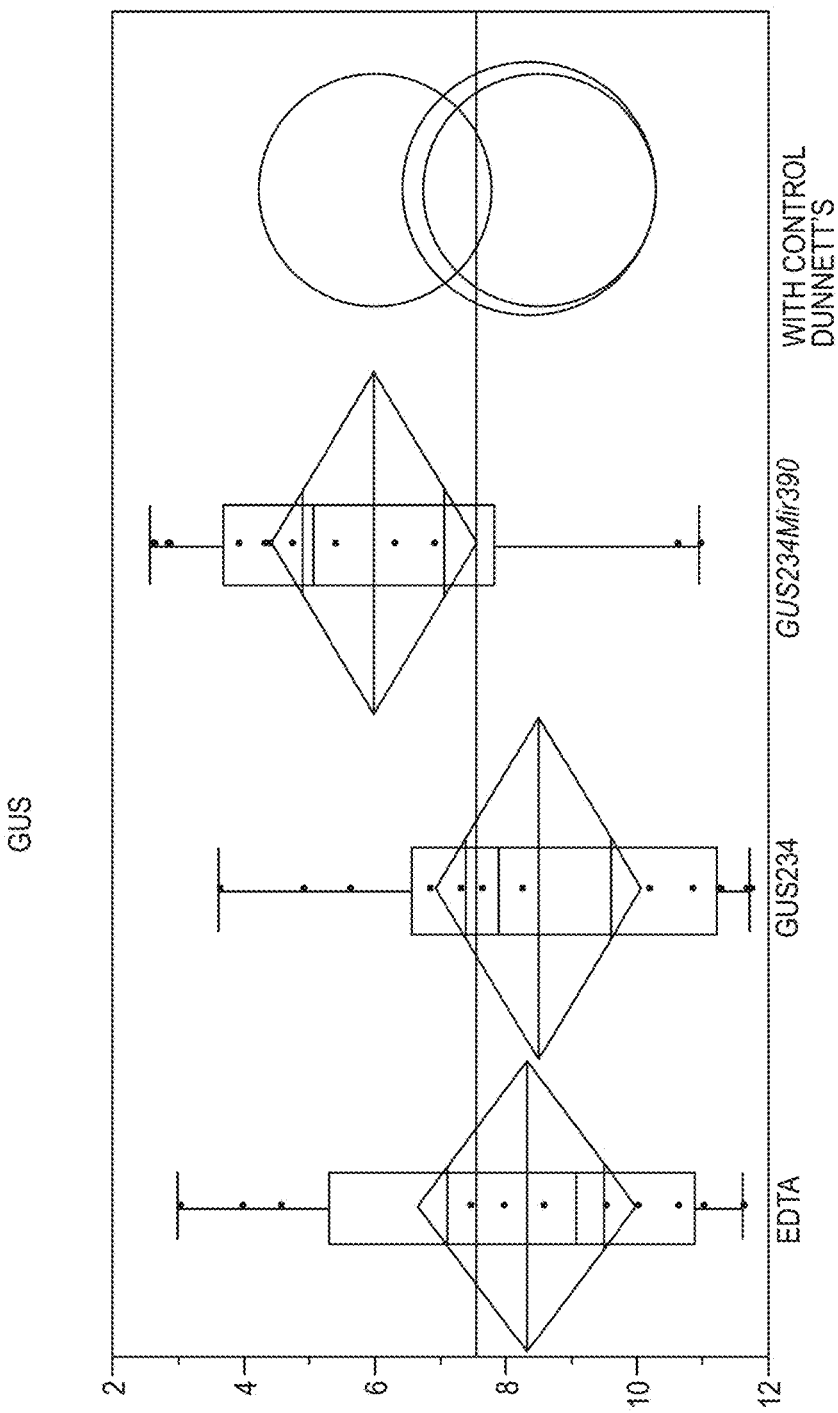

Total RNA was extracted from shoots (including hypocotyl, cotyledon and shoot apical meristem) seven and 14 days after treatment. cDNA was prepared using random primers and the presence of the GUS sequence was determined and quantified by real-time PCR as described in Example 10. A significant increase in GUS levels was observed in plants seven days after treatment with GUS234Mir390 compared to treatment with GUS234 (Dunnett's test, p-value=0.0005). Most of the RNA samples extracted from GUS234-treated plants gave no Ct value, meaning GUS was not detected in those samples. Accordingly, these samples were assigned a value of 40. The resulting difference in the average Ct value between the GUS234 and the GUS234Mir390 treatments was calculated to be about 10, translating into a 994-fold difference in GUS levels. For 14 days old plants, a 12.2-fold difference in GUS levels was observed (Dunnett's test, p-value=0.03865). FIG. 15A shows normalized Ct values seven days after treatment with the two dsRNA constructs. FIG. 15B shows normalized Ct values 14 days after treatment. The analysis was performed as described for FIGS. 14A-B.

Example 15

Small RNA Deep Sequencing of Plants Following Seed Treatment with TA-SI dsRNA Constructs RNA samples from the seven day old shoots described in Examples 11 and 14 were further analyzed by small RNA deep sequencing. cDNA libraries were prepared with an Illumina TruSeq™ Small RNA kit according to the manufacturer's protocol, and sequenced by Illumina MiSeq® instrument. Each cDNA library was prepared from RNA pooled from three plants originating from the same treatment. For GFP-based dsRNAs, a total of ten libraries were prepared. Two libraries (representing a total of six plants) were prepared from GFP234 treated plants, three libraries (nine plants) were prepared from GFP234Mir390 treated plants, one library (three plants) was prepared from GFP234Mir390X2 treated plants, two libraries (six plants) were prepared from GFP234Mir390_Helicase treated plants and two libraries (six plants) were prepared from TAS3Mir390 treated plants. Table 6 shows the average Ct value of each of the pooled RNA samples, according to the real-time PCR analysis shown in FIG. 12A. The values presented in the table were normalized by subtracting the average Ct value of RNA pooled from the TAS3Mir390 treatment. Low quality reads and reads that contain adaptor sequences were filtered out from the raw sequencing data. Table 6 summarizes the number of reads from each library that were mapped to GFP. In accordance with the real-time PCR results, more reads were mapped to the GFP sequence in the GFP234Mir390 and GFP234Mir390_Helicase treatments compared to the GFP234 treatment.

TABLE 6

Small RNA MiSeq analysis of RNA extracted from plants following seed treatment with ta-si-GFP dsRNA constructs

| Treatment | GFP234 | | GFP234Mir390 | | GFP234Mir390_Helicase | GFP234Mir390X2 | TAS3Mir390 | |
|---|---|---|---|---|---|---|---|---|
| RT-PCR normalized Ct value | 1.3 | 2.8 | 3.2 | 6.6 | 9.5 | 7.9 | 5.9 | 2.7 | 0.0 | 4.0 |
| Libraries size ratio | 1.23 | 1.24 | 2.09 | 1.46 | 1.4 | 1.59 | 1.23 | 1 | 1.61 | 1.07 |
| Total # of reads mapped to GFP234 sequence | 36 | 12 | 74 | 130 | 273 | 122 | 117 | 20 | 0 | 2 |
| Normalized # of reads mapped to GFP234 sequence | 29 | 10 | 35 | 89 | 195 | 77 | 95 | 20 | 0 | 2 |

For GUS-based dsRNAs, two libraries were prepared, one library (representing a total of three plants) was prepared from GUS234 treated plants and one library (three plants) was prepared from GUS234Mir390 treated plants. Table 7 shows the average Ct value of each of the pooled RNA samples, according to the real-time PCR analysis shown in FIG. 15A. The values presented in the Table were normalized by subtracting the average Ct value of RNA pooled from the GUS234 treatment. Table 7 summarizes the number of reads from each library that were mapped to GUS. Data was analyzed as described for Table 6. In accordance with the real-time PCR results, no reads were mapped to the GUS sequence in the GUS234 treatment while some reads were mapped to GUS in the GUS234Mir390 treatment.

TABLE 7

Small RNA MiSeq analysis of RNA extracted from plants following seed treatment with ta-si-GUS dsRNA constructs.

| Treatment | GUS234 | GUS234Mir390 |
|---|---|---|
| RT-PCR normalized Ct value | 0 | 7.6 |
| Libraries size ratio | 1 | 1.77 |
| Total # of reads mapped to GUS234 sequence | 0 | 27 |
| Normalized # of reads mapped to GUS234 sequence | 0 | 15 |

Example 16

Additional dsRNA Constructs

Additional dsRNA constructs based on the constructs and sequences provided in Examples 9 and 10 are provided. Deep-Sequencing analysis described in Example 15 indicated that the first nucleotide in the small RNA reads mapped to the endogenous TAS3 transcript is predominantly "T". The most abundant reads mapped to the TAS3 transcript were located at positions 37, 38, 79, 100, 101, 103, 184 and 185 of the 234 nt sequence and with the exception of the reads mapped to position 185, where the first nucleotide was A, the first nucleotide was T. Therefore, the inclusion of a "T" or "A" in the sequence of the target gene of interest that is flanked by the two miR390 binding sites is expected to improve the efficiency of cleavage and direct it to specific sites within the sequence or alternatively improves the interaction of the resulting small RNAs with downstream effectors.

Trigger #14 (SEQ ID No. 314), is designed as a modified GFP234Mir390 sequence (based on Example 9B and trigger #2), where the nucleotides at positions 37, 38, 79, 100, 101, 103 and 184 are "T", and the nucleotide at position 185 is A (only positions 37, 79 and 101 were changed. Sequence appears in 5'-3' orientation, the mentioned positions are in lowercase, bold).

SEQ ID No. 314:
GGTGCTATCCTACCTGAGCTTTTTCCGTCCTCCTTGAAATCAATTCCCTTA

AGCTCGttCCTGTTGACGAGGGTGTCTCCCTCAAACTTGACTTCAGCAtGT

GTCTTGTAGTTCCCGTCGttCtTGAAAGAGATGGTCCTCTCCTGCACGTAT

CCCTCAGGCATGGCGCTCTTGAAGAAGTCGTGCCGCTTCATATGATCTGGG taTCTTGAAAAGCATTGAACACCATAAGAGAAAGTAGTGACAAGTGTTGGC

CCTTGTCTATCCCTCCTGAGCT

Trigger #15 (SEQ ID No. 315) is designed as a modified TAS3Mir390 sequence (based on Example 9I and trigger #11). In this sequence, four 21 nucleotides segments that begin with "TT" are selected from the GFP234 sequence and used to replace the original 21 nucleotide segments from the TAS3Mir390 sequence at positions 37, 79, 100 and 184. These positions are in phase with the miR390-guided cleavage site (sequence appears in 5'-3' orientation, the mentioned four segments are in lowercase, bold).

SEQ ID No. 315:
GGTGCTATCCTACCTGAGCTTTTTCTCACCGCTTTTTTTTTCTGTTGTGT

ATTCTCttttccgtcctccttgaaatcaGTTCCTCTACCTACCCCATTCttc ccttaagctcgatcctgtttgacttcagcacgtgtcttgGTGTTATCTCTT

ACGTCTTTATGTTTTGTTTTTTTGCAAATCTTACGTCATGACTTCTTCATG ttcccgtcgtccttgaaagagCTTCTTTCCTACTCAACTCTCGTTCTCCTT

CCTTGTCTATCCCTCCTGAGCT

Trigger #16 (SEQ ID No.316) is designed as a modified GFP234Mir390 sequence (based on Example 9B and trigger

2), where "T" appears every 21 nucleotides. The most 3' "T" is located at position 226 of the GFP234 sequence, 21 nucleotides upstream to the miR390-guided cleavage site and all other "T" positions are in phase with this site (sequence appears in 5'-3' orientation, only mutated nucleotides are in lowercase, bold).

SEQ ID No. 316:
GGTGCTATCCTACCTGAGCTTTTTCCGTCCTCCTTGtAATCAATTCCCTT

AAGCTCGtTCCTGTTGACGAGGGTGTCTtCCTCAAACTTGACTTCAGCAt

GTGTCTTGTAGTTCCCGTCGTCCTTGAAAGAGATGGTCCTCTCCTGCACG

TATCCCTCAGGCtTGGCGCTCTTGAAGAAGTCGTGCCGCTTCATATGATC

TGGGTATCTTGAAAAGCATTGAACAtCATAAGAGAAAGTAGTGACAtGTG

TTGGCCCTTGTCTATCCCTCCTGAGCT

Trigger #17 (SEQ ID No. 317) is designed as a modified GFP234Mir390 sequence (based on Example 9B and trigger #2), where ten 21 nucleotide segments that originate from the full-length GFP sequence and begins with a "T" are placed in tandem to produce the 234 nucleotide sequence. The first 15 and the last 9 nucleotides are from the endogenous TAS3 sequence, in order to position the ten segments in-phase with the miR390-guided cleavage site (sequence appears in 5'-3' orientation, the first "T" in each segment is in lowercase, bold, and the TAS3 sequence is underlined).

SEQ ID No. 317:
GGTGCTATCCTACCTGAGCTT*TTTCTCACCGCTTTT*tAATGGTTGTCTGG

TAAAAGGtCGCCAATTGGAGTATTTTGTtGATAATGATCAGCGAGTTGCt

CTTCGATGTTGTGGCGGGTCtTGAAGTTGGCTTTGATGCCGtTCTTTTGC

TTGTCGGCCATGtGTATACGTTGTGGGAGTTGTtTGTATTCCAACTTGTG

GCCGtGTTTCCGTCCTCCTTGAAATtTCCCTTAAGCTCGATCCTGT*GTTC*

*TCCTT*CCTTGTCTATCCCTCCTGAGCT

Tomato seeds are treated with dsRNA triggers 14, 15, 16 and 17 as described in Example 10. The seeds are germinated on paper and the seedlings is harvested at 7, 14 and 30 days post treatment and total RNA is extracted from whole seedlings, leaves or roots of the germinated seeds. cDNA is prepared using oligo-dT primers and the expression levels of TAS3, ARF3 and ARF4 are determined by real-time PCR with SYBR Green (Quanta BioSciences). ARF3 and ARF4 genes are regulated by the TAS3 system and their expression is predicted to decrease following trigger treatment.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. An isolated double-stranded RNA (dsRNA) molecule comprising
   (a) a first RNA strand having
      at least one antisense RNA sequence for suppressing expression of a target gene of interest in a corn, rice, tomato, or sorghum plant or an essential target gene of a phytopathogen of a corn, rice, tomato, or sorghum plant,
      a first heterologous smRNA-binding sequence for binding to a first small RNA (smRNA) expressed in said corn, rice, tomato, sorghum plant, wherein said first smRNA comprises 15-30 nucleotides, and wherein said first smRNA comprises a nucleic acid sequence having at least 95% identity or complementarity to a nucleic acid sequence selected from the group consisting of SEQ ID NOs: 41-43, 45, and 47-96,
      a helicase-binding sequence comprising the helicase binding site of SEQ ID NO: 14; and
   (b) a second RNA strand that is a reverse complement of said first RNA strand.

2. The isolated dsRNA molecule of claim 1, wherein said first heterologous smRNA-binding sequence is 5' to said antisense RNA sequence.

3. The isolated dsRNA molecule of claim 1, wherein said first heterologous smRNA-binding sequence is 3' to said antisense RNA sequence.

4. The isolated dsRNA molecule of claim 1, wherein said first heterologous smRNA-binding sequence is the complement of said first smRNA.

5. The isolated dsRNA molecule of claim 1, wherein said first RNA strand further comprises a second heterologous smRNA-binding sequence for binding a second smRNA comprising 15-30 nucleotides expressed in said corn, rice, tomato, or sorghum plant, wherein said second smRNA comprises a nucleic acid sequence having at least 95% identity or complementarity to a nucleic acid sequence selected from the group consisting of SEQ ID NOs: 41-43, 45 and 47-96,and wherein said first heterologous smRNA-binding sequence and said second heterologous smRNA-binding sequence flank said at least one antisense RNA sequence.

6. The isolated dsRNA molecule of claim 5, wherein said first smRNA and said second smRNA comprise a nucleic acid sequence having 100% sequence identity or complementarity to a nucleic acid sequence selected from the group consisting of SEQ ID NOs: 41-43, 45, and 47-96.

7. The isolated dsRNA molecule of claim 5, wherein said second heterologous smRNA-binding sequence is the complement of said second smRNA.

8. The isolated dsRNA molecule of claim 5, wherein said second smRNA is identical to said first smRNA.

9. The isolated dsRNA molecule of claim 5, wherein said second smRNA is non-identical to said first smRNA.

10. The isolated dsRNA molecule of claim 5, wherein said first heterologous smRNA-binding sequence and said second heterologous smRNA-binding sequence comprise a nucleotide sequence selected from the group consisting of:
   a direct sequence of said first smRNA and a direct sequence of said second smRNA;
   a reverse complement of said first smRNA and a direct sequence of said second smRNA;
   a reverse complement of said first smRNA and a reverse complement of said second smRNA;
   a direct sequence of said first smRNA and a reverse complement of said second smRNA;
   a direct sequence of said first smRNA and further comprising a mutation rendering it resistant to cleavage and a direct sequence of said second smRNA;
   a reverse complement of said first smRNA and further comprising a mutation rendering it resistant to cleavage and a direct sequence of said second smRNA;
   a reverse complement of said first smRNA and further comprising a mutation rendering it resistant to cleavage and a reverse complement of said second smRNA;
   a direct sequence of said first smRNA and further comprising a mutation rendering it resistant to cleavage and a reverse complement of said second smRNA;
   a direct sequence of said first smRNA and a direct sequence of said second smRNA and further comprising a mutation rendering it resistant to cleavage;
   a reverse complement of said first smRNA and a direct sequence of said second smRNA and further comprising a mutation rendering it resistant to cleavage;
   a reverse complement of said first smRNA and a reverse complement of said second smRNA and further comprising a mutation rendering it resistant to cleavage;

a direct sequence of said first smRNA and a reverse complement of said second smRNA and further comprising a mutation rendering it resistant to cleavage;

a direct sequence of said first smRNA and further comprising a mutation rendering it resistant to cleavage and a direct sequence of said second smRNA and further comprising a mutation rendering it resistant to cleavage;

a reverse complement of said first smRNA and further comprising a mutation rendering it resistant to cleavage and a direct sequence of said second smRNA and further comprising a mutation rendering it resistant to cleavage;

a reverse complement of said first smRNA and further comprising a mutation rendering it resistant to cleavage and a reverse complement of said second smRNA and further comprising a mutation rendering it resistant to cleavage; and a direct sequence of said first smRNA and further comprising a mutation rendering it resistant to cleavage and a reverse complement of said second smRNA and further comprising a mutation rendering it resistant to cleavage.

11. The isolated dsRNA molecule of claim 1, wherein said helicase binding sequence is positioned within said at least one antisense RNA sequence.

12. The isolated dsRNA molecule of claim 1, wherein said helicase binding sequence is positioned 5' or 3' of said at least one antisense RNA sequence.

13. The isolated dsRNA molecule of claim 12, wherein said first RNA strand further comprises a second heterologous smRNA-binding sequence for binding to a second smRNA expressed in said corn, rice, tomato, or sorghum plant, and wherein said first heterologous smRNA and said second heterologous smRNA-binding sequence flank said at least one antisense RNA sequence and said helicase binding sequence.

14. The isolated dsRNA molecule of claim 1, wherein said first smRNA has a nucleotide sequence selected from the group consisting of an RNA sequence of a microRNA (miRNA) and an RNA sequence of an siRNA.

15. The isolated dsRNA molecule of claim 5, wherein said first smRNA has a nucleotide sequence selected from the group consisting of an RNA sequence of a miRNA and an RNA sequence of an siRNA, and said second smRNA has a nucleotide sequence selected from the group consisting of an RNA sequence of a miRNA and an RNA sequence of an siRNA.

16. The isolated dsRNA molecule of claim 13, wherein said first smRNA is selected from the group consisting of an RNA sequence of a miRNA and an RNA sequence of an siRNA, and said second smRNA is selected from the group consisting of an RNA sequence of a miRNA and an RNA sequence of an siRNA.

17. The isolated dsRNA molecule of claim 1, wherein said first smRNA is a miRNA.

18. The isolated dsRNA molecule of claim 5, wherein said first smRNA is a miRNA and said second smRNA is a miRNA.

19. The isolated dsRNA molecule of claim 13, wherein said first smRNA is a miRNA and said second smRNA is a miRNA.

20. The isolated dsRNA molecule of claim 1, wherein said first smRNA is miR390.

21. The isolated dsRNA molecule of claim 5, wherein said first smRNA is miR390.

22. The isolated dsRNA molecule of claim 13, wherein said first smRNA is miR390.

23. The isolated dsRNA molecule of claim 5, wherein said corn, rice, tomato, or sorghum plant or phytopathogen comprises a trans-acting-siRNA-producing (TAS) locus that comprises a binding site for binding said second smRNA.

24. The isolated dsRNA molecule of claim 5, wherein said corn, rice, tomato, or sorghum plant or phytopathogen comprises a TAS locus, wherein said TAS locus naturally comprises a binding site for binding said first smRNA and a binding site for binding said second smRNA, and wherein said binding sites flank said TAS locus in said corn, rice, tomato, or sorghum plant or phytopathogen.

25. The isolated dsRNA molecule of claim 5, wherein at least one of said first and second smRNA is an smRNA for which binding sites are naturally found flanking a TAS locus in a plant.

26. The isolated dsRNA molecule of claim 1, wherein said plant is a crop plant.

27. The isolated dsRNA molecule of claim 1, wherein said helicase binding site provides for the separation of the two strands of said dsRNA molecule to produce a region of single stranded RNA (ssRNA) when introduced into a plant cell or provided with a helicase and RNA Dependent RNA Polymerase (RDRP) in vitro.

28. The isolated dsRNA molecule of claim 1, wherein said helicase binding site provides for the recruitment of an RNA-dependent RNA Polymerase and transcription of a secondary small interfering RNA (siRNA) complementary to at least one strand of said dsRNA molecule when introduced into a plant cell or provided with a helicase in vitro.

* * * * *

SEQUENCE LISTING

```
<160> NUMBER OF SEQ ID NOS: 332

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      T7 primer sequence

<400> SEQUENCE: 1
taatacgact cactataggg                                              20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 2
ggtgctctga acgtggatg                                               19

<210> SEQ ID NO 3
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      single strand DNA oligonucleotide

<400> SEQUENCE: 3
catcatcgcc atcctcattc tc                                                  22

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 4
taatacgact cactataggg gaagaccctc gaaactaagc                                40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 5
taatacgact cactataggg ggtaagcggc attctaaacc                                40

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 6
actcagcagt cgtaggattg                                                     20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 7
cttcttatgt tcccgtcagg                                                     20

<210> SEQ ID NO 8
<211> LENGTH: 616
<212> TYPE: DNA
<213> ORGANISM: Artificial Sequence
<220> FEATURE:
<223> OTHER INFORMATION: Description of Artificial Sequence: Synthetic
      CGMVV dsRNA product 1 polynucleotide

<400> SEQUENCE: 8
taatacgact cactataggg ggtaagcggc attctaaacc tccaaatcgg aggttggact          60
ctgcttctga agagtccagt tctgtttctt ttgaagatgg cttacaatcc gatcacacct         120
agcaaactta ttgcgtttag tgcttcttat gttcccgtca ggactttact taattttcta         180
gttgcttcac aaggtaccgc tttccagact caagcgggaa gagattcttt ccgcgagtcc         240
```

```
ctgtctgcgt taccctcgtc tgtcgtagat attaattcta gattcccaga tgcgggtttt    300
tacgctttcc tcaacggtcc tgtgttgagg cctatcttcg tttcgcttct cagctccacg    360
gatacgcgta atagggtcat tgaggttgta gatcctagca atcctacgac tgctgagtcg    420
cttaacgccg taaagcgtac tgatgacgcg tctacggccg ctagggctga gatagataat    480
ttaatagagt ctatttctaa gggttttgat gtttacgata gggcttcatt tgaagccgcg    540
ttttcggtag tctggtcaga ggctaccacc tcgaaagctt agtttcgagg gtcttcccct    600
atagtgagtc gtatta                                                    616
```

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 9

```
taatacgact cactataggg catcaccatc gaccctaaac                           40
```

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 10

```
taatacgact cactataggg gctttaccgc cactaagaac                           40
```

<210> SEQ ID NO 11
<211> LENGTH: 598
<212> TYPE: DNA
<213> ORGANISM: Artificial Sequence
<220> FEATURE:
<223> OTHER INFORMATION: Description of Artificial Sequence: Synthetic
      CGMVV dsRNA product 2 polynucleotide

<400> SEQUENCE: 11

```
taatacgact cactataggg gctttaccgc cactaagaac tctgtacact cccttgcggg     60
tggtctgagg cttcttgaat tggaatatat gatgatgcaa gtgccctacg gctcaccttg    120
ttatgacatc ggcggtaact atacgcagca cttgttcaaa ggtagatcat atgtgcattg    180
ctgcaatccg tgcctagatc ttaaagatgt tgcgaggaat gtgatgtaca acgatatgat    240
cacgcaacat gtacagaggc acaagggatc tggcgggtgc agacctcttc aactttcca    300 gatagatgca ttcaggaggt acgatagttc tccctgtgcg gtcacctgtt cagacgtttt    360
ccaagagtgt tcctatgatt ttgggagtgg tagggataat catgcagtct cgttgcattc    420
aatctacgat atcccttatt cttcgatcgg acctgctctt cataggaaaa atgtgcgagt    480
ttgttatgca gcctttcatt tctcggaggc attgctttta ggttcgcctg taggtaattt    540
aaatagtatt ggggctcagt ttagggtcga tggtgatgcc ctatagtgag tcgtatta     598
```

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 12
ggtgctctga acgtggatg                                                    19

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 13
catcatcgcc atcctcattc tc                                                22

<210> SEQ ID NO 14
<211> LENGTH: 166
<212> TYPE: DNA
<213> ORGANISM: Artificial Sequence
<220> FEATURE:
<223> OTHER INFORMATION: Description of Artificial Sequence: Synthetic
      backbone sequence with two smRNA complementary sites and a
      helicase binding site

<400> SEQUENCE: 14
gcatcctcat cttaatctcg gtgctatcct acctgagctt gatatctagg cgaagcagcc       60
cgaatgctgc accctagatg gcgaaagtcc agtagcgata tcgaattcct cgagggatcc      120
aagcttcctt gtctatccct cctgagctgt tgatttatt ccatgt                      166

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 15
taatacgact cactataggg agcattcccg gcgggatagt ctg                         43

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 16
taatacgact cactataggg agcattcccg gcgggatagt ctg                         43

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 17
cagcgcgaag tctttatacc                                                   20

<210> SEQ ID NO 18
<211> LENGTH: 20
<212> TYPE: DNA
<213> ORGANISM: Artificial Sequence

```
<220> FEATURE:
<223> OTHER INFORMATION: Description of Artificial Sequence: Synthetic
      single strand DNA oligonucleotide

<400> SEQUENCE: 18
ctttgccgta atgagtgacc                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 19
ccataaccct ggaggttgag                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      single strand DNA oligonucleotide

<400> SEQUENCE: 20
atcagacgct gctggtctgg                                                    20

<210> SEQ ID NO 21
<211> LENGTH: 443
<212> TYPE: DNA
<213> ORGANISM: Artificial Sequence
<220> FEATURE:
<223> OTHER INFORMATION: Description of Artificial Sequence: Synthetic
      GUS dsRNA product polynucleotide

<400> SEQUENCE: 21
taatacgact cactataggg agatcgacgg cctgtgggca ttcagtctgg atcgcgaaaa        60
ctgtggaatt gatcagcgtt ggtgggaaag cgcgttacaa gaaagccggg ctattgctgt       120
gccaggcagt tttaacgatc agttcgccga tgcagatatt cgtaattatg cgggcaacgt       180
ctggtatcag cgcgaagtct ttataccgaa aggttgggca ggccagcgta tcgtgctgcg       240
tttcgatgcg gtcactcatt acggcaaagt gtgggtcaat aatcaggaag tgatggagca       300
tcagggcggc tatacgccat ttgaagccga tgtcacgccg tatgttattg ccgggaaaag       360
tgtacgtatc accgtttgtg tgaacaacga actgaactgg cagactatcc cgccgggaat       420
gctccctata gtgagtcgta tta                                               443

<210> SEQ ID NO 22
<211> LENGTH: 116
<212> TYPE: DNA
<213> ORGANISM: Artificial Sequence
<220> FEATURE:
<223> OTHER INFORMATION: Description of Artificial Sequence: Synthetic
      backbone sequence with two smRNA complementary sites, without the
      helicase binding site

<400> SEQUENCE: 22
gcatcctcat cttaatctcg gtgctatcct acctgagctt gatatcgata tcgaattcct        60
cgagggatcc aagcttcctt gtctatccct cctgagctgt tgattttatt ccatgt          116
```

```
<210> SEQ ID NO 23
<211> LENGTH: 167
<212> TYPE: DNA
<213> ORGANISM: Artificial Sequence
<220> FEATURE:
<223> OTHER INFORMATION: Description of Artificial Sequence: Synthetic
      backbone sequence with two smRNA complementary sites and an
      helicase binding site

<400> SEQUENCE: 23
gcatcctcat cttaatctcg tgattttcct ctacaagcga agatatctag gcgaagcagc    60
ccgaatgctg caccctagat ggcgaaagtc cagtagcgat atcgaattcc tcgagggatc   120
caagctttct tgctcaaatg agtattccag ttgattttat tccatgt                167

<210> SEQ ID NO 24
<211> LENGTH: 117
<212> TYPE: DNA
<213> ORGANISM: Artificial Sequence
<220> FEATURE:
<223> OTHER INFORMATION: Description of Artificial Sequence: Synthetic
      backbone sequence with two smRNA complementary sites, without the
      helicase binding site

<400> SEQUENCE: 24
gcatcctcat cttaatctcg tgattttcct ctacaagcga agatatcgat atcgaattcc    60
tcgagggatc caagctttct tgctcaaatg agtattccag ttgattttat tccatgt     117

<210> SEQ ID NO 25
<211> LENGTH: 21
<212> TYPE: RNA
<213> ORGANISM: Unknown
<220> FEATURE:
<223> OTHER INFORMATION: Description of Unknown: miR390 oligonucleotide

<400> SEQUENCE: 25
aagcucagga gggauagcgc c                                              21

<210> SEQ ID NO 26
<211> LENGTH: 21
<212> TYPE: RNA
<213> ORGANISM: Unknown
<220> FEATURE:
<223> OTHER INFORMATION: Description of Unknown: miR161.1
      oligonucleotide

<400> SEQUENCE: 26
uugaaaguga cuacaucggg g                                              21

<210> SEQ ID NO 27
<211> LENGTH: 21
<212> TYPE: RNA
<213> ORGANISM: Unknown
<220> FEATURE:
<223> OTHER INFORMATION: Description of Unknown: miR400 oligonucleotide

<400> SEQUENCE: 27
uaugagagua uuauaaguca c                                              21

<210> SEQ ID NO 28
<211> LENGTH: 21
<212> TYPE: RNA
<213> ORGANISM: Unknown
<220> FEATURE:
<223> OTHER INFORMATION: Description of Unknown: TAS2 3'D6(-) smRNA
      oligonucleotide
```

<400> SEQUENCE: 28
auaucccauu ucuaccaucu g                                              21

<210> SEQ ID NO 29
<211> LENGTH: 21
<212> TYPE: RNA
<213> ORGANISM: Unknown
<220> FEATURE:
<223> OTHER INFORMATION: Description of Unknown: TAS1b 3'D4(-) smRNA
      oligonucleotide

<400> SEQUENCE: 29
uucuucuacc auccuaucaa u                                              21

<210> SEQ ID NO 30
<211> LENGTH: 21
<212> TYPE: RNA
<213> ORGANISM: Unknown
<220> FEATURE:
<223> OTHER INFORMATION: Description of Unknown: TAS3 5'D7(+) smRNA
      oligonucleotide

<400> SEQUENCE: 30
uucuugaccu uguaagaccc c                                              21

<210> SEQ ID NO 31
<211> LENGTH: 21
<212> TYPE: RNA
<213> ORGANISM: Unknown
<220> FEATURE:
<223> OTHER INFORMATION: Description of Unknown: TAS3 5'D8(+) smRNA
      oligonucleotide

<400> SEQUENCE: 31
uucuugaccu uguaaggccu u                                              21

<210> SEQ ID NO 32
<211> LENGTH: 21
<212> TYPE: RNA
<213> ORGANISM: Unknown
<220> FEATURE:
<223> OTHER INFORMATION: Description of Unknown: miR168 oligonucleotide

<400> SEQUENCE: 32
ucgcuuggug caggucggga a                                              21

<210> SEQ ID NO 33
<211> LENGTH: 22
<212> TYPE: RNA
<213> ORGANISM: Unknown
<220> FEATURE:
<223> OTHER INFORMATION: Description of Unknown: miR828 oligonucleotide

<400> SEQUENCE: 33
ucuugcuuaa augaguauuc ca                                             22

<210> SEQ ID NO 34
<211> LENGTH: 21
<212> TYPE: RNA
<213> ORGANISM: Unknown
<220> FEATURE:
<223> OTHER INFORMATION: Description of Unknown: miR393 oligonucleotide

<400> SEQUENCE: 34
uccaaaggga ucgcauugau c                                              21

<210> SEQ ID NO 35
<211> LENGTH: 22
<212> TYPE: RNA
<213> ORGANISM: Unknown
<220> FEATURE:
<223> OTHER INFORMATION: Description of Unknown: plant derived smRNA
      oligonucleotide

<400> SEQUENCE: 35
uucgcuugca gagagaaauc ac                                              22

<210> SEQ ID NO 36
<211> LENGTH: 173
<212> TYPE: DNA
<213> ORGANISM: Artificial Sequence
<220> FEATURE:
<223> OTHER INFORMATION: Description of Artificial Sequence: Synthetic
      Endovirus 5' UTR polynucleotide

<400> SEQUENCE: 36
tgaaatgtct tgtacgacca tttcaaattt atgtaaattg aacgcagcaa caacagggg      60 ggggcggaga cgccccccc cttttaaaaa taaaaatgat caaatcaagt acgatcttgg    120
tttgatcaaa tcaaaaaccc ctgttataaa agggttttg aaaagaaggt acc           173

<210> SEQ ID NO 37
<211> LENGTH: 68
<212> TYPE: DNA
<213> ORGANISM: Artificial Sequence
<220> FEATURE:
<223> OTHER INFORMATION: Description of Artificial Sequence: Synthetic
      Endovirus 3' UTR polynucleotide

<400> SEQUENCE: 37
aatattataa ctaactctgt tttgtcaatt tatttttaaa aggatggggc acccctccca     60
aaccccgg                                                             68

<210> SEQ ID NO 38
<211> LENGTH: 571
<212> TYPE: DNA
<213> ORGANISM: Artificial Sequence
<220> FEATURE:
<223> OTHER INFORMATION: Description of Artificial Sequence: Synthetic
      Endovirus RNA Dependent RNA Polymerase (RDRP) coding sequence and
      cloning sites

<400> SEQUENCE: 38
atgatagtat ggcaaaggaa agcagtttgt agtttatttg ccaaattgtt tgtaagatgc     60
aaagacagac tgaaaacttt acttgtggat catatacttt acgtagatgg attgagacca   120
gatgaaatat cagccaaatt aagacaaata tctgatgtat ttggattttt tgaaaacgac   180
ctgactaagc aagatagaca aactgacaaa cccattttag aagtggaaat gttgatgtat   240
cttatgttgg gcgttcatcc taacatcata tctagttggc gttcaagtca tgatgattgg   300
agattcaaat ctacaaatta ttggggtaag agcacggcaa tgagattaac gggacaagct   360
acaaccgcac taggaaattg tatcactaat atgcaagtac actcaaaatt tgtaatcaaa   420
aataaatatt ggttaaagtt tgctttattt cttggggatg atatgtgtat gggtttctca   480
cacaagccaa acacacagca cttacgccag gatatagctt gtaaatttaa tatgcaaagt   540
aaagtgagaa ttcctcgagg gatccaagct t                                  571

-continued

```
<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      T7 Promoter and restriction sites for cloning

<400> SEQUENCE: 39
gagctcctaa tacgactcac tatagggaga gggccc                                 36

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      T7 Promoter reverse complement oligonucleotide sequence

<400> SEQUENCE: 40
tctccctata gtgagtcgta ttag                                              24

<210> SEQ ID NO 41
<211> LENGTH: 21
<212> TYPE: RNA
<213> ORGANISM: Citrus x paradisi

<400> SEQUENCE: 41
ggugcuaucc uaccugagcu u                                                 21

<210> SEQ ID NO 42
<211> LENGTH: 21
<212> TYPE: RNA
<213> ORGANISM: Manihot esculenta

<400> SEQUENCE: 42
ggugcuaucc uaccugagcu u                                                 21

<210> SEQ ID NO 43
<211> LENGTH: 21
<212> TYPE: RNA
<213> ORGANISM: Populus tremula x Populus tremuloides

<400> SEQUENCE: 43
ggugcuaucc uaccugagcu u                                                 21

<210> SEQ ID NO 44
<211> LENGTH: 21
<212> TYPE: RNA
<213> ORGANISM: Pinus taeda

<400> SEQUENCE: 44
gacgcuaucc ccucugagcu u                                                 21

<210> SEQ ID NO 45
<211> LENGTH: 21
<212> TYPE: RNA
<213> ORGANISM: Populus trichocarpa

<400> SEQUENCE: 45
ggugcuaucc uaccugagcu u                                                 21
```

```
<210> SEQ ID NO 46
<211> LENGTH: 21
<212> TYPE: RNA
<213> ORGANISM: Pinus taeda

<400> SEQUENCE: 46
gacgcuaucc ccucugagcu u                                              21

<210> SEQ ID NO 47
<211> LENGTH: 21
<212> TYPE: RNA
<213> ORGANISM: Zea mays

<400> SEQUENCE: 47
gguguuaucc ugauugagcu u                                              21

<210> SEQ ID NO 48
<211> LENGTH: 21
<212> TYPE: RNA
<213> ORGANISM: Gossypium raimondii

<400> SEQUENCE: 48
ggugcuaucc caccugagcu u                                              21

<210> SEQ ID NO 49
<211> LENGTH: 21
<212> TYPE: RNA
<213> ORGANISM: Vitis vinifera

<400> SEQUENCE: 49
ggugcuaucc uaccugagcu u                                              21

<210> SEQ ID NO 50
<211> LENGTH: 21
<212> TYPE: RNA
<213> ORGANISM: Euphorbia esula

<400> SEQUENCE: 50
ggugcuaucc uaucugagcu u                                              21

<210> SEQ ID NO 51
<211> LENGTH: 21
<212> TYPE: RNA
<213> ORGANISM: Lycopersicon esculentum

<400> SEQUENCE: 51
ggugcuaucc uaccugagcu u                                              21

<210> SEQ ID NO 52
<211> LENGTH: 21
<212> TYPE: RNA
<213> ORGANISM: Zea mays

<400> SEQUENCE: 52
gguguuaucc cgacugaacu u                                              21

<210> SEQ ID NO 53
<211> LENGTH: 21
<212> TYPE: RNA
<213> ORGANISM: Vitis vinifera

<400> SEQUENCE: 53
ggugcuaucc uaccugagcu u                                              21
```

```
<210> SEQ ID NO 54
<211> LENGTH: 21
<212> TYPE: RNA
<213> ORGANISM: Gossypium raimondii

<400> SEQUENCE: 54
ggugcuaucc caccugagcu u                                              21

<210> SEQ ID NO 55
<211> LENGTH: 21
<212> TYPE: RNA
<213> ORGANISM: Theobroma cacao

<400> SEQUENCE: 55
ggugcuaucc uaccugagcu u                                              21

<210> SEQ ID NO 56
<211> LENGTH: 21
<212> TYPE: RNA
<213> ORGANISM: Populus euphratica

<400> SEQUENCE: 56
ggugcuaucc uaccugagcu u                                              21

<210> SEQ ID NO 57
<211> LENGTH: 21
<212> TYPE: RNA
<213> ORGANISM: Hordeum vulgare

<400> SEQUENCE: 57
gguguuaucc cgaaugagcu u                                              21

<210> SEQ ID NO 58
<211> LENGTH: 21
<212> TYPE: RNA
<213> ORGANISM: Manihot esculenta

<400> SEQUENCE: 58
ggugcuaucc uaccugagcu u                                              21

<210> SEQ ID NO 59
<211> LENGTH: 21
<212> TYPE: RNA
<213> ORGANISM: Malus x domestica

<400> SEQUENCE: 59
ggugcuaucc uaccugagcu u                                              21

<210> SEQ ID NO 60
<211> LENGTH: 21
<212> TYPE: RNA
<213> ORGANISM: Glycine max

<400> SEQUENCE: 60
ggugcuaucc uaucugagcu u                                              21

<210> SEQ ID NO 61
<211> LENGTH: 21
<212> TYPE: RNA
<213> ORGANISM: Sorghum bicolor

<400> SEQUENCE: 61
ggcguuaucc ugauugagcu u                                              21
```

```
<210> SEQ ID NO 62
<211> LENGTH: 21
<212> TYPE: RNA
<213> ORGANISM: Populus trichocarpa

<400> SEQUENCE: 62
ggugcuaucc uaccugagcu u                                              21

<210> SEQ ID NO 63
<211> LENGTH: 21
<212> TYPE: RNA
<213> ORGANISM: Vitis vinifera

<400> SEQUENCE: 63
ggugcuaucc uaccugagcu u                                              21

<210> SEQ ID NO 64
<211> LENGTH: 21
<212> TYPE: RNA
<213> ORGANISM: Citrus x paradisi x Poncirus trifoliata

<400> SEQUENCE: 64
ggugcuaucc uaccugagcu u                                              21

<210> SEQ ID NO 65
<211> LENGTH: 21
<212> TYPE: RNA
<213> ORGANISM: Bruguiera gymnorhiza

<400> SEQUENCE: 65
ggugcuaucc uaccugagcu u                                              21

<210> SEQ ID NO 66
<211> LENGTH: 21
<212> TYPE: RNA
<213> ORGANISM: Sorghum bicolor

<400> SEQUENCE: 66
ggcguuaucc ugauugagcu u                                              21

<210> SEQ ID NO 67
<211> LENGTH: 21
<212> TYPE: RNA
<213> ORGANISM: Triticum aestivum

<400> SEQUENCE: 67
gguguuaucc ugauugagcu u                                              21

<210> SEQ ID NO 68
<211> LENGTH: 21
<212> TYPE: RNA
<213> ORGANISM: Malus x domestica

<400> SEQUENCE: 68
ggugcuaucc uagcugagcu u                                              21

<210> SEQ ID NO 69
<211> LENGTH: 21
<212> TYPE: RNA
<213> ORGANISM: Oryza sativa

<400> SEQUENCE: 69
gguguuaucc uaacugagcu u                                              21
```

```
<210> SEQ ID NO 70
<211> LENGTH: 21
<212> TYPE: RNA
<213> ORGANISM: Zea mays

<400> SEQUENCE: 70
gguguuaucc ugauugagcu u                                              21

<210> SEQ ID NO 71
<211> LENGTH: 21
<212> TYPE: RNA
<213> ORGANISM: Populus tremula

<400> SEQUENCE: 71
ggugcuaucc uaccugagcu u                                              21

<210> SEQ ID NO 72
<211> LENGTH: 21
<212> TYPE: RNA
<213> ORGANISM: Antirrhinum majus

<400> SEQUENCE: 72
ggugcuaucc uaucugagcu u                                              21

<210> SEQ ID NO 73
<211> LENGTH: 21
<212> TYPE: RNA
<213> ORGANISM: Sorghum bicolor

<400> SEQUENCE: 73
ggcguuaucc ugauugagcu u                                              21

<210> SEQ ID NO 74
<211> LENGTH: 21
<212> TYPE: RNA
<213> ORGANISM: Populus trichocarpa x Populus deltoides

<400> SEQUENCE: 74
ggugcuaucc uaccugagcu u                                              21

<210> SEQ ID NO 75
<211> LENGTH: 21
<212> TYPE: RNA
<213> ORGANISM: Mesembryanthemum crystallinum

<400> SEQUENCE: 75
ggugcuaucc uaccugagcu u                                              21

<210> SEQ ID NO 76
<211> LENGTH: 21
<212> TYPE: RNA
<213> ORGANISM: Zea mays

<400> SEQUENCE: 76
ggcguuaucc uaauugagcu u                                              21

<210> SEQ ID NO 77
<211> LENGTH: 21
<212> TYPE: RNA
<213> ORGANISM: Populus trichocarpa

<400> SEQUENCE: 77
ggugcuaucc uaccugagcu u                                              21
```

```
<210> SEQ ID NO 78
<211> LENGTH: 21
<212> TYPE: RNA
<213> ORGANISM: Populus trichocarpa

<400> SEQUENCE: 78
ggugcuaucc uaccugagcu u                                              21

<210> SEQ ID NO 79
<211> LENGTH: 21
<212> TYPE: RNA
<213> ORGANISM: Antirrhinum majus

<400> SEQUENCE: 79
ggugcuaucc uaucugagcu u                                              21

<210> SEQ ID NO 80
<211> LENGTH: 21
<212> TYPE: RNA
<213> ORGANISM: Zea mays

<400> SEQUENCE: 80
ggcguuaucc uaauugagcu u                                              21

<210> SEQ ID NO 81
<211> LENGTH: 21
<212> TYPE: RNA
<213> ORGANISM: Populus deltoides

<400> SEQUENCE: 81
ggugcuaucc uaccugagcu u                                              21

<210> SEQ ID NO 82
<211> LENGTH: 21
<212> TYPE: RNA
<213> ORGANISM: Triticum aestivum

<400> SEQUENCE: 82
gguguuaucc ugauugagcu u                                              21

<210> SEQ ID NO 83
<211> LENGTH: 21
<212> TYPE: RNA
<213> ORGANISM: Citrus clementina

<400> SEQUENCE: 83
ggugcuaucc uaccugagcu u                                              21

<210> SEQ ID NO 84
<211> LENGTH: 21
<212> TYPE: RNA
<213> ORGANISM: Glycine soja

<400> SEQUENCE: 84
ggugcuaucc uaucugagcu u                                              21

<210> SEQ ID NO 85
<211> LENGTH: 21
<212> TYPE: RNA
<213> ORGANISM: Manihot esculenta

<400> SEQUENCE: 85
ggugcuaucc uaccugagcu u                                              21
```

```
<210> SEQ ID NO 86
<211> LENGTH: 21
<212> TYPE: RNA
<213> ORGANISM: Populus trichocarpa x Populus deltoides

<400> SEQUENCE: 86
ggugcuaucc uaccugagcu u                                              21

<210> SEQ ID NO 87
<211> LENGTH: 21
<212> TYPE: RNA
<213> ORGANISM: Populus deltoides

<400> SEQUENCE: 87
ggugcuaucc uaccugagcu u                                              21

<210> SEQ ID NO 88
<211> LENGTH: 21
<212> TYPE: RNA
<213> ORGANISM: Sorghum bicolor

<400> SEQUENCE: 88
ggcguuaucc ugauugagcu u                                              21

<210> SEQ ID NO 89
<211> LENGTH: 21
<212> TYPE: RNA
<213> ORGANISM: Saccharum officinarum

<400> SEQUENCE: 89
gguguuaucc caauugagcu u                                              21

<210> SEQ ID NO 90
<211> LENGTH: 21
<212> TYPE: RNA
<213> ORGANISM: Zea mays

<400> SEQUENCE: 90
gguguuaucc ugauugagcu u                                              21

<210> SEQ ID NO 91
<211> LENGTH: 21
<212> TYPE: RNA
<213> ORGANISM: Populus trichocarpa

<400> SEQUENCE: 91
ggugcuaucc uaccugagcu u                                              21

<210> SEQ ID NO 92
<211> LENGTH: 21
<212> TYPE: RNA
<213> ORGANISM: Zea mays

<400> SEQUENCE: 92
ggcguuaucc uaauugagcu u                                              21

<210> SEQ ID NO 93
<211> LENGTH: 21
<212> TYPE: RNA
<213> ORGANISM: Zea mays

<400> SEQUENCE: 93
gguguuaucc cgacuaaacu u                                              21
```

```
<210> SEQ ID NO 94
<211> LENGTH: 21
<212> TYPE: RNA
<213> ORGANISM: Triticum aestivum

<400> SEQUENCE: 94
gguguuaucc ugauugagcu u                                              21

<210> SEQ ID NO 95
<211> LENGTH: 21
<212> TYPE: RNA
<213> ORGANISM: Populus trichocarpa

<400> SEQUENCE: 95
ggugcuaucc uaccugagcu u                                              21

<210> SEQ ID NO 96
<211> LENGTH: 21
<212> TYPE: RNA
<213> ORGANISM: Populus deltoides

<400> SEQUENCE: 96
ggugcuaucc uaccugagcu u                                              21

<210> SEQ ID NO 97
<211> LENGTH: 21
<212> TYPE: RNA
<213> ORGANISM: Saccharum officinarum

<400> SEQUENCE: 97
gguguuaucc ugaucgagcu u                                              21

<210> SEQ ID NO 98
<211> LENGTH: 21
<212> TYPE: RNA
<213> ORGANISM: Arabidopsis thaliana

<400> SEQUENCE: 98
gguguuaucc uaucgagcu u                                               21

<210> SEQ ID NO 99
<211> LENGTH: 21
<212> TYPE: RNA
<213> ORGANISM: Arabidopsis thaliana

<400> SEQUENCE: 99
uccaaaugua gucacuuuca g                                              21

<210> SEQ ID NO 100
<211> LENGTH: 21
<212> TYPE: RNA
<213> ORGANISM: Arabidopsis thaliana

<400> SEQUENCE: 100
ccccaauguu guuacuuuca a                                              21

<210> SEQ ID NO 101
<211> LENGTH: 21
<212> TYPE: RNA
<213> ORGANISM: Arabidopsis thaliana

<400> SEQUENCE: 101
cccggaugua aucacuuuca g                                              21
```

-continued

```
<210> SEQ ID NO 102
<211> LENGTH: 21
<212> TYPE: RNA
<213> ORGANISM: Arabidopsis thaliana

<400> SEQUENCE: 102
cccugauguu guuacuuuca g                                              21

<210> SEQ ID NO 103
<211> LENGTH: 21
<212> TYPE: RNA
<213> ORGANISM: Arabidopsis thaliana

<400> SEQUENCE: 103
uccaaaugua gucacuuuca g                                              21

<210> SEQ ID NO 104
<211> LENGTH: 21
<212> TYPE: RNA
<213> ORGANISM: Arabidopsis thaliana

<400> SEQUENCE: 104
uccaaaugua gucacuuuca g                                              21

<210> SEQ ID NO 105
<211> LENGTH: 21
<212> TYPE: RNA
<213> ORGANISM: Arabidopsis thaliana

<400> SEQUENCE: 105
uccaaaugua gucacuuuca a                                              21

<210> SEQ ID NO 106
<211> LENGTH: 21
<212> TYPE: RNA
<213> ORGANISM: Arabidopsis thaliana

<400> SEQUENCE: 106
uccggaugua gucacuuuua g                                              21

<210> SEQ ID NO 107
<211> LENGTH: 21
<212> TYPE: RNA
<213> ORGANISM: Arabidopsis thaliana

<400> SEQUENCE: 107
uccaaaugua gucacuuuca a                                              21

<210> SEQ ID NO 108
<211> LENGTH: 21
<212> TYPE: RNA
<213> ORGANISM: Arabidopsis thaliana

<400> SEQUENCE: 108
cccugauguu gucacuuuca c                                              21

<210> SEQ ID NO 109
<211> LENGTH: 21
<212> TYPE: RNA
<213> ORGANISM: Arabidopsis thaliana

<400> SEQUENCE: 109
cccugaugua uuuacuuuca a                                              21
```

```
<210> SEQ ID NO 110
<211> LENGTH: 21
<212> TYPE: RNA
<213> ORGANISM: Arabidopsis thaliana

<400> SEQUENCE: 110
accugaugua aucacuuuca a                                              21

<210> SEQ ID NO 111
<211> LENGTH: 21
<212> TYPE: RNA
<213> ORGANISM: Arabidopsis thaliana

<400> SEQUENCE: 111
cccugaugua uucacuuuca g                                              21

<210> SEQ ID NO 112
<211> LENGTH: 21
<212> TYPE: RNA
<213> ORGANISM: Arabidopsis thaliana

<400> SEQUENCE: 112
gugacuuaca auacucuuau a                                              21

<210> SEQ ID NO 113
<211> LENGTH: 21
<212> TYPE: RNA
<213> ORGANISM: Arabidopsis thaliana

<400> SEQUENCE: 113
gugacuuaua auacucucau a                                              21

<210> SEQ ID NO 114
<211> LENGTH: 21
<212> TYPE: RNA
<213> ORGANISM: Arabidopsis thaliana

<400> SEQUENCE: 114
guuacauaua auacucucau a                                              21

<210> SEQ ID NO 115
<211> LENGTH: 21
<212> TYPE: RNA
<213> ORGANISM: Arabidopsis thaliana

<400> SEQUENCE: 115
gugacuuaca auacucuuau a                                              21

<210> SEQ ID NO 116
<211> LENGTH: 21
<212> TYPE: RNA
<213> ORGANISM: Arabidopsis thaliana

<400> SEQUENCE: 116
gauacauaua auacucucau a                                              21

<210> SEQ ID NO 117
<211> LENGTH: 21
<212> TYPE: RNA
<213> ORGANISM: Arabidopsis thaliana

<400> SEQUENCE: 117
gugacuuaca auacucuuau u                                              21
```

```
<210> SEQ ID NO 118
<211> LENGTH: 21
<212> TYPE: RNA
<213> ORGANISM: Arabidopsis thaliana

<400> SEQUENCE: 118
gugacauaua acacucucau u                                              21

<210> SEQ ID NO 119
<211> LENGTH: 21
<212> TYPE: RNA
<213> ORGANISM: Arabidopsis thaliana

<400> SEQUENCE: 119
guaacuuaua guauucucau u                                              21

<210> SEQ ID NO 120
<211> LENGTH: 21
<212> TYPE: RNA
<213> ORGANISM: Arabidopsis thaliana

<400> SEQUENCE: 120
guggcuuaua cuucucucau a                                              21

<210> SEQ ID NO 121
<211> LENGTH: 21
<212> TYPE: RNA
<213> ORGANISM: Arabidopsis thaliana

<400> SEQUENCE: 121
gugacuuaua auacgcuuau a                                              21

<210> SEQ ID NO 122
<211> LENGTH: 21
<212> TYPE: RNA
<213> ORGANISM: Arabidopsis thaliana

<400> SEQUENCE: 122
uucccgagcu gcaucaagcu a                                              21

<210> SEQ ID NO 123
<211> LENGTH: 22
<212> TYPE: RNA
<213> ORGANISM: Arabidopsis thaliana

<400> SEQUENCE: 123
gagacaaugc gaucccuuug ga                                             22

<210> SEQ ID NO 124
<211> LENGTH: 22
<212> TYPE: RNA
<213> ORGANISM: Arabidopsis thaliana

<400> SEQUENCE: 124
gagaccaugc gaucccuuug ga                                             22

<210> SEQ ID NO 125
<211> LENGTH: 22
<212> TYPE: RNA
<213> ORGANISM: Arabidopsis thaliana

<400> SEQUENCE: 125
gaaacaaugc gaucccuuug ga                                             22
```

```
<210> SEQ ID NO 126
<211> LENGTH: 22
<212> TYPE: RNA
<213> ORGANISM: Arabidopsis thaliana

<400> SEQUENCE: 126
ggucagagcg aucccuuugg ca                                              22

<210> SEQ ID NO 127
<211> LENGTH: 22
<212> TYPE: RNA
<213> ORGANISM: Arabidopsis thaliana

<400> SEQUENCE: 127
gaaacaaugc gaucccuuug ga                                              22

<210> SEQ ID NO 128
<211> LENGTH: 21
<212> TYPE: RNA
<213> ORGANISM: Acorus americanus

<400> SEQUENCE: 128
aaacaaugcg aucccuuugg a                                               21

<210> SEQ ID NO 129
<211> LENGTH: 21
<212> TYPE: RNA
<213> ORGANISM: Ananas comosus

<400> SEQUENCE: 129
aaacaaugcg aucccuuugg a                                               21

<210> SEQ ID NO 130
<211> LENGTH: 21
<212> TYPE: RNA
<213> ORGANISM: Ananas comosus

<400> SEQUENCE: 130
aaacaaugcg aucccuuugg a                                               21

<210> SEQ ID NO 131
<211> LENGTH: 21
<212> TYPE: RNA
<213> ORGANISM: Aquilegia formosa x Aquilegia pubescens

<400> SEQUENCE: 131
aaacaaugcg aucccuuugg a                                               21

<210> SEQ ID NO 132
<211> LENGTH: 21
<212> TYPE: RNA
<213> ORGANISM: Brassica rapa subsp. pekinesis

<400> SEQUENCE: 132
aaacaaugcg aucccuuugg a                                               21

<210> SEQ ID NO 133
<211> LENGTH: 21
<212> TYPE: RNA
<213> ORGANISM: Citrus sinensis

<400> SEQUENCE: 133
aaucuaugag aucacuuugg a                                               21
```

```
<210> SEQ ID NO 134
<211> LENGTH: 21
<212> TYPE: RNA
<213> ORGANISM: Coffea arabica

<400> SEQUENCE: 134
aaacaaugcg aucccuuugg a                                              21

<210> SEQ ID NO 135
<211> LENGTH: 21
<212> TYPE: RNA
<213> ORGANISM: Coffea canephora

<400> SEQUENCE: 135
aaacaaugcg aucccuuugg a                                              21

<210> SEQ ID NO 136
<211> LENGTH: 21
<212> TYPE: RNA
<213> ORGANISM: Coffea canephora

<400> SEQUENCE: 136
aaacaaugcg aucccuuugg a                                              21

<210> SEQ ID NO 137
<211> LENGTH: 21
<212> TYPE: RNA
<213> ORGANISM: Coffea canephora

<400> SEQUENCE: 137
aaaccaugcu aucccuuugg a                                              21

<210> SEQ ID NO 138
<211> LENGTH: 21
<212> TYPE: RNA
<213> ORGANISM: Coffea canephora

<400> SEQUENCE: 138
aaacaaugcg aucccuuugg a                                              21

<210> SEQ ID NO 139
<211> LENGTH: 21
<212> TYPE: RNA
<213> ORGANISM: Coffea canephora

<400> SEQUENCE: 139
aaacaaugcg aucccuuugg a                                              21

<210> SEQ ID NO 140
<211> LENGTH: 21
<212> TYPE: RNA
<213> ORGANISM: Eucalyptus tereticornis

<400> SEQUENCE: 140
aaacaaugcg aucccuuugg a                                              21

<210> SEQ ID NO 141
<211> LENGTH: 21
<212> TYPE: RNA
<213> ORGANISM: Glycine max

<400> SEQUENCE: 141
aaacaaugcg aucccuuugg a                                              21
```

-continued

<210> SEQ ID NO 142
<211> LENGTH: 21
<212> TYPE: RNA
<213> ORGANISM: Glycine max

<400> SEQUENCE: 142
aaacgaugcg aucccuuugg a					21

<210> SEQ ID NO 143
<211> LENGTH: 21
<212> TYPE: RNA
<213> ORGANISM: Glycine max

<400> SEQUENCE: 143
aaacaaugcg aucccuuugg a					21

<210> SEQ ID NO 144
<211> LENGTH: 21
<212> TYPE: RNA
<213> ORGANISM: Glycine max

<400> SEQUENCE: 144
aaacaaugcg aucccuuugg a					21

<210> SEQ ID NO 145
<211> LENGTH: 21
<212> TYPE: RNA
<213> ORGANISM: Glycine max

<400> SEQUENCE: 145
aaacaaugcg aucccuuugg a					21

<210> SEQ ID NO 146
<211> LENGTH: 21
<212> TYPE: RNA
<213> ORGANISM: Glycine max

<400> SEQUENCE: 146
aaacaaugcg aucccuuugg a					21

<210> SEQ ID NO 147
<211> LENGTH: 21
<212> TYPE: RNA
<213> ORGANISM: Glycine max

<400> SEQUENCE: 147
aaacaaugcg aucccuuugg a					21

<210> SEQ ID NO 148
<211> LENGTH: 21
<212> TYPE: RNA
<213> ORGANISM: Glycine max

<400> SEQUENCE: 148
aaacaaugcg aucccuuugg a					21

<210> SEQ ID NO 149
<211> LENGTH: 21
<212> TYPE: RNA
<213> ORGANISM: Glycine max

<400> SEQUENCE: 149
aaacaaugcg aucccuuugg a					21

```
<210> SEQ ID NO 150
<211> LENGTH: 21
<212> TYPE: RNA
<213> ORGANISM: Glycine max

<400> SEQUENCE: 150
aaacaaugcg aucccuuugg a                                              21

<210> SEQ ID NO 151
<211> LENGTH: 21
<212> TYPE: RNA
<213> ORGANISM: Glycine max

<400> SEQUENCE: 151
aaacaaugcg aucccuuugg a                                              21

<210> SEQ ID NO 152
<211> LENGTH: 21
<212> TYPE: RNA
<213> ORGANISM: Glycine max

<400> SEQUENCE: 152
aaacaaugcg aucccuuugg a                                              21

<210> SEQ ID NO 153
<211> LENGTH: 21
<212> TYPE: RNA
<213> ORGANISM: Glycine max

<400> SEQUENCE: 153
aaacaaugcg aucccuuugg a                                              21

<210> SEQ ID NO 154
<211> LENGTH: 21
<212> TYPE: RNA
<213> ORGANISM: Glycine max

<400> SEQUENCE: 154
aaacaaugcg aucccuuugg a                                              21

<210> SEQ ID NO 155
<211> LENGTH: 21
<212> TYPE: RNA
<213> ORGANISM: Glycine max

<400> SEQUENCE: 155
aaacaaugcg aucccuuugg a                                              21

<210> SEQ ID NO 156
<211> LENGTH: 21
<212> TYPE: RNA
<213> ORGANISM: Glycine max

<400> SEQUENCE: 156
aaacaaugcg aucccuuugg a                                              21

<210> SEQ ID NO 157
<211> LENGTH: 21
<212> TYPE: RNA
<213> ORGANISM: Glycine max

<400> SEQUENCE: 157
aaacaaugcg aucccuuugg a                                              21
```

```
<210> SEQ ID NO 158
<211> LENGTH: 21
<212> TYPE: RNA
<213> ORGANISM: Glycine max

<400> SEQUENCE: 158
aaacaaugcg aucccuuugg a                                              21

<210> SEQ ID NO 159
<211> LENGTH: 21
<212> TYPE: RNA
<213> ORGANISM: Glycine max

<400> SEQUENCE: 159
aaacaaugcg aucccuuugg a                                              21

<210> SEQ ID NO 160
<211> LENGTH: 21
<212> TYPE: RNA
<213> ORGANISM: Glycine soja

<400> SEQUENCE: 160
aaacaaugcg aucccuuugg a                                              21

<210> SEQ ID NO 161
<211> LENGTH: 21
<212> TYPE: RNA
<213> ORGANISM: Gossypium arboreum

<400> SEQUENCE: 161
aaacaaugcg aucccuuugg a                                              21

<210> SEQ ID NO 162
<211> LENGTH: 21
<212> TYPE: RNA
<213> ORGANISM: Gossypium hirsutum

<400> SEQUENCE: 162
aaacaaugcg aucccuuugg a                                              21

<210> SEQ ID NO 163
<211> LENGTH: 21
<212> TYPE: RNA
<213> ORGANISM: Gossypium hirsutum

<400> SEQUENCE: 163
aaacaaugcg aucccuuugg a                                              21

<210> SEQ ID NO 164
<211> LENGTH: 21
<212> TYPE: RNA
<213> ORGANISM: Gossypium hirsutum

<400> SEQUENCE: 164
aaacaaugcg aucccuuugg a                                              21

<210> SEQ ID NO 165
<211> LENGTH: 21
<212> TYPE: RNA
<213> ORGANISM: Helianthus argophyllus

<400> SEQUENCE: 165
agucaaugcg aucccugugg a                                              21
```

```
<210> SEQ ID NO 166
<211> LENGTH: 21
<212> TYPE: RNA
<213> ORGANISM: Helianthus argophyllus

<400> SEQUENCE: 166
agucaaugcg aucccugugg a                                              21

<210> SEQ ID NO 167
<211> LENGTH: 21
<212> TYPE: RNA
<213> ORGANISM: Helianthus petiolaris

<400> SEQUENCE: 167
aaucaaugag gucucuuugg a                                              21

<210> SEQ ID NO 168
<211> LENGTH: 21
<212> TYPE: RNA
<213> ORGANISM: Lactuca sativa

<400> SEQUENCE: 168
aaucaaugag gucucuuugg a                                              21

<210> SEQ ID NO 169
<211> LENGTH: 21
<212> TYPE: RNA
<213> ORGANISM: Lactuca sativa

<400> SEQUENCE: 169
aaucaaugag gucucuuugg a                                              21

<210> SEQ ID NO 170
<211> LENGTH: 21
<212> TYPE: RNA
<213> ORGANISM: Lotus japonicus

<400> SEQUENCE: 170
gcacgaggcg aucccuuugg a                                              21

<210> SEQ ID NO 171
<211> LENGTH: 21
<212> TYPE: RNA
<213> ORGANISM: Malus x domestica

<400> SEQUENCE: 171
aagcaaugcg aucccuuugg a                                              21

<210> SEQ ID NO 172
<211> LENGTH: 21
<212> TYPE: RNA
<213> ORGANISM: Malus x domestica

<400> SEQUENCE: 172
aaacaaugcg aucccuuugg a                                              21

<210> SEQ ID NO 173
<211> LENGTH: 21
<212> TYPE: RNA
<213> ORGANISM: Malus x domestica

<400> SEQUENCE: 173
aagcaaugcg aucccuuugg a                                              21
```

```
<210> SEQ ID NO 174
<211> LENGTH: 21
<212> TYPE: RNA
<213> ORGANISM: Malus x domestica

<400> SEQUENCE: 174
aagcaaugcg aucccuuugg a                                              21

<210> SEQ ID NO 175
<211> LENGTH: 21
<212> TYPE: RNA
<213> ORGANISM: Malus x domestica

<400> SEQUENCE: 175
aagcaaugcg aucccuuugg a                                              21

<210> SEQ ID NO 176
<211> LENGTH: 21
<212> TYPE: RNA
<213> ORGANISM: Malus x domestica

<400> SEQUENCE: 176
aaacaaugcg aucccuuugg a                                              21

<210> SEQ ID NO 177
<211> LENGTH: 21
<212> TYPE: RNA
<213> ORGANISM: Malus x domestica

<400> SEQUENCE: 177
aagcaaugcg aucccuuugg a                                              21

<210> SEQ ID NO 178
<211> LENGTH: 21
<212> TYPE: RNA
<213> ORGANISM: Malus x domestica

<400> SEQUENCE: 178
aagcaaugcg aucccuuugg a                                              21

<210> SEQ ID NO 179
<211> LENGTH: 21
<212> TYPE: RNA
<213> ORGANISM: Malus x domestica

<400> SEQUENCE: 179
aagcaaugcg aucccuuugg a                                              21

<210> SEQ ID NO 180
<211> LENGTH: 21
<212> TYPE: RNA
<213> ORGANISM: Malus x domestica

<400> SEQUENCE: 180
aaacaaugcg aucccuuugg a                                              21

<210> SEQ ID NO 181
<211> LENGTH: 21
<212> TYPE: RNA
<213> ORGANISM: Malus x domestica

<400> SEQUENCE: 181
aaacacugcg aucccuuugg a                                              21
```

```
<210> SEQ ID NO 182
<211> LENGTH: 21
<212> TYPE: RNA
<213> ORGANISM: Malus x domestica

<400> SEQUENCE: 182
aaacaaugcg aucccuuugg a                                        21

<210> SEQ ID NO 183
<211> LENGTH: 21
<212> TYPE: RNA
<213> ORGANISM: Malus x domestica

<400> SEQUENCE: 183
aagcaaugcg aucccuuugg a                                        21

<210> SEQ ID NO 184
<211> LENGTH: 21
<212> TYPE: RNA
<213> ORGANISM: Malus x domestica

<400> SEQUENCE: 184
aagcaaugcg aucccuuugg a                                        21

<210> SEQ ID NO 185
<211> LENGTH: 21
<212> TYPE: RNA
<213> ORGANISM: Malus x domestica

<400> SEQUENCE: 185
aaacaaugcg aucccuuugg a                                        21

<210> SEQ ID NO 186
<211> LENGTH: 21
<212> TYPE: RNA
<213> ORGANISM: Malus x domestica

<400> SEQUENCE: 186
aagcaaugcg aucccuuugg a                                        21

<210> SEQ ID NO 187
<211> LENGTH: 21
<212> TYPE: RNA
<213> ORGANISM: Malus x domestica

<400> SEQUENCE: 187
aagcaaugcg aucccuuugg a                                        21

<210> SEQ ID NO 188
<211> LENGTH: 21
<212> TYPE: RNA
<213> ORGANISM: Manihot esculenta

<400> SEQUENCE: 188
aaacaaugcg aucccuuugg a                                        21

<210> SEQ ID NO 189
<211> LENGTH: 21
<212> TYPE: RNA
<213> ORGANISM: Medicago truncatula

<400> SEQUENCE: 189
aaacaaugcg aucccuuugg a                                        21
```

-continued

<210> SEQ ID NO 190
<211> LENGTH: 21
<212> TYPE: RNA
<213> ORGANISM: Medicago truncatula

<400> SEQUENCE: 190
aaacaaugcg aucccuuugg a                                                 21

<210> SEQ ID NO 191
<211> LENGTH: 21
<212> TYPE: RNA
<213> ORGANISM: Medicago truncatula

<400> SEQUENCE: 191
aaacaaugcg aucccuuugg a                                                 21

<210> SEQ ID NO 192
<211> LENGTH: 21
<212> TYPE: RNA
<213> ORGANISM: Medicago truncatula

<400> SEQUENCE: 192
aaacaaugcg aucccuuugg a                                                 21

<210> SEQ ID NO 193
<211> LENGTH: 21
<212> TYPE: RNA
<213> ORGANISM: Medicago truncatula

<400> SEQUENCE: 193
aaacaaugcg aucccuuugg a                                                 21

<210> SEQ ID NO 194
<211> LENGTH: 21
<212> TYPE: RNA
<213> ORGANISM: Medicago truncatula

<400> SEQUENCE: 194
aaacaaugcg aucccuuugg a                                                 21

<210> SEQ ID NO 195
<211> LENGTH: 21
<212> TYPE: RNA
<213> ORGANISM: Medicago truncatula

<400> SEQUENCE: 195
aaacaaugcg aucccuuugg a                                                 21

<210> SEQ ID NO 196
<211> LENGTH: 21
<212> TYPE: RNA
<213> ORGANISM: Picea glauca

<400> SEQUENCE: 196
aaucaaugcg aucccuuugg a                                                 21

<210> SEQ ID NO 197
<211> LENGTH: 21
<212> TYPE: RNA
<213> ORGANISM: Pinus taeda

<400> SEQUENCE: 197
aaucaaugcg aucccuuugg a                                                 21

-continued

```
<210> SEQ ID NO 198
<211> LENGTH: 21
<212> TYPE: RNA
<213> ORGANISM: Pinus taeda

<400> SEQUENCE: 198
aaucaaugcg aucccuuugg a                                              21

<210> SEQ ID NO 199
<211> LENGTH: 21
<212> TYPE: RNA
<213> ORGANISM: Pinus taeda

<400> SEQUENCE: 199
aaucaaugcg aucccuuugg a                                              21

<210> SEQ ID NO 200
<211> LENGTH: 21
<212> TYPE: RNA
<213> ORGANISM: Pinus taeda

<400> SEQUENCE: 200
aaucaaugcg aucccuuugg a                                              21

<210> SEQ ID NO 201
<211> LENGTH: 21
<212> TYPE: RNA
<213> ORGANISM: Pinus taeda

<400> SEQUENCE: 201
aaucaaugcg aucccuuugg a                                              21

<210> SEQ ID NO 202
<211> LENGTH: 21
<212> TYPE: RNA
<213> ORGANISM: Poncirus trifoliata

<400> SEQUENCE: 202
gaucagagcg aucccuuuga a                                              21

<210> SEQ ID NO 203
<211> LENGTH: 21
<212> TYPE: RNA
<213> ORGANISM: Populus tremula x Populus tremuloides

<400> SEQUENCE: 203
aaacaaugcg aucccuuugg a                                              21

<210> SEQ ID NO 204
<211> LENGTH: 21
<212> TYPE: RNA
<213> ORGANISM: Populus tremula x Populus tremuloides

<400> SEQUENCE: 204
aaacaaugcg aucccuuugg a                                              21

<210> SEQ ID NO 205
<211> LENGTH: 21
<212> TYPE: RNA
<213> ORGANISM: Populus tremula x Populus tremuloides

<400> SEQUENCE: 205
aaacaaugcg aucccuuugg a                                              21
```

```
<210> SEQ ID NO 206
<211> LENGTH: 21
<212> TYPE: RNA
<213> ORGANISM: Populus tremuloides

<400> SEQUENCE: 206
aaacaaugcg aucccuuugg a                                              21

<210> SEQ ID NO 207
<211> LENGTH: 21
<212> TYPE: RNA
<213> ORGANISM: Populus trichocarpa

<400> SEQUENCE: 207
aaacaaugcg aucccuuugg a                                              21

<210> SEQ ID NO 208
<211> LENGTH: 21
<212> TYPE: RNA
<213> ORGANISM: Populus trichocarpa x Populus deltoides

<400> SEQUENCE: 208
aaacaaugcg aucccuuugg a                                              21

<210> SEQ ID NO 209
<211> LENGTH: 21
<212> TYPE: RNA
<213> ORGANISM: Populus trichocarpa x Populus deltoides

<400> SEQUENCE: 209
aaacaaugcg aucccuuugg a                                              21

<210> SEQ ID NO 210
<211> LENGTH: 21
<212> TYPE: RNA
<213> ORGANISM: Populus x canadensis

<400> SEQUENCE: 210
aaacaaugcg aucccuuugg a                                              21

<210> SEQ ID NO 211
<211> LENGTH: 21
<212> TYPE: RNA
<213> ORGANISM: Prunus persica

<400> SEQUENCE: 211
aaucuaugag aucacuuugg a                                              21

<210> SEQ ID NO 212
<211> LENGTH: 21
<212> TYPE: RNA
<213> ORGANISM: Ricinus communis

<400> SEQUENCE: 212
aaacaaugcg aucccuuugg a                                              21

<210> SEQ ID NO 213
<211> LENGTH: 21
<212> TYPE: RNA
<213> ORGANISM: Saruma henryi

<400> SEQUENCE: 213
aaacaaugcg aucccuuugg a                                              21
```

-continued

```
<210> SEQ ID NO 214
<211> LENGTH: 21
<212> TYPE: RNA
<213> ORGANISM: Zingiber officinale

<400> SEQUENCE: 214
aaacaaugcg aucccuuugg a                                              21

<210> SEQ ID NO 215
<211> LENGTH: 21
<212> TYPE: RNA
<213> ORGANISM: Zingiber officinale

<400> SEQUENCE: 215
aaacaaugcg aucccuuugg a                                              21

<210> SEQ ID NO 216
<211> LENGTH: 21
<212> TYPE: RNA
<213> ORGANISM: Arabidopsis thaliana

<400> SEQUENCE: 216
cagauggugg aaaugggaua u                                              21

<210> SEQ ID NO 217
<211> LENGTH: 21
<212> TYPE: RNA
<213> ORGANISM: Arabidopsis thaliana

<400> SEQUENCE: 217
caaauggucg aaaugggaua u                                              21

<210> SEQ ID NO 218
<211> LENGTH: 21
<212> TYPE: RNA
<213> ORGANISM: Arabidopsis thaliana

<400> SEQUENCE: 218
caaauggugg aaauggggua u                                              21

<210> SEQ ID NO 219
<211> LENGTH: 21
<212> TYPE: RNA
<213> ORGANISM: Arabidopsis thaliana

<400> SEQUENCE: 219
caaauggucg aaaugggaua u                                              21

<210> SEQ ID NO 220
<211> LENGTH: 21
<212> TYPE: RNA
<213> ORGANISM: Arabidopsis thaliana

<400> SEQUENCE: 220
cagauggugg aaaugggaua u                                              21

<210> SEQ ID NO 221
<211> LENGTH: 21
<212> TYPE: RNA
<213> ORGANISM: Arabidopsis thaliana

<400> SEQUENCE: 221
caaauggugg aaauggggua u                                              21
```

```
<210> SEQ ID NO 222
<211> LENGTH: 21
<212> TYPE: RNA
<213> ORGANISM: Arabidopsis thaliana

<400> SEQUENCE: 222
caaauggugg aaaugggua u                                          21

<210> SEQ ID NO 223
<211> LENGTH: 21
<212> TYPE: RNA
<213> ORGANISM: Arabidopsis thaliana

<400> SEQUENCE: 223
caaauggugg gaaugggaua u                                         21

<210> SEQ ID NO 224
<211> LENGTH: 21
<212> TYPE: RNA
<213> ORGANISM: Arabidopsis thaliana

<400> SEQUENCE: 224
guugaucgua ugguagaaga a                                         21

<210> SEQ ID NO 225
<211> LENGTH: 21
<212> TYPE: RNA
<213> ORGANISM: Arabidopsis thaliana

<400> SEQUENCE: 225
aaggucuugc aaggucaaga a                                         21

<210> SEQ ID NO 226
<211> LENGTH: 21
<212> TYPE: RNA
<213> ORGANISM: Arabidopsis thaliana

<400> SEQUENCE: 226
agggucuugc aaggucaaga a                                         21

<210> SEQ ID NO 227
<211> LENGTH: 21
<212> TYPE: RNA
<213> ORGANISM: Citrus x paradisi

<400> SEQUENCE: 227
uugucuaucc cuccugagcu g                                         21

<210> SEQ ID NO 228
<211> LENGTH: 21
<212> TYPE: RNA
<213> ORGANISM: Manihot esculenta

<400> SEQUENCE: 228
uugucuaucc cuccugagcu a                                         21

<210> SEQ ID NO 229
<211> LENGTH: 21
<212> TYPE: RNA
<213> ORGANISM: Populus tremula x Populus tremuloides

<400> SEQUENCE: 229
uugucuaucc cuccugagcu g                                         21
```

```
<210> SEQ ID NO 230
<211> LENGTH: 21
<212> TYPE: RNA
<213> ORGANISM: Pinus taeda

<400> SEQUENCE: 230
uacucuaucu cccugagcu a                                              21

<210> SEQ ID NO 231
<211> LENGTH: 21
<212> TYPE: RNA
<213> ORGANISM: Populus trichocarpa

<400> SEQUENCE: 231
uugucuaucc cccugagcu a                                              21

<210> SEQ ID NO 232
<211> LENGTH: 21
<212> TYPE: RNA
<213> ORGANISM: Pinus taeda

<400> SEQUENCE: 232
uacucuaucu cccugagcu a                                              21

<210> SEQ ID NO 233
<211> LENGTH: 21
<212> TYPE: RNA
<213> ORGANISM: Zea mays

<400> SEQUENCE: 233
agcucuaucc cuucugagcu g                                             21

<210> SEQ ID NO 234
<211> LENGTH: 21
<212> TYPE: RNA
<213> ORGANISM: Gossypium raimondii

<400> SEQUENCE: 234
cugucuaucc cccugagcu a                                              21

<210> SEQ ID NO 235
<211> LENGTH: 21
<212> TYPE: RNA
<213> ORGANISM: Vitis vinifera

<400> SEQUENCE: 235
uugucuaucc cccugagcu a                                              21

<210> SEQ ID NO 236
<211> LENGTH: 21
<212> TYPE: RNA
<213> ORGANISM: Euphorbia esula

<400> SEQUENCE: 236
uugucuaucc cccugagcu u                                              21

<210> SEQ ID NO 237
<211> LENGTH: 21
<212> TYPE: RNA
<213> ORGANISM: Lycopersicon esculentum

<400> SEQUENCE: 237
uugucuaucc cccugagcu g                                              21
```

-continued

```
<210> SEQ ID NO 238
<211> LENGTH: 21
<212> TYPE: RNA
<213> ORGANISM: Zea mays

<400> SEQUENCE: 238
ccuucuaucc cuccugagcu a                                              21

<210> SEQ ID NO 239
<211> LENGTH: 21
<212> TYPE: RNA
<213> ORGANISM: Vitis vinifera

<400> SEQUENCE: 239
uugucuaucc cuccugagcu a                                              21

<210> SEQ ID NO 240
<211> LENGTH: 21
<212> TYPE: RNA
<213> ORGANISM: Gossypium raimondii

<400> SEQUENCE: 240
cugucuaucc cuccugagcu a                                              21

<210> SEQ ID NO 241
<211> LENGTH: 21
<212> TYPE: RNA
<213> ORGANISM: Theobroma cacao

<400> SEQUENCE: 241
cuugcuaucc cuccugagcu g                                              21

<210> SEQ ID NO 242
<211> LENGTH: 21
<212> TYPE: RNA
<213> ORGANISM: Populus euphratica

<400> SEQUENCE: 242
uuggcuaucc cuccugagcu g                                              21

<210> SEQ ID NO 243
<211> LENGTH: 21
<212> TYPE: RNA
<213> ORGANISM: Hordeum vulgare

<400> SEQUENCE: 243
cuuucuaucc cuccugagcu a                                              21

<210> SEQ ID NO 244
<211> LENGTH: 21
<212> TYPE: RNA
<213> ORGANISM: Manihot esculenta

<400> SEQUENCE: 244
uugucuaucc cuccugagcu a                                              21

<210> SEQ ID NO 245
<211> LENGTH: 21
<212> TYPE: RNA
<213> ORGANISM: Malus x domestica

<400> SEQUENCE: 245
uugucuaucc cuccugagcu g                                              21
```

-continued

```
<210> SEQ ID NO 246
<211> LENGTH: 21
<212> TYPE: RNA
<213> ORGANISM: Glycine max

<400> SEQUENCE: 246
uugucuaucc cuccugagcu g                                              21

<210> SEQ ID NO 247
<211> LENGTH: 21
<212> TYPE: RNA
<213> ORGANISM: Sorghum bicolor

<400> SEQUENCE: 247
augucuaucc cuucugagcu g                                              21

<210> SEQ ID NO 248
<211> LENGTH: 21
<212> TYPE: RNA
<213> ORGANISM: Populus trichocarpa

<400> SEQUENCE: 248
uugucuaucc cuccugagcu a                                              21

<210> SEQ ID NO 249
<211> LENGTH: 21
<212> TYPE: RNA
<213> ORGANISM: Vitis vinifera

<400> SEQUENCE: 249
uugucuaucc cuccugagcu a                                              21

<210> SEQ ID NO 250
<211> LENGTH: 21
<212> TYPE: RNA
<213> ORGANISM: Citrus x paradise x Poncirus trifoliata

<400> SEQUENCE: 250
uugucuaucc cuccugagcu g                                              21

<210> SEQ ID NO 251
<211> LENGTH: 21
<212> TYPE: RNA
<213> ORGANISM: Bruguiera gymnorhiza

<400> SEQUENCE: 251
uugucuaucc cuccugagcu g                                              21

<210> SEQ ID NO 252
<211> LENGTH: 21
<212> TYPE: RNA
<213> ORGANISM: Sorghum bicolor

<400> SEQUENCE: 252
augucuaucc cuucugagcu g                                              21

<210> SEQ ID NO 253
<211> LENGTH: 21
<212> TYPE: RNA
<213> ORGANISM: Triticum aestivum

<400> SEQUENCE: 253
ccaucuaucc cuccugagcu a                                              21
```

-continued

<210> SEQ ID NO 254
<211> LENGTH: 21
<212> TYPE: RNA
<213> ORGANISM: Malus x domestica

<400> SEQUENCE: 254
uugucuaucc cuccugagcu g                                             21

<210> SEQ ID NO 255
<211> LENGTH: 21
<212> TYPE: RNA
<213> ORGANISM: Oryza sativa

<400> SEQUENCE: 255
cggucuaucc cuccugagcu g                                             21

<210> SEQ ID NO 256
<211> LENGTH: 21
<212> TYPE: RNA
<213> ORGANISM: Zea mays

<400> SEQUENCE: 256
agcucuaucc cuucugagcu u                                             21

<210> SEQ ID NO 257
<211> LENGTH: 21
<212> TYPE: RNA
<213> ORGANISM: Populus tremula

<400> SEQUENCE: 257
uugucuaucc cuccugagcu g                                             21

<210> SEQ ID NO 258
<211> LENGTH: 21
<212> TYPE: RNA
<213> ORGANISM: Antirrhinum majus

<400> SEQUENCE: 258
uugucuaucc cuccugagcu a                                             21

<210> SEQ ID NO 259
<211> LENGTH: 21
<212> TYPE: RNA
<213> ORGANISM: Sorghum bicolor

<400> SEQUENCE: 259
augucuaucc cuucugagcu g                                             21

<210> SEQ ID NO 260
<211> LENGTH: 21
<212> TYPE: RNA
<213> ORGANISM: Populus trichocarpa x Populus deltoides

<400> SEQUENCE: 260
uuaucuaucc cuccugagcu a                                             21

<210> SEQ ID NO 261
<211> LENGTH: 21
<212> TYPE: RNA
<213> ORGANISM: Mesembryanthemum crystallinum

<400> SEQUENCE: 261
gugucuaucc cuccugagcu a                                             21

```
<210> SEQ ID NO 262
<211> LENGTH: 21
<212> TYPE: RNA
<213> ORGANISM: Zea mays

<400> SEQUENCE: 262
augucuaucc cuucugagcu g                                              21

<210> SEQ ID NO 263
<211> LENGTH: 21
<212> TYPE: RNA
<213> ORGANISM: Populus trichocarpa

<400> SEQUENCE: 263
uuaucuaucc cuccugagcu a                                              21

<210> SEQ ID NO 264
<211> LENGTH: 21
<212> TYPE: RNA
<213> ORGANISM: Populus trichocarpa

<400> SEQUENCE: 264
uugucuaucc cuccugagcu a                                              21

<210> SEQ ID NO 265
<211> LENGTH: 21
<212> TYPE: RNA
<213> ORGANISM: Antirrhinum majus

<400> SEQUENCE: 265
uugucuaucc cuccugagcu a                                              21

<210> SEQ ID NO 266
<211> LENGTH: 21
<212> TYPE: RNA
<213> ORGANISM: Zea mays

<400> SEQUENCE: 266
augucuaucc cuucugagcu g                                              21

<210> SEQ ID NO 267
<211> LENGTH: 21
<212> TYPE: RNA
<213> ORGANISM: Populus deltoides

<400> SEQUENCE: 267
uugucuaucc cuccugagcu a                                              21

<210> SEQ ID NO 268
<211> LENGTH: 21
<212> TYPE: RNA
<213> ORGANISM: Triticum aestivum

<400> SEQUENCE: 268
ccaucuaucc cuccggagcu a                                              21

<210> SEQ ID NO 269
<211> LENGTH: 21
<212> TYPE: RNA
<213> ORGANISM: Citrus clementina

<400> SEQUENCE: 269
uugucuaucc cuccugagcu g                                              21
```

```
<210> SEQ ID NO 270
<211> LENGTH: 21
<212> TYPE: RNA
<213> ORGANISM: Glycine soja

<400> SEQUENCE: 270
uugucuaucc cuccugagcu g                                              21

<210> SEQ ID NO 271
<211> LENGTH: 21
<212> TYPE: RNA
<213> ORGANISM: Manihot esculenta

<400> SEQUENCE: 271
uugucuaucc cuccugagcu a                                              21

<210> SEQ ID NO 272
<211> LENGTH: 22
<212> TYPE: RNA
<213> ORGANISM: Populus trichocarpa x Populus deltoides
<220> FEATURE:
<221> NAME/KEY: modified_base
<222> LOCATION: (3)..(5)
<223> OTHER INFORMATION: a, c, u, g, unknown or other
<220> FEATURE:
<221> NAME/KEY: misc_feature
<222> LOCATION: (3)..(5)
<223> OTHER INFORMATION: n is a, c, g, or u

<400> SEQUENCE: 272
uunnnuaucc cuccugagcu au                                             22

<210> SEQ ID NO 273
<211> LENGTH: 21
<212> TYPE: RNA
<213> ORGANISM: Populus deltoides

<400> SEQUENCE: 273
uuaucuaucc cuccugagcu g                                              21

<210> SEQ ID NO 274
<211> LENGTH: 21
<212> TYPE: RNA
<213> ORGANISM: Sorghum bicolor

<400> SEQUENCE: 274
augucuaucc cuucugagcu g                                              21

<210> SEQ ID NO 275
<211> LENGTH: 21
<212> TYPE: RNA
<213> ORGANISM: Saccharum officinarum

<400> SEQUENCE: 275
augucuaucc cuucugagcu g                                              21

<210> SEQ ID NO 276
<211> LENGTH: 21
<212> TYPE: RNA
<213> ORGANISM: Zea mays

<400> SEQUENCE: 276
agcucuaucc cuucugagcu g                                              21
```

```
<210> SEQ ID NO 277
<211> LENGTH: 21
<212> TYPE: RNA
<213> ORGANISM: Populus trichocarpa

<400> SEQUENCE: 277
uuaucuaucc cuccugagcu a                                              21

<210> SEQ ID NO 278
<211> LENGTH: 21
<212> TYPE: RNA
<213> ORGANISM: Zea mays

<400> SEQUENCE: 278
augucuaucc cuucugaacu g                                              21

<210> SEQ ID NO 279
<211> LENGTH: 21
<212> TYPE: RNA
<213> ORGANISM: Zea mays

<400> SEQUENCE: 279
ccuucuaucc cuccugagcu a                                              21

<210> SEQ ID NO 280
<211> LENGTH: 21
<212> TYPE: RNA
<213> ORGANISM: Triticum aestivum

<400> SEQUENCE: 280
ccaucuaucc cuccugagcu a                                              21

<210> SEQ ID NO 281
<211> LENGTH: 21
<212> TYPE: RNA
<213> ORGANISM: Populus trichocarpa

<400> SEQUENCE: 281
uuaucuaucc cuccugagcu a                                              21

<210> SEQ ID NO 282
<211> LENGTH: 21
<212> TYPE: RNA
<213> ORGANISM: Populus deltoides

<400> SEQUENCE: 282
uugucuaucc cuccugagcu a                                              21

<210> SEQ ID NO 283
<211> LENGTH: 21
<212> TYPE: RNA
<213> ORGANISM: Saccharum officinarum

<400> SEQUENCE: 283
augucuaucc cuucugagcu a                                              21

<210> SEQ ID NO 284
<211> LENGTH: 21
<212> TYPE: RNA
<213> ORGANISM: Arabidopsis thaliana

<400> SEQUENCE: 284
uugucuaucc cuccugagcu a                                              21
```

```
<210> SEQ ID NO 285
<211> LENGTH: 21
<212> TYPE: RNA
<213> ORGANISM: Arabidopsis thaliana

<400> SEQUENCE: 285
guuacuuaca acacucucau a                                              21

<210> SEQ ID NO 286
<211> LENGTH: 21
<212> TYPE: RNA
<213> ORGANISM: Arabidopsis thaliana

<400> SEQUENCE: 286
guuacuuaca acacucucau a                                              21

<210> SEQ ID NO 287
<211> LENGTH: 21
<212> TYPE: RNA
<213> ORGANISM: Arabidopsis thaliana

<400> SEQUENCE: 287
agggucuugc aaggucaaga a                                              21

<210> SEQ ID NO 288
<211> LENGTH: 21
<212> TYPE: RNA
<213> ORGANISM: Arabidopsis thaliana

<400> SEQUENCE: 288
aaggucuugc aaggucaaga a                                              21

<210> SEQ ID NO 289
<211> LENGTH: 282
<212> TYPE: DNA
<213> ORGANISM: Unknown
<220> FEATURE:
<223> OTHER INFORMATION: Not known

<400> SEQUENCE: 289
ctaatacgac tcactatagg gagatttccg tcctccttga aatcaattcc cttaagctcg    60
atcctgttga cgagggtgtc tccctcaaac ttgacttcag cacgtgtctt gtagttcccg   120
tcgtccttga aagagatggt cctctcctgc acgtatccct caggcatggc gctcttgaag   180
aagtcgtgcc gcttcatatg atctgggtat cttgaaaagc attgaacacc ataagagaaa   240
gtagtgacaa gtgttggctc tccctatagt gagtcgtatt ag                      282

<210> SEQ ID NO 290
<211> LENGTH: 325
<212> TYPE: DNA
<213> ORGANISM: Unknown
<220> FEATURE:
<223> OTHER INFORMATION: Not known

<400> SEQUENCE: 290
ctaatacgac tcactatagg gagaggtgct atcctacctg agcttttttcc gtcctccttg    60 aaatcaattc ccttaagctc gatcctgttg acgagggtgt ctccctcaaa cttgacttca   120
gcacgtgtct tgtagttccc gtcgtccttg aaagagatgg tcctctcctg cacgtatccc   180
tcaggcatgg cgctcttgaa gaagtcgtgc cgcttcatat gatctgggta tcttgaaaag   240
```

```
cattgaacac cataagagaa agtagtgaca agtgttggcc cttgtctatc cctcctgagc    300
ttctccctat agtgagtcgt attag                                         325

<210> SEQ ID NO 291
<211> LENGTH: 368
<212> TYPE: DNA
<213> ORGANISM: Unknown
<220> FEATURE:
<223> OTHER INFORMATION: Not known

<400> SEQUENCE: 291
ctaatacgac tcactatagg gagaagctca ggagggatag acaaggggtg ctatcctacc     60
tgagcttttt ccgtcctcct tgaaatcaat tcccttaagc tcgatcctgt tgacgagggt    120
gtctccctca aacttgactt cagcacgtgt cttgtagttc ccgtcgtcct tgaaagagat    180
ggtcctctcc tgcacgtatc cctcaggcat ggcgctcttg aagaagtcgt gccgcttcat    240
atgatctggg tatcttgaaa agcattgaac accataagag aaagtagtga caagtgttgg    300
caagctcagg taggatagca ccccttgtct atccctcctg agcttctccc tatagtgagt    360
cgtattag                                                            368

<210> SEQ ID NO 292
<211> LENGTH: 301
<212> TYPE: DNA
<213> ORGANISM: Unknown
<220> FEATURE:
<223> OTHER INFORMATION: Not known

<400> SEQUENCE: 292
ctaatacgac tcactatagg gagaggtgct atcctacctg agcttttcc gtcctccttg      60 aaatcaattc ccttaagctc gatcctgttg acgagggtgt ctccctcaaa cttgacttca    120
gcacgtgtct tgtagttccc gtcgtccttg aaagagatgg tcctctcctg cacgtatccc    180
tcaggcatgg cgctcttgaa gaagtcgtgc cgcttcatat gatctgggta tcttgaaaag    240
cattgaacac cataagagaa agtagtgaca agtgttggcc cttgtctatc cctcctgagc    300
t                                                                   301

<210> SEQ ID NO 293
<211> LENGTH: 258
<212> TYPE: DNA
<213> ORGANISM: Unknown
<220> FEATURE:
<223> OTHER INFORMATION: Not known

<400> SEQUENCE: 293
ctaatacgac tcactatagg gagagccaac acttgtcact actttctctt atggtgttca     60
atgcttttca agatacccag atcatatgaa gcggcacgac ttcttcaaga gcgccatgcc    120
tgagggatac gtgcaggaga ggaccatctc tttcaaggac gacggaaact acaagacacg    180
tgctgaagtc aagtttgagg gagacaccct cgtcaacagg atcgagctta agggaattga    240
tttcaaggag gacggaaa                                                 258

<210> SEQ ID NO 294
<211> LENGTH: 375
<212> TYPE: DNA
<213> ORGANISM: Unknown
<220> FEATURE:
<223> OTHER INFORMATION: Not known
```

```
<400> SEQUENCE: 294
ctaatacgac tcactatagg gagaggtgct atcctacctg agcttttttcc gtcctccttg     60 aaatcaattc ccttaagctc gatcctgttg acgagggtgt ctccctcaaa cttgacttca    120
gcacgtgtct tgtagttccc gtcgtccttg aaagagatgg tcctctcctg cacgtatccc    180
tcaggcatgg cgctcttgaa gaagtcgtgc cgcttcatat gatctgggta tcttgaaaag    240
cattgaacac cataagagaa agtagtgaca agtgttggcg ctactggact ttcgccatct    300
agggtgcagc attcgggctg cttcgcctac cttgtctatc cctcctgagc ttctccctat    360
agtgagtcgt attag                                                     375

<210> SEQ ID NO 295
<211> LENGTH: 344
<212> TYPE: DNA
<213> ORGANISM: Unknown
<220> FEATURE:
<223> OTHER INFORMATION: Not known

<400> SEQUENCE: 295
ctaatacgac tcactatagg gagaagctca ggagggatag acaaggggtg ctatcctacc     60
tgagcttttt ccgtcctcct tgaaatcaat tcccttaagc tcgatcctgt tgacgagggt    120
gtctccctca aacttgactt cagcacgtgt cttgtagttc ccgtcgtcct tgaaagagat    180
ggtcctctcc tgcacgtatc cctcaggcat ggcgctcttg aagaagtcgt gccgcttcat    240
atgatctggg tatcttgaaa agcattgaac accataagag aaagtagtga caagtgttgg    300
caagctcagg taggatagca ccccttgtct atccctcctg agct                     344

<210> SEQ ID NO 296
<211> LENGTH: 394
<212> TYPE: DNA
<213> ORGANISM: Unknown
<220> FEATURE:
<223> OTHER INFORMATION: Not known

<400> SEQUENCE: 296
ctaatacgac tcactatagg gagaagctca ggagggatag acaaggggtg ctatcctacc     60
tgagcttgcc aacacttgtc actactttct cttatggtgt tcaatgcttt tcaagatacc    120
cagatcatat gaagcggcac gacttcttca gagcgccat gcctgaggga tacgtgcagg    180
agaggaccat ctctttcaag gacgacggga actacaagac acgtgctgaa gtcaagtttg    240
agggagacac cctcgtcaac aggatcgagc ttaagggaat tgatttcaag gaggacggaa    300
aaagctcagg taggatagca ccccttgtct atccctcctg agcttaggcg aagcagcccg    360
aatgctgcac cctagatggc gaaagtccag tagc                                394

<210> SEQ ID NO 297
<211> LENGTH: 347
<212> TYPE: DNA
<213> ORGANISM: Unknown
<220> FEATURE:
<223> OTHER INFORMATION: Not known

<400> SEQUENCE: 297
ctaatacgac tcactatagg gagaggtgct atcctacctg agcttttttcc gtcctccttg     60 aaatcaattc ccttaagctc gatcctgttg acgagggtgt ctccctcaaa cttgacttca    120
gcacgtgtct tgtagttccc gtcgtccttg aaagagatgg tcctctcctg cacgtatccc    180
tcaggcatgg cgctcttgaa gaagtcgtgc cgcttcatat gatctgggta tcttgaaaag    240
```

```
cattgaacac cataagagaa agtagtgaca agtgttggct cgcaggagag atgacaccag    300
accttgtcta tccctcctga gcttctccct atagtgagtc gtattag                 347
```

<210> SEQ ID NO 298
<211> LENGTH: 282
<212> TYPE: DNA
<213> ORGANISM: Lycopersicon esculentum

<400> SEQUENCE: 298

```
ctaatacgac tcactatagg gagatttctc accgcttttt tttttctgtt gtgtattctc    60 tttttgact tgttgccttt cgttcctcta cctaccccat tcttcttgac cttgtaagac    120
cttttcttga ccttgtaaga ccccgtgtta tctcttacgt ctttatgttt tgttttttg    180 caaatcttac gtcatgactt cttcatgtaa gctttgtttg gtctccttct tctttcctac    240
tcaactctcg ttctcctttc tccctatagt gagtcgtatt ag                      282
```

<210> SEQ ID NO 299
<211> LENGTH: 325
<212> TYPE: DNA
<213> ORGANISM: Unknown
<220> FEATURE:
<223> OTHER INFORMATION: Not known

<400> SEQUENCE: 299

```
ctaatacgac tcactatagg gagaggtgct atcctacctg agcttttct caccgctttt     60 tttttctgt tgtgtattct cttttttgac ttgttgcctt tcgttcctct acctacccca    120
ttcttcttga ccttgtaaga ccttttcttg accttgtaag accccgtgtt atctcttacg   180
tctttatgtt ttgttttttt gcaaatctta cgtcatgact tcttcatgta agctttgttt   240
ggtctccttc tctttcccta ctcaactctc gttctccttc cttgtctatc cctcctgagc   300
ttctccctat agtgagtcgt attag                                         325
```

<210> SEQ ID NO 300
<211> LENGTH: 21
<212> TYPE: DNA
<213> ORGANISM: Lycopersicon esculentum

<400> SEQUENCE: 300

```
aactacattt ctcccttcca g                                              21
```

<210> SEQ ID NO 301
<211> LENGTH: 20
<212> TYPE: DNA
<213> ORGANISM: Lycopersicon esculentum

<400> SEQUENCE: 301

```
tcacaacaaa cacctgctac                                                20
```

<210> SEQ ID NO 302
<211> LENGTH: 19
<212> TYPE: DNA
<213> ORGANISM: Lycopersicon esculentum

<400> SEQUENCE: 302

```
cgaaagaacc atctactcc                                                 19
```

<210> SEQ ID NO 303
<211> LENGTH: 19
<212> TYPE: DNA
<213> ORGANISM: Lycopersicon esculentum

```
<400> SEQUENCE: 303
aaagcctctc caactcaac                                              19

<210> SEQ ID NO 304
<211> LENGTH: 21
<212> TYPE: DNA
<213> ORGANISM: Lycopersicon esculentum

<400> SEQUENCE: 304
caacccaaag gctgcaaaaa c                                           21

<210> SEQ ID NO 305
<211> LENGTH: 21
<212> TYPE: DNA
<213> ORGANISM: Lycopersicon esculentum

<400> SEQUENCE: 305
ggatgcgaca ctcatcgtta g                                           21

<210> SEQ ID NO 306
<211> LENGTH: 20
<212> TYPE: DNA
<213> ORGANISM: Aequorea victoria

<400> SEQUENCE: 306
cgtcgtcctt gaaagagatg                                             20

<210> SEQ ID NO 307
<211> LENGTH: 20
<212> TYPE: DNA
<213> ORGANISM: Aequorea victoria

<400> SEQUENCE: 307
gagccaacac ttgtcactac                                             20

<210> SEQ ID NO 308
<211> LENGTH: 22
<212> TYPE: DNA
<213> ORGANISM: Lycopersicon esculentum

<400> SEQUENCE: 308
gctaagaacg ctggacctaa tg                                          22

<210> SEQ ID NO 309
<211> LENGTH: 20
<212> TYPE: DNA
<213> ORGANISM: Lycopersicon esculentum

<400> SEQUENCE: 309
agaatagcat ccggtctcag                                             20

<210> SEQ ID NO 310
<211> LENGTH: 24
<212> TYPE: DNA
<213> ORGANISM: Lycopersicon esculentum

<400> SEQUENCE: 310
aacaggtggt gctcgactat gact                                        24

<210> SEQ ID NO 311
<211> LENGTH: 23
<212> TYPE: DNA
<213> ORGANISM: Lycopersicon esculentum
```

```
<400> SEQUENCE: 311
tgctttcgac agtttcactt cca                                              23

<210> SEQ ID NO 312
<211> LENGTH: 236
<212> TYPE: DNA
<213> ORGANISM: Artificial Sequence
<220> FEATURE:
<223> OTHER INFORMATION: Synthetic Construct

<400> SEQUENCE: 312
gccacttgca aagtcccgct agtgccttgt ccagttgcaa ccacctgttg atccgcatca      60
cgcagttcaa cgctgacatc accattggcc accacctgcc agtcaacaga cgcgtggtta    120
cagtcttgcg cgacatgcgt caccacggtg atatcgtcca cccaggtgtt cggcgtggtg    180
tagagcatta cgctgcgatg gattccggca tagttaaaga atcatggaa gtaagc         236

<210> SEQ ID NO 313
<211> LENGTH: 278
<212> TYPE: DNA
<213> ORGANISM: Artificial Sequence
<220> FEATURE:
<223> OTHER INFORMATION: Synthetic Construct

<400> SEQUENCE: 313
ggtgctatcc tacctgagct tccacttgca aagtcccgct agtgccttgt ccagttgcaa     60
ccacctgttg atccgcatca cgcagttcaa cgctgacatc accattggcc accacctgcc   120
agtcaacaga cgcgtggtta cagtcttgcg cgacatgcgt caccacggtg atatcgtcca   180
cccaggtgtt cggcgtggtg tagagcatta cgctgcgatg gattccggca tagttaaaga   240
aatcatggaa gtaagccttg tctatccctc ctgagctc                            278

<210> SEQ ID NO 314
<211> LENGTH: 277
<212> TYPE: DNA
<213> ORGANISM: Artificial Sequence
<220> FEATURE:
<223> OTHER INFORMATION: Synthetic Construct

<400> SEQUENCE: 314
ggtgctatcc tacctgagct ttttccgtcc tccttgaaat caattccctt aagctcgttc     60
ctgttgacga gggtgtctcc ctcaaacttg acttcagcat gtgtcttgta gttcccgtcg   120
ttcttgaaag agatggtcct ctcctgcacg tatccctcag gcatggcgct cttgaagaag   180
tcgtgccgct tcatatgatc tgggtatctt gaaaagcatt gaacaccata agagaaagta   240
gtgacaagtg ttggcccttg tctatccctc ctgagct                             277

<210> SEQ ID NO 315
<211> LENGTH: 277
<212> TYPE: DNA
<213> ORGANISM: Artificial Sequence
<220> FEATURE:
<223> OTHER INFORMATION: Synthetic Construct

<400> SEQUENCE: 315
ggtgctatcc tacctgagct ttttctcacc gctttttttt ttctgttgtg tattctcttt     60
ccgtcctcct tgaaatcagt tcctctacct accccattct tccccttaagc tcgatcctgt   120 ttgacttcag cacgtgtctt ggtgttatct cttacgtctt tatgttttgt ttttttgcaa   180
```

```
atcttacgtc atgacttctt catgttcccg tcgtccttga aagagcttct ttcctactca    240
actctcgttc tccttccttg tctatccctc ctgagct                             277
```

<210> SEQ ID NO 316
<211> LENGTH: 277
<212> TYPE: DNA
<213> ORGANISM: Artificial Sequence
<220> FEATURE:
<223> OTHER INFORMATION: Synthetic Construct

<400> SEQUENCE: 316

```
ggtgctatcc tacctgagct ttttccgtcc tccttgtaat caattccctt aagctcgttc    60
ctgttgacga gggtgtcttc ctcaaacttg acttcagcat gtgtcttgta gttcccgtcg   120
tccttgaaag agatggtcct ctcctgcacg tatccctcag gcttggcgct cttgaagaag   180
tcgtgccgct tcatatgatc tgggtatctt gaaaagcatt gaacatcata agagaaagta   240
gtgacatgtg ttggcccttg tctatccctc ctgagct                            277
```

<210> SEQ ID NO 317
<211> LENGTH: 277
<212> TYPE: DNA
<213> ORGANISM: Artificial Sequence
<220> FEATURE:
<223> OTHER INFORMATION: Synthetic Construct

<400> SEQUENCE: 317

```
ggtgctatcc tacctgagct ttttctcacc gcttttaat ggttgtctgg taaaaggtcg     60
ccaattggag tattttgttg ataatgatca gcgagttgct cttcgatgtt gtggcgggtc   120
ttgaagttgg ctttgatgcc gttcttttgc ttgtcggcca tgtgtatacg ttgtgggagt   180
tgtttgtatt ccaacttgtg gccgtgtttc cgtcctcctt gaaatttccc ttaagctcga   240
tcctgtgttc tccttccttg tctatccctc ctgagct                            277
```

<210> SEQ ID NO 318
<211> LENGTH: 21
<212> TYPE: DNA
<213> ORGANISM: Lycopersicon esculentum

<400> SEQUENCE: 318

```
ggtgctatcc tacctgagct t                                              21
```

<210> SEQ ID NO 319
<211> LENGTH: 22
<212> TYPE: DNA
<213> ORGANISM: Lycopersicon esculentum

<400> SEQUENCE: 319

```
ccttgtctat ccctcttgag ct                                             22
```

<210> SEQ ID NO 320
<211> LENGTH: 282
<212> TYPE: DNA
<213> ORGANISM: Aequorea victoria

<400> SEQUENCE: 320

```
ctaatacgac tcactatagg gagatttccg tcctccttga aatcaattcc cttaagctcg    60
atcctgttga cgagggtgtc tccctcaaac ttgacttcag cacgtgtctt gtagttcccg   120
tcgtccttga aagagatggt cctctcctgc acgtatccct caggcatggc gctcttgaag   180
```

| aagtcgtgcc gcttcatatg atctgggtat cttgaaaagc attgaacacc ataagagaaa | 240 |
| gtagtgacaa gtgttggctc tccctatagt gagtcgtatt ag | 282 |

<210> SEQ ID NO 321
<211> LENGTH: 325
<212> TYPE: DNA
<213> ORGANISM: Artificial Sequence
<220> FEATURE:
<223> OTHER INFORMATION: Lycopersicon esculentum and Aequorea victoria

<400> SEQUENCE: 321

| ctaatacgac tcactatagg gagaggtgct atcctacctg agcttttcc gtcctccttg | 60 |
| aaatcaattc ccttaagctc gatcctgttg acgagggtgt ctccctcaaa cttgacttca | 120 |
| gcacgtgtct tgtagttccc gtcgtccttg aaagagatgg tcctctcctg cacgtatccc | 180 |
| tcaggcatgg cgctcttgaa gaagtcgtgc cgcttcatat gatctgggta tcttgaaaag | 240 |
| cattgaacac cataagagaa agtagtgaca agtgttggcc cttgtctatc cctcctgagc | 300 |
| ttctccctat agtgagtcgt attag | 325 |

<210> SEQ ID NO 322
<211> LENGTH: 368
<212> TYPE: DNA
<213> ORGANISM: Artificial Sequence
<220> FEATURE:
<223> OTHER INFORMATION: Lycopersicon esculentum and Aequorea victoria

<400> SEQUENCE: 322

| ctaatacgac tcactatagg gagaagctca ggagggatag acaagggtg ctatcctacc | 60 |
| tgagcttttt ccgtcctcct tgaaatcaat tcccttaagc tcgatcctgt tgacgagggt | 120 |
| gtctccctca aacttgactt cagcacgtgt cttgtagttc ccgtcgtcct tgaaagagat | 180 |
| ggtcctctcc tgcacgtatc cctcaggcat ggcgctcttg aagaagtcgt gccgcttcat | 240 |
| atgatctggg tatcttgaaa agcattgaac accataagag aaagtagtga caagtgttgg | 300 |
| caagctcagg taggatagca ccccttgtct atccctcctg agcttctccc tatagtgagt | 360 |
| cgtattag | 368 |

<210> SEQ ID NO 323
<211> LENGTH: 301
<212> TYPE: DNA
<213> ORGANISM: Artificial Sequence
<220> FEATURE:
<223> OTHER INFORMATION: Lycopersicon esculentum and Aequorea victoria

<400> SEQUENCE: 323

| ctaatacgac tcactatagg gagaggtgct atcctacctg agcttttcc gtcctccttg | 60 |
| aaatcaattc ccttaagctc gatcctgttg acgagggtgt ctccctcaaa cttgacttca | 120 |
| gcacgtgtct tgtagttccc gtcgtccttg aaagagatgg tcctctcctg cacgtatccc | 180 |
| tcaggcatgg cgctcttgaa gaagtcgtgc cgcttcatat gatctggta tcttgaaaag | 240 |
| cattgaacac cataagagaa agtagtgaca agtgttggcc cttgtctatc cctcctgagc | 300 |
| t | 301 |

<210> SEQ ID NO 324
<211> LENGTH: 258
<212> TYPE: DNA
<213> ORGANISM: Artificial Sequence
<220> FEATURE:
<223> OTHER INFORMATION: Lycopersicon esculentum and Aequorea victoria

<400> SEQUENCE: 324

```
ctaatacgac tcactatagg gagagccaac acttgtcact actttctctt atggtgttca      60
atgcttttca agatacccag atcatatgaa gcggcacgac ttcttcaaga gcgccatgcc     120
tgagggatac gtgcaggaga ggaccatctc tttcaaggac gacgggaact acaagacacg     180
tgctgaagtc aagtttgagg gagacaccct cgtcaacagg atcgagctta agggaattga     240
tttcaaggag gacggaaa                                                   258
```

<210> SEQ ID NO 325
<211> LENGTH: 375
<212> TYPE: DNA
<213> ORGANISM: Artificial Sequence
<220> FEATURE:
<223> OTHER INFORMATION: Lycopersicon esculentum and Aequorea victoria

<400> SEQUENCE: 325

```
ctaatacgac tcactatagg gagaggtgct atcctacctg agcttttcc gtcctccttg       60
aaatcaattc ccttaagctc gatcctgttg acgagggtgt ctccctcaaa cttgacttca     120
gcacgtgtct tgtagttccc gtcgtccttg aaagagatgg tcctctcctg cacgtatccc     180
tcaggcatgg cgctcttgaa gaagtcgtgc cgcttcatat gatctgggta tcttgaaaag     240
cattgaacac cataagagaa agtagtgaca agtgttggcg ctactggact ttcgccatct     300
agggtgcagc attcgggctg cttcgcctac cttgtctatc cctcctgagc ttctccctat     360
agtgagtcgt attag                                                      375
```

<210> SEQ ID NO 326
<211> LENGTH: 344
<212> TYPE: DNA
<213> ORGANISM: Artificial Sequence
<220> FEATURE:
<223> OTHER INFORMATION: Lycopersicon esculentum and Aequorea victoria

<400> SEQUENCE: 326

```
ctaatacgac tcactatagg gagaagctca ggagggatag acaaggggtg ctatcctacc      60
tgagcttttt ccgtcctcct tgaaatcaat tcccttaagc tcgatcctgt tgacgagggt     120
gtctccctca aacttgactt cagcacgtgt cttgtagttc ccgtcgtcct tgaaagagat     180
ggtcctctcc tgcacgtatc cctcaggcat ggcgctcttg aagaagtcgt gccgcttcat     240
atgatctggg tatcttgaaa agcattgaac accataagag aaagtagtga caagtgttgg     300
caagctcagg taggatagca ccccttgtct atccctcctg agct                      344
```

<210> SEQ ID NO 327
<211> LENGTH: 394
<212> TYPE: DNA
<213> ORGANISM: Artificial Sequence
<220> FEATURE:
<223> OTHER INFORMATION: Lycopersicon esculentum and Aequorea victoria

<400> SEQUENCE: 327

```
ctaatacgac tcactatagg gagaagctca ggagggatag acaaggggtg ctatcctacc      60
tgagcttgcc aacacttgtc actactttct cttatggtgt tcaatgcttt tcaagatacc     120
cagatcatat gaagcggcac gacttcttca gagcgccat gcctgagggat acgtgcagg     180
agaggaccat ctctttcaag gacgacggga actacaagac acgtgctgaa gtcaagtttg     240
agggagacac cctcgtcaac aggatcgagc ttaagggaat tgatttcaag gaggacggaa     300
```

```
aaagctcagg taggatagca ccccttgtct atccctcctg agcttaggcg aagcagcccg      360
aatgctgcac cctagatggc gaaagtccag tagc                                  394

<210> SEQ ID NO 328
<211> LENGTH: 347
<212> TYPE: DNA
<213> ORGANISM: Artificial Sequence
<220> FEATURE:
<223> OTHER INFORMATION: Lycopersicon esculentum and Aequorea victoria

<400> SEQUENCE: 328
ctaatacgac tcactatagg gagaggtgct atcctacctg agcttttttcc gtcctccttg     60 aaatcaattc ccttaagctc gatcctgttg acgagggtgt ctccctcaaa cttgacttca    120
gcacgtgtct tgtagttccc gtcgtccttg aaagagatgg tcctctcctg cacgtatccc    180
tcaggcatgg cgctcttgaa gaagtcgtgc cgcttcatat gatctgggta tcttgaaaag    240
cattgaacac cataagagaa agtagtgaca agtgttggct cgcaggagag atgacaccag    300
accttgtcta tccctcctga gcttctccct atagtgagtc gtattag                   347

<210> SEQ ID NO 329
<211> LENGTH: 282
<212> TYPE: DNA
<213> ORGANISM: Lycopersicon esculentum

<400> SEQUENCE: 329
ctaatacgac tcactatagg gagatttctc accgcttttt ttttctgttt gtgtattctc      60 tttttgact tgttgccttt cgttcctcta cctaccccat tcttcttgac cttgtaagac    120
cttttcttga ccttgtaaga ccccgtgtta tctcttacgt ctttatgttt tgttttttg    180 caaatcttac gtcatgactt cttcatgtaa gctttgtttg gtctccttct tctttcctac    240
tcaactctcg ttctcctttc tccctatagt gagtcgtatt ag                        282

<210> SEQ ID NO 330
<211> LENGTH: 325
<212> TYPE: DNA
<213> ORGANISM: Lycopersicon esculentum

<400> SEQUENCE: 330
ctaatacgac tcactatagg gagaggtgct atcctacctg agctttttct caccgctttt      60
ttttttctgt tgtgtattct cttttttgac ttgttgcctt tcgttcctct acctacccca    120
ttcttcttga ccttgtaaga ccttttcttg accttgtaag accccgtgtt atctcttacg    180
tctttatgtt ttgttttttt gcaaatctta cgtcatgact tcttcatgta agctttgttt    240
ggtctccttc ttctttccta ctcaactctc gttctccttc cttgtctatc cctcctgagc    300
ttctccctat agtgagtcgt attag                                           325

<210> SEQ ID NO 331
<211> LENGTH: 236
<212> TYPE: DNA
<213> ORGANISM: Artificial Sequence
<220> FEATURE:
<223> OTHER INFORMATION: Escherichia coli and Lycopersicon esculentum

<400> SEQUENCE: 331
gccacttgca aagtcccgct agtgccttgt ccagttgcaa ccacctgttg atccgcatca      60
cgcagttcaa cgctgacatc accattggcc accacctgcc agtcaacaga cgcgtggtta    120
```

```
cagtcttgcg cgacatgcgt caccacggtg atatcgtcca cccaggtgtt cggcgtggtg    180
tagagcatta cgctgcgatg gattccggca tagttaaaga aatcatggaa gtaagc        236

<210> SEQ ID NO 332
<211> LENGTH: 278
<212> TYPE: DNA
<213> ORGANISM: Artificial Sequence
<220> FEATURE:
<223> OTHER INFORMATION: E. coli and Lycopersicon esculentum

<400> SEQUENCE: 332
ggtgctatcc tacctgagct tccacttgca aagtcccgct agtgccttgt ccagttgcaa     60
ccacctgttg atccgcatca cgcagttcaa cgctgacatc accattggcc accacctgcc   120
agtcaacaga cgcgtggtta cagtcttgcg cgacatgcgt caccacggtg atatcgtcca   180
cccaggtgtt cggcgtggtg tagagcatta cgctgcgatg gattccggca tagttaaaga   240
aatcatggaa gtaagccttg tctatccctc ctgagctc                           278
```